US012774463B2

(12) United States Patent
Desai et al.

(10) Patent No.: US 12,774,463 B2
(45) Date of Patent: Oct. 27, 2026

(54) COMPOSITIONS FOR TREATING CANCER WITH KRAS MUTATIONS AND USES THEREOF

(71) Applicant: Aadigen, LLC, Pacific Palisades, CA (US)

(72) Inventors: Neil P. Desai, Pacific Palisades, CA (US); Gilles Divita, St. André de Sangonis (FR)

(73) Assignee: Aadigen, LLC, Pacific Palisades, CA (US)

( * ) Notice: Subject to any disclaimer, the term of this patent is extended or adjusted under 35 U.S.C. 154(b) by 843 days.

(21) Appl. No.: 17/920,355

(22) PCT Filed: Apr. 23, 2021

(86) PCT No.: PCT/US2021/028995
§ 371 (c)(1),
(2) Date: Oct. 20, 2022

(87) PCT Pub. No.: WO2021/217100
PCT Pub. Date: Oct. 28, 2021

(65) Prior Publication Data

US 2023/0167437 A1 Jun. 1, 2023

(30) Foreign Application Priority Data

Apr. 24, 2020 (FR) ...................................... 2004126

(51) Int. Cl.
*C12N 15/11* (2006.01)
*A61K 9/51* (2006.01)
(Continued)

(52) U.S. Cl.
CPC ................ *C12N 15/11* (2013.01); *A61K 9/51* (2013.01); *A61K 31/337* (2013.01);
(Continued)

(58) Field of Classification Search
None
See application file for complete search history.

(56) References Cited

U.S. PATENT DOCUMENTS

| | | | |
|---|---|---|---|
| 4,966,891 | A | 10/1990 | Fujiu et al. |
| 5,356,802 | A | 10/1994 | Chandrasegaran |

(Continued)

FOREIGN PATENT DOCUMENTS

| | | | |
|---|---|---|---|
| KR | 101796036 B1 | 11/2017 | |
| WO | 2005103293 A1 | 11/2005 | |

(Continued)

OTHER PUBLICATIONS

Kelley et al., Versatility of chemically synthesized guide RNAs for CRISPR-Cas9 genome editing, 2016, Journal of Biotechnology, vol. 233, p. 74-83 (Year: 2016).*

(Continued)

*Primary Examiner* — Tracy Vivlemore
*Assistant Examiner* — Hanna Marie Thueson
(74) *Attorney, Agent, or Firm* — MORRISON & FOERSTER LLP

(57) ABSTRACT

The present application provides guide RNAs and genome-editing complexes or nanoparticles that are useful for specifically targeting a mutated KRAS. Exemplary genome-editing complexes or nanoparticles comprise cell-penetrating peptides, and optionally a DNA nuclease (such as Cas9) or a polynucleotide encoding the DNA nuclease.

21 Claims, 26 Drawing Sheets

Specification includes a Sequence Listing.

(51) Int. Cl.

| | |
|---|---|
| ***A61K 31/337*** | (2006.01) |
| ***A61K 31/7088*** | (2006.01) |
| ***A61K 38/46*** | (2006.01) |
| ***A61P 35/00*** | (2006.01) |
| ***C12N 9/22*** | (2006.01) |

(52) U.S. Cl.

CPC ........ *A61K 31/7088* (2013.01); *A61K 38/465* (2013.01); *A61P 35/00* (2018.01); *C12N 9/22* (2013.01); *C12N 2310/20* (2017.05); *C12N 2310/351* (2013.01); *C12N 2310/3513* (2013.01); *C12N 2320/32* (2013.01); *C12N 2800/80* (2013.01)

(56) References Cited

U.S. PATENT DOCUMENTS

| | | | |
|---|---|---|---|
| 5,436,150 A | 7/1995 | Chandrasegaran | |
| 5,487,994 A | 1/1996 | Chandrasegaran | |
| 6,453,242 B1 | 9/2002 | Eisenberg | |
| 6,503,717 B2 | 1/2003 | Case | |
| 6,534,261 B1 | 3/2003 | Cox, III | |
| 6,599,692 B1 | 7/2003 | Case | |
| 6,689,558 B2 | 2/2004 | Case | |
| 6,794,136 B1 | 9/2004 | Eisenberg | |
| 7,030,215 B2 | 4/2006 | Liu | |
| 7,067,317 B2 | 6/2006 | Rebar | |
| 7,070,934 B2 | 7/2006 | Cox, III | |
| 7,235,273 B2 | 6/2007 | Ruston | |
| 7,262,054 B2 | 8/2007 | Jamieson | |
| 7,361,635 B2 | 4/2008 | Miller | |
| 7,514,530 B2 | 4/2009 | Divita | |
| 8,889,642 B2 * | 11/2014 | Shemi .................. | C12N 15/113 536/23.1 |
| 9,376,468 B2 | 6/2016 | Divita | |
| 9,579,395 B2 | 2/2017 | Divita | |
| 9,598,465 B2 | 3/2017 | Divita | |
| 9,834,581 B2 | 12/2017 | Divita | |
| 10,111,965 B2 | 10/2018 | Divita | |
| 10,118,944 B2 | 11/2018 | Divita | |
| 10,189,876 B2 | 1/2019 | Divita | |
| 10,287,581 B2 | 5/2019 | Divita et al. | |
| 10,421,784 B2 | 9/2019 | Divita et al. | |
| 10,688,194 B2 | 6/2020 | Divita et al. | |
| 10,745,400 B2 | 8/2020 | Hopkins et al. | |
| 2005/0064474 A1 | 3/2005 | Urnov | |
| 2005/0267061 A1 | 12/2005 | Martin | |
| 2007/0218528 A1 | 9/2007 | Miller | |
| 2010/0099626 A2 | 4/2010 | Divita | |
| 2011/0059502 A1 | 3/2011 | Chalasani | |
| 2011/0301073 A1 | 12/2011 | Gregory | |
| 2014/0227344 A1 | 8/2014 | Divita et al. | |
| 2016/0060296 A1 | 3/2016 | Divita et al. | |
| 2016/0089447 A1 | 3/2016 | Divita et al. | |
| 2016/0115199 A1 | 4/2016 | Divita et al. | |
| 2016/0145299 A1 | 5/2016 | Divita | |
| 2017/0081661 A1 | 3/2017 | Divita | |
| 2017/0258928 A1 | 9/2017 | Divita et al. | |
| 2018/0179253 A1 | 6/2018 | Divita et al. | |
| 2019/0002499 A1 | 1/2019 | Divita | |
| 2019/0046652 A1 | 2/2019 | Divita | |
| 2019/0077833 A1 | 3/2019 | Divita | |
| 2019/0211317 A1 | 7/2019 | Divita et al. | |
| 2019/0255094 A1 | 8/2019 | Kim et al. | |
| 2020/0172913 A1 | 6/2020 | Desai et al. | |
| 2020/0323964 A1 | 10/2020 | Desai et al. | |
| 2021/0032290 A1 | 2/2021 | Divita et al. | |
| 2022/0313825 A1 | 10/2022 | Desai et al. | |

FOREIGN PATENT DOCUMENTS

| | | |
|---|---|---|
| WO | 2012137150 A2 | 10/2012 |
| WO | 2014053382 A1 | 4/2014 |
| WO | 2014053879 A1 | 4/2014 |
| WO | 2014053880 A1 | 4/2014 |
| WO | 2014053881 A1 | 4/2014 |
| WO | 2016049024 A2 | 3/2016 |
| WO | 2016102687 A1 | 6/2016 |
| WO | 2017205846 A1 | 11/2017 |
| WO | 2018009525 A1 | 1/2018 |
| WO | 2019032917 A1 | 2/2019 |
| WO | 2019079215 A1 | 4/2019 |
| WO | 2019186275 A1 | 10/2019 |

OTHER PUBLICATIONS

Anzalone, A. et al. (Dec. 5, 2019, e-pub. Oct. 21, 2019). "Search-and-Replace Genome Editing Without Double-Strand Breaks or Donor DNA," Nature 576(7785):149-157, 30 pages.

Athuluri-Divakar, S.K. et al. (Apr. 21, 2016). "A Small Molecule RAS-Mimetic Disrupts RAS Association With Effector Proteins to Block Signaling," Cell 165:643-655.

Batzer, M.A. et al. (Sep. 25, 1991). "Enhanced Evolutionary PCR Using Oligonucleotides With Inosine at the 3'-Terminus," Nucleic Acid Res. 19(18):5081.

Beerli, R. R. et al. (Feb. 1, 2002). "Engineering Polydactyl Zinc-Finger Transcription Factors," Nature Biotechnology 20:135-141.

Bikard, D. et al. (2013, e-pub. Jun. 12, 2013). "Programmable Repression and Activation of Bacterial Gene Expression Using an Engineered CRISPR-Cas System," Nucleic Acids Research 41(15):7429-7437.

Brooks, P.C. et al. (Apr. 22, 1994) "Requirement of Vascular Intergrin αvβ3 for Angiogenesis," Science 264:569-571.

Brummelkamp, T.R. et al. (2002, e-pub. Aug. 22, 2002). "Stable Suppression of Tumorigenicity by Virus-Mediated RNA Interference," Cancer Cell 2:243:1-5.

Burshell, J.V. et al. (Oct. 15, 1987) "Development and Characterization of Breast Cancer Reactive Monoclonal Antibodies Directed to the Core Protein of the Human Milk Mucin," Cancer Res. 47:5476-5482.

Cancer Genome Atlas Research Network. (Jul. 4, 2013). "Comprehensive molecular characterization of clear cell renal cell carcinoma," Nature 499:43-49.

Choo, Y. et al. (Aug. 2000). "Advances in Zinc Finger Engineering," Curr Opin Struct Biol. 10(4):411-416.

Critchlow, S.E. et al. (Oct. 1998). "DNA End-Joining: From Yeast to Man," Trends Biochem. Sci. 23(10):394-398.

Céspedes, M. et al. (2006, e-pub. May 5, 2006). "K-ras Asp12 Mutant Neither Interacts with Raf, Nor Signals Through Erk and is Less Tumorigenic Than K-ras Val12," Carcinogenesis 27(11):2190-2200.

Dickson, M.A. et al. (Apr. 1, 2013). "Extrarenal Perivascular Epithelioid Cell Tumors (PEComas) Respond to mTOR Inhibition: Clinical and Molecular Correlates," International Journal of Cancer 132(7):1711-1717, 14 pages.

Dickson, M.A. et al. (Apr. 1, 2013). "Extrarenal Perivascular Epithelioid Cell Tumors (PEComas) Respond to mTOR Inhibition: Clinical and Molecular Correlates," International Journal of Cancer 132(7):1711-1717.

Divita, G, et al. (2020). "Abstract 1826: CRISPR Mediated KRAS Mutant Gene Editing in Pancreatic and Colorectal Cancer Therapy" Proceedings: AACR Annual Meeting 2020, 80(16)1-4.

Dokurno, P. et al., (1998) "Crystal Structure at 1.95 A Resolution of the Breast Tumour-specific Antibody SM3 Complexed with its Peptide Epitope Reveals Novel Hypervariable Loop Recognition," J. Mol. Biol. 284:713-728.

Dominguez, A.A. et al. (Jan. 2016, e-pub. Dec. 16, 2015). "Beyond Editing: Repurposing CRISP-Cas9 for Precision Genome Regulation and Interrogation," Nature Reviews Molecular Cell Biology 17:1-15.

Dow, L.E. et al. (Apr. 2015). "Inducible in vivo Genome Editing with CRISPR/Cas9," Nature Biotechnology 33(4):390-394, (includes Supplemental Material), 24 pages.

Futreal, A.P. et al. (Oct. 7, 1994) "BRCA1 Mutations in Primary Breast and Ovarian Carcinomas" Science 226:120-122.

Gaj, T. et al. (Jul. 2013, e-pub. May 9, 2013). "ZFN, TALEN, and CRISPR/Cas-Based Methods for Genome Engineering," Trends Biotechnol. 31(7):397-405.

(56) References Cited

OTHER PUBLICATIONS

Girling, A. et al. (1989). "A Core Protein Epitope of the Polymorphic Epithelial Mucin Detected by the Monoclonal Antibody SM-3 is Selectively Exposed in a Range of Primary Carcinomas," Int. J. Cancer 43:1072-1076.
Groenen, P.M.A. et al. (1993). "Nature of DNA Polymorphism in the Direct Repeat Cluster of *Mycobacterium tuberculosis*; Application for Strain Differentiation by a Novel Typing Method," Mol. Microbiol. 10(5):1057-1065.
Gump, J.M. et al. (Oct. 2007). "TAT Transduction: the Molecular Mechanism and Therapeutic Prospects," Trends Mol. Med. 13(10):443-448.
Hanahan, D. (1997). "Signaling Vascular Morphogenesis and Maintenance," Science 277:48-50, 6 pages.
Hareuveni, M. et al. (1990). "A Transcribed Gene, Containing a Variable Number of Tandem Repeats, Codes for a Human Epithelial Tumor Antigen cDNA Cloning, Expression of the Transfected Gene and Over-Expression in Breast Cancer Tissue," Eur. J. Biochem. 189:475-486.
Harris, J.D. et al. (1994). Gene Therapy for Cancer Using Tumour-Specific Prodrug Activation, Gene Therapy 1:170-175.
Hart, T. et al. (Dec. 3, 2015). "High-Resolution CRISPR Screens Reveal Fitness Genes and Genotype-Specific Cancer Liabilities," Cell 163(6):1515-1526.
Heitz, F. et al. (2009, e-pub. Mar. 20, 2009). "Themed Section: Vector Design and Drug Delivery Review. Twenty Years of Cell-Penetrating Peptides: From Molecular Mechanisms to Therapeutics," British Journal of Pharmacology 157:195-206.
International Preliminary Report on Patentability, mailed on Nov. 3, 2022, for PCT Application No. PCT/US2021/028995, filed on Apr. 23, 2021, 11 pages.
International Search Report and Written Opinion, mailed on Jul. 21, 2021, for PCT Application No. PCT/US2021/028995, filed on Apr. 23, 2021, 18 pages.
Isalan, M. et al. (Jul. 2001). "A Rapid, Generally Applicable Method to Engineer zinc Fingers Illustrated by Targeting the HIV-1 Promoter," Nat Biotechnol. 19(7):656-660, 14 pages.
Ishino, Y. et al. (Dec. 1987). "Nucleotide Sequence of the iap Gene, Responsible for Alkaline Phosphatase Isozyme Conversion in *Escherichia coli*, and Identification of the Gene Product," J. Bacteriol. 169(12):5429-5433.
Jansen, R. et al. (2002). "Identification of Genes That are Associated With DNA Repeats in Prokaryotes," Mol. Microbiol. 43(6):1565-1575.
Jones, S. et al. (Sep. 26, 2008). "Core Signaling Pathways in Human Pancreatic Cancers Revelated by Global Genomic Analyses," Science 321:1801-1806.
Kanai, F. et al., (Feb. 1, 1997). "In Vivo Gene Therapy for Alpha-Fetoprotein-Producing Hepatocellular Carcinoma by Adenovirus-Mediated Transfer of Cytosine Deaminase Gene," Cancer Res. 57:461-465.
Khvalevsky, E.Z. et al. (Dec. 17, 2013). "Mutant KRAS is a Druggable Target for Pancreatic Cancer," Proc. Natl. Acad. Sci. USA 110(51):20723-20728.
Kim, Y-G. et al. (Dec. 16, 1994). "Insertion and Deletion Mutants of Fokl Restriction Endonuclease," J.Biol. Chem. 269(50):31978-31982.
Kim, Y-G. et al. (Feb. 1994). "Chimeric Restriction Endonuclease," Proc. Natl. Acad. Sci. USA 91:883-887.
Kim, Y. et al. (Mar. 2013, e-pub. Feb. 17, 2013). "A Library of TAL effector Nucleases Spanning the Human Genome," Nat Biotechnol 31(3):251-258.
Kleinstiver, B.P. et al. (Jul. 23, 2015). "Engineered CRISPR-Cas9 Nucleases With Altered PAM Specificities," Nature 523(7561):481-485, 27 pages.
Komor, A. C. et al. (May 19, 2016). "Programmable Editing of a Target Base in Genomic DNA Without Double-Stranded DNA Cleavage," Nature 533:420-424.
Lee, W, et al. (2018, e-pub. Aug. 8, 2018). "Selective Targeting of KRAS Oncogenic Alleles by CRISPR/Cas9 Inhibits Proliferation of Cancer Cells," Scientific Reports 8:1-7.
Lentsch, E, et al. (2019). "CRISPR/Cas9-Mediated Knock-Out of RrasG12D Mutated Pancreatic Cancer Cell Lines," International Journal of Molecular Sciences 20(5706):1-11.
Li, L. et al. (Apr. 1993). "Alteration of the cleavage distance of Fok I restriction endonuclease by insertion mutagenesis," Proc Natl Acad Sci U S A 90(7):2764-2768.
Li, L. et al. (May 1992). "Functional Domains in Fok I Restriction Endonuclease," Proc. Natl. Acad. Sci. U S A. 89(10):4275-4279.
Lloyd, A. et al. (Aug. 5, 2013). "Beyond the Antigen Receptor: Editing the Genome of T-Cells for Cancer Adoptive Cellular Therapies," Front Immunol. 4(221):1-7.
Michael, S.I. et al. (1995). "Addition of a Short Peptide Ligand to the Adenovirus Fiber Protein," Gene Therapy 2:660-668.
Mickan, A. et al. (2014). "Rational Design of CPP-based Drug Delivery Systems: Considerations from Pharmacokinetics," Current Pharmaceutical Biotechnology 15(3):200-209, 10 pages.
Miki, Y. et al. (Oct. 7, 1994). "A Strong Candidate for the Breast and Ovarian Cancer Susceptibility Gene BRCA1," Science 226:66-71.
Mojica, F.J.M et al. (2000). "MicroCorrespondence," Mol. Microbiol. 36:244-246.
Mojica, F.J.M. et al. (1995). "Long Stretches of Short Tandem Repeats are Present in the Largest Replicon of the Archaea Haloferax Volcanii and Could be Involved in Replicon Partitioning," Mol. Microbiol. 17(1):85-93.
Mojica, F.J.M. et al. (2005). "Intervening Sequences of Regularly Spaced Prokaryotic Repeats Derive From Foreign Genetic Elements," Journal of Molecular Evolution 60:174-182.
Morris, M.C. et al. (1997). "A New Peptide Vector for Efficient Delivery of Oligonucleotides Into Mammalian Cells," Nucleic Acids Res. 25(14):2730-2736.
Morris, M.C. et al. (Dec. 2001). "A Peptide Carrier for the Delivery of Biologically Active Proteins Into Mammalian Cells," Nat. Biotechnol. 19:1173-1176.
Nakamura, Y., et al. (Jan. 1, 2000). "Codon Usage Tabulated From the International DNA Sequence Databases: Status for the Year 2000," Nucl. Acids Res. 28:292.
Nakase, I. et al. (Dec. 2004). "Cellular Uptake of Arginine-Rich Peptides: Roles for Macropinocytosis and Actin Rearrangement," Molecular Therapy 10(6):1011-1022.
Nakata, A. et al. (Jun. 1989). "Unusual Nucleotide Arrangement With Repeated Sequences in the *Escherichia coli* K-12 Chromosome," J. Bacteriol. 171(6):3553-3556.
Ohtsuka, E. et al. (Mar. 10, 1985). "An Alternative Approach to Deoxyoligonucleotides as Hybridization Probes by Insertion of Deoxyinosine at Ambiguous Codon Positions," J. Biol. Chem. 260(5):2605-2608.
Pabo, C. O. et al. (Jul. 2001). "Design and Selection of Novel Cys2His2 Zinc Finger Proteins," Annual Review of Biochemistry 70:313-340.
Patricelli, M.P. et al. (Mar. 2016). "Selective Inhibition of Oncogenic KRAS Output with Small Molecules Targeting the Inactive State," Cancer Discov. 6:316-329.
Polstein, L.R. et al. (Mar. 2015). "A Light-Inducible CRISPR/Cas9 System for Control of Endogenous Gene Activation," Nature Chemical Biology 11(3):198-200, 10 pages.
Qi L.S. et al. (Feb. 28, 2013). "Repurposing CRISPR as an RNA-Guided Platform for Sequence-Specific Control of Gene Expression," Cell 152(5):1173-1183.
Rees, H.A. et al. (Jun. 6, 2017). "Improving DNA Specificity and Applicability of Base Editing Through Protein Engineering and Protein Delivery," Nature Communications 8:15790, pp. 1-10.
Rossolini, G.M. et al. (1994). "Use of Deoxyinosine-containing Primers vs Degenerate Primers for Polymerase Chain Reaction Based on Ambiguous Sequence Information," Molecular and Cellular Probes 8:91-98.
Rothbard, J.B. et al. (2004; e-pub. Jul. 20, 2004). "Role of Membrane Potential and Hydrogen Bonding in the Mechanism of Translocation of Guanidinium-Rich Peptides into Cells," Journal of American Chemical Society 126(31):9506-9507.

(56) References Cited

OTHER PUBLICATIONS

Schrewe, H. et al. (Jun. 1990). "Cloning of the Complete Gene for Carcinoembryonic Antigen: Analysis of Its Promoter Indicates a Region Conveying Cell Type-Specific Expression," Mol. Cell. Biol. 10(6):2738-2748.
Segal, D. J. et al. (Dec. 1, 2001). "Custom DNA-binding Proteins Come of Age: Polydactyl Zinc-Finger Proteins," Current Opinion in Biotechnology 12(6):632-637.
Shukla, R.S. et al. (2014; Aug. 26, 2014). "Peptides Used in the Delivery of Small Noncoding RNA," Molecular Pharmaceuticals 11(10):3395-3408.
Stamey, T.A. et al. (Oct. 8, 1987). "Prostate-Specific Antigen as a Serum Marker for Adenocarcinoma of the Prostate," New England J. Med. 317(15):909-916.
Van Embden, J.D.A et al. (May 2000). "Genetic Variation and Evolutionary Origin of the Direct Repeat Locus of *Mycobacterium tuberculosis* Complex Bacteria," J. Bacteriol. 182(9):2393-2401.
Vile, R.G. et al. (Sep. 1, 1993). "Use of Tissue-Specific Expression of the Herpes Simplex Virus Thrymidine Kinase Gene to Inhibit Growth of Established Murine Melanomas Following Direct Intratumoral Injection of DNA," Cancer Res. 53:3860-3864.
Wagle, N. et al. (May 2014). "Activating mTOR Mutationsin a Patient with an Extraordinary Response on a Phase I Trial of Everolimus and Pazopanib," Cancer Discovery 4:546-553.
Wood, A.D. et al. (Nov. 16, 2007). "The Genomic Landscapes of Human Breast and Colorectal Cancers," Science 318:1108-1113.
Wooster, R. et al. (Dec. 21-28, 1995). "Identification of the Breast Cancer Susceptibility Gene BRCA2," Nature 378:789-792.
Zetsche, B. et al. (Feb. 2015). "A Split-Cas9 Architecture for Inducible Genome Editing and Transcription Modulation," Nature biotechnology 33(2):139-142.
Ahmed, M. (Jan. 1, 2017). "Peptides, Polypeptides and Peptide-Polymer Hybrids as Nucleic Acid Carriers," Biomaterials Science 5(11):2188-2211.
Gonzalez, G.V. et al. (Dec. 1, 2024). "Enhanced CRISPR-Cas9 RNA System Delivery Using Cell Penetrating Peptides-Based Nanoparticles for Efficient in Vitro and in Vivo Applications," Journal of Controlled Release 376:1160-1175.
Kim, W. et al. (Mar. 2018). "Targeting Mutant KRAS With CRISPR-Cas9 Controls Tumor Growth," Genome Research 28:374-382.
Lee, S.H. et al. (Aug. 16, 2013). "Is There a Future for Cell-Penetrating Peptides in Oligonucleotide Delivery?" European Journal of Pharmaceutics and Biopharmaceutics 85(1):5-11.
Rai, J. (Jan. 29, 2019). "Peptide and Protein Mimetics by Retro and Retroinverso Analogs," Chemical Biology & Drug Design 93(5):724-736.
Shen, Y. et al. (2018, e-pub. Sep. 6, 2018). "CRISPR-Delivery Particles targeting Nuclear Receptor-Interacting Protein 1 (Nrip 1) in Adipose cells to Enhance Energy Expenditure," J. Biol. Chem. 293(44):17291-17305.
Jiang, W. et al. (Sep. 16, 2020). "Precise and Efficient Silencing of Mutant KrasG12D by CRISPR-CasRx Controls Pancreatic Cancer Progression," Theranostics 10(25):11507-11519.

* cited by examiner

| | Liver | Spleen | Lung | Kidney | Pancreas | Heart | blood | brain | muscle | lymphnode | tumor |
|---|---|---|---|---|---|---|---|---|---|---|---|
| ADGN-106 | 27 | 2,5 | 3,4 | 4,6 | 0,9 | 1,2 | 1,6 | 1,2 | 1 | 1,9 | 1,9 |
| ADGN-100 | 4,5 | 3,5 | 28 | 4,7 | 4,5 | 4,5 | 1 | 1,2 | 1,2 | 1,8 | 3,1 |
| ADGN-100 Hy5 | 3,1 | 2,5 | 11,4 | 2,8 | 1,2 | 2,5 | 1,5 | 1,2 | 1 | 2,1 | 5,7 |
| ADGN-106 Hy5 | 15 | 2,5 | 3 | 8,7 | 0,8 | 2,1 | 1,2 | 1,2 | 3,8 | 1 | 2,5 |
| ADGN-106 Hy3 | 4,2 | 2,1 | 37 | 3,5 | 2,1 | 3,4 | 1,4 | 1,4 | 7,8 | 1,8 | 7,9 |
| ADGN-100-Hy3 | 4,2 | 2,5 | 3,1 | 2,5 | 3,5 | 2,5 | 1,4 | 1,7 | 2,4 | 1,2 | 11,4 |
| ADGN-100-Hy7 | 3,5 | 2,8 | 2 | 2 | 1 | 1,3 | 0,98 | 1,8 | 1,1 | 1,1 | 12,8 |
| ADGN-106 Hy7 | 4 | 2 | 24 | 5 | 2 | 3,2 | 1,1 | 1,2 | 5,1 | 0,98 | 7,5 |
| mRNA | 1,7 | 1,3 | 1,1 | 2 | 1 | 1,3 | 0,98 | 1,8 | 1,1 | 1,1 | 0,9 |

G1 : control
G2 : ADGN/mRNA CAS9/control gRNA
G3 : G12D targeting ADGN /mRNACAS/gRNA dose 0.5 mg/Kg
G4 : G12D targeting ADGN /mRNACAS/gRNA dose 1.0 mg/Kg
G5 : G12C targeting ADGN/mRNACAS/gRNA dose 1.0 mg/Kg G1 : control
G2 : ADGN/mRNA CAS9/control gRNA
G3 : G12V targeting ADGN /mRNACAS/gRNA dose 0,5 mg/Kg
G4 : G12V targeting ADGN /mRNACAS/gRNA dose 1.0 mg/Kg
G5 : G12C targeting ADGN/mRNACAS/gRNA dose 1.0 mg/Kg G1 : ADGN/mRNA CAS9/control gRNA
G2 : G12D targeting ADGN /mRNACAS/gRNA dose 0,5 mg/Kg
G3 : G12D targeting ADGN /mRNACAS/gRNA dose 1.0 mg/Kg
G4 : G12C targeting ADGN/mRNACAS/gRNA dose 1.0 mg/Kg G1 : ADGN/mRNA CAS9/control gRNA
G2 : G12V targeting ADGN /mRNACAS/gRNA dose 0,5 mg/Kg
G3 : G12V targeting ADGN /mRNACAS/gRNA dose 1.0 mg/Kg
G4 : G12C targeting ADGN/mRNACAS/gRNA dose 1.0 mg/Kg

FIG. 18

Target sequences for the design of sgRNA targeting KRAS WT

| 5' 3' | PAM | |
|---|---|---|
| CTTGTGGTAGTTGGAGCTGG | TGG | gRNAWT1 |
| TTGGATATTCTCGACACAGC | TAG | gRNAWT2 |
| TCTCGACACAGCAGGTCAAG | AGG | gRNAWT3 |
| GATGTACCTATGGTCCTAGT | TGG | gRNAWT4 |
| GTCGAGAATATCCAAGAGAC | GAG | gRNAWT5 |
| TCTCGACACAGCAGGTCAAG | AGG | gRNAWT6 |

Target sequences for KRAS G12D mutation. SgRNA 35G>A .

| 5' 3' | PAM | |
|---|---|---|
| CTT GTG GTA GTT GGA GCT GA | TGG | gRNA35A1 |
| GGT AGT TGG AGC TGA TGG CG | TAG | gRNA35A2 |
| AGC TGA TGG CGT AGG CAA | GAG | gRNA35A3 |
| TGA TGG CGT AGG CAA GAGT | GCC | gRNA35A4 |
| AGT TGG AGC TGA TGG CGT | AGG | gRNA35A5 |
| GTT GGA GCT GAT GGC GT | AGG | gRNA35A6 |
| GTA GTT GGA GCT GAT GGC GT | AGG | gRNA35A7 |
| TTG TGG TAG TTG GAG CTG A | TGG | gRNA35A8 |
| GCT GAT GGC GTA GGC AA | GAG | gRNA35A9 |
| TAG TTG GAG CTG ATG GCG T | AGG | gRNA35A10 |
| TGA TGG CGT AGG CAA GAG TGC CTT G | ACG | gRNA35A11 |

Target sequences for KRAS G12V mutation. SgRNA c.35G>T (p.G12V). .

| 5' 3' | PAM | |
|---|---|---|
| TGG TAG TTG GAG CTG TTG GCG T | AGG | gRNA35T1 |
| CTT GTG GTA GTT GGA GCT GT | TGG | gRNA35T2 |
| GGT AGT TGG AGC TGT TGG CG | TAG | gRNA35T3 |
| AGC TGT TGG CGT AGG CAA | GAG | gRNA35T4 |
| TGT TGG CGT AGG CAA GAGT | GCC | gRNA35T5 |
| GTT GGA GCT GTT GGC GT | AGT | gRNA35T6 |
| TTG TGG TAG TTG GAG CTG T | TGG | gRNA35T7 |
| GTA GTT GGA GCT GTT GGC GT | AGT | gRNA35T8 |
| GCT GTT GGC GTA GGC AA | GAG | gRNA35T9 |
| TAG TTG GAG CTG TTG GCG T | AGG | gRNA35T10 |
| TGT TGG CGT AGG CAA GAG TGC CTT G | ACC | gRNA35T11 |

Target sequences for KRAS G12C mutation. SgRNA 34G>T mutant G12C

| | | |
|---|---|---|
| CTT GTG GTA GTT GGA GCT TG | TGG | gRNA34T1 |
| AGC TTG TGG CGT AGG CAA | GAGT | gRNA34T2 |
| GTT GGA GCT TGT GGC GT | AGG | gRNA34T3 |
| GGT AGT TGG AGC TTG TGG CG | TAG | gRNA34T4 |
| TTG TGG TAG TTG GAG CTT G | TAG | gRNA34T5 |
| GTA GTT GGA GCT TGT GGC GT | AGG | gRNA34T6 |
| GCT TGT GGC GTA GGC AA | GAGT | gRNA34T7 |
| CTT GTG GCG TAG GCA AGA GT | GCC | gRNA34T8 |
| CTT GTG GCG TAG GCA AGA GTG CCT TG | ACG | gRNA34T9 |
| TTG TGG CGT AGG CAA GAG TGC CTT G | ACG | gRNA34T10 |

See Tables 1-3 and Sequence table for SEQ ID Nos of the sequence

FIG. 24

Cancer Cell Lines with Mutant KRAS Genes and or Mutant p53 genes

| INDICATION | Cell Types | KRAS | P53 |
|---|---|---|---|
| PDAC Pancreatic carcinoma | PANC-1 | G12D | R273H |
| | PK-45H | G12D | WT |
| | PK-1 | G12D | M237I |
| | MIA PACA | G12C | R248W |
| | ASPC-1 | G12D | C135A & 403del |
| CRC Colorectal carcinoma | SW-480 | G12V | R273H/P309S |
| | SW-403 | G12V | Q51Ter |
| | LS-513 | G12D | WT |
| | HT-29 | WT | R273H |
| NSCLC Lung carcinoma | NCI H-23 | G12C | M246I |
| | NCI H-358 | G12C | DELETION |
| | H-1299 | WT | DELETION |
| | H-2122 | G12C | Q16L/C176F |
| | H-2444 | G12V | T236C |
| | H-441 | G12V | R158L |
| | CALU-1 | G12C | DELETION |

FIG. 25

$IC_{50}$ and $CC_{50}$ parameters of ADGN-121 in cancer cell lines

| Cell lines | Indication | KRAS | ADGN-121 IC50 (nM) | ADGN-121 CC50 (µM) |
|---|---|---|---|---|
| SW-480 | Colorectal carcinoma | G12V | 17.8±7 | 7.8±0.5 |
| SW-403 | Colorectal carcinoma | G12V | 18.8±3 | 8.5±0.5 |
| LS-513 | Colorectal Carcinoma | G12D | -- | 8.7±0.7 |
| HT-29 | Colorectal Carcinoma | WT | -- | 7.1 ± 0.6 |
| PANC-1 | Pancreatic carcinoma | G12D | -- | 6.8 ± 0.7 |
| H-441 | Lung carcinoma | G12V | 15.6±5 | > 10 |
| H-2444 | Lung carcinoma | G12V | 45.5±8 | > 10 |
| H-358 | Lung carcinoma | G12C | - | 9.7±0.4 |
| CALU-1 | Lung carcinoma | G12C | -- | >10 |
| H-1299 | Lung carcinoma | WT | -- | 8.5±0.5 |

FIG. 26

$IC_{50}$ and $CC_{50}$ parameters of ADGN-123 in cancer cell lines.

| CELL LINES | Indication | KRAS | ADGN-123 IC50 (nM) | ADGN-123 CC50 (μM) |
|---|---|---|---|---|
| PANC-1 | Pancreatic carcinoma | G12D | 22.8±2 | 7.7±0.5 |
| PK-45H | Pancreatic carcinoma | G12D | 25.3±3 | 8.2±0.5 |
| PK-1 | Pancreatic carcinoma | G12D | 15.2±3 | >10 |
| ASPC-1 | Pancreatic carcinoma | G12D | 11.2 ±3 | 9.5±0.5 |
| MIA-PACA | Pancreatic carcinoma | G12C | -- | 7.4 ±0.5 |
| HT-29 | Colorectal carcinoma | WT | -- | >10 |
| LS-513 | Colorectal carcinoma | G12D | 9.8±2 | >10 |
| SW-480 | Colorectal carcinoma | G12V | -- | >10 |
| Sw-403 | Colorectal carcinoma | G12V | -- | 9.8±0.5 |
| H358 | Lung carcinoma | G12C | -- | 8.8±0.5 |
| H-441 | Lung carcinoma | G12V | -- | >10 |

FIG. 27

$IC_{50}$ and $CC_{50}$ parameters of ADGN-122 in cancer cell lines.

| CELL LINES | Indication | KRAS | ADGN-122 IC50 (nM) | ADGN-122 CC50 (μM) |
|---|---|---|---|---|
| H-358 | Lung carcinoma | G12C | 12.8±5 | 9.4 ± 0.7 |
| CALU-1 | Lung carcinoma | G12C | 15.9±3 | > 10 |
| H-2122 | Lung carcinoma | G12C | 11.5±5 | 8.8 ± 0.2 |
| H-441 | Lung carcinoma | G12V | -- | > 10 |
| H-1299 | Lung carcinoma | WT | -- | > 10 |
| MIA-PACA | Pancreatic carcinoma | G12C | 11.8±2 | 7.4 ± 0.5 |
| PANC-1 | Pancreatic carcinoma | G12D | -- | 9.8 ± 0.5 |
| ASPC-1 | Pancreatic carcinoma | G12D | -- | >10 |
| SW-480 | Colorectal carcinoma | G12V | -- | 8.2 ± 0.5 |
| SW-403 | Colorectal carcinoma | G12V | -- | >10 |

FIG. 28

$IC_{50}$ parameters of ADGN-122 and AMG-510 in cancer cell lines.

| CELL LINES | Indication | KRAS | ADGN-122 IC50 (nM) | AMG-510 IC50 (nM) |
|---|---|---|---|---|
| H-358 | Lung carcinoma | G12C | 12.8±5 | 73±2 |
| CALU-1 | Lung carcinoma | G12C | 15.9±3 | 114±8 |
| H-2122 | Lung carcinoma | G12C | 11.5±5 | 43±9 |
| MiA-PACA | Pancreatic carcinoma | G12C | 11.8±2 | 12±4 |

COMPOSITIONS FOR TREATING CANCER WITH KRAS MUTATIONS AND USES THEREOF

CROSS-REFERENCE TO RELATED APPLICATION

This application is a National Stage application under 35 U.S.C. § 371 of International Application No. PCT/US2021/028995, filed internationally on Apr. 23, 2021, which claims priority to French application No. FR2004126, filed Apr. 24, 2020, the contents of each of which are incorporated by reference in their entirety for all purposes.

FIELD OF THE APPLICATION

The present application relates to guide RNAs and genome-editing complexes or nanoparticles that are useful for specifically targeting a mutated KRAS.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 7373720001200SEQLIST.TXT, date recorded: Oct. 19, 2022, size: 88,986 bytes).

BACKGROUND OF THE APPLICATION

The RAS subfamily member KRAS is the most frequently mutated oncogene in cancers, including highly lethal lung, colon, and pancreatic cancers (Cox et al. 2014 Nat Rev Drug Discov 13, 828). Activating mutations in KRAS play potent roles in cancer initiation, propagation, and maintenance, representing important therapeutic targets (Cox et al. 2014). A common cancer-associated mutation occurs in KRAS at the glycine-encoding codon-12. Specifically, the single-nucleotide missense substitutions c.35 G>T and c.35 G>A replace glycine at position 12 with valine (G12V) and aspartic acid (G12D), respectively. G12V and G12D substitutions are among the most commonly observed mutations in pancreatic adenocarcinoma (30% and 51%, respectively) and colorectal adenocarcinomas (27% and 45%, respectively) and have been associated with poor prognosis (Jones, S. et al. 2008, Science 321, 1801; Wood, L. D. et al. 2007, Science 318, 1108).

Today there is an urgent need of a potent strategy to target KRAS mutations. Although several attempts have been made to target RAS-dependent cancers, the direct inhibition of RAS proteins has not been successful and most of the approaches affected the downstream effectors of mutated RAS. The recent development of KRAS (G12C)-specific inhibitors (Patricelli et al. 2016 Cancer Discov 6: 316) and of a non-mutant selective RAS-binding domain inhibitor (Athuluri-Divakar et al. 2016. Cell 165: 643), showed the potential of direct targeting mutated RAS oncogenes. Directly targeting mutated RAS oncogenes has the potential to disrupt the functions of both the aberrant RAS proteins and their downstream effector pathways. However, producing this chemical is challenging due to its complex structure and mutation-specific inhibition was not achieved using small molecules for KRAS (G12D) or KRAS (G12V), which occur more frequently than KRAS (G12C). KRAS silencing using small interfering RNAs (siRNAs) that selectively inhibit mutant KRAS mRNAs have also been reported, but considering the continuous expression of KRAS mutant, permanent delivery is required for target RNA suppression (Zorde Khvalevsky et al. 2013 Proc Natl Acad Sci 110: 20723) to maintain a complete knockdown (Brummelkamp et al. 2002 Cancer Cell 2: 243).

The disclosures of all publications, patents, patent applications and published patent applications referred to herein are hereby incorporated herein by reference in their entirety.

BRIEF SUMMARY OF THE APPLICATION

The present application in one aspect provides a non-naturally occurring polynucleotide comprising a guide RNA for targeting mutated KRAS comprising a specificity-determining CRISPR RNA (crRNA) comprising a nucleotide sequence substantially complementary to a target sequence selected from the group consisting of SEQ ID NOs: 1-37, 241-257 and 271. In some embodiments, the guide RNA further comprises an auxiliary trans-activating crRNA (tracrRNA). In some embodiments, the nucleotide sequence substantially complementary to a target sequence is selected from the group consisting of SEQ ID NOs: 1, 3, 6, 8, 15, 16, 19-21, 23, 29, 31, 33, and 34. In some embodiments, the nucleotide sequence is 100% complementary to a target sequence selected from the group consisting of SEQ ID NOs: 1, 3, 6, 8, 15, 16, 19-21, 23, 29, 31, 33, and 34. In some embodiments, the nucleotide sequence is 100% complementary to a target sequence selected from the group consisting of SEQ ID NOs: 3, 19, and 34.

In some embodiments according to any one of the non-naturally occurring polynucleotides described above, the polynucleotide is chemically modified.

In some embodiments according to any one of the non-naturally occurring polynucleotides described above, the guide RNA has a length of no more than about 200 nucleotides.

The present application in another aspect provides a genome-editing complex comprising a) a first cell-penetrating peptide, and b) a guide RNA targeting a mutated KRAS, wherein the guide RNA comprises any one of the polynucleotides described above. In some embodiments, the genome-editing complex further comprises a DNA nuclease or a nucleotide sequence encoding the DNA nuclease. In some embodiments, the DNA nuclease is selected from the group consisting of a CRISPR-associated protein (Cas) polypeptide, a zinc finger nuclease (ZFN), a transcription activator-like effector nuclease (TALEN), a meganuclease, a variant thereof, a fragment thereof, and a combination thereof. In some embodiments, the DNA nuclease comprises a Cas polypeptide. In some embodiments, the Cas polypeptide is Cas9 or Cas12a.

In some embodiments according to any one of the genome-editing complexes described above, the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides.

In some embodiments according to any one of the genome-editing complexes described above, the first cell-penetrating peptide further comprises one or more moieties covalently linked to N-terminus of the first cell-penetrating peptide, and wherein the one or more moieties are selected from the group consisting of an acetyl, a fatty acid, a cholesterol, a poly-ethylene glycol, a nuclear localization signal, a nuclear export signal, an antibody, a polysaccharide, a linker moiety, and a targeting moiety. In some embodiments, the first cell-penetrating peptide comprises an acetyl group covalently linked to the N-terminus of the first cell-penetrating peptide. In some embodiments, the first cell-penetrating peptide comprises a targeting moiety comprising a targeting peptide covalently linked to the N-terminus of the first cell-penetrating peptide. In some embodiments, the targeting peptide is selected from the group consisting of SEQ ID NOs: 196-205 and 235-240.

In some embodiments according to any one of the genome-editing complexes described above, the first cell-penetrating peptide comprises a linker moiety selected from the group consisting of a polyglycine linker moiety, a PEG moiety, Aun, Ava, and Ahx. In some embodiments, the PEG moiety consists of two to seven ethylene glycol units.

In some embodiments according to any one of the genome-editing complexes described above, the first cell-penetrating peptide comprises, from N-terminus, an acetyl group, a targeting moiety and a linker moiety covalently linked to the N-terminus of the first cell-penetrating peptide.

In some embodiments according to any one of the genome-editing complexes described above, the first cell-penetrating peptide further comprises one or more moieties covalently linked to the C-terminus of the first cell-penetrating peptide, and wherein the one or more moieties are selected from the group consisting of a cysteamide, a cysteine, a thiol, an amide, a nitrilotriacetic acid optionally substituted, a carboxyl, a linear or ramified $C_1$-$C_6$ alkyl optionally substituted, a primary or secondary amine, an osidic derivative, a lipid, a phospholipid, a fatty acid, a cholesterol, a poly-ethylene glycol, a nuclear localization signal, nuclear export signal, an antibody, a polysaccharide, a linker moiety and a targeting moiety. In some embodiments, the first cell-penetrating peptide comprises a cysteamide group covalently linked to its C-terminus.

In some embodiments according to any one of the genome-editing complexes described above, the first cell-penetrating peptide further comprises a carbohydrate moiety. In some embodiments, the carbohydrate moiety is GalNAc.

In some embodiments according to any one of the genome-editing complexes described above, the first cell-penetrating peptide is a retro-inverso peptide.

In some embodiments according to any one of the genome-editing complexes described above, the first cell-penetrating peptide comprises an amino acid sequence selected from the group consisting of SEQ ID NOs: 44-195. In some embodiments, the first cell-penetrating peptide comprises an amino acid sequence selected from the group consisting of SEQ ID NOs: 135-175, 259-260, and 267-269. IN some embodiments, the first cell-penetrating peptide comprises an amino acid sequence selected from the group consisting of SEQ ID NOs: 63-117, 261-266 and 270.

In some embodiments according to any one of the genome-editing complexes described above, the molar ratio of the first cell-penetrating peptide to the guide RNA is between about 1:1 and about 80:1. In some embodiments, the molar ratio of the first cell-penetrating peptide to the guide RNA is between about 2:1 and about 50:1.

In some embodiments according to any one of the genome-editing complexes described above, the molar ratio of the first cell-penetrating peptide to the nucleotide sequence encoding the DNA nuclease is between about 1:1 and about 80:1. In some embodiments, the molar ratio of the first cell-penetrating peptide to the nucleotide sequence encoding the DNA nuclease is between about 2:1 and about 50:1.

In some embodiments according to any one of the genome-editing complexes described above, the guide RNA is complexed with the first cell-penetrating peptide.

In some embodiments according to any one of the genome-editing complexes described above, the nucleotide sequence encoding the DNA nuclease is complexed with the first cell-penetrating peptide.

In some embodiments according to any one of the genome-editing complexes described above, the genome-editing complex further comprises one or more additional guide RNAs comprising different guide sequences. In some embodiments, at least two of the two or more guide RNAs target one single KRAS mutation. In some embodiments, at least two of the two or more guide RNAs target two or more different KRAS mutations. In some embodiments, at least two of the two or more guide RNAs target G12D, G12V, and/or G12C.

In some embodiments according to any one of the genome-editing complexes described above, the average diameter of the genome-editing complex is between about 10 nm and about 300 nm.

The present application in another aspect provides a nanoparticle comprising a core comprising any one of the genome-editing complexes described above. In some embodiments, the core further comprises one or more additional genome-editing complexes such as any one of the genome-editing complexes described above. In some embodiments, the one or more additional genome-editing complex comprises at least one or more the guide RNAs that targets a different KRAS mutation. In some embodiments, the core is complexed with a second cell-penetrating peptide. In some embodiments, the second cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the second cell-penetrating peptide is selected wherein the second cell-penetrating peptide is selected from the group consisting of VEPEP-3 peptides, VEPEP-6 peptides, VEPEP-9 peptides, and ADGN-100 peptides. In some embodiments, the second cell-penetrating peptide comprises an amino acid sequence selected from the group consisting of SEQ ID NOs: 44-175.

In some embodiments according to any one of the nanoparticles described above, the second cell-penetrating peptide in the nanoparticle is covalently linked to a targeting moiety by a linking moiety.

In some embodiments according to any one of the genome-editing complexes described above, the core is coated by a shell comprising a peripheral cell-penetrating peptides. In some embodiments, the peripheral cell-penetrating peptides are selected from the group consisting of VEPEP-3 peptides, VEPEP-6 peptides, VEPEP-9 peptides, and ADGN-100 peptides. In some embodiments, the peripheral cell-penetrating peptide comprises an amino acid sequence selected from the group consisting of SEQ ID NOs: 44-175.

In some embodiments according to any one of the genome-editing complexes described above, the peripheral cell-penetrating peptide in the shell is covalently linked to a targeting moiety by a linking moiety.

In some embodiments according to any one of the genome-editing complexes described above, the average diameter of the nanoparticle is between about 10 nm and about 400 nm.

The present application in another aspect provides a pharmaceutical composition comprising any one of the guide RNAs, any one of the genome-editing complexes, or any one of the nanoparticles described above, and a pharmaceutically acceptable carrier. In some embodiments, the composition comprises two or more nanoparticles, wherein the two or more nanoparticles comprise different guide RNAs that target different KRAS mutations.

The present application in another aspect provides a method of preparing any one of the genome-editing complexes described above, comprising combining the first cell-penetrating peptide with the guide RNA, thereby forming the genome-editing complex.

The present application in another aspect provides a method of modifying mutated KRAS in a cell, comprising contacting the cell with any one of the guide RNAs, any one of the genome-editing complexes, or any one of the nanoparticles described above.

The present application in another aspect provides a method of treating a cancer in an individual comprising administering the individual an effective amount of any one of the pharmaceutical composition described above. In some embodiments, the method further comprises administering a second agent.

BRIEF DESCRIPTION OF THE DRAWINGS

FIG. 1A shows indel frequencies at the endogenous target sequences in different cell lines evaluated 72 hours after transfection by T7E1 method. FIG. 1B shows cell proliferation analyzed over a period of 5 days using CellTiter Glow kits on GlowMax.

FIG. 2A shows indel frequencies at the endogenous target sequences in different cell lines evaluated 72 hours after transfection by T7E1 method. FIG. 2B shows cell proliferation analyzed over a period of 5 days using CellTiter Glow kits on GlowMax.

FIG. 3A shows indel frequencies at the endogenous target sequences in different cell lines evaluated 72 hours after transfection by T7E1 method. FIG. 3B shows cell proliferation analyzed over a period of 5 days using CellTiter Glow kits on GlowMax.

FIG. 4A shows indel frequencies at the endogenous target sequences in different cell lines evaluated 72 hours after transfection by T7E1 method. FIG. 4B shows cell proliferation analyzed over a period of 5 days using CellTiter Glow kits on GlowMax.

FIG. 5A shows the evaluation of gRNAs targeting KRAS 35G>A mutant G12D KRAS on PANC-1 cells. FIG. 5B shows evaluation of gRNAs targeting KRAS 35G>T mutant G12V KRAS on SW403 cells. Western blot analysis (top) and quantification (bottom).

FIGS. 9A and 9B show bioluminescence imaging (FIG. 9B) and a quantification of the total luminescence (FIG. 9A) for the different groups at day 0, 15 and 30.

FIGS. 11A and 11B show bioluminescence imaging and a quantification of the total luminescence for the different groups at day 0, 15 and 30.

FIG. 18 shows various target sequences for the design of sgRNA targeting KRAS wildtype or KRAS with a G12D, G12V, or G12C mutation.

FIG. 24 shows a table listing cancer cell lines with mutant KRAS genes and or mutant p53 genes.

FIG. 25 shows $IC_{50}$ and $CC_{50}$ parameters of ADGN-121 in cancer cell lines.

FIG. 26 shows $IC_{50}$ and $CC_{50}$ parameters of ADGN-123 in cancer cell lines.

FIG. 27 shows $IC_{50}$ and $CC_{50}$ parameters of ADGN-122 in cancer cell lines.

FIG. 28 shows $IC_{50}$ parameters of ADGN-122 and AMG-510 in cancer cell lines.

DETAILED DESCRIPTION OF THE APPLICATION

Figure 1A:
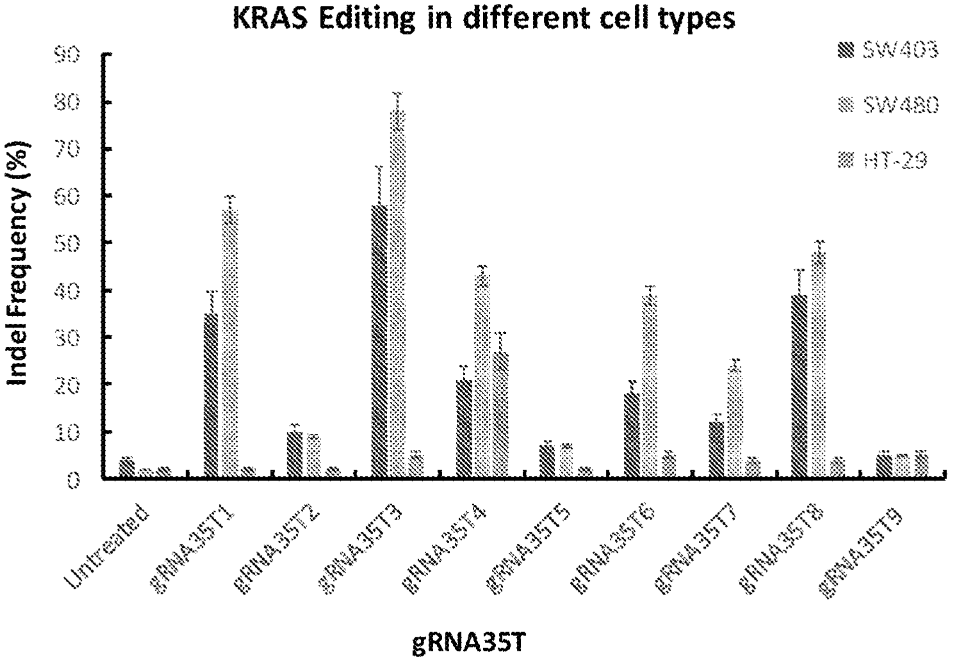
FIGS. 1A-1B show the evaluation of gRNAs targeting KRAS 35G>T mutant G12V KRAS on SW403, SW480, and HT-29 cells. Cancer cells were treated with the different ADGN/Cas9mRNA/gRNA (0.15 μg/0.2 μg) complexes.

The present application in one aspect provides novel guide RNAs that target specific KRAS mutant sequences (such as KRAS with a G12V, G12D, or G12C mutation). As demonstrated in the Examples, the exemplary guide RNAs were able to specifically target KRAS gene that bears a specific mutation (such as G12V, G12D, or G12C) while not affecting KRAS wildtype sequence.

The present application in another aspect provides genome-editing complexes comprising a) a first cell-penetrating peptide, and b) a guide RNA described herein. As demonstrated in the examples, administration of exemplary genome-editing complexes including a cell-penetrating peptide and a guide RNA as described herein successfully treated individuals having tumors with KRAS mutations without inducing any significant toxicity, emergence of off target effects or other KRAS mutations. In some cases, one or two administrations of the exemplary genome-editing complexes resulted in a complete regression of tumors.

Also provided herein are nanoparticles comprising the genome-editing complexes, methods of preparing and using the guide RNAs, genome-editing complexes or nanoparticles as well as kits and articles of manufacture useful for the methods.

I. Definitions

The term "guide RNA" refers to a polynucleotide that cleaves, inserts, or links a target DNA in a cell via RNA editing. The guide RNA may be a single-chain guide RNA (sgRNA). The guide RNA may be a CRISPR RNA (crRNA)

specific to the target nucleotide sequence. The guide RNA may further include a trans-activating crRNA (tracrRNA) interacting with Cas9 nuclease. The tracrRNA may include a polynucleotide forming a loop structure. The guide RNA may have a length of 10 nucleotides to 30 nucleotides. The guide RNA may have a length of, for example, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides.

The guide RNA may include RNA, DNA, PNA, or a combination thereof. The guide RNA may be chemically modified.

The guide RNA may be a component of molecular scissors (programmable nuclease). The molecular scissor refers to all types of nucleases capable of recognizing and cleaving a specific site on the genome. The molecular scissors may be, for example, transcription activator-like effector nuclease (TALEN), zinc-finger nuclease, meganuclease, RNA-guided engineered nuclease (RGEN), Cpf1, and Ago homolog (DNA-guided endonuclease). The RGEN refers to a nuclease including a guide RNA specific to a target DNA and Gas protein as components. The polynucleotide may be, for example, a component of RGEN.

In aspects of the application the term "single guide RNA" or "sgRNA" refers to a polynucleotide sequence comprising a guide sequence, a tracr sequence and a tracr mate sequence. The term "guide sequence" refers to the about 20 bp sequence within the guide RNA that specifies the target site. The term "tracr mate sequence" may also be used interchangeably with the term "direct repeat(s)".

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring," "synthetic," or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Polynucleotide," or "nucleic acid," as used interchangeably herein, refers to polymers of nucleotides of any length, and includes DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (PAC, BAC, YAC, artificial chromosomes), expression cassettes, chimeric sequences, chromosomal DNA, or derivatives and combinations of these groups. RNA may be in the form of siRNA, asymmetrical interfering RNA (aiRNA), microRNA (miRNA), mRNA, tRNA, rRNA, RNA, viral RNA (vRNA), and combinations thereof. Nucleic acids include nucleic acids containing known nucleotide analogs or modified backbone residues or linkages, including for example locked nucleic acid (LNA), unlocked nucleic acid (UNA), and zip nucleic acid (ZNA), which can be synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer e al., Nucleic Acid Res., 19:5081 (1991); Ohtsuka et a., j. Biol. Chern., 260:2605-2608 (1985); Rossolini et al., Mol. Cell. Probes, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylases, and alkylhalides. "Oligonucleotide," as used herein, generally refers to short, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

In general, "CRISPR system" refers collectively to proteins, transcripts and other molecules involved in the activity of CRISPR-associated ("Cas") nucleases (such as RNA-guided endonucleases, or "RGENs"), including Cas gene products, Cas gene sequences, tracr (trans-activating CRISPR) sequences (e.g. tracrRNA or an active partial tracrRNA), tracr-mate sequences (including a "direct repeat" and a tracrRNA-processed partial direct repeat in the context of an endogenous CRISPR system), a guide sequence (also referred to as a "spacer" in the context of an endogenous CRISPR system), or other sequences, transcripts, and products derived from a CRISPR locus. In some embodiments, one or more molecules of a CRISPR system are derived from a type I, type II, or type III CRISPR system. In some embodiments, one or more molecules of a CRISPR system are derived from a particular organism comprising an endogenous CRISPR system, such as *Streptococcus pyogenes*. In general, a CRISPR system is characterized by molecules that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is present in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template," "editing polynucleotide," "editing sequence," "donor sequence," or "donor nucleic acid". In aspects of the application, an exogenous template polynucleotide may be referred to as an editing template. In an aspect of the application the recombination is homologous recombination.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned. In some embodiments, one or more molecules of a CRISPR system are introduced into a host cell such that formation of a CRISPR complex at one or more target sites can occur. For example, a Cas nuclease, a guide sequence linked to a tracr-mate sequence, and a tracr sequence could each be introduced into a host cell to allow formation of a CRISPR complex at a target sequence in the host cell complementary to the guide sequence.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%/, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993). Laboratory Techniques In Biochemistry And Molecular Biology-Hybridization With Nucleic Acid Probes Part I, Second Chapter "Overview of principles of hybridization and the strategy of nucleic acid probe assay". Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating" refers to an approach for obtaining beneficial or desired results including but not limited to a therapeutic benefit. By therapeutic benefit is meant any therapeutically relevant improvement in or effect on one or more diseases, conditions, or symptoms under treatment.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, the singular form "a", "an", and "the" includes plural references unless indicated otherwise.

Reference to "about" a value or parameter herein includes (and describes) embodiments that are directed to that value or parameter per se. For example, description referring to "about X" includes description of "X."

The compositions and methods of the present application may comprise, consist of, or consist essentially of the essential elements and limitations of the application described herein, as well as any additional or optional ingredients, components, or limitations described herein or otherwise useful.

Unless otherwise noted, technical terms are used according to conventional usage.

Guide RNAs

In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-37, 241-257 and 271. In some embodiments, the nucleotide sequence substantially complementary (such as at least about 80%, 85%, 90%, 95%, 96%, 97%, 98%, or 99% complementary) or 100% complementary to a target sequence is selected from the group consisting of SEQ ID NOs: 1, 3, 6, 8, 15, 16, 19-21, 23, 29, 31, 33, and 34. In some embodiments, the guide RNA is a single-guide RNA (sgRNA).

In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 1. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 3. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 6. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 8. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 15. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 16. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence or 99% complementary) or 100% complementary to a target sequence set forth in SEQ ID NO: 19. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 20. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 21. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 23. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 29. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 31. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 33. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 34.

In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 2. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 4. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 5. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 7. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 9. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence or 99% complementary) or 100% complementary to a target sequence set forth in SEQ ID NO: 10. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 11. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 12. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 13. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 14. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 17. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 18. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence or 99% complementary) or 100% complementary to a target sequence set forth in SEQ ID NO: 22. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 24. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 25. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 26. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 27. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 28. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 30. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 32. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 35. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 36. In some embodiments, there is provided a polynucleotide (e.g., a non-naturally occurring polynucleotide) comprising a guide RNA for targeting mutated KRAS comprising a specificity-determining CRISPR RNA (crRNA) comprising a nucleotide sequence substantially complementary (such as at least about 80%, 85%, 90%, 95%, 96%, 97%, 98%, or 99% complementary) or 100% complementary to a target sequence set forth in SEQ ID NO: 37.

Guide RNA Targeting G12V

In some embodiments, there is provided a guide RNA (such as a single-guide RNA) for targeting a mutated KRAS comprising a G12V mutation, wherein the guide RNA comprises a nucleotide sequence substantially complementary (such as at least about 80%, 85%, 90%, 95%, 96%, 97%, 98%, or 99% complementary) to a target sequence selected from the group consisting of SEQ ID NOs: 1-14. In some embodiments, the target sequence is selected from the group consisting of SEQ ID NOs: 1, 3, 4, and 6-8. In some embodiments, the target sequence is selected from the group consisting of SEQ ID NOs: 1, 3, 6, and 8. In some embodiments, the target sequence is selected from the group consisting of SEQ ID NOs: 3, 6, and 8. In some embodiments, the target sequence is set forth in SEQ ID NO: 3.

In some embodiments, the guide RNA comprises a nucleotide sequence 100% complementary to a target sequence selected from the group consisting of SEQ ID NOs: 1, 3, 6, and 8. In some embodiments, the guide RNA comprises a nucleotide sequence 100% complementary to a target sequence of SEQ ID NO: 3.

In some embodiments, the guide RNA (such as a single-guide RNA) for targeting a mutated KRAS comprising G12V, wherein the guide RNA comprises a guide sequence complementary to the target sequence flanked by a PAM sequence of AGG at position 42-44. In some embodiments, the guide sequence has a length of about 20-24 base pairs, 20-22 base pairs, or 20-21 base pairs.

In some embodiments, the guide RNA (such as a single-guide RNA) for targeting a mutated KRAS comprising G12V, wherein the guide RNA comprises a guide sequence complementary to the target sequence flanked by a PAM sequence of TAG at position 41-43. In some embodiments, the guide sequence has a length of about 20-24 base pairs, 20-22 base pairs, or 20-21 base pairs.

In some embodiments, the guide RNA (such as a single-guide RNA) for targeting a mutated KRAS comprising G12V, wherein the guide RNA comprises a guide sequence complementary to the target sequence flanked by a PAM sequence of TGG at position 36-38. In some embodiments, the guide sequence has a length of about 20-24 base pairs, 20-22 base pairs, or 20-21 base pairs.

KRAS G12V mutation was present in various diseases (such as a solid cancer or a liquid cancer, such as myelodysplastic syndrome). Exemplary cancers include lung cancer (e.g., NSCLC, small cell lung cancer, squamous cell lung cancer), colorectal cancer, acute myeloid leukemia, pancreatic cancer, rectal cancer, multiple myeloma, and glioma. In some embodiments, the cancer is a malignant or advanced cancer. Guide RNA described herein can be used for treating any of the above diseases (such as via methods described herein).

Guide RNA Targeting G12D

In some embodiments, there is provided a guide RNA (such as a single-guide RNA) for targeting a mutated KRAS comprising a G12D mutation, wherein the guide sequence comprises a nucleotide sequence substantially complementary (such as at least about 80%, 85%, 90%, 95%, 96%, 97%, 98%, or 99% complementary) to a target sequence selected from the group consisting of SEQ ID NOs: 15-28. In some embodiments, the target sequence is selected from the group consisting of SEQ ID NOs: 15, 16, 19-21, and 23. In some embodiments, the target sequence is selected from the group consisting of SEQ ID NOs: 16, 19-21, and 23. In some embodiments, the target sequence is selected from the group consisting of SEQ ID NO: 19.

In some embodiments, the guide RNA comprises a nucleotide sequence 100% complementary to a target sequence selected from the group consisting of SEQ ID NOs: 15, 16, 19-21, and 23. In some embodiments, the guide RNA comprises a nucleotide sequence 100% complementary to a target sequence of SEQ ID NO: 19.

In some embodiments, the guide RNA (such as a single-guide RNA) for targeting a mutated KRAS comprising G12D, wherein the guide RNA comprises a guide sequence complementary to the target sequence flanked by a PAM sequence of AGG at position 42-44. In some embodiments, the guide sequence has a length of about 20-24 base pairs, 20-22 base pairs, or 20-21 base pairs.

In some embodiments, the guide RNA (such as a single-guide RNA) for targeting a mutated KRAS comprising G12D, wherein the guide RNA comprises a guide sequence complementary to the target sequence flanked by a PAM sequence of TAG at position 41-43. In some embodiments, the guide sequence has a length of about 20-24 base pairs, 20-22 base pairs, or 20-21 base pairs.

KRAS G12D mutation was present in various diseases (such as a solid cancer or a liquid cancer, such as myelodysplastic syndrome). Exemplary cancers include lung cancer (e.g., NSCLC, small cell lung cancer, squamous cell lung cancer), colorectal cancer, acute myeloid leukemia, pancreatic cancer, rectal cancer, multiple myeloma, and glioma. In some embodiments, the cancer is a malignant or advanced cancer. Guide RNA described herein can be used for treating any of the above diseases (such as via methods described herein).

Guide RNA Targeting G12C

In some embodiments, there is provided a guide RNA (such as a single-guide RNA) for targeting a mutated KRAS comprising a G12C mutation, wherein the guide sequence comprises a nucleotide sequence substantially complementary (such as at least about 80%, 85%, 90%, 95%, 96%, 97%, 98%, or 99% complementary) to a target sequence selected from the group consisting of SEQ ID NOs: 29-37. In some embodiments, the target sequence is selected from the group consisting of SEQ ID NOs: 29, 31, 33, and 34. In some embodiments, the target sequence is set forth in SEQ ID NO: 34.

In some embodiments, the guide RNA comprises a nucleotide sequence 100% complementary to a target sequence selected from the group consisting of SEQ ID NOs: 29, 31, 33, and 34. In some embodiments, the guide RNA comprises a nucleotide sequence 100% complementary to a target sequence of SEQ ID NO: 34.

In some embodiments, the guide RNA (such as a single-guide RNA) for targeting a mutated KRAS comprising G12C, wherein the guide RNA comprises a guide sequence complementary to the target sequence flanked by a PAM sequence of AGG at position 42-44. In some embodiments, the guide sequence has a length of about 20-24 base pairs, 20-22 base pairs, or 20-21 base pairs.

In some embodiments, the guide RNA (such as a single-guide RNA) for targeting a mutated KRAS comprising G12C, wherein the guide RNA comprises a guide sequence complementary to the target sequence flanked by a PAM sequence of TAG at position 41-43. In some embodiments, the guide sequence has a length of about 20-24 base pairs, 20-22 base pairs, or 20-21 base pairs.

In some embodiments, the guide RNA (such as a single-guide RNA) for targeting a mutated KRAS comprising G12C, wherein the guide RNA comprises a guide sequence complementary to the target sequence flanked by a PAM sequence of TGG at position 36-38. In some embodiments, the guide sequence has a length of about 20-24 base pairs, 20-22 base pairs, or 20-21 base pairs.

KRAS G12C mutation was present in various diseases (such as a solid cancer or a liquid cancer, such as myelodysplastic syndrome). Exemplary cancers include lung cancer (e.g., NSCLC, small cell lung cancer, squamous cell lung cancer), colorectal cancer, acute myeloid leukemia, pancreatic cancer, rectal cancer, esophageal squamous cell carcinoma, gastrointestinal stromal tumor, head and neck squamous cancer, pancreatic ductal adenocarcinoma, multiple myeloma, and glioma. In some embodiments, the cancer is a malignant or advanced cancer. Guide RNA described herein can be used for treating any of the above diseases (such as via methods described herein).

In some embodiments, the guide RNA is in the form of RNA.

In other embodiments, the guide RNA is in the form of DNA encoding the RNA (i.e., gDNA). In some embodiments, the DNA is a plasmid DNA. In some embodiments, the plasmid DNA further comprises a DNA encoding a DNA nuclease (such as Cas9).

In some embodiments, the guide RNA further comprises a DNA nuclease recruiting sequence.

In some embodiments, the guide RNA is a single guide RNA (sgRNA) further comprising an auxiliary trans-activating crRNA (tracrRNA).

In some embodiments, the guide RNA further comprises a tracr mate sequence, a tracr sequence, and/or a tail sequence. In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the guide sequence, tracr sequence and tracr mate sequence are contained within a single RNA (referred to herein as a "single-guide RNA," or "sgRNA"), such that hybridization between the tracr sequence and the tracr mate sequence produces a secondary structure, such as a hairpin. Preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In some embodiments, the sgRNA has at least two or more hairpins. In some embodiments, the sgRNA has two, three, four or five hairpins. In some embodiments, the sgRNA has at most five hairpins. In some embodiments, the sgRNA further includes a transcription termination sequence; preferably this is a polyT sequence, for example six T nucleotides.

In some embodiments, the guide RNA is a prime editing guide RNA (pegRNA) that further comprises a primer binding sequence and/or a desired RNA sequence (for example at the 3'end of the guide RNA). PegRNA can form a complex with a prime editor (such as a fusion protein comprising a modified Cas9 protein and a reverse transcriptase), thereby allowing prime editing of targeted sequences. See for example, Anzalone & Liu et al., Nature. 2019 December; 576 (7785):149-157.

In some embodiments, the guide RNA comprises one or more modification (e.g., chemical modification). In some embodiments, the gRNA has one or more modified nucleotides, including nucleobase modification and/or backbone modification. Exemplary modifications to the guide RNA include, but are not limited to, phosphorothioate backbone modification, 2'-substitutions in the ribose (such as 2'-O-methyl and 2'-fluoro substitutions), LNA, and L-RNA. In some embodiments, the guide RNA does not have modifications to the nucleobase or backbone.

In some embodiments, the guide RNA comprises a moiety that promotes the annealing of guide sequence. In some embodiments, the moiety comprises a synthetic nucleotide sequence, wherein the synthetic sequence is about 1-200 nucleotides, such as about 5 to about 100 nucleotides, such as about 8 to about 80 nucleotides, such as about 10 to about 50 nucleotides, such as about 12 to about 40 nucleotides.

In some embodiments, the guide RNA (such as a single-guide RNA) has a length of no more than about 200 nucleotides, such as about 5 to about 100 nucleotides, such as about 8 to about 80 nucleotides, such as about 10 to about 50 nucleotides, such as about 12 to about 40 nucleotides.

Also provided herein are complexes, nanoparticles, compositions that comprise any of the guide RNAs described above including, but not limited to the complexes, nanoparticles and compositions described as following.

Many delivery systems can be employed to deliver any of the guide RNAs, complexes, nanoparticles, and compositions described in this application, including but not limited to, viral, liposome, electroporation, microinjection and conjugation, to achieve the introduction of the gRNA into a host cell. Conventional viral and non-viral based gene transfer methods can be used to introduce nucleic acids into mammalian cells or target tissues. Such methods can be used to administer nucleic acids encoding gRNA of the present invention to cells in culture, or in a host organism. Non-viral vector delivery systems include DNA plasmids, RNA (e.g. a transcript of a construct described herein), naked nucleic acid, and nucleic acid complexed with a delivery vehicle, such as a liposome. Viral vector delivery systems include DNA and RNA viruses, which have either episomal or integrated genomes for delivery to the host cell.

Methods of non-viral delivery of nucleic acids include lipofection, nucleofection, microinjection, biolistics, virosomes, liposomes, immunoliposomes, polycation or lipid: nucleic acid conjugates, electroporation, nanoparticles, exosomes, microvesicles, or gene-gun, naked DNA and artificial virions.

The use of RNA or DNA viral based systems for the delivery of nucleic acids has high efficiency in targeting a virus to specific cells and trafficking the viral payload to the cellular nuclei.

Complexes

The present application provides genome-editing complexes comprising a) a first cell-penetrating peptide, and b) a polynucleotide comprising a guide RNA targeting mutated KRAS comprising a nucleotide sequence substantially complementary (such as at least about 80%, 85%, 90%, 95%, 96%, 97%, 98%, or 99% complementary) to a target sequence selected from the group consisting of SEQ ID NOs: 1-37, 241-257 and 271. In some embodiments, the genome-editing complex further comprises a DNA nuclease (e.g., Cas9) or a nucleotide sequence encoding the DNA nuclease. In some embodiments, the DNA nuclease is selected from the group consisting of a CRISPR-associated protein (Cas) polypeptide, a zinc finger nuclease (ZFN), a transcription activator-like effector nuclease (TALEN), a meganuclease, a variant thereof, a fragment thereof, and a combination thereof. In some embodiments, the guide RNA comprises a nucleotide sequence substantially complementary (such as at least about 80%, 85%, 90%, 95%, 96%, 97%, 98%, or 99% complementary) to a target sequence selected from the group consisting of SEQ ID NOs: 1, 3, 6, 8, 15, 16, 19-21, 23, 29, 31, 33, and 34.

In some embodiments, there is provided a genome-editing complex comprising a) a first cell-penetrating peptide, and b) a guide RNA targeting KRAS G12V comprising a nucleotide sequence substantially complementary (such as at least about 80%, 85%, 90%, 95%, 96%, 97%, 98%, or 99% complementary) to a target sequence selected from the group consisting of SEQ ID NOs: 1, 3, 4, and 6-8. In some embodiments, the target sequence is selected from the group consisting of SEQ ID NOs: 3, 6, and 8. In some embodiments, the target sequence is set forth in SEQ ID NO: 3. In some embodiments, the guide RNA further comprising an auxiliary trans-activating crRNA (tracrRNA). In some embodiments, the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first cell-penetrating peptide comprises a targeting moiety comprising a targeting peptide covalently linked to the N-terminus of the first cell-penetrating peptide. In some embodiments, the first cell-penetrating peptide comprises a linker moiety selected from the group consisting of a polyglycine linker moiety, a PEG moiety, Aun, Ava, and Ahx. In some embodiments, the first cell-penetrating peptide further comprises a carbohydrate moiety (such as GalNAc). In some embodiments, the first cell-penetrating peptide is an ADGN-100 peptide. In some embodiments, the first cell-penetrating peptide comprises an amino acid sequence selected from the group consisting of SEQ ID NOs: 135-175, 259-260, and 267-269. In some embodiments, the first cell-penetrating peptide is a VEPEP-3 peptide. In some embodiments, the first cell-penetrating peptide comprises an amino acid sequence selected from the group consisting of SEQ ID NOs: 44-62. In some embodiments, the first cell-penetrating peptide is a VEPEP-6 peptide. In some embodiments, the first cell-penetrating peptide comprises an amino acid sequence selected from the group consisting of SEQ ID NOs: 63-117, 261-266 and 270. In some embodiments, the first cell-penetrating peptide is a VEPEP-9 peptide. In some embodiments, the first cell-penetrating peptide comprises an amino acid sequence selected from the group consisting of SEQ ID NOs: 118-134. In some embodiments, the molar ratio of the first cell-penetrating peptide to the guide RNA is between about 1:1 and about 80:1 (such as between about 5:1 and about 20:1, such as between about 2:1 to about 50:1). In some embodiments, the molar ratio of the first cell-penetrating peptide to the nucleotide sequence encoding the Cas polypeptide is between about 1:1 and about 80:1 (such as between about 5:1 to about 20:1, such as between about 2:1 to about 50:1). In some embodiments, the molar ratio of the nucleotide sequence encoding the Cas polypeptide to the guide RNA is between about 1:10 and about 50:1 (such as between about 1:1 and about 10:1). In some embodiments, the guide RNA is complexed with the first cell-penetrating peptide. In some embodiments, the genome-editing complex further comprises a DNA nuclease (e.g., Cas9) or a nucleotide sequence encoding the DNA nuclease.

In some embodiments, there is provided a genome-editing complex comprising a) a first cell-penetrating peptide, and b) a guide RNA targeting KRAS G12D comprising a nucleotide sequence substantially complementary (such as at least about 80%, 85%, 90%, 95%, 96%, 97%, 98%, or 99% complementary) to a target sequence selected from the group consisting of SEQ ID NOs: 15, 16, 19-21, and 23. In some embodiments, the target sequence is selected from the group consisting of SEQ ID NOs: 16, 19-21, and 23. In some embodiments, the target sequence is selected from the group consisting of SEQ ID NO: 19. In some embodiments, the guide RNA further comprising an auxiliary trans-activating crRNA (tracrRNA). In some embodiments, the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first cell-penetrating peptide comprises a targeting moiety comprising a targeting peptide covalently linked to the N-terminus of the first cell-penetrating peptide. In some embodiments, the first cell-penetrating peptide comprises a linker moiety selected from the group consisting of a polyglycine linker moiety, a PEG moiety, Aun, Ava, and Ahx. In some embodiments, the first cell-penetrating peptide further comprises a carbohydrate moiety (such as GalNAc). In some embodiments, the first cell-penetrating peptide is an ADGN-100 peptide. In some embodiments, the first cell-penetrating peptide comprises an amino acid sequence selected from the group consisting of SEQ ID NOs: 135-175, 259-260, and 267-269. In some embodiments, the first cell-penetrating peptide is a VEPEP-3 peptide. In some embodiments, the first cell-penetrating peptide comprises an amino acid sequence selected from the group consisting of SEQ ID NOs: 44-62. In some embodiments, the first cell-penetrating peptide is a VEPEP-6 peptide. In some embodiments, the first cell-penetrating peptide comprises an amino acid sequence selected from the group consisting of SEQ ID NOs: 63-117, 261-266 and 270. In some embodiments, the first cell-penetrating peptide is a VEPEP-9 peptide. In some embodiments, the first cell-penetrating peptide comprises an amino acid sequence selected from the group consisting of SEQ ID NOs: 118-134. In some embodiments, the molar ratio of the first cell-penetrating peptide to the guide RNA is between about 1:1 and about 80:1 (such as between about 5:1 and about 20:1, such as between about 2:1 to about 50:1). In some embodiments, the molar ratio of the first cell-penetrating peptide to the nucleotide sequence encoding the Cas polypeptide is between about 1:1 and about 80:1 (such as between about 5:1 to about 20:1, such as between about 2:1 to about 50:1). In some embodiments, the molar ratio of the nucleotide sequence encoding the Cas polypeptide to the guide RNA is between about 1:10 and about 50:1 (such as between about 1:1 and about 10:1). In some embodiments, the guide RNA is complexed with the first cell-penetrating peptide. In some embodiments, the guide RNA is complexed with the first cell-penetrating peptide. In some embodiments, the genome-editing complex further comprises a DNA nuclease (e.g., Cas9) or a nucleotide sequence encoding the DNA nuclease.

In some embodiments, there is provided a genome-editing complex comprising a) a first cell-penetrating peptide, and b) a guide RNA targeting KRAS G12C comprising a nucleotide sequence substantially complementary (such as at least about 80%, 85%, 90%, 95%, 96%, 97%, 98%, or 99% complementary) to a target sequence selected from the group consisting of SEQ ID NOs: 29, 31, 33, and 34. In some embodiments, the target sequence is set forth in SEQ ID NO: 34. In some embodiments, the guide RNA further comprising an auxiliary trans-activating crRNA (tracrRNA). In some embodiments, the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first cell-penetrating peptide comprises a targeting moiety comprising a targeting peptide covalently linked to the N-terminus of the first cell-penetrating peptide. In some embodiments, the first cell-penetrating peptide comprises a linker moiety selected from the group consisting of a polyglycine linker moiety, a PEG moiety, Aun, Ava, and Ahx. In some embodiments, the first cell-penetrating peptide further comprises a carbohydrate moiety (such as GalNAc). In some embodiments, the first cell-penetrating peptide is an ADGN-100 peptide. In some embodiments, the first cell-penetrating peptide comprises an amino acid sequence selected from the group consisting of SEQ ID NOs: 135-175, 259-260, and 267-269. In some embodiments, the first cell-penetrating peptide is a VEPEP-3 peptide. In some embodiments, the first cell-penetrating peptide comprises an amino acid sequence selected from the group consisting of SEQ ID NOs: 44-62. In some embodiments, the first cell-penetrating peptide is a VEPEP-6 peptide. In some embodiments, the first cell-penetrating peptide comprises an amino acid sequence selected from the group consisting of SEQ ID NOs: 63-117, 261-266 and 270. In some embodiments, the first cell-penetrating peptide is a VEPEP-9 peptide. In some embodiments, the first cell-penetrating peptide comprises an amino acid sequence selected from the group consisting of SEQ ID NOs: 118-134. In some embodiments, the molar ratio of the first cell-penetrating peptide to the guide RNA is between about 1:1 and about 80:1 (such as between about 5:1 and about 20:1, such as between about 2:1 to about 50:1). In some embodiments, the molar ratio of the first cell-penetrating peptide to the nucleotide sequence encoding the Cas polypeptide is between about 1:1 and about 80:1 (such as between about 5:1 to about 20:1, such as between about 2:1 to about 50:1). In some embodiments, the molar ratio of the nucleotide sequence encoding the Cas polypeptide to the guide RNA is between about 1:10 and about 50:1 (such as between about 1:1 and about 10:1). In some embodiments, the guide RNA is complexed with the first cell-penetrating peptide. In some embodiments, the guide RNA is complexed with the first cell-penetrating peptide. In some embodiments, the genome-editing complex further comprises a DNA nuclease (e.g., Cas9) or a nucleotide sequence encoding the DNA nuclease.

In some embodiments, there is provided a genome-editing complex comprising a) a first cell-penetrating peptide, wherein the first cell-penetrating peptide is an ADGN-100 peptide; and b) a guide RNA targeting a mutated KRAS comprising a nucleotide sequence substantially complementary (such as at least about 80%, 85%, 90%, 95%, 96%, 97%, 98%, or 99% complementary) to a target sequence selected from the group consisting of SEQ ID NOs: 1, 3, 6, 8, 15, 16, 19-21, 23, 29, 31, 33, and 34. In some embodiments, the first cell-penetrating peptide comprises an amino acid sequence selected from the group consisting of SEQ ID NOs: 135-175, 259-260, and 267-269. In some embodiments, the first cell-penetrating peptide comprises an amino acid sequence selected from the group consisting of 153-175. In some embodiments, the first cell-penetrating peptide comprises an amino acid sequence selected from the group consisting of 154, 155, 157, 158, 162, 167-170, and 172. In some embodiments, the guide RNA further comprising an auxiliary trans-activating crRNA (tracrRNA). In some embodiments, the molar ratio of the first cell-penetrating peptide to the guide RNA is between about 1:1 and about 80:1 (such as between about 5:1 and about 20:1, such as between about 2:1 to about 50:1). In some embodiments, the molar ratio of the first cell-penetrating peptide to the nucleotide sequence encoding the Cas polypeptide is between about 1:1 and about 80:1 (such as between about 5:1 to about 20:1, such as between about 2:1 to about 50:1). In some embodiments, the molar ratio of the nucleotide sequence encoding the Cas polypeptide to the guide RNA is between about 1:10 and about 50:1 (such as between about 1:1 and about 10:1). In some embodiments, the guide RNA is complexed with the first cell-penetrating peptide. In some embodiments, the guide RNA is complexed with the first cell-penetrating peptide. In some embodiments, the genome-editing complex further comprises a DNA nuclease (e.g., Cas9) or a nucleotide sequence encoding the DNA nuclease.

In some embodiments, there is provided a genome-editing complex comprising a) a first cell-penetrating peptide, wherein the first cell-penetrating peptide is a VEPEP-6 peptide; and b) a guide RNA targeting a mutated KRAS comprising a nucleotide sequence substantially complementary (such as at least about 80%, 85%, 90%, 95%, 96%, 97%, 98%, or 99% complementary) to a target sequence selected from the group consisting of SEQ ID NOs: 1, 3, 6, 8, 15, 16, 19-21, 23, 29, 31, 33, and 34. In some embodiments, the first cell-penetrating peptide comprises an amino acid sequence selected from the group consisting of SEQ ID NOs: 63-117, 261-266 and 270. In some embodiments, the first cell-penetrating peptide comprises an amino acid sequence selected from the group consisting of 81, 92-103, 105-107, and 111-114. In some embodiments, the guide RNA further comprising an auxiliary trans-activating crRNA (tracrRNA). In some embodiments, the molar ratio of the first cell-penetrating peptide to the guide RNA is between about 1:1 and about 80:1 (such as between about 5:1 and about 20:1, such as between about 2:1 to about 50:1). In some embodiments, the molar ratio of the first cell-penetrating peptide to the nucleotide sequence encoding the Cas polypeptide is between about 1:1 and about 80:1 (such as between about 5:1 to about 20:1, such as between about 2:1 to about 50:1). In some embodiments, the molar ratio of the nucleotide sequence encoding the Cas polypeptide to the guide RNA is between about 1:10 and about 50:1 (such as between about 1:1 and about 10:1). In some embodiments, the guide RNA is complexed with the first cell-penetrating peptide. In some embodiments, the guide RNA is complexed with the first cell-penetrating peptide. In some embodiments, the genome-editing complex further comprises a DNA nuclease (e.g., Cas9) or a nucleotide sequence encoding the DNA nuclease.

In some embodiments, there is provided a genome-editing complex comprising a) a first cell-penetrating peptide, wherein the first cell-penetrating peptide is a VEPEP-9 peptide; and b) a guide RNA targeting a mutated KRAS comprising a nucleotide sequence substantially complementary (such as at least about 80%, 85%, 90%, 95%, 96%, 97%, 98%, or 99% complementary) to a target sequence selected from the group consisting of SEQ ID NOs: 1, 3, 6, 8, 15, 16, 19-21, 23, 29, 31, 33, and 34. In some embodiments, the first cell-penetrating peptide comprises an amino acid sequence selected from the group consisting of SEQ ID NOs: 118-134. In some embodiments, the guide RNA further comprising an auxiliary trans-activating crRNA (tracrRNA). In some embodiments, the molar ratio of the first cell-penetrating peptide to the guide RNA is between about 1:1 and about 80:1 (such as between about 5:1 and about 20:1, such as between about 2:1 to about 50:1). In some embodiments, the molar ratio of the first cell-penetrating peptide to the nucleotide sequence encoding the Cas polypeptide is between about 1:1 and about 80:1 (such as between about 5:1 to about 20:1, such as between about 2:1 to about 50:1). In some embodiments, the molar ratio of the nucleotide sequence encoding the Cas polypeptide to the guide RNA is between about 1:10 and about 50:1 (such as between about 1:1 and about 10:1). In some embodiments, the guide RNA is complexed with the first cell-penetrating peptide. In some embodiments, the guide RNA is complexed with the first cell-penetrating peptide. In some embodiments, the genome-editing complex further comprises a DNA nuclease (e.g., Cas9) or a nucleotide sequence encoding the DNA nuclease.

In some embodiments, there is provided a genome-editing complex comprising a) a first cell-penetrating peptide, wherein the first cell-penetrating peptide is an ADGN-100 peptide, a VEPEP-6 peptide, or a VEPEP-9 peptide; b) one or more guide RNA targeting a mutated KRAS comprising a nucleotide sequence substantially complementary (such as at least about 80%, 85%, 90%, 95%, 96%, 97%, 98%, or 99% complementary) to a target sequence selected from the group consisting of SEQ ID NOs: 1, 3, 6, 8, 15, 16, 19-21, 23, 29, 31, 33, and 34; and c) a DNA nuclease (e.g., a CRISPR-associated endonuclease) or a polynucleotide encoding the DNA nuclease. In some embodiments, there is provided a genome-editing complex comprising a) a first cell-penetrating peptide, wherein the first cell-penetrating peptide is an ADGN-100 peptide, a VEPEP-6 peptide, or a VEPEP-9 peptide; b) one or more guide RNA targeting a mutated KRAS comprising a nucleotide sequence 100% complementary to a target sequence selected from the group consisting of SEQ ID NOs: 1, 3, 6, 8, 15, 16, 19-21, 23, 29, 31, 33, and 34; and c) a DNA nuclease (e.g., a CRISPR-associated endonuclease) or a polynucleotide encoding the DNA nuclease. In some embodiments, the first cell-penetrating peptide is an ADGN-100 peptide. In some embodiments, the first cell-penetrating peptide comprises an amino acid sequence selected from the group consisting of SEQ ID NOs: 135-175 (such as an amino acid sequence selected from the group consisting of 153-175, such as an amino acid sequence selected from the group consisting of 154, 155, 157, 158, 162, 167-170, and 172). In some embodiments, the first cell-penetrating peptide comprises a VEPEP-6 peptide. In some embodiments, the first cell-penetrating peptide comprises an amino acid sequence selected from the group consisting of SEQ ID NOs: 63-117, 261-266 and 270. In some embodiments, the first cell-penetrating peptide comprises an amino acid sequence selected from the group consisting of 81, 92-103, 105-107, and 111-114. In some embodiments, the first cell-penetrating peptide comprises a VEPEP-9 peptide. In some embodiments, the first cell-penetrating peptide comprises an amino acid sequence selected from the group consisting of SEQ ID NOs: 118-134. In some embodiments, the DNA nuclease is a Cas9 polypeptide. In some embodiments, the DNA nuclease comprises a modified Cas9 (e.g., a catalytically impaired Cas9). In some embodiments, the DNA nuclease is a fusion protein, wherein the fusion protein further comprises a second enzyme that will allow base editing or prime editing. In some embodiments, the second enzyme comprises a reverse transcriptase or a nucleobase deaminase enzyme. In some embodiments, the one or more guide RNA comprise at least two guide RNA that specifically target at least two different KRAS mutations selected from G12V, G12D, and G12C. In some embodiments, the guide RNA further comprising an auxiliary trans-activating crRNA (tracrRNA). In some embodiments, the molar ratio of the first cell-penetrating peptide to the guide RNA is between about 1:1 and about 80:1 (such as between about 5:1 and about 20:1, such as between about 2:1 to about 50:1). In some embodiments, the molar ratio of the first cell-penetrating peptide to the nucleotide sequence encoding the Cas polypeptide is between about 1:1 and about 80:1 (such as between about 5:1 to about 20:1, such as between about 2:1 to about 50:1). In some embodiments, the molar ratio of the nucleotide sequence encoding the Cas polypeptide to the guide RNA is between about 1:10 and about 50:1 (such as between about 1:1 and about 10:1). In some embodiments, the guide RNA is complexed with the first cell-penetrating peptide. In some embodiments, the guide RNA is complexed with the first cell-penetrating peptide.

In some embodiments, there is provided a genome-editing complex comprising a) a first cell-penetrating peptide, wherein the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides; and b) one or more guide RNA targeting a mutated KRAS comprising a nucleotide sequence 100% complementary to a target sequence set forth in SEQ ID NO: 3. In some embodiments, there is provided a genome-editing complex comprising a) a first cell-penetrating peptide, wherein the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides; b) one or more guide RNA targeting a mutated KRAS comprising a nucleotide sequence 100% complementary to a target sequence set forth in SEQ ID NO: 3; and c) a DNA nuclease (e.g., a CRISPR-associated endonuclease, e.g., a Cas polypeptide, e.g., Cas9 or Cas12a) or a polynucleotide encoding the DNA nuclease. In some embodiments, the first cell-penetrating peptide is an ADGN-100 peptide, a VEPEP-6 peptide, or a VEPEP-9 peptide. In some embodiments, the first cell-penetrating peptide is an ADGN-100 peptide. In some embodiments, the first cell-penetrating peptide comprises an amino acid sequence selected from the group consisting of SEQ ID NOs: 135-175 (such as an amino acid sequence selected from the group consisting of 153-175, such as an amino acid sequence selected from the group consisting of 154, 155, 157, 158, 162, 167-170, and 172). In some embodiments, the first cell-penetrating peptide comprises a VEPEP-6 peptide. In some embodiments, the first cell-penetrating peptide comprises an amino acid sequence selected from the group consisting of SEQ ID NOs: 63-117, 261-266 and 270. In some embodiments, the first cell-penetrating peptide comprises an amino acid sequence selected from the group consisting of 81, 92-103, 105-107, and 111-114. In some embodiments, the first cell-penetrating peptide comprises a VEPEP-9 peptide. In some embodiments, the first cell-penetrating peptide comprises an amino acid sequence selected from the group consisting of SEQ ID NOs: 118-134. In some embodiments, the guide RNA further comprising an auxiliary trans-activating crRNA (tracrRNA). In some embodiments, the molar ratio of the first cell-penetrating peptide to the guide RNA is between about 1:1 and about 80:1 (such as between about 5:1 and about 20:1, such as between about 2:1 to about 50:1). In some embodiments, the molar ratio of the first cell-penetrating peptide to the nucleotide sequence encoding the Cas polypeptide is between about 1:1 and about 80:1 (such as between about 5:1 to about 20:1, such as between about 2:1 to about 50:1). In some embodiments, the molar ratio of the nucleotide sequence encoding the Cas polypeptide to the guide RNA is between about 1:10 and about 50:1 (such as between about 1:1 and about 10:1). In some embodiments, the guide RNA is complexed with the first cell-penetrating peptide. In some embodiments, the guide RNA is complexed with the first cell-penetrating peptide.

In some embodiments, there is provided a genome-editing complex comprising a) a first cell-penetrating peptide, wherein the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides; and b) one or more guide RNA targeting a mutated KRAS comprising a nucleotide sequence 100% complementary to a target sequence set forth in SEQ ID NO: 19. In some embodiments, there is provided a genome-editing complex comprising a) a first cell-penetrating peptide, wherein the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides; b) one or more guide RNA targeting a mutated KRAS comprising a nucleotide sequence 100% complementary to a target sequence set forth in SEQ ID NO: 19; and c) a DNA nuclease (e.g., a CRISPR-associated endonuclease, e.g., a Cas polypeptide, e.g., Cas9 or Cas12a) or a polynucleotide encoding the DNA nuclease. In some embodiments, the first cell-penetrating peptide is an ADGN-100 peptide, a VEPEP-6 peptide, or a VEPEP-9 peptide. In some embodiments, the first cell-penetrating peptide is an ADGN-100 peptide. In some embodiments, the first cell-penetrating peptide comprises an amino acid sequence selected from the group consisting of SEQ ID NOs: 135-175 (such as an amino acid sequence selected from the group consisting of 153-175, such as an amino acid sequence selected from the group consisting of 154, 155, 157, 158, 162, 167-170, and 172). In some embodiments, the first cell-penetrating peptide comprises a VEPEP-6 peptide. In some embodiments, the first cell-penetrating peptide comprises an amino acid sequence selected from the group consisting of SEQ ID NOs: 63-117, 261-266 and 270. In some embodiments, the first cell-penetrating peptide comprises an amino acid sequence selected from the group consisting of 81, 92-103, 105-107, and 111-114. In some embodiments, the first cell-penetrating peptide comprises a VEPEP-9 peptide. In some embodiments, the first cell-penetrating peptide comprises an amino acid sequence selected from the group consisting of SEQ ID NOs: 118-134. In some embodiments, the guide RNA further comprising an auxiliary trans-activating crRNA (tracrRNA). In some embodiments, the molar ratio of the first cell-penetrating peptide to the guide RNA is between about 1:1 and about 80:1 (such as between about 5:1 and about 20:1, such as between about 2:1 to about 50:1). In some embodiments, the molar ratio of the first cell-penetrating peptide to the nucleotide sequence encoding the Cas polypeptide is between about 1:1 and about 80:1 (such as between about 5:1 to about 20:1, such as between about 2:1 to about 50:1). In some embodiments, the molar ratio of the nucleotide sequence encoding the Cas polypeptide to the guide RNA is between about 1:10 and about 50:1 (such as between about 1:1 and about 10:1). In some embodiments, the guide RNA is complexed with the first cell-penetrating peptide. In some embodiments, the guide RNA is complexed with the first cell-penetrating peptide.

In some embodiments, there is provided a genome-editing complex comprising a) a first cell-penetrating peptide, wherein the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides; and b) one or more guide RNA targeting a mutated KRAS comprising a nucleotide sequence 100% complementary to a target sequence set forth in SEQ ID NO: 34. In some embodiments, there is provided a genome-editing complex comprising a) a first cell-penetrating peptide, wherein the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides; b) one or more guide RNA targeting a mutated KRAS comprising a nucleotide sequence 100% complementary to a target sequence set forth in SEQ ID NO: 34; and c) a DNA nuclease (e.g., a CRISPR-associated endonuclease, e.g., a Cas polypeptide, e.g., Cas9 or Cas12a) or a polynucleotide encoding the DNA nuclease. In some embodiments, the first cell-penetrating peptide is an ADGN-100 peptide, a VEPEP-6 peptide, or a VEPEP-9 peptide. In some embodiments, the first cell-penetrating peptide is an ADGN-100 peptide. In some embodiments, the first cell-penetrating peptide comprises an amino acid sequence selected from the group consisting of SEQ ID NOs: 135-175 (such as an amino acid sequence selected from the group consisting of 153-175, such as an amino acid sequence selected from the group consisting of 154, 155, 157, 158, 162, 167-170, and 172). In some embodiments, the first cell-penetrating peptide comprises a VEPEP-6 peptide. In some embodiments, the first cell-penetrating peptide comprises an amino acid sequence selected from the group consisting of SEQ ID NOs: 63-117, 261-266 and 270. In some embodiments, the first cell-penetrating peptide comprises an amino acid sequence selected from the group consisting of 81, 92-103, 105-107, and 111-114. In some embodiments, the first cell-penetrating peptide comprises a VEPEP-9 peptide. In some embodiments, the first cell-penetrating peptide comprises an amino acid sequence selected from the group consisting of SEQ ID NOs: 118-134. In some embodiments, the guide RNA further comprising an auxiliary trans-activating crRNA (tracrRNA). In some embodiments, the molar ratio of the first cell-penetrating peptide to the guide RNA is between about 1:1 and about 80:1 (such as between about 5:1 and about 20:1, such as between about 2:1 to about 50:1). In some embodiments, the molar ratio of the first cell-penetrating peptide to the nucleotide sequence encoding the Cas polypeptide is between about 1:1 and about 80:1 (such as between about 5:1 to about 20:1, such as between about 2:1 to about 50:1). In some embodiments, the molar ratio of the nucleotide sequence encoding the Cas polypeptide to the guide RNA is between about 1:10 and about 50:1 (such as between about 1:1 and about 10:1). In some embodiments, the guide RNA is complexed with the first cell-penetrating peptide. In some embodiments, the guide RNA is complexed with the first cell-penetrating peptide.

Cell-Penetrating Peptides

Cell Penetrating Peptides (CPP) are one of the promising non-viral strategies. Although definition of CPPs is constantly evolving, they are generally described as short peptides of less than 30 amino acids either derived from proteins or from chimeric sequences. They are usually amphipathic and possess a net positive charge (Langel U (2007) *Handbook of Cell-Penetrating Peptides* (CRC Taylor & Francis, Boca Raton); Heitz et al. (2009) *Br J Pharmacol* 157, 195-206). CPPs are able to penetrate biological membranes, to trigger the movement of various biomolecules across cell membranes into the cytoplasm and to improve their intracellular routing, thereby facilitating interactions with the target. CPPs can be subdivided into two main classes, the first requiring chemical linkage with the cargo and the second involving the formation of stable, non-covalent complexes. CPPs from both strategies have been reported to favour the delivery of a large panel of cargos (plasmid DNA, oligonucleotide, siRNA, PNA, protein, peptide, liposome, nanoparticle . . . ) into a wide variety of cell types and in vivo models (Langel U (2007) *Handbook of Cell-Penetrating Peptides* (CRC Taylor & Francis, Boca Raton); Heitz et al. (2009) *Br J Pharmacol* 157, 195-206; Mickan et al. (2014) *Curr Pharm Biotechnol* 15, 200-209; Shukla et al. (2014) *Mol Pharm* 11, 3395-3408).

The concept of protein transduction domain (PTD) was initially proposed based on the observation that some proteins, mainly transcription factors, could shuttle within cells and from one cell to another (for review see Langel U (2007) *Handbook of Cell-Penetrating Peptides* (CRC Taylor & Francis, Boca Raton); Heitz et al. (2009) *Br J Pharmacol* 157, 195-206). The first observation was made in 1988, by Frankel and Pabo. They showed that the transcription-transactivating (Tat) protein of HIV-1 could enter cells and translocate into the nucleus. In 1991, the group of Prochiantz reached the same conclusions with the *Drosophila* Antennapedia homeodomain and demonstrated that this domain was internalized by neuronal cells. These works were at the origin of the discovery in 1994 of the first Protein Transduction Domain: a 16 mer-peptide derived from the third helix of the homeodomain of Antennapedia named Penetratin. In 1997, the group of Lebleu identified the minimal sequence of Tat required for cellular uptake, and the first proofs-of-concept of the application of PTD in vivo were reported by the group of Dowdy for the delivery of small peptides and large proteins (Gump J M, and Dowdy S F (2007) *Trends Mol Med* 13, 443-448.). Historically, the notion of Cell Penetrating Peptide (CPP) was introduced by the group of Langel, in 1998, with the design of the first chimeric peptide carrier, the Transportan, which derived from the N-terminal fragment of the neuropeptide galanin, linked to mastoparan, a wasp venom peptide. Transportan has been originally reported to improve the delivery of PNAs (peptide nucleic acids) both in cultured cells and in vivo (Langel U (2007) *Handbook of Cell-Penetrating Peptides* (CRC Taylor & Francis, Boca Raton)). In 1997, the group of Heitz and Divita proposed a new strategy involving CPP in the formation of stable but non-covalent complexes with their cargo (Morris et al. (1997) *Nucleic Acids Res* 25, 2730-2736). The strategy was first based on the short peptide carrier (MPG) consisting of two domains: a hydrophilic (polar) domain and a hydrophobic (apolar) domain. MPG was designed for the delivery of nucleic acids. The primary amphipathic peptide Pep-1 was then proposed for non-covalent delivery of proteins and peptides (Morris et al. (2001) *Nat Biotechnol* 19, 1173-1176). Then the groups of Wender and of Futaki demonstrated that polyarginine sequences (Arg8) are sufficient to drive small and large molecules into cells and in vivo (Nakase et al. (2004) *Mol Ther* 10, 1011-1022; Rothbard et al. (2004) *J Am Chem Soc* 126, 9506-9507). Ever since, many CPPs derived from natural or unnatural sequences have been identified and the list is constantly increasing. Peptides have been derived from VP22 protein of Herpes Simplex Virus, from calcitonin, from antimicrobial or toxin peptides, from proteins involved in cell cycle regulation, as well as from polyproline-rich peptides (Heitz et al. (2009) *Br J Pharmacol* 157, 195-206). More recently, a new non-covalent strategy based on secondary amphipathic CPPs has been described. These peptides such as CADY and VEPEP-families are able to self-assemble in a helical shape with hydrophilic and hydrophobic residues on different side of the molecule. WO2014/053879 discloses VEPEP-3 peptides; WO2014/053881 discloses VEPEP-4 peptides; WO2014/053882 discloses VEPEP-5 peptides; WO2012/137150 discloses VEPEP-6 peptides; WO2014/053880 discloses VEPEP-9 peptides; WO 2016/102687 discloses ADGN-100 peptides; US2010/0099626 discloses CADY peptides; and. U.S. Pat. No. 7,514,530 discloses MPG peptides; the disclosures of which are hereby incorporated herein by reference in their entirety.

The cell-penetrating peptides in the genome-editing complexes or nanoparticles of the present application are capable of forming stable complexes and nanoparticles with various molecules of a genome-editing system, such as nucleases (e.g., ZFNs, TALENs, and CRISPR-associated nucleases (such as Cas9 and Cpf1)), integrases (such as bacteriophage integrases, e.g., ΦC31), and nucleic acids (e.g., guide RNAs, guide DNAs, and donor nucleic acids). Any of the cell-penetrating peptides in any of the genome-editing complexes or nanoparticles described herein may comprise or consist of any of the cell-penetrating peptide sequences described in this section.

In some embodiments, a genome-editing complex or nanoparticle described herein comprises a cell-penetrating peptide selected from the group consisting of CADY, PEP-1, MPG, VEPEP-3 peptides, VEPEP-4 peptides, VEPEP-5 peptides, VEPEP-6 peptides, VEPEP-9 peptides, and ADGN-100 peptides. In some embodiments, the cell-penetrating peptide is present in a genome-editing complex. In some embodiments, the cell-penetrating peptide is present in a genome-editing complex present in the core of a nanoparticle. In some embodiments, the cell-penetrating peptide is present in the core of a nanoparticle. In some embodiments, the cell-penetrating peptide is present in the core of a nanoparticle and is associated with a DNA nuclease (such as a CRISPR-associated endonuclease, such as Cas9). In some embodiments, the cell-penetrating peptide is present in the core of a nanoparticle and is associated with a gRNA. In some embodiments, the cell-penetrating peptide is present in the core of a nanoparticle and is associated with the guide RNA. In some embodiments, the cell-penetrating peptide is present in the core of a nanoparticle and is associated with a donor nucleic acid. In some embodiments, the cell-penetrating peptide is present in an intermediate layer of a nanoparticle. In some embodiments, the cell-penetrating peptide is present in the surface layer of a nanoparticle. In some embodiments, the cell-penetrating peptide is linked to a targeting moiety. In some embodiments, the linkage is covalent. WO2014/053879 discloses VEPEP-3 peptides; WO2014/053881 discloses VEPEP-4 peptides; WO2014/053882 discloses VEPEP-5 peptides; WO2012/137150 discloses VEPEP-6 peptides; WO2014/053880 discloses VEPEP-9 peptides; WO 2016/102687 discloses ADGN-100 peptides; US2010/0099626 discloses CADY peptides; and. U.S. Pat. No. 7,514,530 discloses MPG peptides; the disclosures of which are hereby incorporated herein by reference in their entirety.

VEPEP-3 Peptides

In some embodiments, a genome-editing complex or nanoparticle described herein comprises a VEPEP-3 cell-penetrating peptide comprising the amino acid sequence $X_1X_2X_3X_4X_5X_2X_3X_4X_6X_7X_3X_8X_9X_{10}X_{11}X_{12}X_{13}$ (SEQ ID NO: 44), wherein $X_1$ is beta-A ("beta-alanine) or S, $X_2$ is K, R or L (independently from each other), $X_3$ is F or W (independently from each other), $X_4$ is F, W or Y (independently from each other), $X_5$ is E, R or S, $X_6$ is R, T or S, $X_7$ is E, R, or S, $X_8$ is none, F or W, $X_9$ is P or R, $X_{10}$ is R or L, $X_{11}$ is K, W or R, $X_{12}$ is R or F, and $X_{13}$ is R or K. In some embodiments, the VEPEP-3 peptide comprises the amino acid sequence $X_1X_2WX_4EX_2WX_4X_6X_7X_3PRX_{11}RX_{13}$ (SEQ ID NO: 45), wherein $X_1$ is beta-A or S, $X_2$ is K, R or L, $X_3$ is F or W, $X_4$ is F, W or Y, $X_5$ is E, R or S, $X_6$ is R, T or S, $X_7$ is E, R, or S, $X_8$ is none, F or W, $X_9$ is P or R, $X_{10}$ is R or L, $X_{11}$ is K, W or R, $X_{12}$ is R or F, and $X_{13}$ is R or K. In some embodiments, the VEPEP-3 peptide comprises the amino acid sequence $X_1$KWFERWFREWPRKRR (SEQ ID NO: 46), $X_1$KWWERWWREWPRKRR (SEQ ID NO: 47), $X_1$KWWERWWREWPRKRK (SEQ ID NO: 48), $X_1$RWWEKWWTRWPRKRK (SEQ ID NO: 49), or $X_1$RWYEKWYTEFPRRRR (SEQ ID NO: 50), wherein $X_1$ is beta-A or S. In some embodiments, the VEPEP-3 peptide comprises the amino acid sequence of any one of SEQ ID NOs: 1-7, wherein the cell-penetrating peptide is modified by replacement of the amino acid in position 10 by a non-natural amino acid, addition of a non-natural amino acid between the amino acids in positions 2 and 3, and addition of a hydrocarbon linkage between the two non-natural amino acids. In some embodiments, the VEPEP-3 peptide comprises the amino acid sequence $X_1KX_{14}$WWERWWR$X_{14}$WPRKRK (SEQ ID NO: 51), wherein $X_1$ is beta-A or S and $X_{14}$ is a non-natural amino acid, and wherein there is a hydrocarbon linkage between the two non-natural amino acids. In some embodiments, the VEPEP-3 peptide comprises the amino acid sequence $X_1X_2X_3WX_5X_{10}X_3WX_6X_7WX_8X_9X_{10}WX_{12}R$ (SEQ ID NO: 52), wherein $X_1$ is beta-A or S, $X_2$ is K, R or L, $X_3$ is F or W, $X_5$ is R or S, $X_6$ is R or S, $X_7$ is R or S, $X_8$ is F or W, $X_9$ is R or P, $X_{10}$ is L or R, and $X_{12}$ is R or F. In some embodiments, the VEPEP-3 peptide comprises the amino acid sequence $X_1$RWWRLWWRSWFRLWRR (SEQ ID NO: 53), $X_1$LWWRRWWSRWWPRWRR (SEQ ID NO: 54), $X_1$LWWSRWWRSWFRLWFR (SEQ ID NO: 55), or $X_1$KFWSRFWRSWFRLWRR (SEQ ID NO: 56), wherein $X_1$ is beta-A or S. In some embodiments, the VEPEP-3 peptide comprises the amino acid sequence of any one of SEQ ID NOs: 44 and 52-56, wherein the cell-penetrating peptide is modified by replacement of the amino acids in position 5 and 12 by non-natural amino acids, and addition of a hydrocarbon linkage between the two non-natural amino acids. In some embodiments, the VEPEP-3 peptide comprises the amino acid sequence $X_1$RWW$X_{14}$LWWRSW$X_{14}$RLWRR (SEQ ID NO: 57), wherein $X_1$ is a beta-alanine or a serine and $X_{14}$ is a non-natural amino acid, and wherein there is a hydrocarbon linkage between the two non-natural amino acids. In some embodiments, the VEPEP-3 peptide comprises the amino acid sequence beta-AKWFERWFREWPRKRR (SEQ ID NO: 58). In some embodiments, the VEPEP-3 peptide comprises the amino acid sequence beta-AKWWERWWREWPRKRR (SEQ ID NO: 59). In some embodiments, the VEPEP-3 peptide comprises the amino acid sequence ASSLNIA-Ava-KWWERWWREWPRKRR (SEQ ID NO: 60). In some embodiments, the VEPEP-3 peptide comprises the amino acid sequence LSSRLDA-Ava-KWWERWWREWPRKRR (SEQ ID NO: 61). In some embodiments, the VEPEP-3 peptide comprises the amino acid sequence Ac-SYTSSTM-ava-KWWERWWREWPRKRR (SEQ ID NO: 62). In some embodiments, the VEPEP-3 peptide is present in a genome-editing complex. In some embodiments, the VEPEP-3 peptide is present in a genome-editing complex in the core of a nanoparticle. In some embodiments, the VEPEP-3 peptide is present in the core of a nanoparticle. In some embodiments, the VEPEP-3 peptide is present in the core of a nanoparticle and is associated with the guide RNA. In some embodiments, the VEPEP-3 peptide is present in the core of a nanoparticle and is associated with a guide RNA. In some embodiments, the VEPEP-3 peptide is present in the core of a nanoparticle and is associated with the guide RNA. In some embodiments, the VEPEP-3 peptide is present in the core of a nanoparticle and is associated with a donor nucleic acid. In some embodiments, the VEPEP-3 peptide is present in an intermediate layer of a nanoparticle. In some embodiments, the VEPEP-3 peptide is present in the surface layer of a nanoparticle. In some embodiments, the VEPEP-3 peptide is linked to a targeting moiety. In some embodiments, the linkage is covalent.

VEPEP-6 Peptides

In some embodiments, a genome-editing complex or nanoparticle described herein comprises a VEPEP-6 cell-penetrating peptide. In some embodiments, the VEPEP-6 peptide comprises an amino acid sequence selected from the group consisting of $X_1LX_2RALWX_9LX_3X_9X_4LWX_9LX_5X_6X_7X_8$ (SEQ ID NO: 63), $X_1LX_2LARWX_9LX_3X_9X_4LWX_9LXSX_6X_7X_8$ (SEQ ID NO: 64) and $X_1LX_2ARLWX_9LX_3X_9X_4LWX_9LX_5X_6X_7X_8$ (SEQ ID NO: 65), wherein $X_1$ is beta-A or S, $X_2$ is F or W, $X_3$ is L, W, C or I, $X_4$ is S, A, N or T, $X_5$ is L or W, $X_6$ is W or R, $X_7$ is K or R, $X_8$ is A or none, and $X_9$ is R or S. In some embodiments, the VEPEP-6 peptide comprises the amino acid sequence $X_1LX_2RALWRLX_3RX_4LWRLX_5X_6X_7X_8$ (SEQ ID NO: 66), wherein $X_1$ is beta-A or S, $X_2$ is F or W, $X_3$ is L, W, C or I, $X_4$ is S, A, N or T, $X_5$ is L or W, $X_6$ is W or R, $X_7$ is K or R, and $X_8$ is A or none. In some embodiments, the VEPEP-6 peptide comprises the amino acid sequence $X_1LX_2RALWRLX_3RX_4LWRLXSX_6KX_7$ (SEQ ID NO: 67), wherein $X_1$ is beta-A or S, $X_2$ is F or W, $X_3$ is L or W, $X_4$ is S, A or N, $X_5$ is L or W, $X_6$ is W or R, $X_7$ is A or none. In some embodiments, the VEPEP-6 peptide comprises an amino acid sequence selected from the group consisting of $X_1LFRALWRLLRX_2LWRLLWX_3$ (SEQ ID NO: 68), $X_1LWRALWRLWRX_2LWRLLWX_3A$ (SEQ ID NO: 69), $X_1LWRALWRLX_4RX_2LWRLWRX_3A$ (SEQ ID NO: 70), $X_1LWRALWRLWRX_2LWRLWRX_3A$ (SEQ ID NO: 71), $X_1LWRALWRLX_5RALWRLLWX_3A$ (SEQ ID NO: 72), and $X_1LWRALWRLX_4RNLWRLLWX_3A$ (SEQ ID NO: 73), wherein $X_1$ is beta-A or S, $X_2$ is S or T, $X_3$ is K or R, $X_4$ is L, C or I and $X_5$ is L or I. In some embodiments, the VEPEP-6 peptide comprises an amino acid sequence selected from the group consisting of Ac-$X_1$LFRALWRLLRSLWRLLWK-cysteamide (SEQ ID NO: 74), Ac-$X_1$LWRALWRLWRSLWRLLWKA-cysteamide (SEQ ID NO: 75), Ac-$X_1$LWRALWRLLRSLWRLWRKA-cysteamide (SEQ ID NO: 76), Ac-$X_1$LWRALWRLWRSLWRLWRKA-cysteamide (SEQ ID NO: 77), Ac-$X_1$LWRALWRLLRALWRLLWKA-cysteamide (SEQ ID NO: 78), and Ac-$X_1$LWRALWRLLRNLWRLLWKA-cysteamide (SEQ ID NO: 79), wherein $X_1$ is beta-A or S. In some embodiments, the VEPEP-6 peptide comprises the amino acid sequence of any one of SEQ ID NOs: 63-79, further comprising a hydrocarbon linkage between two residues at positions 8 and 12. In some embodiments, the VEPEP-6 peptide comprises an amino acid sequence selected from the group consisting of Ac-$X_1$LFRALWR$_S$LLRS$_S$LWRLLWK-cysteamide (SEQ ID NO: 80), Ac-$X_1$LFLARWR$_S$LLRS$_S$LWRLLWK-cysteamide (SEQ ID NO: 81), Ac-$X_1$LFRALWS$_S$LLRS$_S$LWRLLWK-cysteamide (SEQ ID NO: 82), Ac-$X_1$LFLARWS$_S$LLRS$_S$LWRLLWK-cysteamide (SEQ ID NO: 83), Ac-$X_1$LFRALWRLLR$_S$SLWS$_S$LLWK-cysteamide (SEQ ID NO: 84), Ac-$X_1$LFLARWRLLR$_S$SLWS$_S$LLWK-cysteamide (SEQ ID NO: 85), Ac-$X_1$LFRALWRLLS$_S$SLWS$_S$LLWK-cysteamide (SEQ ID NO: 86), Ac-$X_1$LFLARWRLLS$_S$SLWS$_S$LLWK-cysteamide (SEQ ID NO: 87), and Ac-$X_1$LFAR$_S$LWRLLRS$_S$LWRLLWK-cysteamide (SEQ ID NO: 88), wherein $X_1$ is beta-A or S and wherein the residues followed by an inferior "S" are those which are linked by said hydrocarbon linkage. In some embodiments, the VEPEP-6 peptide comprises an amino acid sequence beta-ALWRALWRLWRSLWRLLWKA (SEQ ID NO: 89). In some embodiments, the VEPEP-6 peptide comprises an amino acid sequence set forth in any one of SEQ ID NOs 90-117. In some embodiments, the VEPEP-6 peptide comprises an amino acid sequence beta-ALWRALWRLWRSLWRLLWKA-NH2 (SEQ ID NO: 90). In some embodiments, the VEPEP-6 peptide comprises a retro-inverso amino acid sequence AKWLLRWLSRWLRWLARWLR (SEQ ID NO: 91). In some embodiments, the VEPEP-6 peptide comprises an amino acid sequence Ac-(PEG)7-βALWRALWRLWRSLWRLLWKA-NH2 (SEQ ID NO: 92) or Ac-(PEG)2-βALWRALWRLWRSLWRLLWKA-NH2 (SEQ ID NO: 93). In some embodiments, the VEPEP-6 peptide comprises an amino acid sequence set forth in any one of SEQ ID NOS: 94-103. In some embodiments, the VEPEP-6 peptide comprises an amino acid sequence beta-A-Ac-YIGSR-Ava-ALWRALWRLWRSLWRLLWKA-NH2 (SEQ ID NO: 96). In some embodiments, the VEPEP-6 peptide comprises an amino acid sequence beta-A-Ac-YIGSR-Aun-ALWRALWRLWRSLWRLLWKA-NH2 (SEQ ID NO: 98). In some embodiments, the VEPEP-6 peptide comprises an amino acid sequence Ac-YIGSR-Ahx-ALWRALWRLWRSLWRLLWK-NH2 (SEQ ID NO: 100) or Ac-YIGSR-Ahx-ALWRALWRLWRSLWRLLWKA-NH2 (SEQ ID NO: 101). In some embodiments, the VEPEP-6 peptide comprises an amino acid sequence beta-Ac-GYVS-Ahx-ALWRALWRLWRSLWRLLWKA-NH2 (SEQ ID NO: 102) or Ac-YIGSR-βALWRALWRLWRSLWRLLWKA-NH2 (SEQ ID NO: 103). In some embodiments, the VEPEP-6 peptide comprises an amino acid sequence Stearyl-βA-ALWRALWRLWRSLWRLLWKA-NH2 (SEQ ID NO: 104). In some embodiments, the VEPEP-6 peptide comprises an amino acid sequence set forth in any one of SEQ ID NOS: 105-107. In some embodiments, the VEPEP-6 peptide comprises an amino acid sequence ALWRA(GalNac)LWRLWRSLWRLLWKA-NH2 (SEQ ID NO: 111). In some embodiments, the VEPEP-6 peptide comprises an amino acid sequence Ac-SYTSSTM-ava-βALWRALWRLWRSLWRLLWKA-NH2 (SEQ ID NO: 112). In some embodiments, the VEPEP-6 peptide comprises an amino acid sequence Ac-THRPPNWSPVWPRALWRLWRSLWRLRWKA-NH2 (SEQ ID NO: 113). In some embodiments, the VEPEP-6 peptide comprises an amino acid sequence Ac-CKTRRVP-WRALWRLWRSLWRLLWKA-NH2 (SEQ ID NO: 114). In some embodiments, the VEPEP-6 peptide comprises an amino acid sequence Ac-CKTRRVP-ava-WRALWRLWRSLWRLLWKA-NH2 (SEQ ID NO: 115). In some embodiments, the VEPEP-6 peptide comprises an amino acid sequence Ac-CARPAR-ava-WRALWRLWRSLWRLLWK-NH2 (SEQ ID NO: 116). In some embodiments, the VEPEP-6 peptide comprises an amino acid sequence Ac-THRPPNWSPV-ava-WRALWRLWRSLWRLRWK-NH2 (SEQ ID NO: 117). In some embodiments, the VEPEP-6 peptide is present in a genome-editing complex. In some embodiments, the VEPEP-6 peptide is present in a genome-editing complex in the core of a nanoparticle. In some embodiments, the VEPEP-6 peptide is present in the core of a nanoparticle. In some embodiments, the VEPEP-6 peptide is present in the core of a nanoparticle and is associated with a DNA nuclease (such as a CRISPR-associated endonuclease, such as Cas9). In some embodiments, the VEPEP-6 peptide is present in the core of a nanoparticle and is associated with a gRNA. In some embodiments, the VEPEP-6 peptide is present in the core of a nanoparticle and is associated with the guide RNA. In some embodiments, the VEPEP-6 peptide is present in the core of a nanoparticle and is associated with a donor nucleic acid. In some embodiments, the VEPEP-6 peptide is present in an intermediate layer of a nanoparticle. In some embodiments, the VEPEP-6 peptide is present in the surface layer of a nanoparticle. In some embodiments, the VEPEP-6 peptide is linked to a targeting moiety. In some embodiments, the linkage is covalent.

VEPEP-9 Peptides

In some embodiments, a genome-editing complex or nanoparticle described herein comprises a VEPEP-9 cell-penetrating peptide comprising the amino acid sequence $X_1X_2X_3WWX_4X_5WAX_6X_3X_7X_8X_9X_{10}X_{11}X_{12}WX_{13}R$ (SEQ ID NO: 118), wherein $X_1$ is beta-A or S, $X_2$ is L or none, $X_3$ is R or none, $X_4$ is L, R or G, $X_5$ is R, W or S, $X_6$ is S, P or T, $X_7$ is W or P, $X_8$ is F, A or R, $X_9$ is S, L, P or R, $X_{10}$ is R or S, $X_{11}$ is W or none, $X_{12}$ is A, R or none and $X_{13}$ is W or F, and wherein if $X_3$ is none, then $X_2$, $X_{11}$ and $X_{12}$ are none as well. In some embodiments, the VEPEP-9 peptide comprises the amino acid sequence $X_1X_2RWWLRWAX_6RWX_8X_9X_{10}WX_{12}WX_{13}R$ (SEQ ID NO: 119), wherein $X_1$ is beta-A or S, $X_2$ is L or none, $X_6$ is S or P, $X_8$ is F or A, $X_9$ is S, L or P, $X_{10}$ is R or S, $X_{12}$ is A or R, and $X_{13}$ is W or F. In some embodiments, the VEPEP-9 peptide comprises an amino acid sequence selected from the group consisting of $X_1$LRWWLRWASRWFSRWAWWR (SEQ ID NO: 120), $X_1$LRWWLRWASRWASRWAWFR (SEQ ID NO: 121), $X_1$RWWLRWASRWALSWRWWR (SEQ ID NO: 122), $X_1$RWWLRWASRWFLSWRWWR (SEQ ID NO: 123), $X_1$RWWLRWAPRWFPSWRWWR (SEQ ID NO: 124), and $X_1$RWWLRWASRWAPSWRWWR (SEQ ID NO: 125), wherein $X_1$ is beta-A or S. In some embodiments, the VEPEP-9 peptide comprises the amino acid sequence of $X_1WWX_4X_5WAX_6X_7X_8RX_{10}WWR$ (SEQ ID NO: 126), wherein $X_1$ is beta-A or S, $X_4$ is R or G, $X_5$ is W or S, $X_6$ is S, T or P, $X_7$ is W or P, $X_8$ is A or R, and $X_{10}$ is S or R. In some embodiments, the VEPEP-9 peptide comprises an amino acid sequence selected from the group consisting of $X_1$WWRWWASWARSWWR (SEQ ID NO: 127), $X_1$WWGSWATPRRRWWR (SEQ ID NO: 128), and $X_1$WWRWWAPWARSWWR (SEQ ID NO: 129), wherein $X_1$ is beta-A or S. In some embodiments, the VEPEP-9 peptide comprises the amino acid sequence beta-ALRWWLRWASRWFSRWAWWR (SEQ ID NO: 130). In some embodiments, the VEPEP-9 peptide comprises the amino acid sequence KSYDTY-ava-ALRWLRWAS-RWFSRWAWR (SEQ ID NO: 131). In some embodiments, the VEPEP-9 peptide comprises the amino acid sequence ac-CKRAVRWWLRWASRWFSRWAWWR (SEQ ID NO: 132). In some embodiments, the VEPEP-9 peptide comprises the amino acid sequence beta-A-RWWLRWAS-RWFSRWAWR (SEQ ID NO: 133). In some embodiments, the VEPEP-9 peptide comprises the amino acid sequence KSYDTYAAETRRWASRWFSRWAWWR (SEQ ID NO: 134). In some embodiments, the VEPEP-9 peptide is present in a genome-editing complex. In some embodiments, the VEPEP-9 peptide is present in a genome-editing complex in the core of a nanoparticle. In some embodiments, the VEPEP-9 peptide is present in the core of a nanoparticle. In some embodiments, the VEPEP-9 peptide is present in the core of a nanoparticle and is associated with a DNA nuclease (such as a CRISPR-associated endonuclease, such as Cas9). In some embodiments, the VEPEP-9 peptide is present in the core of a nanoparticle and is associated with a gRNA. In some embodiments, the VEPEP-9 peptide is present in the core of a nanoparticle and is associated with the guide RNA. In some embodiments, the VEPEP-9 peptide is present in the core of a nanoparticle and is associated with a donor nucleic acid. In some embodiments, the VEPEP-9 peptide is present in an intermediate layer of a nanoparticle. In some embodiments, the VEPEP-9 peptide is present in the surface layer of a nanoparticle. In some embodiments, the VEPEP-9 peptide is linked to a targeting moiety. In some embodiments, the linkage is covalent.

ADGN-100 Peptides

In some embodiments, a genome-editing complex or nanoparticle described herein comprises an ADGN-100 cell-penetrating peptide comprising the amino acid sequence $X_1KWRSX_2X_3X_4RWRLWRX_5X_6X_7X_8SR$ (SEQ ID NO: 135), wherein $X_1$ is any amino acid or none, and $X_2$-$X_8$ are any amino acid. In some embodiments, the ADGN-100 peptide comprises the amino acid sequence $X_1KWRSX_2X_3X_4RWRLWRX_5X_6X_7X_8SR$ (SEQ ID NO: 136), wherein $X_1$ is PA, S, or none, $X_2$ is A or V, $X_3$ is or L, $X_4$ is W or Y, $X_5$ is V or S, $X_6$ is R, V, or A, $X_7$ is S or L, and $X_8$ is W or Y. In some embodiments, the ADGN-100 peptide comprises the amino acid sequence KWR-SAGWRWRLWRVRSWSR (SEQ ID NO: 137), KWR-SALYRWRLWRVRSWSR (SEQ ID NO: 138), KWR-SALYRWRLWRSRSWSR (SEQ ID NO: 139), or KWRSALYRWRLWRSALYSR (SEQ ID NO: 140). In some embodiments, the ADGN-100 peptide comprises two residues separated by three or six residues that are linked by a hydrocarbon linkage. In some embodiments, the ADGN-100 peptide comprises the amino acid sequence KWRS$_S$AGWR$_S$WRLWRVRSWSR (SEQ ID NO: 141), KWR$_S$-SAGWRWR$_S$LWRVRSWSR (SEQ ID NO: 142), KWR-SAGWR$_S$WRLWRVR$_S$SWSR (SEQ ID NO: 143), KWRS$_S$ALYR$_S$WRLWRSRSWSR (SEQ ID NO: 144), KWR$_S$-SALYRWR$_S$LWRSRSWSR (SEQ ID NO: 145), KWR-SALYR$_S$WRLWRSR$_S$SWSR (SEQ ID NO: 146), KWR-SALYRWR$_S$LWRS$_S$RSWSR (SEQ ID NO: 147), KWRSALYRWRLWRS$_S$RSWS$_S$R (SEQ ID NO: 148), KWR$_S$SALYRWR$_S$LWRSALYSR (SEQ ID NO: 149), KWRS$_S$ALYR$_S$WRLWRSALYSR (SEQ ID NO: 150), KWRSALYRWR$_S$LWRS$_S$ALYSR (SEQ ID NO: 151), or KWRSALYRWRLWRS$_S$ALYS$_S$R (SEQ ID NO: 152), wherein the residues marked with a subscript "S" are linked by a hydrocarbon linkage. In some embodiments, the ADGN-100 peptide comprises an amino acid sequence of any one of SEQ ID NOs: 153-171. In some embodiments, the ADGN-100 peptide comprises an amino acid sequence of beta-AKWRSAGWRWRLWRVRSWSR-NH2 (SEQ ID NO: 153). In some embodiments, the ADGN-100 peptide comprises an amino acid sequence of beta-AKWR-SAGWRWRLWRVRSWSR (SEQ ID NO: 154) or beta-AKWRSALYRWRLWRVRSWSR (SEQ ID NO: 155). In some embodiments, the ADGN-100 peptide comprises a retro-inverso amino acid sequence of RSWSRVRWLRWRWGASRWK (SEQ ID NO: 156). In some embodiments, the ADGN-100 peptide comprises an amino acid sequence of Ac-(PEG)7-bA-KWR- SALWRWRLWRVRSWSR-NH2 (SEQ ID NO: 157) or beta-Ac-(PEG)2-βA-KWRSALWRWRLWRVRSWSR-NH2 (SEQ ID NO: 158). In some embodiments, the ADGN-100 peptide comprises an amino acid sequence of Stearyl-βA-KWRSALWRWRLWRVRSWSR-NH2 (SEQ ID NO: 159). In some embodiments, the ADGN-100 peptide comprises an amino acid sequence of any one of SEQ ID NOS: 160-169. In some embodiments, the ADGN-100 peptide comprises an amino acid sequence Ac-YIGSR-Ava-KWR-SALWRWRLWRVRSWSR-NH2 (ava is a 5-amino pentanoic acid) (SEQ ID NO: 162). In some embodiments, the ADGN-100 peptide comprises an amino acid sequence Ac-YIGSR-Ahx-KWRSALWRWRLWRVRSWSR-NH2 (SEQ ID NO: 167). In some embodiments, the ADGN-100 peptide comprises an amino acid sequence Ac-YIGSR-(PEG)n-βA-KWRSALWRWRLWRVRSWSR-NH2 (n=2, 4, or 7) (SEQ ID NO: 170). In some embodiments, the ADGN-100 peptide comprises an amino acid sequence Ac-KWRSA(GALNAC)LWRWRLWRVRSWSR-NH2 (SEQ ID NO: 172). In some embodiments, the ADGN-100 peptide comprises an amino acid sequence Ac-CAR-PARWRSAGWRWRLWRVRSWSR-NH2 (SEQ ID NO: 173). In some embodiments, the ADGN-100 peptide comprises a core motif comprising an amino acid sequence of RWRLWRWSR (SEQ ID NO: 168). In some embodiments, the ADGN-100 peptide comprises an amino acid sequence TGNYKALHPDHNGWRSALRWRLWRWSR-NH2 (SEQ ID NO: 174) or Ac-TGNYKALHPDHNG-ava-WR-SALRWRLWRWSR-NH2 (SEQ ID NO: 175). In some embodiments, the ADGN-100 peptide is present in a genome-editing complex. In some embodiments, the ADGN-100 peptide is present in a genome-editing complex in the core of a nanoparticle. In some embodiments, the ADGN-100 peptide is present in the core of a nanoparticle. In some embodiments, the ADGN-100 peptide is present in the core of a nanoparticle and is associated with a DNA nuclease (such as a CRISPR-associated endonuclease, such as Cas9). In some embodiments, the ADGN-100 peptide is present in the core of a nanoparticle and is associated with a gRNA. In some embodiments, the ADGN-100 peptide is present in the core of a nanoparticle and is associated with the guide RNA. In some embodiments, the ADGN-100 peptide is present in the core of a nanoparticle and is associated with a donor nucleic acid. In some embodiments, the ADGN-100 peptide is present in an intermediate layer of a nanoparticle. In some embodiments, the ADGN-100 peptide is present in the surface layer of a nanoparticle. In some embodiments, the ADGN-100 peptide is linked to a targeting moiety. In some embodiments, the linkage is covalent.

VEPEP-4 Peptides

In some embodiments, a genome-editing complex or nanoparticle described herein comprises a VEPEP-4 cell-penetrating peptide comprising the amino acid sequence XWXRLXXXXXX (SEQ ID NO: 176), wherein X in position 1 is beta-A or S; X in positions 3, 9 and 10 are, independently from each other, W or F; X in position 6 is R if X in position 8 is S, and X in position 6 is S if X in position 8 is R; X in position 7 is L or none; X in position 11 is R or none, and X in position 7 is L if X in position 11 is none. In some embodiments, the VEPEP-4 peptide comprises an amino acid sequence of any one of SEQ ID NOs: 177-180. In some embodiments, the VEPEP-4 peptide is present in a genome-editing complex. In some embodiments, the VEPEP-4 peptide is present in a genome-editing complex in the core of a nanoparticle. In some embodiments, the VEPEP-4 peptide is present in the core of a nanoparticle. In some embodiments, the VEPEP-4 peptide is present in the core of a nanoparticle and is associated with a DNA nuclease (such as a CRISPR-associated endonuclease, such as Cas9). In some embodiments, the VEPEP-4 peptide is present in the core of a nanoparticle and is associated with a gRNA. In some embodiments, the VEPEP-4 peptide is present in the core of a nanoparticle and is associated with the guide RNA. In some embodiments, the VEPEP-4 peptide is present in the core of a nanoparticle and is associated with a donor nucleic acid. In some embodiments, the VEPEP-4 peptide is present in an intermediate layer of a nanoparticle. In some embodiments, the VEPEP-4 peptide is present in the surface layer of a nanoparticle. In some embodiments, the VEPEP-4 peptide is linked to a targeting moiety. In some embodiments, the linkage is covalent.

VEPEP-5 Peptides

In some embodiments, a genome-editing complex or nanoparticle described herein comprises a VEPEP-5 cell-penetrating peptide comprising the amino acid sequence RXWXRLWXRLR (SEQ ID NO: 181), wherein X in position 2 is R or S; and X in positions 4 and 8 are, independently from each other, W or F. In some embodiments, the VEPEP-5 peptide comprises an amino acid sequence of any one of SEQ ID NOs: 182-187. In some embodiments, the VEPEP-5 peptide is present in a genome-editing complex. In some embodiments, the VEPEP-5 peptide is present in a genome-editing complex in the core of a nanoparticle. In some embodiments, the VEPEP-5 peptide is present in the core of a nanoparticle. In some embodiments, the VEPEP-5 peptide is present in the core of a nanoparticle and is associated with a DNA nuclease (such as a CRISPR-associated endonuclease, such as Cas9). In some embodiments, the VEPEP-5 peptide is present in the core of a nanoparticle and is associated with a gRNA. In some embodiments, the VEPEP-5 peptide is present in the core of a nanoparticle and is associated with the guide RNA. In some embodiments, the VEPEP-5 peptide is present in the core of a nanoparticle and is associated with a donor nucleic acid. In some embodiments, the VEPEP-5 peptide is present in an intermediate layer of a nanoparticle. In some embodiments, the VEPEP-5 peptide is present in the surface layer of a nanoparticle. In some embodiments, the VEPEP-5 peptide is linked to a targeting moiety. In some embodiments, the linkage is covalent.

Cell-Penetrating Peptide Modification

In some embodiments, the CPP described herein (e.g., VEPEP-3 peptide, VEPEP-6 peptide, VEPEP-9 peptide, or ADGN-100 peptide) further comprises one or more moieties linked to (e.g., covalently linked to) the N-terminus of the CPP. In some embodiments, the one or more moieties is covalently linked to the N-terminus of the CPP. In some embodiments, the one or more moieties are selected from the group consisting of an acetyl group, a stearyl group, a fatty acid, a cholesterol, a poly-ethylene glycol, a nuclear localization signal, a nuclear export signal, an antibody or antibody fragment thereof, a peptide, a polysaccharide, a linker moiety, and a targeting moiety. In some embodiments, the one or more moieties comprise an acetyl group covalently linked to the N-terminus of the CPP.

In some embodiments, the CPP described herein (e.g., VEPEP-3 peptide, VEPEP-6 peptide, VEPEP-9 peptide, or ADGN-100 peptide) further comprises one or more moieties linked to (e.g., covalently linked to) the C-terminus of the CPP. In some embodiments, the one or more moieties are selected from the group consisting of a cysteamide group, a cysteine, a thiol, an amide, a nitrilotriacetic acid, a carboxyl group, a linear or ramified $C_1$-$C_6$ alkyl group, a primary or secondary amine, an osidic derivative, a lipid, a phospholipid, a fatty acid, a cholesterol, a poly-ethylene glycol, a nuclear localization signal, a nuclear export signal, an antibody or antibody fragment thereof, a peptide, a polysaccharide, a linker moiety, and a targeting moiety. In some embodiments, the one or more moieties comprises a cysteamide group.

In some embodiments, the CPP described herein (e.g., PEP-1, PEP-2, VEPEP-3 peptide, VEPEP-4 peptide, VEPEP-5 peptide, VEPEP-6 peptide, VEPEP-9 peptide, or ADGN-100 peptide) is stapled. "Stapled" as used herein refers to a chemical linkage between two residues in a peptide. In some embodiments, the CPP is stapled, comprising a chemical linkage between two amino acids of the peptide. In some embodiments, the two amino acids linked by the chemical linkage are separated by 3 or 6 amino acids. In some embodiments, two amino acids linked by the chemical linkage are separated by 3 amino acids. In some embodiments, the two amino acids linked by the chemical linkage are separated by 6 amino acids. In some embodiments, each of the two amino acids linked by the chemical linkage is R or S. In some embodiments, each of the two amino acids linked by the chemical linkage is R. In some embodiments, each of the two amino acids linked by the chemical linkage is S. In some embodiments, one of the two amino acids linked by the chemical linkage is R and the other is S. In some embodiments, the chemical linkage is a hydrocarbon linkage.

In some embodiments, the CPP is an L-peptide comprising L-amino acids. In some embodiments, the CPP is a retro-inverso peptide (e.g., a peptide made up of D-amino acids in a reversed sequence and, when extended, assumes a side chain topology similar to that of its parent molecule but with inverted amide peptide bonds). In some embodiments, the retro-inverso peptide comprises a sequence of SEQ ID NO: 91 or 156.

In some embodiments, the CPP comprises, from N-terminus, an acetyl group, a targeting moiety and a linker moiety covalently linked to the N-terminus of the cell-penetrating peptide.

Targeting Moiety

In some embodiments, the one or more moieties comprise a targeting moiety. In some embodiments, the targeting moiety is conjugated to the N-terminus the CPP. In some embodiments, the targeting moiety is conjugated to the C-terminus the CPP. In some embodiments, a first targeting moiety is conjugated to the N-terminus of the CPP and a second targeting moiety is conjugated to the C-terminus of the CPP.

In some embodiments, the targeting moiety comprises a targeting peptide that targets one or more organs. In some embodiments, the one or more organs are selected from the group consisting of muscle, heart, brain, spleen, lymph node, liver, lung, and kidney. In some embodiments, the targeting peptide targets brain. In some embodiments, the targeting peptide targets muscle. In some embodiments, the targeting peptide targets heart.

In some embodiments, the targeting moiety comprises at least about 3, 4, or 5 amino acids. In some embodiments, the targeting moiety comprises no more than about 8, 7, 6, 5, or 4 amino acids. In some embodiments, the targeting moiety comprises about 3, 4, or 5 amino acids. In some embodiments, the targeting moiety comprises a sequence selected from the group consisting of GY, YV, VS, SK, GYV, YVS, VSK, GYVS, YVSK, YI, IG, GS, SR, YIG, IGS, GSR, YIGS, IGSR. In some embodiments, the sequence (e.g., a targeting sequence) is selected from the group consisting of GYVSK, GYVS, YIGS, and YIGSR.

In some embodiments, the targeting moiety comprises a targeting sequence selected from the group consisting of SEQ ID NOs: 196-205 and 235-240. In some embodiments, the targeting moiety comprises a targeting sequence SYTSSTM (SEQ ID NO: 196). In some embodiments, the targeting moiety comprises a targeting sequence CKTRRVP (SEQ ID NO: 197). In some embodiments, the targeting moiety comprises a targeting sequence THRPPNWSPV (SEQ ID NO: 198). In some embodiments, the targeting moiety comprises a targeting sequence TGNYKALHPDHNG (SEQ ID NO: 199). In some embodiments, the targeting moiety comprises a targeting sequence CARPAR (SEQ ID NO: 200). In some embodiments, the targeting moiety comprises a targeting sequence ASSLNIA (SEQ ID NO: 203). In some embodiments, the targeting moiety comprises a targeting sequence LSSRLDA (SEQ ID NO: 204). In some embodiments, the targeting moiety comprises a targeting sequence KSYDTY (SEQ ID NO: 205).

In some embodiments, the targeting moiety is conjugated to the CPP via a linker moiety such as any one of the linker moieties described herein.

Linker Moiety

In some embodiments, the one or more moieties comprise a linker moiety.

In some embodiments, the linker moiety comprises a polyglycine linker. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS or SGGGG sequence. In some embodiments, the linker comprises a Glycine-β-Alanine motif.

In some embodiments, the one or more moieties comprise a polymer (e.g., PEG, polylysine, PET). In some embodiments, the polymer is conjugated to the N-terminus of the CPP. In some embodiments, the polymer is conjugated to the C-terminus of the CPP. In some embodiments, a first polymer is conjugated to the N-terminus of the CPP and a second polymer is conjugated to the C-terminus of the CPP. In some embodiments, the polymer is a PEG. In some embodiments, the PEG is a linear PEG. In some embodiments, the PEG is a branched PEG. In some embodiments, the molecular weight of the PEG is no more than about 5 kDa, 10 kDa, 15 kDa, 20 kDa, 30 kDa, or 40 kDa. In some embodiments, the molecular weight of the PEG is at least about 5 kDa, 10 kDa, 15 kDa, 20 kDa, 30 kDa, or 40 kDa. In some embodiments, the molecular weight of the PEG is about 5 kDa to about 10 kDa, about 10 kDa to about 15 kDa, about 15 kDa to about 20 kDa, about 20 kDa to about 30 kDa, or about 30 kDa to about 40 kDa. In some embodiments, the molecular weight of the PEG is about 5 kDa, 10 kDa, 20 kDa, or 40 kDa. In some embodiments, the molecular weight of the PEG is selected from the group consisting of 5 kDa, 10 kDa, 20 kDa or 40 kDa. In some embodiments, the molecular weight of the PEG is about 5 kDa. In some embodiments, the molecular weight of the PEG is about 10 kDa. In some embodiments, the PEG comprises at least about 1, 2, or 3 ethylene glycol units. In some embodiments, the PEG consists of no more than about 10, 9, 8 or 7 ethylene glycol units. In some embodiments, the PEG consists of about 1, 2, or 3 ethylene glycol units. In some embodiments, the PEG moiety consists of about one to eight, or about two to seven ethylene glycol units.

In some embodiments, the linker moiety is selected from the group consisting of beta alanine, cysteine, cysteamide bridge, poly glycine (such as G2 or G4), Aun (11-amino-undecanoic acid), Ava (5-amino pentanoic acid), and Ahx (aminocaproic acid). In some embodiments, the linker moiety comprises Aun (11-amino-undecanoic acid). In some embodiments, the linker moiety comprises Ava (5-amino pentanoic acid). In some embodiments, the linker moiety comprises Ahx (aminocaproic acid).

Carbohydrate Moiety

In some embodiments, the cell-penetrating peptide further comprises a carbohydrate moiety. In some embodiments, the carbohydrate moiety is GalNAc. In some embodiments, the cell-penetrating peptide is an ADGN-106 peptide. In some embodiments, the cell-penetrating peptide is an ADGN-100 peptide. In some embodiments, the carbohydrate moiety modifies an alanine within the cell-penetrating peptide. In some embodiments, the cell-penetrating peptide is set forth in SEQ ID NO: 111 or 172.

Cell-Penetrating Peptide Mixture

In some embodiments, the cell-penetrating peptide in the genome-editing complexes is a mixture of a) a first peptide comprising a first cell-penetrating peptide (such as any of the cell-penetrating peptide described herein); b) a second peptide comprising a second cell-penetrating peptide (such as any of the cell-penetrating peptide described herein), wherein the second peptide comprises a polyethylene glycol (PEG) moiety that is covalently linked to the second cell-penetrating peptide, and wherein the first peptide does not have a PEG moiety. In some embodiments, the first and/or the second cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the first and the second cell-penetrating peptides are selected from the group consisting of CADY, PEP-1 peptides, PEP-2 peptides, PEP-3 peptides, VEPEP-3 peptides, VEPEP-4 peptides, VEPEP-5 peptides, VEPEP-6 peptides, VEPEP-9 peptides, and ADGN-100 peptides. In some embodiments, the molar ratio of the cell-penetrating peptide to the cargo (such as the guide RNA optionally with a DNA nuclease or a nucleotide encoding the DNA nuclease) is between about 1:1 and about 100:1 (such as about between about 1:1 and about 50:1, or about 2:1 to about 50:1). In some embodiments, the average diameter of the genome-editing complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, the ratio of the first cell-penetrating peptide to the second cell-penetrating peptide is about 20:1 to about 1:1 (such as about 15:1 to about 2:1, about 10:1 to about 4:1).

In some embodiments, the first and/or the second cell-penetrating peptides are selected from VEPEP-3 peptides, VEPEP-6 peptides, VEPEP-9 peptides, and ADGN-100 peptides. In some embodiments, the first and/or the second cell-penetrating peptide are selected from VEPEP-6 peptides, and ADGN-100 peptides.

In some embodiments, the PEG moiety is a linear PEG. In some embodiments, the PEG moiety is a branched PEG.

Cargo Molecules

In some embodiments, cell-penetrating peptides described herein are complexed with the one or more cargo molecules. In some embodiments, the cell-penetrating peptides are non-covalently complexed with at least one of the one or more cargo molecules. In some embodiments, the cell-penetrating peptides are non-covalently complexed with each of the one or more cargo molecules. In some embodiments, the cell-penetrating peptides are covalently complexed with at least one of the one or more cargo molecule. In some embodiments, the cell-penetrating peptides are covalently complexed with each of the one or more cargo molecules.

As described above, the genome-editing complex or nanoparticles described herein comprise a guide RNA as described above. In some embodiments, the genome-editing complex or nanoparticle comprises one or more genome-editing molecules (such as a DNA nuclease or a polynucleotide encoding the DNA nuclease).

Guide RNA

The genome-editing complex or nanoparticle described herein comprises a guide RNA that targets a mutated KRAS, such as any of the guide RNA described in the "synthetic guide RNAs" section. In some embodiments, the mutated KRAS comprises one or more mutations selected from the group consisting of G12C, G12S, G12R, G12F, G12L, G12N, G12A, G12D, G12S, G12V, G13C, G13S, G13R, G13A, G13D, G13V, G13P, S17G, P34S, Q61E, Q61K, Q61L, Q61R, Q61P, Q61H, K117N, A146P, A146T and A146V. In some embodiments, the mutated KRAS comprises one or more mutations selected from the group consisting of G12D, G12C, G12V, G12A, G12S, G12R, G13D and G13C.

DNA Nuclease

In some embodiments, the genome-editing complex or nanoparticle described herein further comprises a DNA nuclease or a nucleotide encoding the DNA nuclease. In some embodiments, the DNA nuclease is selected from the group consisting of a CRISPR-associated protein (Cas) polypeptide, a zinc finger nuclease (ZFN), a transcription activator-like effector nuclease (TALEN), a meganuclease, a variant thereof, a fragment thereof, and a combination thereof.

For example, in some embodiments, a genome-editing complex or nanoparticle described herein comprises an RGEN (e.g., Cas9). In some embodiments, the protein or polypeptide is between about 10 kDa and about 200 kDa (such as about any of 10, 20, 30, 40, 50, 60, 70, 80, 90, 100, 110, 120, 130, 140, 150, 160, 170, 180, 190, and 200 kDa, including any ranges between these values). In some embodiments, the genome-editing complex or nanoparticle comprises a plurality of proteins or polypeptides, wherein each of the plurality of protein or polypeptides is between about 10 kDa and about 200 kDa (such as about any of 10, 20, 30, 40, 50, 60, 70, 80, 90, 100, 110, 120, 130, 140, 150, 160, 170, 180, 190, and 200 kDa, including any ranges between these values).

In some embodiments, a genome-editing complex or nanoparticle described herein further comprises a nucleic acid encoding a DNA nuclease. In some embodiments, the nucleic acid is between about 20 nt and about 20 kb (such as about any of 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, and 20 kb, including any ranges between these values). In some embodiments, the nucleic acid is DNA, such as a DNA plasmid encoding a genome-editing system molecule. In some embodiments, the DNA plasmid comprises an expression cassette for expressing the genome-editing system molecule. In some embodiments, the DNA plasmid is between about 1 kb and about 20 kb (such as about any of 1, 2, 3, 4, 5, 6, 7, 8, 9, 10, 11, 12, 13, 14, 15, 16, 17, 18, 19, and 20 kb, including any ranges between these values). In some embodiments, the nucleic acid is RNA, such as mRNA encoding a genome-editing system molecule. In some embodiments, the mRNA is between about 100 nt and about 10 kb (such as about any of 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, and 10 kb, including any ranges between these values).

In some embodiments, the genome-editing complex or nanoparticle comprises a plurality of nucleic acids, such as any of the nucleic acids described herein. For example, in some embodiments, the genome-editing complex or nanoparticle comprises a gRNA and a nucleic acid encoding a genome-editing system molecule (e.g., a DNA plasmid or mRNA encoding the DNA nuclease). In some embodiments, the genome-editing complex or nanoparticle comprises nucleic acid encoding a plurality of genome-editing system molecules (e.g., one or more DNA plasmid encoding the plurality of genome-editing system molecules, or a plurality of mRNAs encoding the plurality of genome-editing system molecules).

In some embodiments, the nucleic acids are single stranded oligonucleotides. In some embodiments, the nucleic acids are double stranded oligonucleotides. The nucleic acids described herein may be any of a range of length of up to, but not necessarily 200 nucleotides in the case of antisense oligonucleotides, RNAi, siRNA, shRNA, iRNA, antagomirs or up to 1000 kilo bases in the case of plasmid DNA.

In some embodiments, the nucleic acids are plasmid DNA or DNA fragments (for example DNA fragments of lengths of up to about 1000 bp). In addition, the plasmid DNA or DNA fragments may be hypermethylated or hypomethylated. In some embodiments, the plasmid DNA or DNA fragments encode one or more genes, and may contain regulatory elements necessary for the expression of said one or more genes. In some embodiments, the plasmid DNA or DNA fragments may comprise one or more genes that encode a selectable marker, allowing for maintenance of the plasmid DNA or DNA fragment in an appropriate host cell.

CRISPR-Associated Nuclease

In some embodiments, the DNA nuclease is a CRISPR-associated nuclease. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401) [2000]). CRISPR loci have been identified in more than 40 prokaryotes (See e.g., Jansen et al., Mol. Microbiol., 43:1565-1575 [2002]; and Mojica et al., [2005]) including, but not limited to Aeropyrum, *Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella. Acinetobacter, Erwinia, Escherichia, Legionella, Methylococcus, Pasteurella, Photobacterium, Salmonella, Xanthomonas, Yersinia, Treponema*, and *Thermotoga*.

In some embodiments, the DNA nuclease is a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof, such as inducible, inactivated, or split Cas proteins (see for example Dominguez et al. (2015). Nature Reviews Molecular Cell Biology; Polstein, L. R., & Gersbach, C. A. (2015). *Nature chemical biology,* 11(3):198-200; Dow et al. (2015). *Nature biotechnology,* 33(4):390-394; Zetsche et al. (2015). *Nature biotechnology,* 33(2):139-142; Kleinstiver et al. (2015). *Nature.* 523:481-485; Bikard et al. (2013). *Nucleic acids research,* 41(15):7429-7437; Qi et al. (2013). *Cell,* 152(5): 1173-1183). These enzymes are known to those of skill in the art; for example, the amino acid sequence of *S. pyogenes* Cas9 protein may be found in the SwissProt database under accession number Q99ZW2, and the amino acid sequence of Acidaminococcus sp. Cpf1 protein may be found in the SwissProt database under accession number U2UMQ6.

In some embodiments, the DNA nuclease comprises an unmodified or modified CRISPR enzyme that has DNA cleavage activity, such as Cas9. In some embodiments, the CRISPR enzyme is Cas9, and may be Cas9 from *S. pyogenes* or *S. pneumoniae*. In some embodiments, the CRISPR enzyme is Cpf1, and may be Cpf1 from Acidaminococcus or Lachnospiraceae. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, the CRISPR enzyme is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S.*

*pyogenes* converts Cas9 from a nuclease that cleaves both strands to a nickase (cleaves a single strand). Other examples of mutations that render Cas9 a nickase include, without limitation, H840A, N854A, and N863A. In some embodiments, a Cas9 nickase may be used in combination with guide sequences, e.g., two guide sequences, which target respectively sense and antisense strands of the DNA target. This combination allows both strands to be nicked and used to induce NHEJ.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some embodiments, the Cas protein (such as Cas9) is a split Cas protein comprising an N-terminal Cas protein fragment, Cas(N), and a C-terminal Cas protein fragment, Cas(C), wherein Cas(N) is fused to a first dimerization domain and Cas(C) is fused to a second dimerization domain, and wherein the first and second dimerization domains facilitate dimerization of Cas(N) and Cas(C) to form a complex with a functional Cas nuclease activity. In some embodiments, dimerization of the first and second dimerization domains is sensitive to a dimerization agent. For example, in some embodiments, the first and second dimerization domains comprise the FK506 binding protein 12 (FKBP) and FKBP rapamycin binding (FRB) domains of the mammalian target of rapamycin (mTOR), and the dimerization agent is rapamycin.

In some embodiments, the complex or nanoparticle described herein comprises a nucleotide sequence encoding a CRISPR enzyme (such as Cas9 endonuclease) is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, the CRISPR enzyme described herein comprises one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In some embodiments, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, but other types of NLS are known. Non-limiting examples of NLSs include an NLS sequence derived from: the NLS of the SV40 virus large T-antigen, having the amino acid sequence PKKKRKV (SEQ ID NO: 212); the NLS from nucleoplasmin (e.g. the nucleoplasmin bipartite NLS with the sequence KRPAATKKAGQAKKKK (SEQ ID NO: 213)); the c-myc NLS having the amino acid sequence PAAKRVKLD (SEQ ID NO: 214) or RQRRNELKRSP (SEQ ID NO: 215); the hRNPA1 M9 NLS having the sequence NQSSNFGPMKGGNFGGRSSGPYGGGGQYFAKPRNQGGY (SEQ ID NO: 216); the sequence RMRIZFKNKGKDTAELRRRRVEVSVELRKAKKDEQILKRRNV (SEQ ID NO: 217) of the IBB domain from importin-alpha; the sequences VSRKRPRP (SEQ ID NO: 218) and PPKKARED (SEQ ID NO: 219) of the myoma T protein; the sequence PQPKKKPL (SEQ ID NO: 220) of human p53; the sequence SALIKKKKKMAP (SEQ ID NO: 221) of mouse c-abl IV; the sequences DRLRR (SEQ ID NO: 222) and PKQKKRK (SEQ ID NO: 223) of the influenza virus NS1; the sequence RKLKKKIKKL (SEQ ID NO: 224) of the Hepatitis virus delta antigen; the sequence REKKKFLKRR (SEQ ID NO: 225) of the mouse Mx1 protein; the sequence KRKGDEVDGVDEVAKKKSKK (SEQ ID NO: 226) of the human poly(ADP-ribose) polymerase; and the sequence RKCLQAGMNLEARKTKK (SEQ ID NO: 227) of the steroid hormone receptors (human) glucocorticoid.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, the cargo comprises a base editor. Base editors have been developed that convert Cas endonucleases into programmable nucleotide deaminases, thus facilitating the introduction of C-to-T mutations (by C-to-U deamination) or A-to-G mutations (by A-to-I deamination) without induction of a double-strand break. Base editors comprise a nickase form of SpCas9 (nSpCas9, to stimulate cellular DNA mismatch repair) fused to a nucleobase deaminase enzyme as well as an inhibitor of base excision repair such as uracil glycosylase inhibitor (UGI). See Rees et al., *Nature Communications* Improving the DNA specificity and applicability of base editing through protein engineering and protein delivery volume 8, Article number: 15790 (2017); Komor et al. Programmable editing of a target base in genomic DNA without double-stranded DNA cleavage. *Nature* 533, 420-424 (2016).

In some embodiments, the cargo comprises a prime editor. Prime editing is a versatile and precise genome editing method that directly writes new genetic information into a specified DNA site. It uses a fusion protein, consisting of a catalytically impaired Cas9 endonuclease fused to an engineered reverse transcriptase enzyme, and a prime editing guide RNA (pegRNA), capable of identifying the target site and provide the new genetic information to replace the target DNA nucleotides. It mediates targeted insertions, deletions, and base-to-base conversions without the need for double strand breaks (DSBs) or donor DNA templates. See Anzalone et al. Search-and-replace genome editing without double-strand breaks or donor DNA. *Nature volume* 576, pages 149-157(2019).

In some embodiments, the cargo comprises a fusion protein comprising a catalytically disabled nuclease (such as a catalytically disabled Cas9 endonuclease) and a reversed transcriptase (such as a pentamutant of M-MLV reverse transcriptase). See for example, Anzalone & Liu et al., Nature. 2019 December; 576 (7785):149-157. In some embodiments, the cargo comprises a polynucleotide encoding the fusion protein.

In some embodiments, the cargo comprises a fusion protein comprising a catalytically disabled nuclease (such as a catalytically disabled Cas9 endonuclease) and a nucleobase deaminase enzyme. In some embodiments, the nucleobase deaminase enzyme is APOBEC1 cytidine deaminase. In some embodiments, the nucleobase deaminase enzyme is cytidine deaminase CDA1. In some embodiments, the fusion protein further comprises a DNA glycosylase inhibitor. In some embodiments, the DNA glycosylase inhibitor is uracil DNA glycosylase inhibitor (UGI). In some embodiments, the cargo comprises a polynucleotide encoding the fusion protein.

ZFPs and ZFNs; TALs, TALEs, and TALENs

In some embodiments, the cargo molecule includes a DNA-binding protein such as one or more zinc finger protein (ZFP) or transcription activator-like protein (TAL), fused to an effector protein such as an endonuclease (or nucleic acid encoding the DNA-binding protein/effector protein fusion). Examples include ZFNs, TALEs, and TALENs. See Lloyd et al., Fronteirs in Immunology, 4(221), 1-7 (2013). In some embodiments, the guide RNA described herein can be in the form of a DNA (i.e., guide DNA, gDNA) encoding the RNA that guides ZFP or TAL to the target set.

ZFPs and ZFNs

In some embodiments, the cargo molecule comprises one or more zinc-finger proteins (ZFPs) or domains thereof that bind to DNA in a sequence-specific manner. A ZFP or domain thereof is a protein or domain within a larger protein that binds DNA in a sequence-specific manner through one or more zinc fingers, regions of amino acid sequence within the binding domain whose structure is stabilized through coordination of a zinc ion. The term zinc finger DNA binding protein is often abbreviated as zinc finger protein or ZFP.

Among the ZFPs are artificial ZFP domains targeting specific DNA sequences, typically 9-18 nucleotides long, generated by assembly of individual fingers.

ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

In some embodiments, the cargo molecule includes a zinc-finger DNA binding domain fused to a DNA cleavage domain to form a zinc-finger nuclease (ZFN). In some embodiments, fusion proteins comprise the cleavage domain (or cleavage half-domain) from at least one Type IIS restriction enzyme and one or more zinc finger binding domains, which may or may not be engineered. In some embodiments, the cleavage domain is from the Type IIS restriction endonuclease Fok I. Fok I generally catalyzes double-stranded cleavage of DNA, at 9 nucleotides from its recognition site on one strand and 13 nucleotides from its recognition site on the other. See, for example, U.S. Pat. Nos. 5,356,802;

5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982.]

In some embodiments, ZFNs target a gene present in a target cell. In some aspects, the ZFNs efficiently generate a double strand break (DSB), for example at a predetermined site in the coding region of the gene. Typical regions targeted include exons, regions encoding N-terminal regions, first exon, second exon, and promoter or enhancer regions. In some embodiments, transient expression of the ZFNs promotes highly efficient and permanent disruption of the target gene in target cells. In particular, in some embodiments, delivery of the ZFNs results in the permanent disruption of the gene with efficiencies surpassing 50%.

Many gene-specific engineered zinc fingers are available commercially. For example, Sangamo Biosciences (Richmond, CA, USA) has developed a platform (CompoZr) for zinc-finger construction in partnership with Sigma-Aldrich (St. Louis, MO, USA), allowing investigators to bypass zinc-finger construction and validation altogether, and provides specifically targeted zinc fingers for thousands of proteins. Gaj et al., *Trends in Biotechnology,* 2013, 31(7), 397-405. In some embodiments, commercially available zinc fingers are used or are custom designed. (See, for example, Sigma-Aldrich catalog numbers CSTZFND, CSTZFN, CTI1-1KT, and PZD0020).

TALEs and TALENs

In some embodiments, the cargo molecule includes a naturally occurring or engineered (non-naturally occurring) transcription activator-like protein (TAL) DNA binding domain, such as in a transcription activator-like protein effector (TALE) protein, See, e.g., U.S. Patent Publication No. 20110301073, incorporated by reference in its entirety herein.

A TALE DNA binding domain or TALE is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Each TALE repeat unit includes 1 or 2 DNA-binding residues making up the Repeat Variable Diresidue (RVD), typically at positions 12 and/or 13 of the repeat. The natural (canonical) code for DNA recognition of these TALEs has been determined such that an HD sequence at positions 12 and 13 leads to a binding to cytosine (C), NG binds to T, NI to A, NN binds to G or A, and NG binds to T and non-canonical (atypical) RVDs are also known. See, U.S. Patent Publication No. 20110301073. In some embodiments, TALEs may be targeted to any gene by design of TAL arrays with specificity to the target DNA sequence. The target sequence generally begins with a thymidine.

In some embodiments, the cargo molecule includes a DNA binding endonuclease, such as a TALE-nuclease (TALEN). In some aspects the TALEN is a fusion protein comprising a DNA-binding domain derived from a TALE and a nuclease catalytic domain to cleave a nucleic acid target sequence. In some embodiments, the TALE DNA-binding domain has been engineered to bind a target sequence within a target gene.

In some embodiments, the TALEN recognizes and cleaves the target sequence in the gene. In some aspects, cleavage of the DNA results in double-stranded breaks. In some aspects the breaks stimulate the rate of homologous recombination or non-homologous end joining (NHEJ). Generally, NHEJ is an imperfect repair process that often results in changes to the DNA sequence at the site of the cleavage. In some aspects, repair mechanisms involve rejoining of what remains of the two DNA ends through direct re-ligation (Critchlow and Jackson, *Trends Biochem Sci.* 1998 October; 23(10):394-8) or via the so-called micro-homology-mediated end joining. In some embodiments, repair via NHEJ results in small insertions or deletions and can be used to disrupt and thereby repress the gene. In some embodiments, the modification may be a substitution, deletion, or addition of at least one nucleotide. In some aspects, cells in which a cleavage-induced mutagenesis event, i.e. a mutagenesis event consecutive to an NHEJ event, has occurred can be identified and/or selected by well-known methods in the art.

In some embodiments, TALE repeats are assembled to specifically target a gene. (Gaj et al., *Trends in Biotechnology,* 2013, 31(7), 397-405). A library of TALENs targeting 18,740 human protein-coding genes has been constructed (Kim et al., *Nature Biotechnology.* 31, 251-258 (2013)). Custom-designed TALE arrays are commercially available through Cellectis Bioresearch (Paris, France), Transposagen Biopharmaceuticals (Lexington, KY, USA), and Life Technologies (Grand Island, NY, USA).

In some embodiments the TALENs are introduced as transgenes encoded by one or more plasmid vectors. In some aspects, the plasmid vector can contain a selection marker which provides for identification and/or selection of cells which received said vector.

Donor Nucleic Acid

In some embodiments, the genome-editing complex or nanoparticles described herein further comprises a donor nucleic acid. In some embodiments, the donor nucleic acid is designed to serve as a template in homologous recombination, such as within or near a target sequence nicked or cleaved by a CRISPR enzyme as a part of a CRISPR complex. A donor nucleic acid may be of any suitable length, such as about or more than about 10, 15, 20, 25, 50, 75, 100, 150, 200, 500, 1000, or more nucleotides in length. In some embodiments, the donor nucleic acid comprises a sequence that is complementary to a portion of a polynucleotide comprising the target sequence. In some embodiments, when a donor nucleic acid and a polynucleotide comprising a target sequence are optimally aligned, the donor nucleic acid overlaps with one or more nucleotides of the target sequence (e.g. about or more than about 1, 5, 10, 15, 20, 25, 30, 35, 40, 45, 50, 60, 70, 80, 90, 100 or more nucleotides). In some embodiments, when a donor nucleic acid and a polynucleotide comprising a target sequence are optimally aligned, the nearest nucleotide of the donor nucleic acid in the region of complementarity is within about 1, 5, 10, 15, 20, 25, 50, 75, 100, 200, 300, 400, 500, 1000, 5000, 10000, or more nucleotides from the target sequence.

RNAi Targeting Mutant Form of KRAS

In some embodiments, the cargo further comprises one or more RNAi (e.g., siRNA) that targets a mutant form of KRAS. In some embodiments, the mutant form of KRAS comprises an aberration of KRAS, wherein the aberration of KRAS comprises a mutation on codon 12, 13, 17, 34 and/or 61 of KRAS. In some embodiments, the aberration of KRAS comprises a mutation on codon 12, or 61 of KRAS. In some embodiments, the aberration of KRAS is selected from the group consisting of G12C, G12S, G12R, G12F, G12L, G12N, G12A, G12D, G12S, G12V, G13C, G13S, G13R, G13A, G13D, G13V, G13P, S17G, P34S, Q61E, Q61K, Q61L, Q61R, Q61P, Q61H, K117N, A146P, A146T and A146V. In some embodiments, the aberration of KRAS is selected from the group consisting of G12C, G12S, G12R, G12F, G12L, G12N, G12A, G12D, G12V, G13C, G13S, G13D, G13V, G13P, S17G, P34S, Q61K, Q61L, Q61R, and Q61H. In some embodiments, the aberration of KRAS is selected from the group consisting of G12C, G12R, G12S, G12A, G12D, G12V, G13C, G13R, G13S, G13A, G13D, G13V, Q61K, Q61L, Q61R, Q61H, K117N, A146P, A146T and A146V. In some embodiments, the aberration of KRAS is selected from the group consisting of KRAS G12A, G12C, G12D, G12R, G12S, G12V, G13A, G13C, G13D, G13R, G13S, G13V, Q61E, Q61H, Q61K, Q61L, Q61P, and Q61R. In some embodiments, the aberration of KRAS is selected from the group consisting of KRAS G12C, G12D, G12R, G12S, G12V and G13D. In some embodiments, the aberration of KRAS is selected from G12C, G12D and Q61K.

In some embodiments, the one or more RNAi (e.g., siRNA) is selected from the group consisting of SEQ ID NOs: 228-234.

Modifications

In some embodiments, a genome-editing complex or nanoparticle as described herein comprises a targeting moiety, wherein the targeting moiety is a ligand capable of cell-specific and/or nuclear targeting. A cell membrane surface receptor and/or cell surface marker is a molecule or structure which can bind said ligand with high affinity and preferably with high specificity. Said cell membrane surface receptor and/or cell surface marker is preferably specific for a particular cell, i.e. it is found predominantly in one type of cell rather than in another type of cell (e.g. galactosyl residues to target the asialoglycoprotein receptor on the surface of hepatocytes). The cell membrane surface receptor facilitates cell targeting and internalization into the target cell of the ligand (e.g. the targeting moiety) and attached molecules (e.g. the complex or nanoparticle of the application). A large number of ligand moieties/ligand binding partners that may be used in the context of the present application are widely described in the literature. Such a ligand moiety is capable of conferring to the complex or nanoparticle of the application the ability to bind to a given binding-partner molecule or a class of binding-partner molecules localized at the surface of at least one target cell. Suitable binding-partner molecules include without limitation polypeptides selected from the group consisting of cell-specific markers, tissue-specific markers, cellular receptors, viral antigens, antigenic epitopes and tumor-associated markers. Binding-partner molecules may moreover consist of or comprise, for example, one or more sugar, lipid, glycolipid, antibody molecules or fragments thereof, or aptamer. According to the application, a ligand moiety may be for example a lipid, a glycolipid, a hormone, a sugar, a polymer (e.g. PEG, polylysine, PET), an oligonucleotide, a vitamin, an antigen, all or part of a lectin, all or part of a polypeptide, such as for example JTS1 (WO 94/40958), an antibody or a fragment thereof, or a combination thereof. In some embodiments, the ligand moiety used in the present application is a peptide or polypeptide having a minimal length of 7 amino acids. It is either a native polypeptide or a polypeptide derived from a native polypeptide. “Derived” means containing (a) one or more modifications with respect to the native sequence (e.g. addition, deletion and/or substitution of one or more residues), (b) amino acid analogs, including non-naturally occurring amino acids, (c) substituted linkages, or (d) other modifications known in the art. The polypeptides serving as ligand moiety encompass variant and chimeric polypeptides obtained by fusing sequences of various origins, such as for example a humanized antibody which combines the variable region of a mouse antibody and the constant region of a human immunoglobulin. In addition, such polypeptides may have a linear or cyclized structure (e.g. by flanking at both extremities a polypeptide ligand by cysteine residues). Additionally, the polypeptide in use as a ligand moiety may include modifications of its original structure by way of substitution or addition of chemical moieties (e.g. glycosylation, alkylation, acetylation, amidation, phosphorylation, addition of sulfhydryl groups and the like). The application further contemplates modifications that render the ligand moiety detectable. For this purpose, modifications with a detectable moiety can be envisaged (i.e. a scintigraphic, radioactive, or fluorescent moiety, or a dye label and the like). Such detectable labels may be attached to the ligand moiety by any conventional techniques and may be used for diagnostic purposes (e.g. imaging of tumoral cells). In some embodiments, the binding-partner molecule is an antigen (e.g. a target cell-specific antigen, a disease-specific antigen, an antigen specifically expressed on the surface of engineered target cells) and the ligand moiety is an antibody, a fragment or a minimal recognition unit thereof (e.g. a fragment still presenting an antigenic specificity) such as those described in detail in immunology manuals (see for example Immunology, third edition 1993, Roitt, Brostoff and Male, ed Gambli, Mosby). The ligand moiety may be a monoclonal antibody. Many monoclonal antibodies that bind many of these antigens are already known, and using techniques known in the art in relation to monoclonal antibody technology, antibodies to most antigens may be prepared. The ligand moiety may be a part of an antibody (for example a Fab fragment) or a synthetic antibody fragment (for example, ScFv). In some embodiments, the ligand moiety is selected among antibody fragments, rather than whole antibodies. Effective functions of whole antibodies, such as complement binding, are removed. ScFv and dAb antibody fragments may be expressed as a fusion with one or more other polypeptides. Minimal recognition units may be derived from the sequence of one or more of the complementary-determining regions (CDR) of the Fv fragment. Whole antibodies, and F(ab')2 fragments are “bivalent”. By “bivalent” it is meant that said antibodies and F(ab')2 fragments have two antigen binding sites. In contrast, Fab, Fv, ScFv, dAb fragments and minimal recognition units are monovalent, having only one antigen binding sites. In some embodiments, the ligand moiety allows targeting to a tumor cell and is capable of recognizing and binding to a molecule related to the tumor status, such as a tumor-specific antigen, a cellular protein differentially or over-expressed in tumor cells or a gene product of a cancer-associated vims. Examples of tumor-specific antigens include but are not limited to MUC-1 related to breast cancer (Hareuven i et al., 990, Eur. J. Biochem 189, 475-486), the products encoded by the mutated BRCA1 and BRCA2 genes related to breast and ovarian cancers (Miki et al, 1994, Science 226, 66-7 1; Fuireal et al, 1994, Science 226, 120-122; Wooster et al., 1995, Nature 378, 789-792), APC related to colon cancer (Poiakis, 1995, Curr. Opin. Genet. Dev. 5, 66-71), prostate specific antigen (PSA) related to prostate cancer, (Stamey et al., 1987, New England J. Med. 317, 909), carcinoma embryonic antigen (CEA) related to colon cancers (Schrewe et al., 1990, Mol. Cell. Biol. 10, 2738-2748), tyrosinase related to melanomas (Vile et al, 1993, Cancer Res. 53, 3860-3864), receptor for melanocyte-stimulating hormone (MSH) which is highly expressed in melanoma cells, ErbB-2 related to breast and pancreas cancers (Harris et al., 1994, Gene Therapy 1, 170-175), and alpha-foetoprotein related to liver cancers (Kanai et al., 1997, Cancer Res. 57, 46 1-465). In some embodiments, the ligand moiety is a fragment of an antibody capable of recognizing and binding to the MUC-1 antigen and thus targeting MUC-1 positive tumor cells. In some embodiments, the ligand moiety is the scFv fragment of the SM3 monoclonal antibody which recognizes the tandem repeat region of the MUC-1 antigen (Burshell et al., 1987, Cancer Res. 47, 5476-5482; Girling et al., 1989, Int. J. Cancer 43, 1072-1076; Dokurno et al., 1998, J. Mol. Biol. 284, 713-728). Examples of cellular proteins differentially or overexpressed in tumor cells include but are not limited to the receptor for interleukin 2 (IL-2) overexpressed in some lymphoid tumors, GRP (Gastrin Release Peptide) overexpressed in lung carcinoma cells, pancreas, prostate and stomach tumors (Michael et al., 1995, Gene Therapy 2, 660-668), TNF (Tumor Necrosis Factor) receptor, epidermal growth factor receptors, Fas receptor, CD40 receptor, CD30 receptor, CD27 receptor, OX-40, α-v integrins (Brooks et al, 994, Science 264, 569) and receptors for certain angiogenic growth factors (Hanahan, 1997, Science 277, 48). Based on these indications, it is within the scope of those skilled in the art to define an appropriate ligand moiety capable of recognizing and binding to such proteins. To illustrate, IL-2 is a suitable ligand moiety to bind to TL-2 receptor. In the case of receptors that are specific to fibrosis and inflammation, these include the TGFbeta receptors or the Adenosine receptors that are identified above and are suitable targets for application compositions. Cell surface markers for multiple myeloma include, but are not limited to, CD56, CD40, FGFR3, CS1, CD138, IGF1R, VEGFR, and CD38, and are suitable targets for application compositions. Suitable ligand moieties that bind to these cell surface markers include, but are not limited to, anti-CD56, anti-CD40, PRO-001, Chir-258, HuLuc63, anti-CD138-DM1, anti-IGF1R and bevacizumab.

In some embodiments, a genome-editing complex or nanoparticle described herein comprises one or more molecules of a genome-editing system (such as the entire genome-editing system) targeting one or more genes including, but are not limited to, Adenosine receptor A2A, Adenosine receptor A2B, Adenylyl cyclase, Akt, ALK, ALK/Met, angiopoietin receptor, Angiotensin II, APC, AR, ARKS, arrestin, ATF1, ATF-2, B7-1, B7-h1 (pdl-1), β-catenin, Bcl-2, BCL2L12, Bcl6, Bcr-Abl, BRAF, BRCA1, BRCA2, BTK, caspase-2, caspase-9, CCL2, CCN1, Ccnd2, CDK-activating kinases, CEBPA, Chop, c-Jun, c-Myc, CREB, CREB1, CS1, CTGF, CTNNB1, CXCR4, Cyclin d1-2, cyclin-dependent kinases (Cdk1 to 13), DEPTOR, DNMT3B, DPC4, EBOV polymerase L, EGF, EGFR, eIF5A, Elk-1, ER, Erbb4, ERK, ESR1, Ets1, EWSR1, FAK, FGF, FGFR, FOXO1, Frizzled family receptors (FZD-1 to 10), Fyn, GATA1, GATA3, GLI1, GM-CSF, GP/sGP, GSK, HBV conserved sequences, HDACs, HDGF, HDGFR, Her2, Her3, Hexokinase II, HGF, HGFR, HIF-1, HIF-1α, histone methyltransferase EZH2, HIV TAR RNA, HIV Tat, HLA-B7/Beta 2-Microglobulin, HMGA2, HNF1A, HNF1B, Hsp27, HSP47, human CCRS, Idh1, Idh2, IGF, IGFR, IKK, IKZF1, IL-12, IL-2, INK4, interferon-gamma, IRF1, IRF4, JAK, JNK, keratin 16, keratin 17, keratin K6A, keratin K6B, KGFR, KLF6, KRAS, LMO, LMO1, LMP2, LMP7, LOXL2, LPL, LYL1, MADR2, MAPK, Max, Mcl-1, MDA-7, MDM2, MDR-1, MDS1-EVI1, MECL-1, MEF2C, MEK, MEKK, MKK, MLH1, MLST8, MMP-2, MMP-9, MSFR, MSH2, MSH6, MSIN1, mTOR, MUC-1, mutant DDX3X, MYC, NCAP-D2, NCAP-D3, NCAP-G, NCAP-G2, NCAP-H, NCAP-H2, NF1, NF2, NFAT4, NF-κB, Notch1, NPC1, NR4A3, NRAS, Olig2, osteopontin, p53, PAI-1, PARP-1, patched, PAX3, PAX5, PAX7, PBX1, PDCD4, PDGF, PDGFR, PDK1, PHOX2B, PI3K, PKA, PKC, PKN3, PLK-1, PML, PR, PRAS40, PRDM16, Prdx1 and Prdx2 (burkitts lymphoma), Pre-gen/Pre-C, Pre-S1, Pre-S2/S, PTC, PTEN, Pyk2, Rad51, RAF, Raptor, Rb, RET, Rictor, RPN13, RRM2, RSV nucleocapsid, RUNX1, S6 kinase, Sap1a, SETBP1, Shc, SLAMF7, Smad, Smad 3, Smad 4, Smad 7, SMC-2, SMC-4, smoothened, SOX9, SPARC, Spry2, Src, ß-2 adrenergic receptors (ADRB2), ß-Globin, STAT5B, STATs, survivin, Syk, Tal, TAL1, TGFR, TGF-α, TGF-β, TGFβ receptors 1, TGFβ receptors 2, TGFβ receptors 3, TGFβ1, thrombospondin, thymidine kinase, TIM-1, TIMP, TNF-α, TP53, Transthyretin, TRPV1, ubiquitin ligase, uPAR, VEGF, VEGFR, VEGFR1, VEGFR2, VEGFR3, VHL, VP24, VP30, VP35, VP40, wnt, WT1, WT2, XBP1 (spliced and unspliced), XIAP, and ZBTB16, including mutants thereof (e.g., mutant PTEN, mutant KRAS, mutant p53, and the like). For example, in some embodiments, the genome-editing complex or nanoparticle comprises one or more molecules of an RGEN-based genome-editing system (e.g., a CRISPR/Cas9 genome-editing system), wherein the RGEN-based genome-editing system comprises a gRNA targeting one of the genes described herein. In some embodiments, the genome-editing complex or nanoparticle comprises one or more molecules of a ZFN-based genome-editing system, wherein the ZFN targets one of the genes described herein. In some embodiments, the genome-editing complex or nanoparticle comprises one or more molecules of a TALEN-based genome-editing system, wherein the TALEN targets one of the genes described herein. In some embodiments, the genome-editing complex or nanoparticle comprises one or more molecules of a homing endonuclease-based genome-editing system, wherein the homing endonuclease targets one of the genes described herein. In some embodiments, the genome-editing complex or nanoparticle comprises one or more molecules of an integrase-based genome-editing system, wherein the integrase targets one of the genes described herein.

Nanoparticles

The present application in one aspect provides a nanoparticle comprising a core comprising any one or more of genome-editing complexes described above.

In some embodiments, there is provided a nanoparticle comprising a core comprising a genome-editing complex described herein, wherein the cell-penetrating peptide in the genome-editing delivery complex is associated with the cargo. In some embodiments, the association is non-covalent. In some embodiments, the association is covalent.

In some embodiments, the nanoparticle further comprises a surface layer (e.g., a shell) comprising a peripheral cell-penetrating peptide (i.e., CPP), wherein the core is coated by the shell. In some embodiments, the peripheral CPP is the same as a CPP in the core. In some embodiments, the peripheral CPP is different than any of the CPPs in the core. In some embodiments, the peripheral CPP includes, but is not limited to, a PTD-based peptide, an amphipathic peptide, a poly-arginine-based peptide, an MPG peptide, a CADY peptide, a VEPEP peptide (such as a VEPEP-3, VEPEP-4, VEPEP-5, VEPEP-6, or VEPEP-9 peptide), an ADGN-100 peptide, a Pep-1 peptide, and a Pep-2 peptide. In some embodiments, the peripheral CPP is a VEPEP-3 peptide, a VEPEP-6 peptide, a VEPEP-9 peptide, or an ADGN-100 peptide. IN some embodiments, the peripheral cell-penetrating peptide is selected from the group consisting of PEP-1 peptides, PEP-2 peptides, PEP-3 peptides, VEPEP-3 peptides, VEPEP-6 peptides, VEPEP-9 peptides, and ADGN- 100 peptides. In some embodiments, at least some of the peripheral cell-penetrating peptides in the surface layer are linked to a targeting moiety. In some embodiments, the linkage is covalent. In some embodiments, the covalent linkage is by chemical coupling. In some embodiments, the covalent linkage is by genetic methods. In some embodiments, the nanoparticle further comprises an intermediate layer between the core of the nanoparticle and the surface layer. In some embodiments, the intermediate layer comprises an intermediate CPP. In some embodiments, the intermediate CPP is the same as a CPP in the core. In some embodiments, the intermediate CPP is different than any of the CPPs in the core. In some embodiments, the intermediate CPP includes, but is not limited to, a PTD-based peptide, an amphipathic peptide, a poly-arginine-based peptide, an MPG peptide, a CADY peptide, a VEPEP peptide (such as a VEPEP-3, VEPEP-6, or VEPEP-9 peptide), an ADGN-100 peptide, a Pep-1 peptide, and a Pep-2 peptide. In some embodiments, the intermediate CPP is a VEPEP-3 peptide, a VEPEP-6 peptide, a VEPEP-9 peptide, or an ADGN-100 peptide.

In some embodiments, the nanoparticle comprises two or more guide RNAs such as any one of the guide RNAs described herein. In some embodiments, the two or more guide RNAs targets two or more different KRAS mutations. In some embodiments, the two or more different KRAS mutations are selected from the group consisting of G12D, G12V, and G12C. In some embodiments, the two or more guide RNAs are contained in the same genome-editing complex. In some embodiments, the two or more guide RNAs are contained in different genome-editing complex.

In some embodiments, the nanoparticle core comprises a plurality of genome-editing complexes. In some embodiments, the nanoparticle core comprises a plurality of genome-editing complexes present in a predetermined ratio. In some embodiments, the predetermined ratio is selected to allow the most effective use of the nanoparticle in any of the methods described below in more detail. In some embodiments, the nanoparticle core further comprises one or more additional guide RNAs, one or more additional cell-penetrating peptides, one or more additional genome-editing nucleases, and/or one or more additional donor nucleic acids.

In some embodiments, the one or more additional genome-editing complex comprises at least one or more the guide RNAs that targets a different KRAS mutation. In some embodiments, the nanoparticle described herein comprises a) a first genome-editing complex comprising a first guide RNA that specifically targeting G12D (such as any one of the guide RNA targeting G12D described herein), and b) a second genome-editing complex comprising a second guide RNA that specifically targeting G12V (such as any one of the guide RNA targeting G12V described herein). In some embodiments, the nanoparticle described herein comprises a) a first genome-editing complex comprising a first guide RNA that specifically targeting G12D (such as any one of the guide RNA targeting G12D described herein), and b) a second genome-editing complex comprising a second guide RNA that specifically targeting G12C (such as any one of the guide RNA targeting G12C described herein). In some embodiments, the nanoparticle described herein comprises a) a first genome-editing complex comprising a first guide RNA that specifically targeting G12C (such as any one of the guide RNA targeting G12C described herein), and b) a second genome-editing complex comprising a second guide RNA that specifically targeting G12V (such as any one of the guide RNA targeting G12V described herein). In some embodiments, the nanoparticle described herein comprises a) a first genome-editing complex comprising a first guide RNA that specifically targeting G12D (such as any one of the guide RNA targeting G12D described herein), b) a second genome-editing complex comprising a second guide RNA that specifically targeting G12V (such as any one of the guide RNA targeting G12V described herein), and c) a second genome-editing complex comprising a second guide RNA that specifically targeting G12V (such as any one of the guide RNA targeting G12V described herein).

In some embodiments, the nanoparticle further comprises one or more additional cell-penetrating peptides. In some embodiments, the one or more additional cell-penetrating peptides include, but are not limited to, a PTD-based peptide, an amphipathic peptide, a poly-arginine-based peptide, an MPG peptide, a CADY peptide, a VEPEP peptide (such as a VEPEP-3, VEPEP-6, or VEPEP-9 peptide), an ADGN-100 peptide, a Pep-1 peptide, and a Pep-2 peptide. In some embodiments, at least some of the one or more additional cell-penetrating peptides are linked to a targeting moiety. In some embodiments, the linkage is covalent.

In some embodiments, according to any of the nanoparticles described herein, the mean size (diameter) of the nanoparticle is from about 20 nm to about 1000 nm, including for example from about 50 nm to about 800 nm, from about 75 nm to about 600 nm, from about 100 nm to about 600 nm, and from about 200 nm to about 400 nm. In some embodiments, the mean size (diameter) of the nanoparticle is no greater than about 1000 nanometers (nm), such as no greater than about any of 900, 800, 700, 600, 500, 400, 300, 200, or 100 nm. In some embodiments, the average or mean diameter of the nanoparticle is no greater than about 200 nm. In some embodiments, the average or mean diameters of the nanoparticles is no greater than about 150 nm. In some embodiments, the average or mean diameter of the nanoparticle is no greater than about 100 nm. In some embodiments, the average or mean diameter of the nanoparticle is about 20 nm to about 400 nm. In some embodiments, the average or mean diameter of the nanoparticle is about 30 nm to about 400 nm. In some embodiments, the average or mean diameter of the nanoparticle is about 40 nm to about 300 nm. In some embodiments, the average or mean diameter of the nanoparticle is about 50 nm to about 200 nm. In some embodiments, the average or mean diameter of the nanoparticle is about 60 nm to about 150 nm. In some embodiments, the average or mean diameter of the nanoparticle is about 70 nm to about 100 nm. In some embodiments, the nanoparticles are sterile-filterable.

In some embodiments, the zeta potential of the nanoparticle is from about −30 mV to about 60 mV (such as about any of −30, −25, −20, −15, −10, −5, 0, 5, 10, 15, 20, 25, 30, 35, 40, 45, 50, 55, and 60 mV, including any ranges between these values). In some embodiments, the zeta potential of the nanoparticle is from about −30 mV to about 30 mV, including for example from about −25 mV to about 25 mV, from about −20 mV to about 20 mV, from about −15 mV to about 15 mV, from about −10 mV to about 10 mV, and from about −5 mV to about 10 mV. In some embodiments, the polydispersity index (PI) of the nanoparticle is from about 0.05 to about 0.6 (such as about any of 0.05, 0.1, 0.15, 0.2, 0.25, 0.3, 0.35, 0.4, 0.45, 0.5, 0.55, and 0.6, including any ranges between these values). In some embodiments, the nanoparticle is substantially non-toxic.

Compositions

In some embodiments, there is provided a composition (e.g., a pharmaceutical composition) comprising a genome-editing complex or nanoparticle as described herein. In some embodiments, the composition is a pharmaceutical composition comprising a genome-editing complex or nanoparticle as described herein and a pharmaceutically acceptable diluent, excipient, and/or carrier.

In some embodiments, the composition comprises a mixture of two or more nanoparticles, wherein the two or more nanoparticles comprise different guide RNAs that target different KRAS mutations. For example, in some embodiments, the composition comprises a) a first nanoparticle as described above comprising a first guide RNA that specifically targets KRAS G12D, and b) a second nanoparticle comprising a second guide RNA that specifically targets KRAS G12V. In some embodiments, the composition comprises a) a first nanoparticle as described above comprising a first guide RNA that specifically targets KRAS G12D, and b) a second nanoparticle comprising a second guide RNA that specifically targets KRAS G12C. In some embodiments, the composition comprises a) a first nanoparticle as described above comprising a first guide RNA that specifically targets KRAS G12C, and b) a second nanoparticle comprising a second guide RNA that specifically targets KRAS G12V. In some embodiments, the composition comprises a) a first nanoparticle as described above comprising a first guide RNA that specifically targets KRAS G12D, b) a third nanoparticle comprising a second guide RNA that specifically targets KRAS G12V, c) a second nanoparticle comprising a second guide RNA that specifically targets KRAS G12C.

In some embodiments, the concentration of the complex or nanoparticle in the composition is from about 1 nM to about 100 mM, including for example from about 10 nM to about 50 mM, from about 25 nM to about 25 mM, from about 50 nM to about 10 mM, from about 100 nM to about 1 mM, from about 500 nM to about 750 μM, from about 750 nM to about 500 μM, from about 1 μM to about 250 μM, from about 10 μM to about 200 μM, and from about 50 μM to about 150 μM. In some embodiments, the pharmaceutical composition is lyophilized.

The term "pharmaceutically acceptable diluent, excipient, and/or carrier" as used herein is intended to include any and all solvents, dispersion media, coatings, antibacterial and antifungal agents, isotonic and absorption delaying agents, and the like, compatible with administration to humans or other vertebrate hosts. Typically, a pharmaceutically acceptable diluent, excipient, and/or carrier is a diluent, excipient, and/or carrier approved by a regulatory agency of a Federal, a state government, or other regulatory agency, or listed in the U.S. Pharmacopeia or other generally recognized pharmacopeia for use in animals, including humans as well as non-human mammals. The term diluent, excipient, and/or "carrier" refers to a diluent, adjuvant, excipient, or vehicle with which the pharmaceutical composition is administered. Such pharmaceutical diluent, excipient, and/or carriers can be sterile liquids, such as water and oils, including those of petroleum, animal, vegetable or synthetic origin. Water, saline solutions and aqueous dextrose and glycerol solutions can be employed as liquid diluents, excipients, and/or carriers, particularly for injectable solutions. Suitable pharmaceutical diluents and/or excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like, including lyophilization aids. The composition, if desired, can also contain minor amounts of wetting, bulking, emulsifying agents, or pH buffering agents. These compositions can take the form of solutions, suspensions, emulsion, sustained release formulations and the like. Examples of suitable pharmaceutical diluent, excipient, and/or carriers are described in "Remington's Pharmaceutical Sciences" by E. W. Martin. The formulation should suit the mode of administration. The appropriate diluent, excipient, and/or carrier will be evident to those skilled in the art and will depend in large part upon the route of administration.

In some embodiments, a composition comprising a genome-editing complex or nanoparticle as described herein further comprises a pharmaceutically acceptable diluent, excipient, and/or carrier. In some embodiments, the pharmaceutically acceptable diluent, excipient, and/or carrier affects the level of aggregation of a genome-editing complex or nanoparticle in the composition and/or the efficiency of intracellular delivery mediated by a genome-editing complex or nanoparticle in the composition. In some embodiments, the extent and/or direction of the effect on aggregation and/or delivery efficiency mediated by the pharmaceutically acceptable diluent, excipient, and/or carrier is dependent on the relative amount of the pharmaceutically acceptable diluent, excipient, and/or carrier in the composition.

For example, in some embodiments, the presence of a pharmaceutically acceptable diluent, excipient, and/or carrier (such as a salt, sugar, chemical buffering agent, buffer solution, cell culture medium, or carrier protein) at one or more concentrations in the composition does not promote and/or contribute to aggregation of the genome-editing complex or nanoparticle, or promotes and/or contributes to the formation of aggregates of the genome-editing complex or nanoparticles having a size no more than about 200% (such as no more than about any of 190, 180, 170, 160, 150, 140, 130, 120, 110, 100, 90, 80, 70, 60, 50, 40, 30, 20, 10, 9, 8, 7, 6, 5, 4, 3, 2, or 1%, including any ranges between any of these values) larger than the size of the genome-editing complex or nanoparticle. In some embodiments, the composition comprises the pharmaceutically acceptable diluent, excipient, and/or carrier at a concentration that does not promote and/or contribute to aggregation of the genome-editing complex or nanoparticle, or promotes and/or contributes to the formation of aggregates of the genome-editing complex or nanoparticles having a size no more than about 200% (such as no more than about any of 190, 180, 170, 160, 150, 140, 130, 120, 110, 100, 90, 80, 70, 60, 50, 40, 30, 20, 10, 9, 8, 7, 6, 5, 4, 3, 2, or 1%, including any ranges between any of these values) larger than the size of the genome-editing complex or nanoparticle. In some embodiments, the composition comprises the pharmaceutically acceptable diluent, excipient, and/or carrier at a concentration that promotes and/or contributes to the formation of aggregates of the genome-editing complex or nanoparticles having a size no more than about 150% larger than the size of the genome-editing complex or nanoparticle. In some embodiments, the composition comprises the pharmaceutically acceptable diluent, excipient, and/or carrier at a concentration that promotes and/or contributes to the formation of aggregates of the genome-editing complex or nanoparticles having a size no more than about 100% larger than the size of the genome-editing complex or nanoparticle. In some embodiments, the composition comprises the pharmaceutically acceptable diluent, excipient, and/or carrier at a concentration that promotes and/or contributes to the formation of aggregates of the genome-editing complex or nanoparticles having a size no more than about 50% larger than the size of the genome-editing complex or nanoparticle. In some embodiments, the composition comprises the pharmaceutically acceptable diluent, excipient, and/or carrier at a concentration that promotes and/or contributes to the formation of aggregates of the genome-editing complex or nanoparticles having a size no more than about 20% larger than the size of the genome-editing complex or nanoparticle. In some embodiments, the composition comprises the pharmaceutically acceptable diluent, excipient, and/or carrier at a concentration that promotes and/or contributes to the formation of aggregates of the genome-editing complex or nanoparticles having a size no more than about 15% larger than the size of the genome-editing complex or nanoparticle. In some embodiments, the composition comprises the pharmaceutically acceptable diluent, excipient, and/or carrier at a concentration that promotes and/or contributes to the formation of aggregates of the genome-editing complex or nanoparticles having a size no more than about 10% larger than the size of the genome-editing complex or nanoparticle. In some embodiments, the pharmaceutically acceptable diluent, excipient, and/or carrier is a salt, including, without limitation, NaCl. In some embodiments, the pharmaceutically acceptable diluent, excipient, and/or carrier is a sugar, including, without limitation, sucrose, glucose, and mannitol. In some embodiments, the pharmaceutically acceptable diluent, excipient, and/or carrier is a chemical buffering agent, including, without limitation, HEPES. In some embodiments, the pharmaceutically acceptable diluent, excipient, and/or carrier is a buffer solution, including, without limitation, PBS. In some embodiments, the pharmaceutically acceptable diluent, excipient, and/or carrier is a cell culture medium, including, without limitation, DMEM. Particle size can be determined using any means known in the art for measuring particle size, such as by dynamic light scattering (DLS). For example, in some embodiments, an aggregate having a Z-average as measured by DLS that is 10% greater than the Z-average as measured by DLS of a genome-editing complex or nanoparticle is 10% larger than the genome-editing complex or nanoparticle.

In some embodiments, the composition comprises a salt (e.g., NaCl) at a concentration that does not promote and/or contribute to aggregation of the genome-editing complex or nanoparticle, or promotes and/or contributes to the formation of aggregates of the genome-editing complex or nanoparticles having a size no more than about 100% (such as no more than about any of 90, 80, 70, 60, 50, 40, 30, 20, 10, 9, 8, 7, 6, 5, 4, 3, 2, or 1%, including any ranges between any of these values) larger than the size of the genome-editing complex or nanoparticle. In some embodiments, the composition comprises a salt (e.g., NaCl) at a concentration that promotes and/or contributes to the formation of aggregates of the genome-editing complex or nanoparticles having a size no more than about 75% larger than the size of the genome-editing complex or nanoparticle. In some embodiments, the composition comprises a salt (e.g., NaCl) at a concentration that promotes and/or contributes to the formation of aggregates of the genome-editing complex or nanoparticles having a size no more than about 50% larger than the size of the genome-editing complex or nanoparticle. In some embodiments, the composition comprises a salt (e.g., NaCl) at a concentration that promotes and/or contributes to the formation of aggregates of the genome-editing complex or nanoparticles having a size no more than about 20% larger than the size of the genome-editing complex or nanoparticle. In some embodiments, the composition comprises a salt (e.g., NaCl) at a concentration that promotes and/or contributes to the formation of aggregates of the genome-editing complex or nanoparticles having a size no more than about 15% larger than the size of the genome-editing complex or nanoparticle. In some embodiments, the composition comprises a salt (e.g., NaCl) at a concentration that promotes and/or contributes to the formation of aggregates of the genome-editing complex or nanoparticles having a size no more than about 10% larger than the size of the genome-editing complex or nanoparticle. In some embodiments, the concentration of the salt in the composition is no more than about 100 mM (such as no more than about any of 90, 80, 70, 60, 50, 40, 30, 20, 10, 9, 8, 7, 6, 5, 4, 3, 2, or 1 mM, including any ranges between any of these values). In some embodiments, the salt is NaCl.

In some embodiments, the composition comprises a sugar (e.g., sucrose, glucose, or mannitol) at a concentration that does not promote and/or contribute to aggregation of the genome-editing complex or nanoparticle, or promotes and/or contributes to the formation of aggregates of the genome-editing complex or nanoparticles having a size no more than about 25% (such as no more than about any of 24, 23, 22, 21, 20, 19, 18, 17, 16, 15, 14, 13, 12, 11, 10, 9, 8, 7, 6, 5, 4, 3, 2, or 1%, including any ranges between any of these values) larger than the size of the genome-editing complex or nanoparticle. In some embodiments, the composition comprises a sugar (e.g., sucrose, glucose, or mannitol) at a concentration that promotes and/or contributes to the formation of aggregates of the genome-editing complex or nanoparticles having a size no more than about 75% larger than the size of the genome-editing complex or nanoparticle. In some embodiments, the composition comprises a sugar (e.g., sucrose, glucose, or mannitol) at a concentration that promotes and/or contributes to the formation of aggregates of the genome-editing complex or nanoparticles having a size no more than about 50% larger than the size of the genome-editing complex or nanoparticle. In some embodiments, the composition comprises a sugar (e.g., sucrose, glucose, or mannitol) at a concentration that promotes and/or contributes to the formation of aggregates of the genome-editing complex or nanoparticles having a size no more than about 20% larger than the size of the genome-editing complex or nanoparticle. In some embodiments, the composition comprises a sugar (e.g., sucrose, glucose, or mannitol) at a concentration that promotes and/or contributes to the formation of aggregates of the genome-editing complex or nanoparticles having a size no more than about 15% larger than the size of the genome-editing complex or nanoparticle. In some embodiments, the composition comprises a sugar (e.g., sucrose, glucose, or mannitol) at a concentration that promotes and/or contributes to the formation of aggregates of the genome-editing complex or nanoparticles having a size no more than about 10% larger than the size of the genome-editing complex or nanoparticle. In some embodiments, the concentration of the sugar in the composition is no more than about 20% (such as no more than about any of 18, 16, 14, 12, 10, 9, 8, 7, 6, 5, 4, 3, 2, or 1%, including any ranges between any of these values). In some embodiments, the sugar is sucrose. In some embodiments, the sugar is glucose. In some embodiments, the sugar is mannitol.

In some embodiments, the composition comprises a chemical buffering agent (e.g., HEPES or phosphate) at a concentration that does not promote and/or contribute to aggregation of the genome-editing complex or nanoparticle, or promotes and/or contributes to the formation of aggregates of the genome-editing complex or nanoparticles having a size no more than about 10% (such as no more than about any of 9, 8, 7, 6, 5, 4, 3, 2, or 1%, including any ranges between any of these values) larger than the size of the genome-editing complex or nanoparticle. In some embodiments, the composition comprises a chemical buffering agent (e.g., HEPES or phosphate) at a concentration that promotes and/or contributes to the formation of aggregates of the genome-editing complex or nanoparticles having a size no more than about 7.5% larger than the size of the genome-editing complex or nanoparticle. In some embodiments, the composition comprises a chemical buffering agent (e.g., HEPES or phosphate) at a concentration that promotes and/or contributes to the formation of aggregates of the genome-editing complex or nanoparticles having a size no more than about 5% larger than the size of the genome-editing complex or nanoparticle. In some embodiments, the composition comprises a chemical buffering agent (e.g., HEPES or phosphate) at a concentration that promotes and/or contributes to the formation of aggregates of the genome-editing complex or nanoparticles having a size no more than about 3% larger than the size of the genome-editing complex or nanoparticle. In some embodiments, the composition comprises a chemical buffering agent (e.g., HEPES or phosphate) at a concentration that promotes and/or contributes to the formation of aggregates of the genome-editing complex or nanoparticles having a size no more than about 1% larger than the size of the genome-editing complex or nanoparticle. In some embodiments, the composition comprises a chemical buffering agent (e.g., HEPES or phosphate) at a concentration that does not promote and/or contribute to the formation of aggregates of the genome-editing complex or nanoparticles. In some embodiments, the chemical buffering agent is HEPES. In some embodiments, the HEPES is added to the composition in the form of a buffer solution comprising HEPES. In some embodiments, the solution comprising HEPES has a pH between about 5 and about 9 (such as about any of 5, 5.5, 6, 6.5, 7, 7.5, 8, 8.5, and 9, including any ranges between these values). In some embodiments, the composition comprises HEPES at a concentration of no more than about 75 mM (such as no more than about any of 70, 65, 60, 55, 50, 45, 40, 35, 30, 25, 20, 15, 10 mM or less, including any ranges between any of these values). In some embodiments, the chemical buffering agent is phosphate. In some embodiments, the phosphate is added to the composition in the form of a buffer solution comprising phosphate. In some embodiments, the composition does not comprise PBS.

In some embodiments, the composition comprises a cell culture medium (e.g., DMEM or Opti-MEM) at a concentration that does not promote and/or contribute to aggregation of the genome-editing complex or nanoparticle, or promotes and/or contributes to the formation of aggregates of the genome-editing complex or nanoparticles having a size no more than about 200% (such as no more than about any of 190, 180, 170, 160, 150, 140, 130, 120, 110, 100, 90, 80, 70, 60, 50, 40, 30, 20, 10, 9, 8, 7, 6, 5, 4, 3, 2, or 1%, including any ranges between any of these values) larger than the size of the genome-editing complex or nanoparticle. In some embodiments, the composition comprises a cell culture medium (e.g., DMEM or Opti-MEM) at a concentration that promotes and/or contributes to the formation of aggregates of the genome-editing complex or nanoparticles having a size no more than about 150% larger than the size of the genome-editing complex or nanoparticle. In some embodiments, the composition comprises a cell culture medium (e.g., DMEM or Opti-MEM) at a concentration that promotes and/or contributes to the formation of aggregates of the genome-editing complex or nanoparticles having a size no more than about 100% larger than the size of the genome-editing complex or nanoparticle. In some embodiments, the composition comprises a cell culture medium (e.g., DMEM or Opti-MEM) at a concentration that promotes and/or contributes to the formation of aggregates of the genome-editing complex or nanoparticles having a size no more than about 50% larger than the size of the genome-editing complex or nanoparticle. In some embodiments, the composition comprises a cell culture medium (e.g., DMEM or Opti-MEM) at a concentration that promotes and/or contributes to the formation of aggregates of the genome-editing complex or nanoparticles having a size no more than about 25% larger than the size of the genome-editing complex or nanoparticle. In some embodiments, the composition comprises a cell culture medium (e.g., DMEM or Opti-MEM) at a concentration that promotes and/or contributes to the formation of aggregates of the genome-editing complex or nanoparticles having a size no more than about 10% larger than the size of the genome-editing complex or nanoparticle. In some embodiments, the cell culture medium is DMEM. In some embodiments, the composition comprises DMEM at a concentration of no more than about 70% (such as no more than about any of 65, 60, 55, 50, 45, 40, 35, 30, 25, 20, 15, 10%, or less, including any ranges between any of these values).

In some embodiments, the composition comprises a carrier protein (e.g., albumin) at a concentration that does not promote and/or contribute to aggregation of the genome-editing complex or nanoparticle, or promotes and/or contributes to the formation of aggregates of the genome-editing complex or nanoparticles having a size no more than about 200% (such as no more than about any of 190, 180, 170, 160, 150, 140, 130, 120, 110, 100, 90, 80, 70, 60, 50, 40, 30, 20, 10, 9, 8, 7, 6, 5, 4, 3, 2, or 1%, including any ranges between any of these values) larger than the size of the genome-editing complex or nanoparticle. In some embodiments, the composition comprises a carrier protein (e.g., albumin) at a concentration that promotes and/or contributes to the formation of aggregates of the genome-editing complex or nanoparticles having a size no more than about 150% larger than the size of the genome-editing complex or nanoparticle. In some embodiments, the composition comprises a carrier protein (e.g., albumin) at a concentration that promotes and/or contributes to the formation of aggregates of the genome-editing complex or nanoparticles having a size no more than about 100% larger than the size of the genome-editing complex or nanoparticle. In some embodiments, the composition comprises a carrier protein (e.g., albumin) at a concentration that promotes and/or contributes to the formation of aggregates of the genome-editing complex or nanoparticles having a size no more than about 50% larger than the size of the genome-editing complex or nanoparticle. In some embodiments, the composition comprises a carrier protein (e.g., albumin) at a concentration that promotes and/or contributes to the formation of aggregates of the genome-editing complex or nanoparticles having a size no more than about 25% larger than the size of the genome-editing complex or nanoparticle. In some embodiments, the composition comprises a carrier protein (e.g., albumin) at a concentration that promotes and/or contributes to the formation of aggregates of the genome-editing complex or nanoparticles having a size no more than about 10% larger than the size of the genome-editing complex or nanoparticle. In some embodiments, the carrier protein is albumin. In some embodiments, the albumin is human serum albumin.

In some embodiments, a pharmaceutical composition as described herein is formulated for intravenous, intratumoral, intraarterial, topical, intraocular, ophthalmic, intraportal, intracranial, intracerebral, intracerebroventricular, intrathecal, intravesicular, intradermal, subcutaneous, intramuscular, intranasal, intratracheal, pulmonary, intracavity, or oral administration, or nebulization (NB) or intratracheal instillation.

Exemplary dosing frequencies include, but are not limited to, no more than once every three days.

Methods of Preparation

In some embodiments, there is provided a method of preparing a genome-editing complex or nanoparticle as described herein.

In some embodiments, there is provided a method of preparing the genome-editing complex comprising a peptide and a cargo molecule (e.g., a guide RNA) as described above, comprising combining the peptide with the cargo molecule, thereby forming the genome-editing complex.

In some embodiments, there is provided a method of preparing the genome-editing complex comprising a first cell-penetrating peptide and a second cell-penetrating peptide as described above, comprising a) combining the first cell-penetrating peptide and the second cell-penetrating peptide, thereby forming a peptide mixture; b) combining the peptide mixture with the cargo, thereby forming the genome-editing complex.

In some embodiments, the peptide or the peptide mixture and the cargo molecule are combined at a molar ratio from about 1:1 to about 100:1 (such as about between about 1:1 and about 50:1, such as about 2:1 to about 50:1), respectively.

In some embodiments, the method comprises mixing a first solution comprising the cargo molecule with a second solution comprising the peptide or peptide mixture to form a third solution, wherein the third solution comprises or is adjusted to comprise i) about 0-5% sucrose, ii) about 0-5% glucose, iii) about 0-50% DMEM, iv) about 0-80 mM NaCl, or v) about 0-20% PBS, and wherein the third solution is incubated to allow formation of the genome-editing complex. In some embodiments, the first solution comprises the cargo in sterile water and/or wherein the second solution comprises the peptide or peptide mixture in sterile water. In some embodiments, the third solution is adjusted to comprise i) about 0-5% sucrose, ii) about 0-5% glucose, iii) about 0-50% DMEM, iv) about 0-80 mM NaCl, or v) about 0-20% PBS after incubating to form the genome-editing complex.

In some embodiments, the method further comprises a filtration process, wherein the genome-editing complex is filtered through a pore-sized membrane. In some embodiments, the pore has a diameter of at least about 0.1 μm (such as at least about 0.1 μm, 0.15 μm, 0.2 μm, 0.25 μm, 0.3 μm, 0.35 μm, 0.4 μm, 0.45 μm, 0.5 μm, 0.6 μm, 0.7 μm, 0.8 0.9 1.0 μm, 1.1 μm or 1.2 μm). In some embodiments, the pore has a diameter of no more about 1.2 1.0 0.8 0.6 0.5 0.45 0.4 0.35 0.3 or 0.25 In some embodiments, the port has a diameter of about 0.1 μm to about 1.2 μm (such as about 0.1 to about 0.8 μm, about 0.2 to about 0.5 μm).

In some embodiments, for a stable composition comprising a cargo molecule delivery complex or nanoparticle of the application, the average diameter of the complex or nanoparticle does not change by more than about 10%, and the polydispersity index does not change by more than about 10%.

Also provided are methods of preparing any of the peptides comprising cell-penetrating peptides described herein.

Method of Use (e.g., Method of Treatment)

The present application in one aspect provides a method of treating a disease (such as a cancer) in an individual comprising administering to the individual a genome-editing complex or nanoparticle comprising a guide RNA as described above. The present application in another aspect provides a method of modifying mutated KRAS in a cell comprising contacting the cell with the genome-editing complex or nanoparticle comprising a guide RNA as described above.

In some embodiments, there is provided a method of treating a cancer (such as a pancreatic cancer, colorectal cancer or a lung cancer) in an individual comprising administering to the individual a genome-editing complex or nanoparticle comprising a guide RNA targeting mutated KRAS comprising a nucleotide sequence substantially complementary (such as at least about 80%, 85%, 90%, 95%, 96%, 97%, 98%, or 99% complementary) to a target sequence selected from the group consisting of SEQ ID NOs: 1-37, 241-257 and 271. In some embodiments, the guide RNA comprises a nucleotide sequence substantially complementary (such as at least about 80%, 85%, 90%, 95%, 96%, 97%, 98%, or 99% complementary) to a target sequence selected from the group consisting of SEQ ID NOs: 1, 3, 6, 8, 15, 16, 19-21, 23, 29, 31, 33, and 34. In some embodiments, the guide RNA comprises a nucleotide sequence 100% complementary to a target sequence selected from the group consisting of SEQ ID NOs: 1, 3, 6, 8, 15, 16, 19-21, 23, 29, 31, 33, and 34. In some embodiments, the genome-editing complex or nanoparticle is intravenously administered to the individual.

In some embodiments, there is provided a method of modifying mutated KRAS in a cell, comprising contacting the cell with a genome-editing complex or nanoparticle comprising a guide RNA targeting mutated KRAS comprising a nucleotide sequence substantially complementary (such as at least about 80%, 85%, 90%, 95%, 96%, 97%, 98%, or 99% complementary) to a target sequence selected from the group consisting of SEQ ID NOs: 1-37, 241-257 and 271. In some embodiments, the guide RNA comprises a nucleotide sequence substantially complementary (such as at least about 80%, 85%, 90%, 95%, 96%, 97%, 98%, or 99% complementary) to a target sequence selected from the group consisting of SEQ ID NOs: 1, 3, 6, 8, 15, 16, 19-21, 23, 29, 31, 33, and 34. In some embodiments, the guide RNA comprises a nucleotide sequence 100% complementary to a target sequence selected from the group consisting of SEQ ID NOs: 1, 3, 6, 8, 15, 16, 19-21, 23, 29, 31, 33, and 34.

In some embodiments, the guide RNA targets KRAS G12V. In some embodiments, the guide RNA comprises a nucleotide sequence substantially complementary (such as at least about 80%, 85%, 90%, 95%, 96%, 97%, 98%, or 99% complementary) to a target sequence selected from the group consisting of SEQ ID NOs: 1, 3, 4, and 6-8. In some embodiments, the target sequence is selected from the group consisting of SEQ ID NOs: 3, 6, and 8. In some embodiments, the target sequence is set forth in SEQ ID NO: 3. In some embodiments, the guide RNA further comprising an auxiliary trans-activating crRNA (tracrRNA).

In some embodiments, the guide RNA targets KRAS G12D. In some embodiments, the guide RNA comprises a nucleotide sequence substantially complementary (such as at least about 80%, 85%, 90%, 95%, 96%, 97%, 98%, or 99% complementary) to a target sequence selected from the group consisting of SEQ ID NOs: 15, 16, 19-21, and 23. In some embodiments, the target sequence is selected from the group consisting of SEQ ID NOs: 16, 19-21, and 23. In some embodiments, the target sequence is selected from the group consisting of SEQ ID NO: 19. In some embodiments, the guide RNA further comprising an auxiliary trans-activating crRNA (tracrRNA).

In some embodiments, the guide RNA targets KRAS G12C. In some embodiments, the guide RNA comprises a nucleotide sequence substantially complementary (such as at least about 80%, 85%, 90%, 95%, 96%, 97%, 98%, or 99% complementary) to a target sequence selected from the group consisting of SEQ ID NOs: 29, 31, 33, and 34. In some embodiments, the target sequence is set forth in SEQ ID NO: 34. In some embodiments, the guide RNA further comprising an auxiliary trans-activating crRNA (tracrRNA).

In some embodiments, the genome-editing complex further comprises a first cell-penetrating peptide. In some embodiments, the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first cell-penetrating peptide comprises a targeting moiety comprising a targeting peptide covalently linked to the N-terminus of the first cell-penetrating peptide. In some embodiments, the first cell-penetrating peptide comprises a linker moiety selected from the group consisting of a polyglycine linker moiety, a PEG moiety, Aun, Ava, and Ahx. In some embodiments, the first cell-penetrating peptide further comprises a carbohydrate moiety (such as GalNAc). In some embodiments, the first cell-penetrating peptide is an ADGN-100 peptide. In some embodiments, the first cell-penetrating peptide comprises an amino acid sequence selected from the group consisting of SEQ ID NOs: 135-175, 259-260, and 267-269. In some embodiments, the first cell-penetrating peptide is a VEPEP-3 peptide. In some embodiments, the first cell-penetrating peptide comprises an amino acid sequence selected from the group consisting of SEQ ID NOs: 44-62. In some embodiments, the first cell-penetrating peptide is a VEPEP-6 peptide. In some embodiments, the first cell-penetrating peptide comprises an amino acid sequence selected from the group consisting of SEQ ID NOs: 63-117, 261-266 and 270. In some embodiments, the first cell-penetrating peptide is a VEPEP-9 peptide. In some embodiments, the first cell-penetrating peptide comprises an amino acid sequence selected from the group consisting of SEQ ID NOs: 118-134. In some embodiments, the molar ratio of the first cell-penetrating peptide to the guide RNA is between about 1:1 and about 80:1 (such as between about 5:1 and about 20:1, such as between about 2:1 to about 50:1). In some embodiments, the molar ratio of the first cell-penetrating peptide to the nucleotide sequence encoding the Cas polypeptide is between about 1:1 and about 80:1 (such as between about 5:1 to about 20:1, such as between about 2:1 to about 50:1). In some embodiments, the molar ratio of the nucleotide sequence encoding the Cas polypeptide to the guide RNA is between about 1:10 and about 50:1 (such as between about 1:1 and about 10:1). In some embodiments, the guide RNA is complexed with the first cell-penetrating peptide. In some embodiments, the guide RNA is complexed with the first cell-penetrating peptide. In some embodiments, the genome-editing complex further comprises a DNA nuclease (e.g., Cas9) or a nucleotide sequence encoding the DNA nuclease.

In some embodiments of the methods described herein, the individual is a mammal. In some embodiments, the individual is human.

In some embodiments, there is provided a method of treating a cancer that has a KRAS G12V mutation, wherein the method comprises administering a composition comprising a polynucleotide comprising a guide RNA comprising a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-14. In some embodiments, the target sequence selected from the group consisting of SEQ ID NOs: 1, 3, 4, and 6-8. In some embodiments, the target sequence is selected from the group consisting of SEQ ID NOs: 3, 6, and 8. In some embodiments, the target sequence is set forth in SEQ ID NO: 3. In some embodiments, the guide RNA further comprising an auxiliary trans-activating crRNA (tracrRNA). In some embodiments, the guide RNA is a single guide RNA. In some embodiments, the composition further comprises a DNA nuclease (e.g., Cas9) or a nucleotide encoding the DNA nuclease. In some embodiments, the polynucleotide is chemically modified. In some embodiments, the genome-editing complex is administered intravenously, intramuscularly, subcutaneously, or via nebulization or intratracheal instillation.

In some embodiments, there is provided a method of treating a cancer that has a KRAS G12D mutation, wherein the method comprises administering a composition comprising a polynucleotide comprising a guide RNA comprising a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 15-28. In some embodiments, the target sequence is selected from the group consisting of SEQ ID NOs: 15, 16, 19-21, and 23. In some embodiments, the target sequence is selected from the group consisting of SEQ ID NOs: 16, 19-21, and 23. In some embodiments, the target sequence is selected from the group consisting of SEQ ID NO: 19. In some embodiments, the guide RNA further comprising an auxiliary trans-activating crRNA (tracrRNA). In some embodiments, the guide RNA is a single guide RNA. In some embodiments, the composition further comprises a DNA nuclease (e.g., Cas9) or a nucleotide encoding the DNA nuclease. In some embodiments, the polynucleotide is chemically modified. In some embodiments, the genome-editing complex is administered intravenously, intramuscularly, subcutaneously, or via nebulization or intratracheal instillation.

In some embodiments, there is provided a method of treating a cancer that has a KRAS G12C mutation, wherein the method comprises administering a composition comprising a polynucleotide comprising a guide RNA comprising a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 29-37. In some embodiments, the target sequence is selected from the group consisting of SEQ ID NOs: 29, 31, 33, and 34. In some embodiments, the target sequence is set forth in SEQ ID NO: 34. In some embodiments, the guide RNA further comprising an auxiliary trans-activating crRNA (tracrRNA). In some embodiments, the guide RNA is a single guide RNA. In some embodiments, the composition further comprises a DNA nuclease (e.g., Cas9) or a nucleotide encoding the DNA nuclease. In some embodiments, the polynucleotide is chemically modified. In some embodiments, the genome-editing complex is administered intravenously, intramuscularly, subcutaneously, or via nebulization or intratracheal instillation.

In some embodiments, there is provided a method of treating a cancer that has a KRAS G12V mutation, wherein the method comprises administering a genome-editing complex comprising a) a guide RNA comprising a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-14, and b) a cell-penetrating peptide. In some embodiments, the target sequence selected from the group consisting of SEQ ID NOs: 1, 3, 4, and 6-8. In some embodiments, the target sequence is selected from the group consisting of SEQ ID NOs: 3, 6, and 8. In some embodiments, the target sequence is set forth in SEQ ID NO: 3. In some embodiments, the guide RNA further comprising an auxiliary trans-activating crRNA (tracrRNA). In some embodiments, the cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the cell-penetrating peptide comprises an acetyl group covalently linked to the N-terminus of the first cell-penetrating peptide. In some embodiments, the cell-penetrating peptide comprises a targeting moiety comprising a targeting peptide covalently linked to the N-terminus of the first cell-penetrating peptide. In some embodiments, the targeting peptide is selected from the group consisting of SEQ ID NOs: 196-205 and 235-240. In some embodiments, the cell-penetrating peptide comprises a linker moiety selected from the group consisting of a polyglycine linker moiety, a PEG moiety, Aun, Ava, and Ahx. In some embodiments, the cell-penetrating peptide comprises an amino acid sequence selected from the group consisting of SEQ ID NOs: 44-195. In some embodiments, the genome-editing complex is administered intravenously, intramuscularly, subcutaneously, or via nebulization or intratracheal instillation.

In some embodiments, there is provided a method of treating a cancer that has a KRAS G12D mutation, wherein the method comprises administering a genome-editing complex comprising a guide RNA comprising a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 15-28, and b) a cell-penetrating peptide. In some embodiments, the target sequence is selected from the group consisting of SEQ ID NOs: 15, 16, 19-21, and 23. In some embodiments, the target sequence is selected from the group consisting of SEQ ID NOs: 16, 19-21, and 23. In some embodiments, the target sequence is selected from the group consisting of SEQ ID NO: 19. In some embodiments, the guide RNA further comprising an auxiliary trans-activating crRNA (tracrRNA). In some embodiments, the cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the cell-penetrating peptide comprises an acetyl group covalently linked to the N-terminus of the first cell-penetrating peptide. In some embodiments, the cell-penetrating peptide comprises a targeting moiety comprising a targeting peptide covalently linked to the N-terminus of the first cell-penetrating peptide. In some embodiments, the targeting peptide is selected from the group consisting of SEQ ID NOs: 196-205 and 235-240. In some embodiments, the cell-penetrating peptide comprises a linker moiety selected from the group consisting of a polyglycine linker moiety, a PEG moiety, Aun, Ava, and Ahx. In some embodiments, the cell-penetrating peptide comprises an amino acid sequence selected from the group consisting of SEQ ID NOs: 44-195. In some embodiments, the genome-editing complex is administered intravenously, intramuscularly, subcutaneously, or via nebulization or intratracheal instillation.

In some embodiments, there is provided a method of treating a cancer that has a KRAS G12C mutation, wherein the method comprises administering a genome-editing complex comprising a guide RNA comprising a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 29-37, and b) a cell-penetrating peptide. In some embodiments, the target sequence is selected from the group consisting of SEQ ID NOs: 29, 31, 33, and 34. In some embodiments, the target sequence is set forth in SEQ ID NO: 34. In some embodiments, the guide RNA further comprising an auxiliary trans-activating crRNA (tracrRNA). In some embodiments, the cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the cell-penetrating peptide comprises an acetyl group covalently linked to the N-terminus of the first cell-penetrating peptide. In some embodiments, the cell-penetrating peptide comprises a targeting moiety comprising a targeting peptide covalently linked to the N-terminus of the first cell-penetrating peptide. In some embodiments, the targeting peptide is selected from the group consisting of SEQ ID NOs: 196-205 and 235-240. In some embodiments, the cell-penetrating peptide comprises a linker moiety selected from the group consisting of a polyglycine linker moiety, a PEG moiety, Aun, Ava, and Ahx. In some embodiments, the cell-penetrating peptide comprises an amino acid sequence selected from the group consisting of SEQ ID NOs: 44-195. In some embodiments, the genome-editing complex is administered intravenously, intramuscularly, subcutaneously, or via nebulization or intratracheal instillation. In some embodiments, there is provided a method of treating a cancer that has a KRAS G12V mutation, wherein the method comprises administering a genome-editing complex comprising a) a guide RNA comprising a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-14, b) a cell-penetrating peptide, and c) a DNA nuclease or a polynucleotide encoding the DNA nuclease. In some embodiments, the target sequence selected from the group consisting of SEQ ID NOs: 1, 3, 4, and 6-8. In some embodiments, the target sequence is selected from the group consisting of SEQ ID NOs: 3, 6, and 8. In some embodiments, the target sequence is set forth in SEQ ID NO: 3. In some embodiments, the DNA nuclease is a Cas9 polypeptide. In some embodiments, the DNA nuclease comprises a modified Cas9 (e.g., a catalytically impaired Cas9). In some embodiments, the DNA nuclease is a fusion protein, wherein the fusion protein further comprises a second enzyme that will allow base editing or prime editing. In some embodiments, the second enzyme comprises a reverse transcriptase or a nucleobase deaminase enzyme. In some embodiments, the guide RNA further comprising an auxiliary trans-activating crRNA (tracrRNA). In some embodiments, the cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the cell-penetrating peptide comprises an acetyl group covalently linked to the N-terminus of the first cell-penetrating peptide. In some embodiments, the cell-penetrating peptide comprises a targeting moiety comprising a targeting peptide covalently linked to the N-terminus of the first cell-penetrating peptide. In some embodiments, the targeting peptide is selected from the group consisting of SEQ ID NOs: 196-205 and 235-240. In some embodiments, the cell-penetrating peptide comprises a linker moiety selected from the group consisting of a polyglycine linker moiety, a PEG moiety, Aun, Ava, and Ahx. In some embodiments, the cell-penetrating peptide comprises an amino acid sequence selected from the group consisting of SEQ ID NOs: 44-195. In some embodiments, the genome-editing complex is administered intravenously, intramuscularly, subcutaneously, or via nebulization or intratracheal instillation.

In some embodiments, there is provided a method of treating a cancer that has a KRAS G12D mutation, wherein the method comprises administering a genome-editing complex comprising a) a guide RNA comprising a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 15-28, b) a cell-penetrating peptide, and c) a DNA nuclease or a polynucleotide encoding the DNA nuclease. In some embodiments, the target sequence is selected from the group consisting of SEQ ID NOs: 15, 16, 19-21, and 23. In some embodiments, the target sequence is selected from the group consisting of SEQ ID NOs: 16, 19-21, and 23. In some embodiments, the target sequence is selected from the group consisting of SEQ ID NO: 19. In some embodiments, the DNA nuclease is a Cas9 polypeptide. In some embodiments, the DNA nuclease comprises a modified Cas9 (e.g., a catalytically impaired Cas9). In some embodiments, the DNA nuclease is a fusion protein, wherein the fusion protein further comprises a second enzyme that will allow base editing or prime editing. In some embodiments, the second enzyme comprises a reverse transcriptase or a nucleobase deaminase enzyme. In some embodiments, the guide RNA further comprising an auxiliary trans-activating crRNA (tracrRNA). In some embodiments, the cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the cell-penetrating peptide comprises an acetyl group covalently linked to the N-terminus of the first cell-penetrating peptide. In some embodiments, the cell-penetrating peptide comprises a targeting moiety comprising a targeting peptide covalently linked to the N-terminus of the first cell-penetrating peptide. In some embodiments, the targeting peptide is selected from the group consisting of SEQ ID NOs: 196-205 and 235-240. In some embodiments, the cell-penetrating peptide comprises a linker moiety selected from the group consisting of a polyglycine linker moiety, a PEG moiety, Aun, Ava, and Ahx. In some embodiments, the cell-penetrating peptide comprises an amino acid sequence selected from the group consisting of SEQ ID NOs: 44-195. In some embodiments, the genome-editing complex is administered intravenously, intramuscularly, subcutaneously, or via nebulization or intratracheal instillation.

In some embodiments, there is provided a method of treating a cancer that has a KRAS G12C mutation, wherein the method comprises administering a genome-editing complex comprising a) a guide RNA comprising a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 29-37, b) a cell-penetrating peptide, and c) a DNA nuclease or a polynucleotide encoding the DNA nuclease. In some embodiments, the target sequence is selected from the group consisting of SEQ ID NOs: 29, 31, 33, and 34. In some embodiments, the target sequence is set forth in SEQ ID NO: 34. In some embodiments, the DNA nuclease is a Cas9 polypeptide. In some embodiments, the DNA nuclease comprises a modified Cas9 (e.g., a catalytically impaired Cas9). In some embodiments, the DNA nuclease is a fusion protein, wherein the fusion protein further comprises a second enzyme that will allow base editing or prime editing. In some embodiments, the second enzyme comprises a reverse transcriptase or a nucleobase deaminase enzyme. In some embodiments, the guide RNA further comprising an auxiliary trans-activating crRNA (tracrRNA). In some embodiments, the cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the cell-penetrating peptide comprises an acetyl group covalently linked to the N-terminus of the first cell-penetrating peptide. In some embodiments, the cell-penetrating peptide comprises a targeting moiety comprising a targeting peptide covalently linked to the N-terminus of the first cell-penetrating peptide. In some embodiments, the targeting peptide is selected from the group consisting of SEQ ID NOs: 196-205 and 235-240. In some embodiments, the cell-penetrating peptide comprises a linker moiety selected from the group consisting of a polyglycine linker moiety, a PEG moiety, Aun, Ava, and Ahx. In some embodiments, the cell-penetrating peptide comprises an amino acid sequence selected from the group consisting of SEQ ID NOs: 44-195. In some embodiments, the genome-editing complex is administered intravenously, intramuscularly, subcutaneously, or via nebulization or intratracheal instillation.

In some embodiments, there is provided a method of treating a cancer that has a KRAS G12V mutation, wherein the method comprises administering a genome-editing complex comprising a) a guide RNA comprising a nucleotide sequence 100% complementary to a target sequence selected from the group consisting of SEQ ID NOs: 1, 3, 4, and 6-8 (e.g., SEQ ID NOs: 3, 6, and 8); b) a cell-penetrating peptide, wherein the cell-penetrating peptide comprises the amino acid sequence selected from the group consisting of SEQ ID NOs: 89, 92-103, 105-107, 112-114, 137-138, 154-155, 157-158, 162, 167, 170 and 172, and c) a DNA nuclease or a polynucleotide encoding the DNA nuclease. In some embodiments, the target sequence has the amino acid sequence set forth in SEQ ID NO: 3. In some embodiments, the DNA nuclease is a Cas9 polypeptide. In some embodiments, the DNA nuclease comprises a modified Cas9 (e.g., a catalytically impaired Cas9). In some embodiments, the DNA nuclease is a fusion protein, wherein the fusion protein further comprises a second enzyme that will allow base editing or prime editing. In some embodiments, the second enzyme comprises a reverse transcriptase or a nucleobase deaminase enzyme. In some embodiments, the genome-editing complex is administered intravenously, intramuscularly, subcutaneously, or via nebulization or intratracheal instillation.

In some embodiments, there is provided a method of treating a cancer that has a KRAS G12D mutation, wherein the method comprises administering a genome-editing complex comprising a) a guide RNA comprising a nucleotide sequence 100% complementary to a target sequence selected from the group consisting of SEQ ID NOs: 15, 16, 19-21, and 23; b) a cell-penetrating peptide, wherein the cell-penetrating peptide comprises the amino acid sequence selected from the group consisting of SEQ ID NOs: 89, 92-103, 105-107, 112-114, 137-138, 154-155, 157-158, 162, 167, 170 and 172, and c) a DNA nuclease or a polynucleotide encoding the DNA nuclease. In some embodiments, the target sequence has the amino acid sequence set forth in SEQ ID NO: 19. In some embodiments, the DNA nuclease is a Cas9 polypeptide. In some embodiments, the DNA nuclease comprises a modified Cas9 (e.g., a catalytically impaired Cas9). In some embodiments, the DNA nuclease is a fusion protein, wherein the fusion protein further comprises a second enzyme that will allow base editing or prime editing. In some embodiments, the second enzyme comprises a reverse transcriptase or a nucleobase deaminase enzyme. In some embodiments, the genome-editing complex is administered intravenously, intramuscularly, subcutaneously, or via nebulization or intratracheal instillation.

In some embodiments, there is provided a method of treating a cancer that has a KRAS G12C mutation, wherein the method comprises administering a genome-editing complex comprising a) a guide RNA comprising a nucleotide sequence 100% complementary to a target sequence selected from the group consisting of SEQ ID NOs: 29, 31, 33, and 34; b) a cell-penetrating peptide, wherein the cell-penetrating peptide comprises the amino acid sequence selected from the group consisting of SEQ ID NOs: 89, 92-103, 105-107, 112-114, 137-138, 154-155, 157-158, 162, 167, 170 and 172, and c) a DNA nuclease or a polynucleotide encoding the DNA nuclease. In some embodiments, the target sequence has the amino acid sequence set forth in SEQ ID NO: 34. In some embodiments, the DNA nuclease is a Cas9 polypeptide. In some embodiments, the DNA nuclease comprises a modified Cas9 (e.g., a catalytically impaired Cas9). In some embodiments, the DNA nuclease is a fusion protein, wherein the fusion protein further comprises a second enzyme that will allow base editing or prime editing. In some embodiments, the second enzyme comprises a reverse transcriptase or a nucleobase deaminase enzyme. In some embodiments, the genome-editing complex is administered intravenously, intramuscularly, subcutaneously, or via nebulization or intratracheal instillation.

In some embodiments, there is provided a method of treating a disease or condition in heart comprising administering a composition comprising a genome-editing complex comprising a) cell-penetrating peptide, and b) a guide RNA and/or a DNA nuclease or a nucleotide sequence encoding the DNA nuclease. In some embodiments, the cell-penetrating peptide comprises the amino acid sequence of any of SEQ ID NOs: 114, 153, 154, 96, 100, and 101. In some embodiments, the cell-penetrating peptide comprises the amino acid sequence of SEQ ID NO: 114. In some embodiments, the genome-editing complex is administered intravenously, intramuscularly, subcutaneously, or via nebulization or intratracheal instillation. In some embodiments, the guide RNA targets a KRAS mutation (e.g., a G12D, a G12V, or a G12C mutation). In some embodiments, the guide RNA comprises a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-37, 241-257 and 271. In some embodiments, the target sequence is selected from the group consisting of SEQ ID NOs: 1, 3, 4, 6-8, 15, 16, 19-21, 23, 29, 31, 33, and 34. In some embodiments, the target sequence is selected from the group consisting of SEQ ID NOs: 3, 6, 8, 16, 19-21, 23, 29, 31, 33, and 34. In some embodiments, the target sequence is selected from the group consisting of SEQ ID NOs: 3, 19, and 34. In some embodiments, the guide RNA further comprising an auxiliary trans-activating crRNA (tracrRNA). In some embodiments, the guide RNA is a single guide RNA. In some embodiments, the guide RNA is chemically modified. In some embodiments, the DNA nuclease is a Cas9 or Cas12a polynucleotide.

In some embodiments, there is provided a method of treating a disease or condition in brain (e.g., a brain tumor) comprising administering a composition comprising a genome-editing complex comprising a) cell-penetrating peptide, and b) a guide RNA and/or a DNA nuclease or a nucleotide sequence encoding the DNA nuclease. In some embodiments, the cell-penetrating peptide comprises the amino acid sequence of any of SEQ ID NOs: 97, 112, and 113. In some embodiments, the genome-editing complex is administered intravenously, intramuscularly, subcutaneously, or via nebulization or intratracheal instillation. In some embodiments, the guide RNA targets a KRAS mutation (e.g., a G12D, a G12V, or a G12C mutation). In some embodiments, the guide RNA comprises a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-37, 241-257 and 271. In some embodiments, the target sequence is selected from the group consisting of SEQ ID NOs: 1, 3, 4, 6-8, 15, 16, 19-21, 23, 29, 31, 33, and 34. In some embodiments, the target sequence is selected from the group consisting of SEQ ID NOs: 3, 6, 8, 16, 19-21, 23, 29, 31, 33, and 34. In some embodiments, the target sequence is selected from the group consisting of SEQ ID NOs: 3, 19, and 34. In some embodiments, the guide RNA further comprising an auxiliary trans-activating crRNA (tracrRNA). In some embodiments, the guide RNA is a single guide RNA. In some embodiments, the guide RNA is chemically modified. In some embodiments, the DNA nuclease is a Cas9 or Cas12a polynucleotide.

In some embodiments, there is provided a method of treating a disease or condition in muscle comprising administering a composition comprising a genome-editing complex comprising a) cell-penetrating peptide, and b) a guide RNA and/or a DNA nuclease or a nucleotide sequence encoding the DNA nuclease. In some embodiments, the cell-penetrating peptide comprises the amino acid sequence of any of SEQ ID NOs: 95, 98, 114, 100, and 101. In some embodiments, the genome-editing complex is administered intravenously, intramuscularly, subcutaneously, or via nebulization or intratracheal instillation. In some embodiments, the guide RNA targets a KRAS mutation (e.g., a G12D, a G12V, or a G12C mutation). In some embodiments, the guide RNA comprises a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-37, 241-257 and 271. In some embodiments, the target sequence is selected from the group consisting of SEQ ID NOs: 1, 3, 4, 6-8, 15, 16, 19-21, 23, 29, 31, 33, and 34. In some embodiments, the target sequence is selected from the group consisting of SEQ ID NOs: 3, 6, 8, 16, 19-21, 23, 29, 31, 33, and 34. In some embodiments, the target sequence is selected from the group consisting of SEQ ID NOs: 3, 19, and 34. In some embodiments, the guide RNA further comprising an auxiliary trans-activating crRNA (tracrRNA). In some embodiments, the guide RNA is a single guide RNA. In some embodiments, the guide RNA is chemically modified. In some embodiments, the DNA nuclease is a Cas9 or Cas12a polynucleotide.

In some embodiments, there is provided a method of treating a disease or condition in lung (e.g., a lung cancer) comprising administering a composition comprising a genome-editing complex comprising a) cell-penetrating peptide, and b) a guide RNA and/or a DNA nuclease or a nucleotide sequence encoding the DNA nuclease. In some embodiments, the cell-penetrating peptide comprises the amino acid sequence of any of SEQ ID NOs: 89, 90, 92-94, 96, 98, 99, 100, 101, 105-107, 113, 137, 138, 153-155, 157, 158, 162, 164, 167, and 170. In some embodiments, the genome-editing complex is administered intravenously, intramuscularly, subcutaneously, or via nebulization or intratracheal instillation. In some embodiments, the guide RNA targets a KRAS mutation (e.g., a G12D, a G12V, or a G12C mutation). In some embodiments, the guide RNA comprises a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-37, 241-257 and 271. In some embodiments, the target sequence is selected from the group consisting of SEQ ID NOs: 1, 3, 4, 6-8, 15, 16, 19-21, 23, 29, 31, 33, and 34. In some embodiments, the target sequence is selected from the group consisting of SEQ ID NOs: 3, 6, 8, 16, 19-21, 23, 29, 31, 33, and 34. In some embodiments, the target sequence is selected from the group consisting of SEQ ID NOs: 3, 19, and 34. In some embodiments, the guide RNA further comprising an auxiliary trans-activating crRNA (tracrRNA). In some embodiments, the guide RNA is a single guide RNA. In some embodiments, the guide RNA is chemically modified. In some embodiments, the DNA nuclease is a Cas9 or Cas12a polynucleotide.

In some embodiments, there is provided a method of treating a disease or condition in liver (e.g., a liver cancer) comprising administering a composition comprising a genome-editing complex comprising a) cell-penetrating peptide, and b) a guide RNA and/or a DNA nuclease or a nucleotide sequence encoding the DNA nuclease. In some embodiments, the cell-penetrating peptide comprises the amino acid sequence of any of SEQ ID NOs: 89, 90, 95, 96, 98, 112, 137, 138, 153-155, 157, 158, 172, 164, 153, 162, 167, 100, and 101. In some embodiments, the cell-penetrating peptide comprises the amino acid sequence of any of SEQ ID NOs: 89, 90, 95, 98, 112, 137, 138, 153-155, 157, 158, and 172. In some embodiments, the genome-editing complex is administered intravenously, intramuscularly, subcutaneously, or via nebulization or intratracheal instillation. In some embodiments, the guide RNA targets a KRAS mutation (e.g., a G12D, a G12V, or a G12C mutation). In some embodiments, the guide RNA comprises a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-37, 241-257 and 271. In some embodiments, the target sequence is selected from the group consisting of SEQ ID NOs: 1, 3, 4, 6-8, 15, 16, 19-21, 23, 29, 31, 33, and 34. In some embodiments, the target sequence is selected from the group consisting of SEQ ID NOs: 3, 6, 8, 16, 19-21, 23, 29, 31, 33, and 34. In some embodiments, the target sequence is selected from the group consisting of SEQ ID NOs: 3, 19, and 34. In some embodiments, the guide RNA further comprising an auxiliary trans-activating crRNA (tracrRNA). In some embodiments, the guide RNA is a single guide RNA. In some embodiments, the guide RNA is chemically modified. In some embodiments, the DNA nuclease is a Cas9 or Cas12a polynucleotide.

In some embodiments, there is provided a method of treating a disease or condition in kidney (e.g., a kidney cancer) comprising administering a composition comprising a genome-editing complex comprising a) cell-penetrating peptide, and b) a guide RNA and/or a DNA nuclease or a nucleotide sequence encoding the DNA nuclease. In some embodiments, the cell-penetrating peptide comprises the amino acid sequence of any of SEQ ID NOs: 89, 90, 93, 96-98, 137, 100, 101, 138, 154, 155, and 172. In some embodiments, the cell-penetrating peptide comprises the amino acid sequence of any of SEQ ID NOs: 93, 97, 98, 137, 100, 101, 138, 154, and 155. In some embodiments, the genome-editing complex is administered intravenously, intramuscularly, subcutaneously, or via nebulization or intratracheal instillation. In some embodiments, the guide RNA targets a KRAS mutation (e.g., a G12D, a G12V, or a G12C mutation). In some embodiments, the guide RNA comprises a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-37, 241-257 and 271. In some embodiments, the target sequence is selected from the group consisting of SEQ ID NOs: 1, 3, 4, 6-8, 15, 16, 19-21, 23, 29, 31, 33, and 34. In some embodiments, the target sequence is selected from the group consisting of SEQ ID NOs: 3, 6, 8, 16, 19-21, 23, 29, 31, 33, and 34. In some embodiments, the target sequence is selected from the group consisting of SEQ ID NOs: 3, 19, and 34. In some embodiments, the guide RNA further comprising an auxiliary trans-activating crRNA (tracrRNA). In some embodiments, the guide RNA is a single guide RNA. In some embodiments, the guide RNA is chemically modified. In some embodiments, the DNA nuclease is a Cas9 or Cas12a polynucleotide.

In some embodiments, there is provided a method of treating a disease or condition in pancreas (e.g., a pancreas cancer) comprising administering a composition comprising a genome-editing complex comprising a) cell-penetrating peptide, and b) a guide RNA and/or a DNA nuclease or a nucleotide sequence encoding the DNA nuclease. In some embodiments, the cell-penetrating peptide comprises the amino acid sequence of any of SEQ ID NOs: 98, 99, 137, 138, 153, 154, 155, and 162. In some embodiments, the cell-penetrating peptide comprises the amino acid sequence of any of SEQ ID NOs: 98, 99, 137, 138, 153, 154, and 155. In some embodiments, the genome-editing complex is administered intravenously, intramuscularly, subcutaneously, or via nebulization or intratracheal instillation. In some embodiments, the guide RNA targets a KRAS mutation (e.g., a G12D, a G12V, or a G12C mutation). In some embodiments, the guide RNA comprises a nucleotide sequence or 99% complementary) or 100% complementary to a target sequence selected from the group consisting of SEQ ID NOs: 1-37, 241-257 and 271. In some embodiments, the target sequence is selected from the group consisting of SEQ ID NOs: 1, 3, 4, 6-8, 15, 16, 19-21, 23, 29, 31, 33, and 34. In some embodiments, the target sequence is selected from the group consisting of SEQ ID NOs: 3, 6, 8, 16, 19-21, 23, 29, 31, 33, and 34. In some embodiments, the target sequence is selected from the group consisting of SEQ ID NOs: 3, 19, and 34. In some embodiments, the guide RNA further comprising an auxiliary trans-activating crRNA (tracrRNA). In some embodiments, the guide RNA is a single guide RNA. In some embodiments, the guide RNA is chemically modified. In some embodiments, the DNA nuclease is a Cas9 or Cas12a polynucleotide.

In some embodiments, there is provided a method of treating a disease or condition in spleen comprising administering a composition comprising a genome-editing complex comprising a) cell-penetrating peptide, and b) a guide RNA and/or a DNA nuclease or a nucleotide sequence encoding the DNA nuclease. In some embodiments, the cell-penetrating peptide comprises the amino acid sequence of any of SEQ ID NOs: 93, 153, 154, and 158. In some embodiments, the cell-penetrating peptide comprises the amino acid sequence of any of SEQ ID NOs: 93 and 158. In some embodiments, the genome-editing complex is administered intravenously, intramuscularly, subcutaneously, or via nebulization or intratracheal instillation. In some embodiments, the guide RNA targets a KRAS mutation (e.g., a G12D, a G12V, or a G12C mutation). In some embodiments, the guide RNA comprises a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-37, 241-257 and 271. In some embodiments, the target sequence is selected from the group consisting of SEQ ID NOs: 1, 3, 4, 6-8, 15, 16, 19-21, 23, 29, 31, 33, and 34. In some embodiments, the target sequence is selected from the group consisting of SEQ ID NOs: 3, 6, 8, 16, 19-21, 23, 29, 31, 33, and 34. In some embodiments, the target sequence is selected from the group consisting of SEQ ID NOs: 3, 19, and 34. In some embodiments, the guide RNA further comprising an auxiliary trans-activating crRNA (tracrRNA). In some embodiments, the guide RNA is a single guide RNA. In some embodiments, the guide RNA is chemically modified. In some embodiments, the DNA nuclease is a Cas9 or Cas12a polynucleotide.

In some embodiments, there is provided a method of treating a disease or condition in a tumor (e.g., solid tumor) comprising administering a composition comprising a genome-editing complex comprising a) cell-penetrating peptide, and b) a guide RNA and/or a DNA nuclease or a nucleotide sequence encoding the DNA nuclease. In some embodiments, the cell-penetrating peptide comprises the amino acid sequence of any of SEQ ID NOs: 94, 96, 98-101, 105-107, 153, 154, 162, 164, 167, and 170. In some embodiments, the cell-penetrating peptide comprises the amino acid sequence of any of SEQ ID NOs: 94, 96, 98-101, 105-107, 162, 164, 167, and 170. In some embodiments, the genome-editing complex is administered intravenously, intramuscularly, subcutaneously, or via nebulization or intratracheal instillation. In some embodiments, the guide RNA targets a KRAS mutation (e.g., a G12D, a G12V, or a G12C mutation). In some embodiments, the guide RNA comprises a nucleotide sequence substantially complementary (such as at least about 80%, 85%, 90%, 95%, 96%, 97%, 98%, or 99% complementary) or 100% complementary to a target sequence selected from the group consisting of SEQ ID NOs: 1-37, 241-257 and 271. In some embodiments, the target sequence is selected from the group consisting of SEQ ID NOs: 1, 3, 4, 6-8, 15, 16, 19-21, 23, 29, 31, 33, and 34. In some embodiments, the target sequence is selected from the group consisting of SEQ ID NOs: 3, 6, 8, 16, 19-21, 23, 29, 31, 33, and 34. In some embodiments, the target sequence is selected from the group consisting of SEQ ID NOs: 3, 19, and 34. In some embodiments, the guide RNA further comprising an auxiliary trans-activating crRNA (tracrRNA). In some embodiments, the guide RNA is a single guide RNA. In some embodiments, the guide RNA is chemically modified. In some embodiments, the DNA nuclease is a Cas9 or Cas12a polynucleotide.

KRAS Aberration

In some embodiments, the cancer tissue has a KRAS aberration. In some embodiments, the aberration of KRAS comprises a mutation on codon 12. In some embodiments, the aberration of KRAS is selected from the group consisting of G12C, G12D, and G12V. In some embodiments, the aberration of KRAS is G12C, G12D and/or G12V.

The genetic aberrations of KRAS may be assessed based on a sample, such as a sample from the individual and/or reference sample. In some embodiments, the sample is a tissue sample or nucleic acids extracted from a tissue sample. In some embodiments, the sample is a cell sample (for example a CTC sample) or nucleic acids extracted from a cell sample. In some embodiments, the sample is a tumor biopsy. In some embodiments, the sample is a tumor sample or nucleic acids extracted from a tumor sample. In some embodiments, the sample is a biopsy sample or nucleic acids extracted from the biopsy sample. In some embodiments, the sample is a Formaldehyde Fixed-Paraffin Embedded (FFPE) sample or nucleic acids extracted from the FFPE sample. In some embodiments, the sample is a blood sample. In some embodiments, cell-free DNA is isolated from the blood sample. In some embodiments, the biological sample is a plasma sample or nucleic acids extracted from the plasma sample.

The genetic aberrations of KRAS may be determined by any method known in the art. See, for example, Dickson et al. *Int. J. Cancer,* 2013, 132(7): 1711-1717; Wagle N. *Cancer Discovery,* 2014, 4:546-553; and Cancer Genome Atlas Research Network. *Nature* 2013, 499: 43-49. Exemplary methods include, but are not limited to, genomic DNA sequencing, bisulfite sequencing or other DNA sequencing-based methods using Sanger sequencing or next generation sequencing platforms; polymerase chain reaction assays; in situ hybridization assays; and DNA microarrays. The epigenetic features (such as DNA methylation, histone binding, or chromatin modifications) of one or more genes from a sample isolated from the individual may be compared with the epigenetic features of the one or more genes from a control sample. The nucleic acid molecules extracted from the sample can be sequenced or analyzed for the presence of the genetic aberrations relative to a reference sequence, such as the wildtype sequences of KRAS.

In some embodiments, the genetic aberration of KRAS is assessed using cell-free DNA sequencing methods. In some embodiments, the genetic aberration of KRAS is assessed using next-generation sequencing. In some embodiments, the genetic aberration of KRAS isolated from a blood sample is assessed using next-generation sequencing. In some embodiments, the genetic aberration of KRAS is assessed using exome sequencing. In some embodiments, the genetic aberration of KRAS is assessed using fluorescence in-situ hybridization analysis. In some embodiments, the genetic aberration of KRAS is assessed prior to initiation of the methods of treatment described herein. In some embodiments, the genetic aberration of KRAS is assessed after initiation of the methods of treatment described herein. In some embodiments, the genetic aberration of KRAS is assessed prior to and after initiation of the methods of treatment described herein. An aberrant level of KRAS may refer to an aberrant expression level or an aberrant activity level.

Diseases (Such as Cancer)

In some embodiments, the disease is a cancer. In some embodiments, the diseases is myelodysplastic syndrome.

In some embodiments, the cancer is a leukemia or lymphoma. In some embodiments, the cancer is a solid tumor.

In some embodiments, the solid tumor includes, but is not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Kaposi's sarcoma, soft tissue sarcoma, uterine sacronomasynovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In some embodiments, the disease is selected from the group consisting of myelodysplastic syndrome, lung cancer (e.g., NSCLC, small cell lung cancer, squamous cell lung cancer), colorectal cancer, acute myeloid leukemia, pancreatic cancer, rectal cancer, esophageal squamous cell carcinoma, gastrointestinal stromal tumor, head and neck squamous cancer, pancreatic ductal adenocarcinoma, multiple myeloma, and glioma.

In some embodiments, the cancer is pancreatic cancer (e.g., pancreatic ductal adenocarcinoma).

In some embodiments, the cancer is colorectal cancer.

In some embodiments, the cancer is lung cancer (e.g., NSCLC).

In some embodiments, the cancer is a malignant and/or advanced cancer.

Combination Therapy

Also provided herein are combination therapies for treating a disease (such as a cancer) discussed above in an individual comprising: a) administering into the individual a genome-editing complex or nanoparticle described herein, and b) administering to the individual a second agent or therapy. The second agent described herein can be any medication or therapy that is useful for treating the disease (such as a standard therapy for the disease). In some embodiments, the second agent comprises a chemotherapeutic agent. In some embodiments, the second agent comprises a taxane. In some embodiments, the second agent comprises a cytotoxic nucleoside analogue.

In some embodiments, there is provided a method of treating a cancer (such as pancreatic cancer) in an individual comprising a) administering to the individual a genome-editing complex or nanoparticle comprising an effective amount of guide RNA described herein, and b) administering to the individual an effective amount of a second agent selected from the group consisting of gemcitabine, 5-FU, oxaliplatin, a taxane (e.g., paclitaxel, docetaxel, albumin-bound paclitaxel (e.g., Abraxane)), capecitabine (e.g., xeloda), cisplatin, irinotecan (e.g., camptosar), an EGFR inhibitor (e.g., erlotinib), a PARP inhibitor (e.g., olaparib), a NTRK inhibitor (e.g., larotrectinib, e.g., entrectinib), and a checkpoint inhibitor (such as a PD-1 inhibitor, e.g., pembrolizumab). In some embodiments, the second agent is a taxane (e.g., paclitaxel, docetaxel, albumin-bound paclitaxel (e.g., Abraxane)). In some embodiments, the second agent is Abraxane. In some embodiments, Abraxane is administered at a frequency of about once a week. In some embodiments, Abraxane is administered at a dose of about 5-25 mg to a human. In some embodiments, the second agent is capecitabine (e.g., xeloda). In some embodiments, capecitabine is administered at a frequency of about once a week. In some embodiments, capecitabine is administered at a dose of about 25-100 mg to a human.

In some embodiments, there is provided a method of treating a cancer (such as pancreatic cancer) in an individual comprising a) administering to the individual a genome-editing complex or nanoparticle comprising an effective amount of guide RNA described herein, and b) administering to the individual an effective amount of a nanoparticle composition comprising a taxane (e.g., paclitaxel) or an mTOR inhibitor (e.g., rapamycin) and a carrier protein (e.g., albumin, e.g., human serum albumin). In some embodiments, the cancer tissue has a KRAS G12D mutation. In some embodiments, the taxane is paclitaxel. In some embodiments, the other agent is nab-paclitaxel. In some embodiments, the mTOR inhibitor is rapamycin. In some embodiments, the other agent is nab-rapamycin. In some embodiments, the method further comprises administering a chemotherapeutic agent (e.g., gemcitabine). In some embodiments, the individual is a human. In some embodiments, the nanoparticles comprising a taxane (e.g., paclitaxel) or an mTOR inhibitor (e.g., rapamycin) have an average diameter of no greater than 200 nm. In some embodiments, the taxane (e.g., paclitaxel) or the mTOR inhibitor (e.g., rapamycin) in the nanoparticles are coated with the carrier protein (e.g., albumin). In some embodiments, the weight ratio of the carrier protein (e.g., albumin) and the taxane (e.g., paclitaxel) or the mTOR inhibitor (e.g., rapamycin) in the nanoparticle composition is about 9:1 or less. In some embodiments, the albumin is human albumin. In some embodiments, the dose of the taxane (e.g., paclitaxel) or the mTOR inhibitor (e.g., rapamycin) in the nanoparticle composition for each administration in an individual (such as a human) is about 1 $mg/m^2$ to about 150 $mg/m^2$.

In some embodiments, there is provided a method of treating a cancer (such as colorectal cancer) in an individual comprising a) administering to the individual a genome-editing complex or nanoparticle comprising an effective amount of guide RNA described herein, and b) administering to the individual an effective amount of a second agent selected from the group consisting of 5-FU, capecitabine, irinotecan, oxaliplatin, a combination of trifluridein and tipiracil, an angiogenesis inhibitor (such as a VEGF or VEGFR antagonist, e.g., bevacizumab, e.g., ramucirumab, e.g., aflibercept), and a checkpoint inhibitor (such as a PD-1 or CTLA-4 inhibitor, e.g., pembrolizumab, e.g., nivolumab, e.g., lpilimumab).

In some embodiments, there is provided a method of treating a cancer (such as colorectal cancer) in an individual comprising a) administering to the individual a genome-editing complex or nanoparticle comprising an effective amount of guide RNA described herein, and b) administering to the individual an effective amount of a cytotoxic nucleoside analogue (such as capecitabine or an analog thereof). A series of capecitabine analogues containing "an easily hydrolysable radical under physiological conditions" has been claimed by Fujiu et al. (U.S. Pat. No. 4,966,891) and is herein incorporated by reference. The series described by Fujiu includes N4 alkyl and aralkyl carbamates of 5'-deoxy-5-fluorocytidine and the implication that these compounds will be activated by hydrolysis under normal physiological conditions to provide 5'-deoxy-5-fluorocytidine. In some embodiments, the cancer tissue has a KRAS G12V mutation. In some embodiments, the dose of capecitabine for each administration in an individual (such as a human) is about 1 mg/m$^2$ to about 150 mg/m$^2$.

In some embodiments, the dose of the taxane (e.g., paclitaxel) or the mTOR inhibitor (e.g., rapamycin) for each administration in an individual (such as a human) in the nanoparticle composition is about 10 mg/m$^2$ to about 50 mg/m$^2$. In some embodiments, the dose of the guide RNA for each administration in an individual (such as a human) is about 0.001 mg/kg to about 10 mg/kg (e.g., about 0.01 mg/kg to about 1 mg/kg, about 0.1 mg/kg to about 1 mg/kg, about 0.01 mg/kg to about 0.1 mg/kg). In some embodiments, the dose of the guide RNA for each administration in an individual (such as a human) is about 0.01 mg/m$^2$ to about 400 mg/m$^2$ (e.g., about 0.1 mg/m$^2$ to about 100 mg/m$^2$, about 1 mg/m$^2$ to about 50 mg/m$^2$).

In some embodiments, the genome-editing complex or nanoparticle further comprises a polynucleotide encoding a DNA nuclease (such as Cas9). In some embodiments, the dose of the polynucleotide encoding a DNA nuclease (such as Cas9) for each administration in an individual (such as a human) is about 0.001 mg/kg to about 10 mg/kg (e.g., about 0.01 mg/kg to about 1 mg/kg, about 0.1 mg/kg to about 1 mg/kg, about 0.01 mg/kg to about 0.1 mg/kg). In some embodiments, the dose of the polynucleotide encoding a DNA nuclease (such as Cas9) for each administration in an individual (such as a human) is about 0.01 mg/m$^2$ to about 400 mg/m$^2$ (e.g., about 0.1 mg/m$^2$ to about 100 mg/m$^2$, about 1 mg/m$^2$ to about 50 mg/m$^2$).

Dosing and Method of Administering the Combination Therapy

In some embodiments, the genome-editing complex or nanoparticle composition and/or the second agent/therapy are administered simultaneously. In some embodiments, the genome-editing complex or nanoparticle composition and/or the second agent/therapy are administered sequentially. In some embodiments, the genome-editing complex or nanoparticle composition and/or the second agent/therapy are administered concurrently.

The dosing frequency of the genome-editing complex or nanoparticle composition and/or the second agent/therapy may be adjusted over the course of the treatment, based on the judgment of the administering physician. When administered separately, the genome-editing complex or nanoparticle composition and/or the second agent/therapy can be administered at different dosing frequency or intervals. In some embodiments, sustained continuous release formulation of the genome-editing complex or nanoparticle composition and/or the second agent/therapy may be used. Various formulations and devices for achieving sustained release are known in the art. A combination of the administration configurations described herein can also be used.

In some embodiments, the genome-editing complex or nanoparticle composition is administered to the individual at a frequency of about twice a week to about once every two weeks (e.g., about once a week). In some embodiments, the genome-editing complex or nanoparticle composition is administered to the individual at least twice.

The genome-editing complex or nanoparticle composition and/or the second agent/therapy can be administered using the same route of administration or different routes of administration. In some embodiments of the methods described herein, the genome-editing complex or second agent/therapy described herein is administered to the individual by any of intravenous, intratumoral, intraarterial, topical, intraocular, ophthalmic, intraportal, intracranial, intracerebral, intracerebroventricular, intrathecal, intravesicular, intradermal, subcutaneous, intramuscular, intranasal, intratracheal, pulmonary, intracavity, or oral administration, or nebulization (NB) or intratracheal instillation.

In some embodiments, the genome-editing complex or nanoparticle composition and/or the second agent/therapy as described herein is formulated for systemic or tropical administration. In some embodiments, the genome-editing complex or nanoparticle composition and/or the second agent/therapy as described herein is formulated for intravenous, intratumoral, intraarterial, topical, intraocular, ophthalmic, intraportal, intracranial, intracerebral, intracerebroventricular, intrathecal, intravesicular, intradermal, subcutaneous, intramuscular, intranasal, intratracheal, pulmonary, intracavity, or oral administration, or nebulization (NB) or intratracheal instillation.

In some embodiments, dosages of the guide RNA or the total nucleic acid in the cargo (e.g., the guide RNA and the polynucleotide encoding a DNA nuclease) for treatment of human or mammalian subjects are in the range of about 0.001 mg/kg to about 100 mg/kg for each administration. In some embodiments, the exemplary dosage the guide RNA or the total nucleic acid in the cargo (e.g., the guide RNA and the polynucleotide encoding a DNA nuclease) is about 0.005 mg/kg to about 0.5 mg/kg (e.g., about 0.01 mg/kg to about 0.05 mg/kg, about 0.02 mg/kg to about 0.04 mg/kg) for each administration in the individual. In some embodiments, the individual is a human being.

In some embodiments, dosages of the guide RNA or the total nucleic acid in the cargo (e.g., the guide RNA and the polynucleotide encoding a DNA nuclease) for treatment of human or mammalian subjects are in the range of about 0.01 mg/m$^2$ to about 1000 mg/m$^2$ for each administration. In some embodiments, the exemplary dosage of the guide RNA or the total nucleic acid in the cargo (e.g., the guide RNA and the polynucleotide encoding a DNA nuclease) is about 0.01 mg/m$^2$ to about 50 mg/m$^2$ (e.g., about 0.1 mg/m$^2$ to about 5 mg/m$^2$, about 0.5 mg/m$^2$ to about 3 mg/m$^2$) for each administration in the individual. In some embodiments, the individual is a human being.

Exemplary effective amounts of a taxane (e.g., paclitaxel) or an mTOR inhibitor (e.g., rapamycin) in the nanoparticle composition include, but not limited to, about 1 mg/m$^2$ to 150 mg/m$^2$ of a taxane (e.g., paclitaxel) or an mTOR inhibitor (e.g., rapamycin) for each administration. In some embodiments, the dosing frequency of the nanoparticle composition comprising a taxane or mTOR inhibitor is once every two days for one time, two times, three times, four times, five times, six times, seven times, eight times, nine times, ten times, and eleven times. In some embodiments, the dosing frequency is once every two days for five times. In some embodiments, the taxane (e.g., paclitaxel) or the mTOR inhibitor (e.g., rapamycin) is administered over a period of at least ten days, wherein the interval between each administration is no more than about two days, and wherein the dose of the taxane (e.g., paclitaxel) or the mTOR inhibitor (e.g., rapamycin) at each administration is about 1 mg/m$^2$ to about 150 mg/m$^2$. In some embodiments, the taxane (e.g., paclitaxel) or the mTOR inhibitor (e.g., rapamycin) is administered on days 1, 8, and 15 on a 28-day cycle, wherein the dose of the taxane (e.g., paclitaxel) or the mTOR inhibitor (e.g., rapamycin) at each administration is about 1 mg/$m^2$ to about 150 mg/$m^2$. In some embodiments, the taxane (e.g., paclitaxel) or the mTOR inhibitor (e.g., rapamycin) is administered intravenously over 30 minutes on days 1, 8, and 15 on a 28-day cycle, wherein the dose of the taxane (e.g., paclitaxel) or the mTOR inhibitor (e.g., rapamycin) at each administration is about 1 mg/$m^2$ to about 150 mg/$m^2$. In some embodiments, the taxane is paclitaxel. In some embodiments, the dosage of a taxane (e.g., paclitaxel) or an mTOR inhibitor (e.g., rapamycin) in a nanoparticle composition can be in the range of 5-150 mg/$m^2$ (such as 80-150 mg/$m^2$, for example 100-120 mg/$m^2$) when given on a weekly schedule. Other exemplary dosing schedules for the administration of the nanoparticle composition (e.g., paclitaxel/albumin nanoparticle composition) include, but are not limited to, 100 mg/$m^2$, weekly, without break; 75 mg/$m^2$ weekly, 3 out of 4 weeks; 100 mg/$m^2$, weekly, 3 out of 4 weeks; 125 mg/$m^2$, weekly, 3 out of 4 weeks; 125 mg/$m^2$, weekly, 2 out of 3 weeks; 130 mg/$m^2$, weekly, without break; and 20-150 mg/$m^2$ twice a week. The dosing frequency of the composition may be adjusted over the course of the treatment based on the judgment of the administering physician. In some embodiments, the individual is treated for at least about any of one, two, three, four, five, six, seven, eight, nine, or ten treatment cycles. Other exemplary dose of the taxane (in some embodiments paclitaxel) in the nanoparticle composition include, but is not limited to, about any of 50 mg/$m^2$, 60 mg/$m^2$, 75 mg/$m^2$, 80 mg/$m^2$, 90 mg/$m^2$, 100 mg/$m^2$, 120 mg/$m^2$, and 150 mg/$m^2$. For example, the dosage of paclitaxel in a nanoparticle composition can be in the range of about 50-150 mg/$m^2$ when given on a weekly schedule.

Exemplary dosing frequencies of the guide RNA or the second agent/therapy include, but are not limited to, weekly without break; weekly, three out of four weeks; once every three weeks; once every two weeks; weekly, two out of three weeks. In some embodiments, the guide RNA or the second agent/therapy is administered about once every 2 weeks, once every 3 weeks, once every 4 weeks, once every 6 weeks, or once every 8 weeks. In some embodiments, the guide RNA or the second agent/therapy is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week. In some embodiments, the schedule of administration of the guide RNA or the second agent/therapy to an individual ranges from a single administration that constitutes the entire treatment to daily administration. The administration of the guide RNA or the second agent/therapy can be extended over an extended period of time, such as from about a month up to about seven years. In some embodiments, the guide RNA or the second agent/therapy is administered over a period of at least about any of 2, 3, 4, 5, 6, 7, 8, 9, 10, 11, 12, 18, 24, 30, 36, 48, 60, 72, or 84 months.

The doses required for the guide RNA or the second agent/therapy may (but not necessarily) be lower than what is normally required when each agent is administered alone. Thus, in some embodiments, a subtherapeutic amount of the guide RNA or the second agent/therapy is administered. "subtherapeutic amount" or "subtherapeutic level" refer to an amount that is less than the therapeutic amount, that is, less than the amount normally used when the drug in the nanoparticle composition and/or the other agent are administered alone. The reduction may be reflected in terms of the amount administered at a given administration and/or the amount administered over a given period of time (reduced frequency).

In some embodiments, the dose of both the guide RNA or the second agent/therapy are reduced as compared to the corresponding normal dose of each when administered alone. In some embodiments, the guide RNA or the second agent/therapy are administered at a subtherapeutic, i.e., reduced, level. In some embodiments, the dose of guide RNA or the second agent/therapy is substantially less than the established maximum toxic dose (MTD). For example, the dose of the guide RNA or the second agent/therapy is less than about 50%, 40%, 30%, 20%, or 10% of the MTD.

A combination of the administration configurations described herein can be used. The methods described herein (including combination therapy methods described herein) may be performed alone or in conjunction with another therapy, such as chemotherapy, radiation therapy, surgery, hormone therapy, gene therapy, immunotherapy, chemoimmunotherapy, hepatic artery-based therapy, cryotherapy, ultrasound therapy, liver transplantation, local ablative therapy, radiofrequency ablation therapy, photodynamic therapy, and the like.

Additionally, a person having a greater risk of developing a cancer (e.g., a pancreatic cancer) may receive treatments to inhibit or and/or delay the development of the disease.

The compositions described herein allow infusion of the composition to an individual over an infusion time that is shorter than about 24 hours. For example, in some embodiments, the composition is administered over an infusion period of less than about any of 24 hours, 12 hours, 8 hours, 5 hours, 3 hours, 2 hours, 1 hour, 30 minutes, 20 minutes, or 10 minutes. In some embodiments, the composition is administered over an infusion period of about 30 minutes.

Kits

Also provided herein are kits, reagents, and articles of manufacture useful for the methods described herein. In some embodiments, kit contains vials containing the guide RNA, cell-penetrating peptides, other genome-editing molecules and/or other cell-penetrating peptides, combined in one vial or separately in different vials. At the time of patient treatment, it is first determined what particular pathology is to be treated based on for example, gene expression analysis or proteomic or histological analysis of patient samples. Having obtained those results, the cell-penetrating peptides and any molecules (such as a modified Cas9 protein or mRNA encoding the modified Cas9) and/or cell-penetrating peptides are combined accordingly with the appropriate one or more guide RNA to result in complexes or nanoparticles that can be administered to the patient for an effective treatment. Thus, in some embodiments, there is provided a kit comprising: 1) a CPP, 2) a guide RNA, and optionally 3) one or more DNA nuclease or polynucleotide encoding the DNA nuclease. In some embodiments, the kit further comprises other genome-editing molecules and/or other cell-penetrating peptides. In some embodiments, the kit further comprises agents for determining gene expression profiles. In some embodiment, the kit further comprises a pharmaceutically acceptable carrier.

In some embodiments, a kit described herein comprises a) one or more guide RNAs targeting KRAS G12C, G12D and/or G12V as described herein, b) a cell-penetrating peptide, and/or c) an mRNA encoding a CRISPR-associated endonuclease (e.g., unmodified or modified Cas9). In some embodiments, a kit described herein comprises a) one or more guide RNAs targeting KRAS G12C, G12D and/or G12V as described herein, b) a cell-penetrating peptide, and/or c) a CRISPR-associated endonuclease (e.g., unmodified or modified Cas9). In some embodiments, a kit described herein comprises a) one or more guide RNAs targeting KRAS G12C, G12D and/or G12V as described herein, b) a cell-penetrating peptide, and/or c) a fusion protein comprising a CRISPR-associated endonuclease (e.g., unmodified or modified Cas9) and a second enzyme (such as a reversed transcriptase or a nucleobase deaminase enzyme). In some embodiments, a kit described herein comprises a) one or more guide RNAs targeting KRAS G12C, G12D and/or G12V as described herein, b) a cell-penetrating peptide, and/or c) a polynucleotide encoding a fusion protein comprising a CRISPR-associated endonuclease (e.g., unmodified or modified Cas9) and a second enzyme (such as a reversed transcriptase or a nucleobase deaminase enzyme). In some embodiments, the kit further comprises an agent to assess a mutation of KRAS in an individual.

The kits described herein may further comprise instructions for using the components of the kit to practice the subject methods (for example instructions for making the pharmaceutical compositions described herein and/or for use of the pharmaceutical compositions). The instructions for practicing the subject methods are generally recorded on a suitable recording medium. For example, the instructions may be printed on a substrate, such as paper or plastic, etc. As such, the instructions may be present in the kits as a package insert, in the labeling of the container of the kits or components thereof (i.e., associated with the packaging or sub packaging) etc. In some embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate The various components of the kit may be in separate containers, where the containers may be contained within a single housing, e.g., a box.

EXEMPLARY EMBODIMENTS

Embodiment 1. A non-naturally occurring polynucleotide comprising a guide RNA for targeting mutated KRAS comprising a specificity-determining CRISPR RNA (crRNA) comprising a nucleotide sequence substantially complementary to a target sequence selected from the group consisting of SEQ ID NOs: 1-37, 241-257 and 271.

Embodiment 2. The non-naturally occurring polynucleotide of embodiment 1, wherein the guide RNA further comprises an auxiliary trans-activating crRNA (tracrRNA).

Embodiment 3. The non-naturally occurring polynucleotide of embodiment 1 or embodiment 2, wherein the nucleotide sequence substantially complementary to a target sequence is selected from the group consisting of SEQ ID NOs: 1, 3, 6, 8, 15, 16, 19-21, 23, 29, 31, 33, and 34.

Embodiment 4. The non-naturally occurring polynucleotide of embodiment 3, wherein the nucleotide sequence is 100% complementary to a target sequence selected from the group consisting of SEQ ID NOs: 1, 3, 6, 8, 15, 16, 19-21, 23, 29, 31, 33, and 34.

Embodiment 5. The non-naturally occurring polynucleotide of embodiment 4, wherein the nucleotide sequence is 100% complementary to a target sequence selected from the group consisting of SEQ ID NOs: 3, 19, and 34.

Embodiment 6. The non-naturally occurring polynucleotide of any one of embodiments 1-5, wherein the polynucleotide is chemically modified.

Embodiment 7. The non-naturally occurring polynucleotide of any one of embodiments 1-6, wherein the guide RNA has a length of no more than about 200 nucleotides.

Embodiment 8. A genome-editing complex comprising a) a first cell-penetrating peptide, and b) a guide RNA targeting a mutated KRAS, wherein the guide RNA comprises a polynucleotide of any one of embodiments 1-7.

Embodiment 9. The genome-editing complex of embodiment 8, further comprising a DNA nuclease or a nucleotide sequence encoding the DNA nuclease.

Embodiment 10. The genome-editing complex of embodiment 9, wherein the DNA nuclease is selected from the group consisting of a CRISPR-associated protein (Cas) polypeptide, a zinc finger nuclease (ZFN), a transcription activator-like effector nuclease (TALEN), a meganuclease, a variant thereof, a fragment thereof, and a combination thereof.

Embodiment 11. The genome-editing complex of embodiment 10, wherein the DNA nuclease comprises a Cas polypeptide.

Embodiment 12. The genome-editing complex of embodiment 10 or embodiment 11, wherein the Cas polypeptide is Cas9.

Embodiment 13. The genome-editing complex of any one of embodiments 8-12, wherein the first cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides.

Embodiment 14. The genome-editing complex of any one of embodiments 8-13, wherein the first cell-penetrating peptide further comprises one or more moieties covalently linked to N-terminus of the first cell-penetrating peptide, and wherein the one or more moieties are selected from the group consisting of an acetyl, a fatty acid, a cholesterol, a poly-ethylene glycol, a nuclear localization signal, a nuclear export signal, an antibody, a polysaccharide, a linker moiety, and a targeting moiety.

Embodiment 15. The genome-editing complex of embodiment 14, wherein the first cell-penetrating peptide comprises an acetyl group covalently linked to the N-terminus of the first cell-penetrating peptide.

Embodiment 16. The genome-editing complex of embodiment 14 or embodiment 15, wherein the first cell-penetrating peptide comprises a targeting moiety comprising a targeting peptide covalently linked to the N-terminus of the first cell-penetrating peptide.

Embodiment 17. The genome-editing complex of embodiment 16, wherein the targeting peptide is selected from the group consisting of SEQ ID NOs: 196-205 and 235-240.

Embodiment 18. The genome-editing complex of any one of embodiments 8-17, wherein the first cell-penetrating peptide comprises a linker moiety selected from the group consisting of a polyglycine linker moiety, a PEG moiety, Aun, Ava, and Ahx.

Embodiment 19. The genome-editing complex of embodiment 18, wherein the PEG moiety consists of two to seven ethylene glycol units.

Embodiment 20. The genome-editing complex of any one of embodiments 14-19, wherein the first cell-penetrating peptide comprises, from N-terminus, an acetyl group, a targeting moiety and a linker moiety covalently linked to the N-terminus of the first cell-penetrating peptide.

Embodiment 21. The genome-editing complex of any one of embodiments 8-20, wherein the first cell-penetrating peptide further comprises one or more moieties covalently linked to the C-terminus of the first cell-penetrating peptide, and wherein the one or more moieties are selected from the group consisting of a cysteamide, a cysteine, a thiol, an amide, a nitrilotriacetic acid optionally substituted, a carboxyl, a linear or ramified $C_1$-$C_6$ alkyl optionally substituted, a primary or secondary amine, an osidic derivative, a lipid, a phospholipid, a fatty acid, a cholesterol, a polyethylene glycol, a nuclear localization signal, nuclear export signal, an antibody, a polysaccharide, a linker moiety and a targeting moiety.

Embodiment 22. The genome-editing complex of embodiment 21, wherein the first cell-penetrating peptide comprises a cysteamide group covalently linked to its C-terminus.

Embodiment 23. The genome-editing complex of any one of embodiments 8-22, wherein the first cell-penetrating peptide further comprises a carbohydrate moiety.

Embodiment 24. The genome-editing complex of embodiment 23, wherein the carbohydrate moiety is GalNAc.

Embodiment 25. The genome-editing complex of any one of embodiments 8-24, wherein the first cell-penetrating peptide is a retro-inverso peptide.

Embodiment 26. The genome-editing complex of any one of embodiments 8-25, wherein the first cell-penetrating peptide comprises an amino acid sequence selected from the group consisting of SEQ ID NOs: 44-195.

Embodiment 27. The genome-editing complex of embodiment 26, wherein the first cell-penetrating peptide comprises an amino acid sequence selected from the group consisting of SEQ ID NOs: 135-175, 259-260 and 267-269.

Embodiment 28. The genome-editing complex of embodiment 26, wherein the first cell-penetrating peptide comprises an amino acid sequence selected from the group consisting of SEQ ID NOs: 63-117, 261-266 and 270.

Embodiment 29. The genome-editing complex of any one of embodiments 1-28, wherein the molar ratio of the first cell-penetrating peptide to the guide RNA is between about 1:80 and about 1:1.

Embodiment 30. The genome-editing complex of embodiment 29, wherein the molar ratio of the first cell-penetrating peptide to the guide RNA is between about 1:50 and about 1:2.

Embodiment 31. The genome-editing complex of any one of embodiments 9-30, wherein the molar ratio of the first cell-penetrating peptide to the nucleotide sequence encoding the DNA nuclease is between about 1:1 and about 80:1.

Embodiment 32. The genome-editing complex of embodiment 31, wherein the molar ratio of the first cell-penetrating peptide to the nucleotide sequence encoding the DNA nuclease is between about 2:1 and about 50:1.

Embodiment 33. The genome-editing complex of any one of embodiments 8-32, wherein the guide RNA is complexed with the first cell-penetrating peptide.

Embodiment 34. The genome-editing complex of any one of embodiments 9-33, wherein the nucleotide sequence encoding the DNA nuclease is complexed with the first cell-penetrating peptide.

Embodiment 35. The genome-editing complex of any one of embodiments 8-34, further comprising one or more additional guide RNAs comprising different guide sequences.

Embodiment 36. The genome-editing complex of embodiment 35, wherein at least two of the two or more guide RNAs target one single KRAS mutation.

Embodiment 37. The genome-editing complex of embodiment 36, wherein at least two of the two or more guide RNAs target two or more different KRAS mutations.

Embodiment 38. The genome-editing complex of embodiment 36 or 37, wherein at least two of the two or more guide RNAs target G12D, G12V, and/or G12C.

Embodiment 39. The genome-editing complex of any one of embodiments 1-38, wherein the average diameter of the genome-editing complex is between about 10 nm and about 300 nm.

Embodiment 40. A nanoparticle comprising a core comprising the genome-editing complex of any one of embodiments 1-39.

Embodiment 41. The nanoparticle of embodiment 40, wherein the core further comprises one or more additional genome-editing complexes of any one of embodiments 1-40.

Embodiment 42. The nanoparticle of embodiment 41, wherein the one or more additional genome-editing complex comprises at least one or more the guide RNAs that targets a different KRAS mutation.

Embodiment 43. The nanoparticle of any one of embodiments 40-42, wherein the core is complexed with a second cell-penetrating peptide.

Embodiment 44. The nanoparticle of embodiment 43, wherein the second cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides.

Embodiment 45. The nanoparticle of embodiment 44, wherein the second cell-penetrating peptide is selected wherein the second cell-penetrating peptide is selected from the group consisting of VEPEP-3 peptides, VEPEP-6 peptides, VEPEP-9 peptides, and ADGN-100 peptides.

Embodiment 46. The nanoparticle of embodiment 45, wherein the second cell-penetrating peptide comprises an amino acid sequence selected from the group consisting of SEQ ID NOs: 44-175.

Embodiment 47. The nanoparticle of any one of embodiments 41-46, wherein the second cell-penetrating peptide in the nanoparticle is covalently linked to a targeting moiety by a linking moiety.

Embodiment 48. The nanoparticle of any one of embodiments 40-47, wherein the core is coated by a shell comprising a peripheral cell-penetrating peptides.

Embodiment 49. The nanoparticle of embodiment 48, wherein the peripheral cell-penetrating peptides are selected from the group consisting of VEPEP-3 peptides, VEPEP-6 peptides, VEPEP-9 peptides, and ADGN-100 peptides.

Embodiment 50. The nanoparticle of embodiment 49, wherein the peripheral cell-penetrating peptide comprises an amino acid sequence selected from the group consisting of SEQ ID NOs: 44-175.

Embodiment 51. The nanoparticle of any one of embodiments 40-50, wherein the peripheral cell-penetrating peptide in the shell is covalently linked to a targeting moiety by a linking moiety.

Embodiment 52. The nanoparticle of any one of embodiments 40-51, wherein the average diameter of the nanoparticle is between about 10 nm and about 400 nm.

Embodiment 53. A pharmaceutical composition comprising the guide RNA of any one of embodiments 1-7, the genome-editing complex of any one of embodiments 8-39, or the nanoparticle of any one of embodiments 40-52, and a pharmaceutically acceptable carrier.

Embodiment 54. The pharmaceutical composition of embodiment 53, wherein the composition comprises two or more nanoparticles, wherein the two or more nanoparticles comprise different guide RNAs that target different KRAS mutations.

Embodiment 55. A method of preparing the genome-editing complex of any one of embodiments 8-39, comprising combining the first cell-penetrating peptide with the guide RNA, thereby forming the genome-editing complex.

Embodiment 56. A method of modifying mutated KRAS in a cell, comprising contacting the cell with guide RNA of any one of embodiments 1-7, the genome-editing complex of any one of embodiments 8-39, or the nanoparticle of any one of embodiments 40-52.

Embodiment 57. A method of treating a cancer in an individual comprising administering the individual an effective amount of the pharmaceutical composition of embodiment 53.

Embodiment 58. The method of embodiment 57, further comprising administering a second agent.

EXAMPLES

The examples below are intended to be purely exemplary of the application and should therefore not be considered to limit the application in any way. The following examples and detailed description are offered by way of illustration and not by way of limitation.

Example 1. Design of sgRNAs Targeting a Single-Nucleotide Substitution on Codon-12 of KRAS A new strategy was developed to impair cancer cell proliferation by directly targeting specific mutations at codon-12 (G12V, G12D and G12C) of the KRAS oncogene. A selective ADGN/CRISPR/Cas9 system that selectively targets and disrupts the oncogenic allele of KRAS mutants was designed for in vivo systemic administration and leading to inhibition of cancer cell proliferation and tumor growth. In order to target mutant KRAS alleles in cancer cells with the CRISPR-Cas9 system, Specific guide RNAs targeting c.35G>T (G12V), c.35G>A (G12D) and c.34G>T (G12C) KRAS mutations were designed and their potency on different cancer cells using ADGN nanoparticles delivery system was validated. Then it was evaluated whether targeting mutant KRAS can suppress tumor growth in vivo when administered intravenously using ADGN nanoparticles.

Major oncogenic mutations occur on codon-12 of KRAS exon-2. In order to target mutant KRAS alleles in cancer cells with the CRISPR-Cas9 system, specific guide RNAs targeting the following single nucleotide missense substitution c.35G>T (G12V), c.35G>A (G12D) and c.34G>T (G12C) were identified. These mutated target nucleotides are located within the region adjacent to the PAM sequence, and was thus chosen to be targeted by CRISPR/Cas9. sgRNAs to target the wild-type KRAS (sgRNAWT) was also designed as a negative control for the cell lines. See FIG. 18.

TABLE 1 sgRNA target KRAS G12V mutation. SgRNA c.35G > T

| SEQUENCE | PAM | NAME |
|---|---|---|
| TGG TAG TTG GAG CTG TTG GCG T (SEQ ID NO: 241) | AGG | gRNA35T1 |
| CTT GTG GTA GTT GGA GCT GT (SEQ ID NO: 2) | TGG | gRNA35T2 |
| GGT AGT TGG AGC TGT TGG CG (SEQ ID NO: 3) | TAG | gRNA35T3 |
| AGC TGT TGG CGT AGG CAA (SEQ ID NO: 242) | GAG | gRNA35T4 |
| TGT TGG CGT AGG CAA GAGT (SEQ ID NO: 243) | GCC | gRNA35T5 |
| GTT GGA GCT GTT GGC GT (SEQ ID NO: 244) | AGG | gRNA35T6 |
| TTG TGG TAG TTG GAG CTG T (SEQ ID NO: 245) | TGG | gRNA35T7 |
| GTA GTT GGA GCT GTT GGC GT (SEQ ID NO: 8) | AGG | gRNA35T8 |
| GCT GTT GGC GTA GGC AA (SEQ ID NO: 246) | GAG | gRNA35T9 |
| TAG TTG GAG CTG TTG GCG T (SEQ ID NO: 10) | AGG | gRNA35T10 |
| TGT TGG CGT AGG CAA GAG TGC CTT G (SEQ ID NO: 11) | ACG | gRNA35T11 |

TABLE 2 sgRNA target KRAS G12D mutation. SgRNA 35G > A.

| SEQUENCES | PAM | NAME |
|---|---|---|
| CTT GTG GTA GTT GGA GCT GA (SEQ ID NO: 15) | TGG | gRNA35A1 |
| GGT AGT TGG AGC TGA TGG CG (SEQ ID NO: 247) | TAG | gRNA35A2 |
| AGC TGA TGG CGT AGG CAA (SEQ ID NO: 248) | GAG | gRNA35A3 |
| TGA TGG CGT AGG CAA GAGT (SEQ ID NO: 249) | GCC | gRNA35A4 |
| AGT TGG AGC TGA TGG CGT (SEQ ID NO: 19) | AGG | gRNA35A5 |
| GTT GGA GCT GAT GGC GT (SEQ ID NO: 250) | AGG | gRNA35A6 |
| GTA GTT GGA GCT GAT GGC GT (SEQ ID NO: 21) | AGG | gRNA35A7 |
| TTG TGG TAG TTG GAG CTG A (SEQ ID NO: 251) | TGG | gRNA35A8 |
| GCT GAT GGC GTA GGC AA (SEQ ID NO: 252) | GAG | gRNA35A9 |

TABLE 2-continued

| sgRNA target KRAS G12D mutation. SgRNA 35G > A. | | |
|---|---|---|
| SEQUENCES | PAM | NAME |
| TAG TTG GAG CTG ATG GCG T (SEQ ID NO: 24) | AGG | gRNA35A10 |
| TGA TGG CGT AGG CAA GAG TGC CTT G (SEQ ID NO: 25) | ACG | gRNA35A11 |

TABLE 3

| sgRNA target KRAS G12C mutation. SgRNA 34G > T | | |
|---|---|---|
| SEQUENCES | PAM | NAME |
| CTT GTG GTA GTT GGA GCT TG (SEQ ID NO: 29) | TGG | gRNA34T1 |
| AGC TTG TGG CGT AGG CAA (SEQ ID NO: 253) | GAG | gRNA34T2 |
| GTT GGA GCT TGT GGC GT (SEQ ID NO: 254) | AGG | gRNA34T3 |
| GGT AGT TGG AGC TTG TGG CG (SEQ ID NO: 255) | TAG | gRNA34T4 |
| TTG TGG TAG TTG GAG CTT G (SEQ ID NO: 33) | TGG | gRNA34T5 |
| GTA GTT GGA GCT TGT GGC GT (SEQ ID NO: 34) | AGG | gRNA34T6 |
| GCT TGT GGC GTA GGC AA (SEQ ID NO: 256) | GAG | gRNA34T7 |
| CTT GTG GCG TAG GCA AGAGT ((SEQ ID NO: 257) | GCC | gRNA34T8 |
| CTT GTG GCG TAG GCA AGA GTG CCT TG (SEQ ID NO: 37) | ACG | gRNA34T9 |
| TTGTGGCGTAGGCAAGAGTGCCTTG (SEQ ID NO: 271) | ACG | gRNA34T10 |

Example 2 Preparation of ADGN Peptide/Cas9 mRNA/sgRNA Complexes

Materials

Lipofectamine 2000, RNAiMAX, TranscriptAid T7 transcription kit, MEGAclear transcription Clean Up kit, GeneArt Genomic Cleavage Detection kit, and Platinum Green Hot Start PCR mix were obtained from Thermo Fisher life Science (France). AST/ALT/BUN and Creatinine activity assay kits were obtained from Sigma (France) and Thermo Fisher life Science (France). Antibodies: phospho-Akt (Ser 473) (CST, #9271, RRID:AB_329825) and phospho-p44/42 MAPK (Erk1/2) (Thr202/Tyr204) (CST, #4370, RRID:AB_2315112) are from CST.

mRNA: CleanCap™ Cas9mRNA (5moU) and CleanCap™ Luc mRNA (5 moU) were obtained for Trilink Biotechnology (USA).

gRNA: Luciferase gRNA was obtained by in vitro transcription using an sgRNA expression plasmid (Addgene #74190, plasmid pLCKO_Luciferase_sgRNA) according to Hart, T., et al. (2015). *Cell,* 163(6), 1515-1526. Luciferase target site: ACAACTTTACCGACCGCGCC. Generation of sgRNA was performed using a generic sgRNA expression plasmid containing a T7 promoter adapter sequence as template for a PCR product, which can be in vitro transcribed. Linear DNA fragments containing the T7 promoter binding site followed by the about 20-bp sgRNA target sequence were transcribed in vitro using TranscriptAid T7 high Yield transcription Kit (Thermo Fisher life science, France) following the manufacturer's instructions. In vitro transcribed gRNAs were precipitated with ethanol and further purified using MEGAclear transcription clean up Kit (Thermo Fisher life Science).

KRAS sgRNAs targeting KRAS mutation at codon 12 were obtained from Thermo Fisher Life science (France) and Trilink Biotechnology (USA).

Stock solutions of sgRNAs were solubilized in water, quantified by UV absorbance and stored at −80° C.

ADGN Peptides: The following peptide sequences were used.

TABLE 4

| | |
|---|---|
| ADGN-100 | beta-AKWRSAGWRWRLWRVRSWSR-NH2 |
| ADGN-100-Hydro-3 | Ac-YIGSR-Ava-KWRSALWRWRLWRVRSWSR-NH2 |
| ADGN-100-Hydro-5 | Ac-YIGSR-Aun-KWRSALWRWRLWRVRSWSR-NH2 |
| ADGN-100 Hydro-7 | Ac-YIGSR-Ahx-KWRSALWRWRLWRVRSWSR-NH2 |
| ADGN-100-PEG2 | Ac-(PEG)2-A-KWRSALWRWRLWRVRSWSR-NH2 |
| ADGN-100-HYPEG2 | Ac-YIGSR-(PEG)2-βA-KWRSALWRWRLWRVRSWSR-NH2 |
| ADGN-106 | beta-ALWRALWRLWRSLWRLLWKA-NH2 |
| ADGN-106-Hydro-3 | Ac-YIGSR-Ava-ALWRALWRLWRSLWRLLWK-NH2 |
| ADGN-106-Hydro-5 | Ac-YIGSR-Aun-ALWRALWRLWRSLWRLLWK-NH2 |
| ADGN-106 hydro-7 | Ac-YIGSR-Ahx-ALWRALWRLWRSLWRLLWK-NH2 |
| ADGN-106-PEG2 | Ac-(PEG)2-βALWRALWRLWRSLWRLLWK-NH2 |
| ADGN-106-HYPEG2 | Ac-YIGSR-(PEG)2-βALWRALWRLWRSLWRLLWK-NH2 |

Cell lines: All cell lines were obtained from the ATCC. Pancreatic cancer (PDAC): PANC1 Heterozygous for KRAS p.Gly12Asp (c.35G>A), PK 45H Homozygous for KRAS p.Gly12Asp (c.35G>A), PK1 Heterozygous for KRAS p.Gly12Asp (c.35G>A), MIA-PACA Homozygous for KRAS p.Gly12Cys (c.34G>T)

Colorectal cancer (CRC) SW480 Homozygous for KRAS p.Gly12Val (c.35G>T), SW403 Heterozygous for KRAS p.Gly12Val (c.35G>T), LS513 Heterozygous for KRAS p.Gly12Asp (c.35G>A), HT-29 WT KRAS and Homozygous for TP53 p.Arg273His (c.818G>A), HT-29 WT for KRAS Lung Cancer (NSCLC), NCI H23 and H358 Heterozygous for KRAS p.Gly12Cys (c.34G>T), H1299 WT for KRAS Methods:

Complex formation with mRNA:gRNA: ADGN peptide/mRNA/gRNA particles were prepared at a 20:1:1 molar ratio. ADGN/Cas9mRNA/sgRNA complexes were prepared at a 20/1/1 molar ratio with 0.5 μg mRNA: 1.5 μg sgRNA and 5% Glucose or DMEM (example for 96 well plates). It is suggested to prepare a minimum volume of complexes for 6 wells of 96 well. Premixed Cas9 mRNA/gRNA were prepared in sterile water at room temperature in a glass vial (1-4 ml). ADGN-peptide solution was added dropwise (1 drop/sec) under magnetic agitation at 400 rpm to obtain a 1:2 ratio, and incubated for 30 min at room temperature or 37° C. Just before transfection, 150 µl Glucose or DMEM was added and the solution was mixed under magnetic agitation at 400 rpm for 1 minute. Then the solution was incubated for 5 min at 37° C. Then the complexes was ready for cell transfection or IV administration. Prior to IV administration, complexes were diluted in sucrose 5% solution.

Transfection protocol. The following protocols are reported for 24/48/96 well plate format transfection. Cells should be trypsinized and seeded a day prior transfection Cells were cultured in Dulbecco's Modified Eagle's Medium (DMEM), supplemented with 2 mM glutamine, 1% antibiotics (streptomycin 10,000 µg/mL, penicillin, 10,000 IU/mL) and 10% (w/v) foetal calf serum (FCS), at 37° C. in a humidified atmosphere containing 5% CO2. 96 well plates seeded with 50,000 cells, the day prior transfection, grown to 60-80% confluence and set up to be at around 70% confluence at the day of transfection. Before transfection, cells are washed twice with DMEM (without FBS and pen/strep) (100 µl/well). Cells were then overlaid with 25 µl of complex solution, mixed gently and incubated for 10 min at 37° C.+5% $CO_2$. 50 µl of fresh DMEM (without FBS and Antibiotics) was added and cells were incubated for 2 h at 37° C.+5% $CO_2$ (time of exposure can be adjusted based on sensitivity of the cells). 250 µL of DMEM (containing 10% FCS and 1% antibiotics) were then added without removing the overlay of ADGN peptide/mRNA complexes. Cells were returned to the incubator (37° C., 5% $CO_2$) and analyzed 48 hours to 72 hours post transfection.

TABLE 5

| Plate format | 24 well | 48 well | 96 well |
|---|---|---|---|
| ADGN-mRNA Complexes | 225 µl | 100 µl | 25 µl |
| DMEM | 450 µl | 200 µl | 30 µl |
| DMEM (+10% FBS) | 2.250 µl | 1000 µl | 250 µl |
| Final volume | 2925 µl | 1300 µl | 305 µl |

Figure 19A:
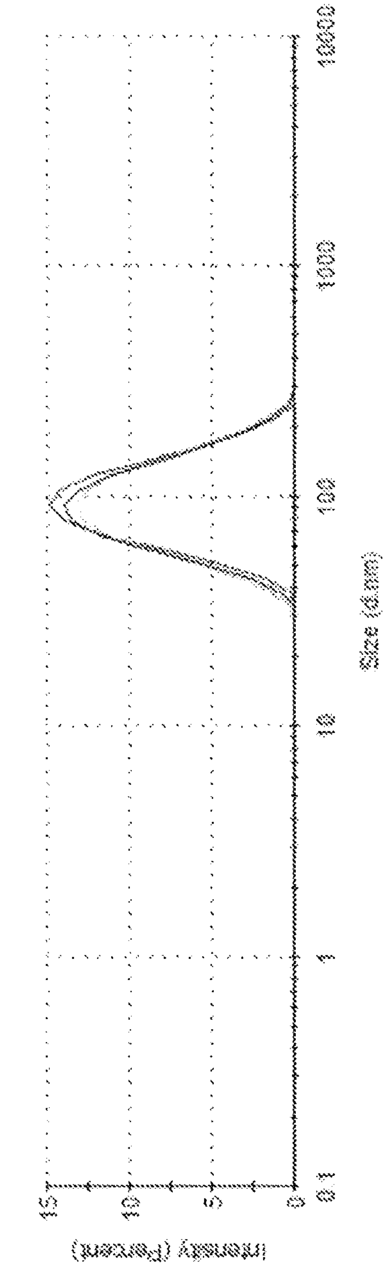
FIGS. 19A-19B shows the particle sizes and level of aggregation of the ADGN/mRNA/gRNA complexes measured on DLS NanoZS (Malvern Ltd). ADGN-Hy3/mRNA/gRNA particles were prepared at a 20/1/1 molar ratio in either 5% Glucose or DMEM. Data are reported in size distribution by intensity (FIG. 19A) and size distribution by volume (FIG. 19B).
Figure 19B:
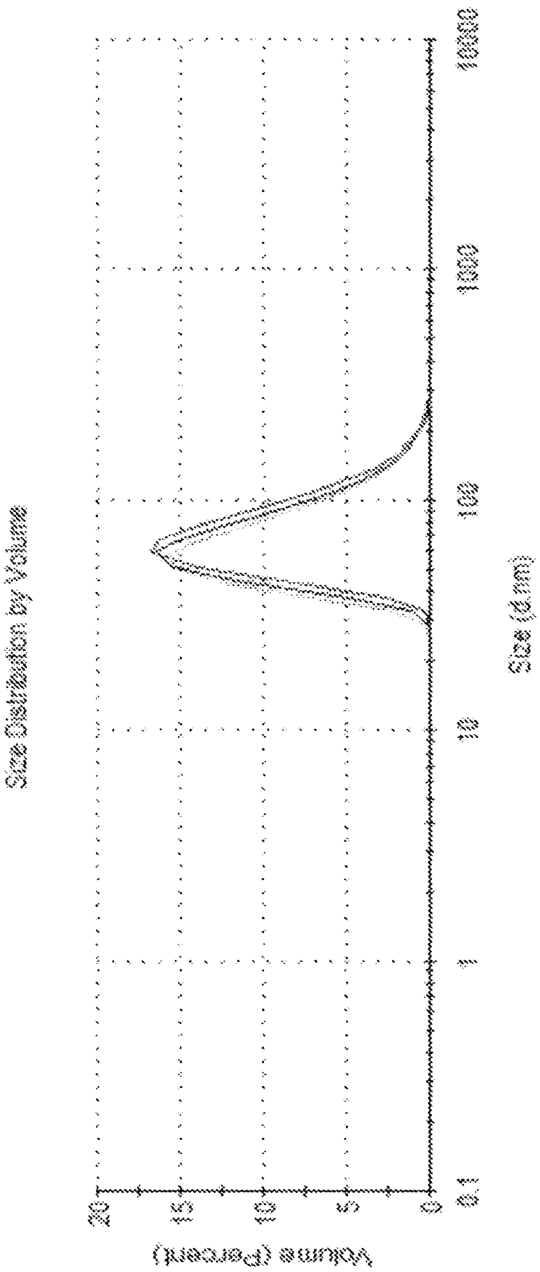

The ability of ADGN-peptides to form stable nanoparticles with CAS9mRNA/gRNA was analyzed. The particle sizes and level of aggregation were measured on DLS NanoZS (Malvern Ltd). The mean size and the polydispersity of the ADGN/mRNA/gRNA complexes were determined at 25° C. for 3 minute per measurement. Data are shown in FIGS. 19A-19B for a mean of 3 separate experiments.

ADGN peptide-mRNA:sgRNA complexes were characterized by dynamic light scattering (DLS Malvern Nanosizer) prior transfection. As reported in FIGS19 ADGN peptides formed stable highly homogenous nanoparticles with mRNA/gRNA with a mean size ranging between 80 to 100 nm and polydispersity index of 0.183.

Example 3. ADGN Mediated CRISPR Targeting KRAS Mutation at Codon-12 Selective and Efficient Disruption of Mutant KRAS in Cancer Cells In order to target mutant KRAS alleles in cancer cells with the CRISPR-Cas9 system, we have identified specific guide RNAs targeting c.35G>T (G12V), c.35G>A (G12D) and c.34G>T (G12C) KRAS mutations and evaluated their potency on different cancer cells using ADGN nanoparticles delivery system. ADGN-100, ADGN-106, and different variant have been used for formulation and both ex vivo and in vivo evaluation.

For pancreatic cancer (PDAC), the following cell lines and KRAS targets were used: PANC1 Heterozygous for KRAS p.Gly12Asp (c.35G>A), PK 45H Homozygous for KRAS p.Gly12Asp (c.35G>A), PK1 Heterozygous for KRAS p.Gly12Asp (c.35G>A), MIA-PACA Homozygous for KRAS p.Gly12Cys (c.34G>T)

For colorectal cancer (CRC), the following cell lines and KRAS targets were used: SW480 Homozygous for KRAS p.Gly12Val (c.35G>T), SW403 Heterozygous for KRAS p.Gly12Val (c.35G>T), and LS513 Heterozygous for KRAS p.Gly12Asp (c.35G>A). Results were compared to control cell lines including HT-29 WT KRAS and Homozygous for TP53 p.Arg273His (c.818G>A), HT-29 WT for KRAS.

For lung cancer (NSCLC), NCI H23 and H358 Heterozygous for KRAS p.Gly12Cys (c.34G>T) cell lines and mutations were compared to H1299 WT for KRAS as controls.

Nine different gRNAs targeting KRAS 35G>T mutant G12V (gRNA35T1, gRNA35T2, gRNA35T3, gRNA35T4, gRNA35T5, gRNA35T6, gRNA35T7, gRNA35T8 and gRNA35T9 (see FIG. 18)) were evaluated on SW403 and SW480 cancer cells harboring G12V KRAS mutation. Cas9 mRNA (0.15 µg) and gRNA (0.2 µg) were associated with ADGN-peptides as reported in experimental procedure. SW403, SW480 and HT-29 cells were cultured in 48 well plate format and treated with free mRNACas9-gRNA, or ADGN-100/mRNACas9:gRNA complex. Indel frequencies at the endogenous target sequences was evaluated 72 hours after transfection by either T7E1 method and by deep sequencing. Cell proliferation was analyzed over a period of 5 days using CellTiter Glow kits on GlowMax (Promega).

As reported in FIG. 1A, gRNA35T1, 35T3, 35T6, 35T7 and 35T8 specifically induced indel editing and efficient disruption of G12V mutant KRAS in cancer cells, but not in wild type KRAS HT29 cells. Deep sequencing showed that ADGN-mediated delivery of gRNA35T3 sgRNA resulted in indel frequencies of 65% in SW403 cells, which are heterozygous for the 35G>T mutation, and 81% in SW480 cells, which are homozygous for the 35G>T mutation. 35T6 sgRNA resulted in indel frequencies of 18% in SW403 cells, and 39% in SW480 cells. 35T1 sgRNA resulted in indel frequencies of 35% in SW403 cells, and 57% in SW480 cells. 35T8 sgRNA resulted in indel frequencies of 40% in SW403 cells, and 51% in SW480 cells. In contrast, gRNA35T2, 35T5 and 35T9 induced less than 15% G12V KRAS gene editing. Although, gRNA35T4 resulted in a significant G12V KRAS mutant editing (22% in SW403 and 41% in SW480), this sgRNA sequence is not specific for G12V mutant KRAS and also induced disruption of WT KRAS in HT29 cells.

Figure 1B:
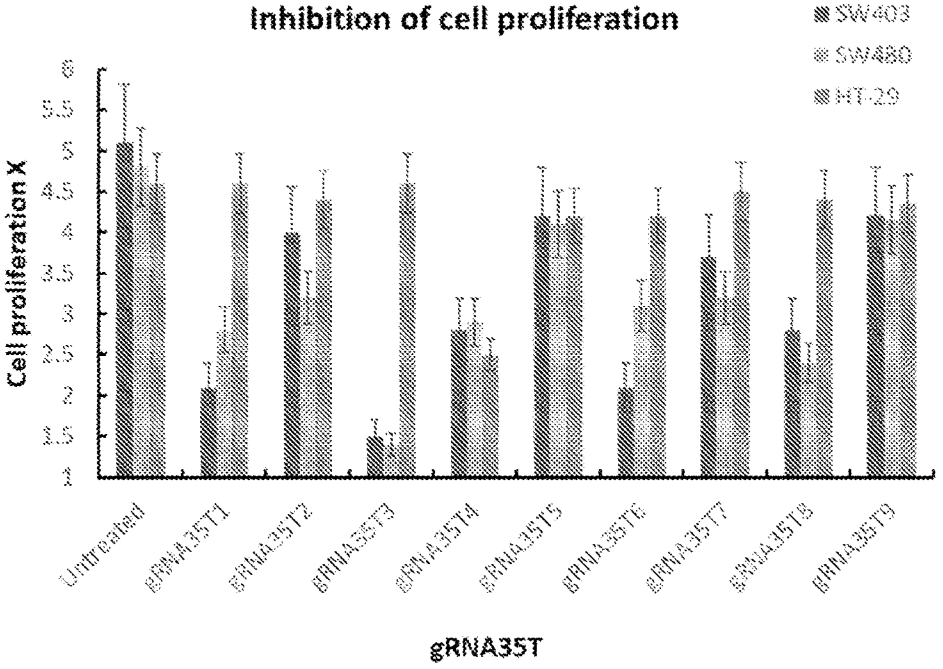

We next determined whether disruption of mutant KRAS can affect cancer cells proliferation. As reported in FIG. 1B, gRNA35T1, 35T3, 35T6 and 35T8 specifically inhibit proliferation or survival of SW480 and SW403 cells, and did not affect HT29 cells harboring KRAS WT. As reported for gene editing results, the best response was obtained with gRNA35T3>gRNA35T8>gRNA35T6/35T1. Cell proliferation analysis confirmed the fact that gRNA35T4 is not specific to G12V mutation and also altered also HT-29 proliferation. gRNA35T3 blocked SW403 and SW480 cell proliferation by 75% and is 1.5 and 2 fold more efficient than gRNA35T8 and gRNA35T6. gRNA35T3 guide efficiently target 35G>T (G12V) mutant KRAS without alteration of the wild-type allele and was selected for further evaluation.

Nine different gRNAs targeting KRAS 35G>A mutant G12D (gRNA35A1, gRNA35A2, gRNA35A3, gRNA35A4, gRNA35A5, gRNA35A6; gRNA35A7, gRNA35A8, gRNA35A9) were evaluated on LS513, Panc1, PK-45H, and PK1 cancer cells harboring G12D KRAS mutation. Cas9 mRNA (0.1 μg) and gRNA (0.2 μg) were associated with ADGN-peptide at molar ratio 20/1 (peptide/nucleic acid). LS513, Panc1, PK-45H, PK1, HS-68 and HT-29 cells were cultured in 48 well plate format and treated with free mRNACas9-gRNA, or ADGN/mRNACas9:gRNA complex. Indel frequencies at the endogenous target sequences was evaluated 72 hours after transfection by either T7E1 method or deep sequencing. Cell proliferation was analyzed over a period of 5 days using CellTiter Glow kits on GlowMax (Promega).

Figure 2A:
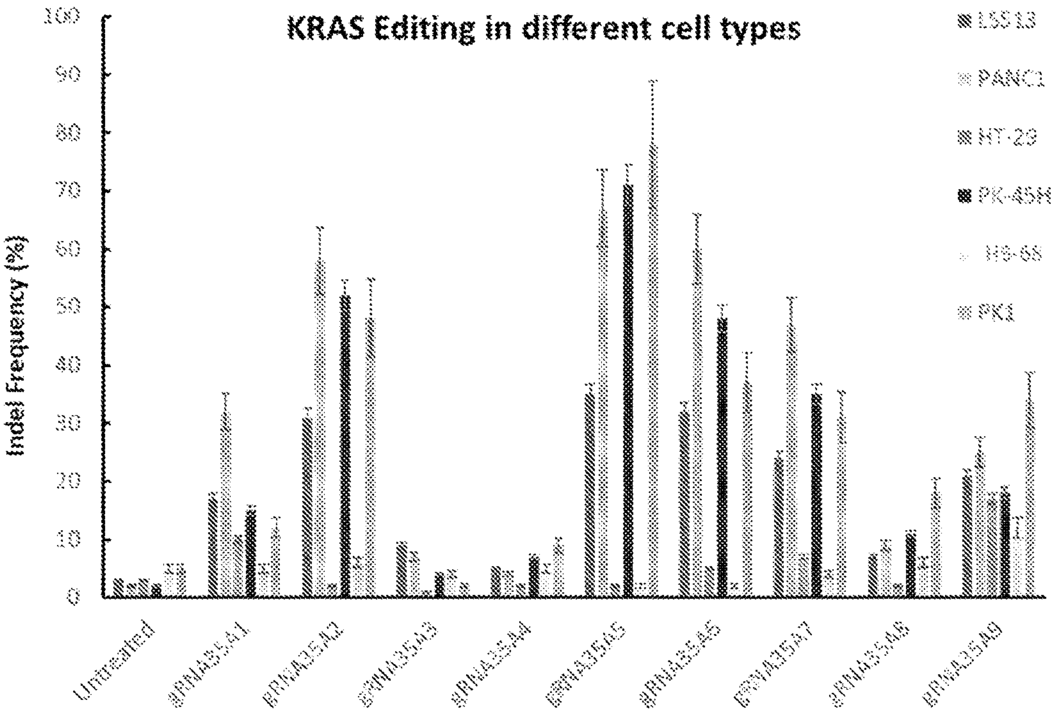
FIGS. 2A-2B show the evaluation of gRNAs targeting KRAS 35G>A mutant G12D KRAS on Panc1, LS513, PK-45H, PK-1, HS-68 and HT-29 cells. Cancer cells were treated with the different ADGN/Cas9mRNA/gRNA (0.15 μg/0.2 μg) complexes.

As reported in FIG. 2A, gRNA35A2, 35A5, 35A7, 35A6 and 35A9 induced efficient disruption of G12D mutant KRAS in cancer cells, but not in wild type KRAS cells (HT29 or HS-68 cells). In contrast, gRNA35A3, 35A4 and 35A8 induced less than 15% G12D KRAS gene editing and gRNA35A1 in not specific for G12D mutation and also affected wild type KRAS cells (HT-29 and HS-68).

TABLE 6

| Cell lines | LS513 | PANC1 | HT-29 | PK-45H | HS68 | PK1 |
|---|---|---|---|---|---|---|
| Untreated | 3 ± 1 | 2 ± 1 | 3 ± 1 | 2 ± 0.4 | 5 ± 1 | 5 ± 1 |
| gRNA35A1 | 17 ± 2 | 32 ± 2 | 10 ± 1 | 15 ± 0.8 | 8 ± 1 | 12 ± 1 |
| gRNA35A2 | 31 ± 2 | 58 ± 4 | 2 ± 1 | 52 ± 5 | 6 ± 2 | 48 ± 2 |
| gRNA35A3 | 9 ± 1 | 7 ± 1 | 1 ± 0.5 | 4 ± 1 | 4 ± 1 | 2 ± 0.5 |
| gRNA35A4 | 5 ± 2 | 4 ± 1 | 2 ± 1 | 7 ± 2 | 5 ± 0.7 | 9 ± 0.1 |
| gRNA35A5 | 35 ± 4 | 67 ± 5 | 2 ± 1 | 75 ± 7 | 2 ± 1 | 78 ± 8 |
| gRNA35A6 | 32 ± 5 | 60 ± 2 | 5 ± 1 | 48 ± 1 | 2 ± 1 | 37 ± 0.4 |
| gRNA35A7 | 24 ± 2 | 47 ± 1 | 7 ± 2 | 35 ± 0.5 | 4 ± 0.4 | 31 ± 2 |
| gRNA35A8 | 7 ± 1 | 9 ± 2 | 2 ± 0.2 | 11 ± 1 | 6 ± 0.1 | 18 ± 1 |
| gRNA35A9 | 21 ± 3 | 25 ± 3 | 17 ± 3 | 18 ± 2 | 12 ± 1 | 34 ± 1 |

As reported in Table 6, deep sequencing showed that delivery of gRNA35A5 sgRNA resulted in indel frequencies of 78% in PK1 and 75% in PK-45H cells, which are heterozygous for the 35G>A mutation, of 67% in PANC-1 cells and 42% in LS513 cells, which are homozygous for the 35G>A mutation.

Figure 2B:
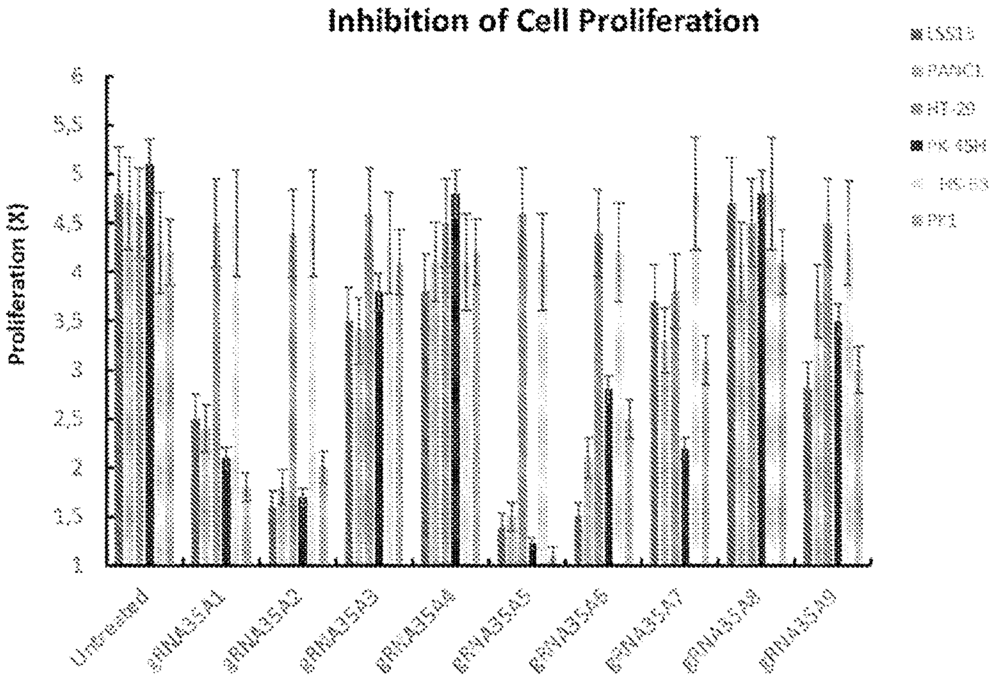

We next determined whether disruption of mutant KRAS can affect cancer cells proliferation. As reported in FIG. 2B, gRNA35A5, 35A2, 35A1, 35A6 and 35A7 specifically inhibit proliferation or survival of PANC1, PK1, LS513 and PK-45H cells and do not affected HT29 or HS-68 cells harboring KRAS WT. We have selected gRNA35A5 guide that efficiently target 35G>A (G12D) mutant KRAS without alteration of the wild-type allele. gRNA35A5 blocked PANC1; PK1, LS513 and PK-45H cells proliferation by 80% and is 2 and 3 fold more efficient than gRNA35A2 and gRNA35A6.

Example 4. ADGN Mediated CRISPR Targeting KRAS G12C Mutation

Eight different gRNAs targeting KRAS 34G>T mutant G12C (gRNA34T1, gRNA34T2, gRNA34T3, gRNA34T4, gRNA34T5, gRNA34T6, gRNA34T7 and gRNA34T8) were evaluated on MIA-PACA, H23, H358, H29 and PANC1 cells. Cas9 mRNA (0.1 μg) and gRNA (0.2 μg) were associated with ADGN peptide at molar ratio 20/1 (peptide/nucleic acid). MIA-PACA, H23, H358, PANC1 and HT29 cells were cultured in 48 well plate format and treated with free mRNACas9-gRNA, or ADGN/mRNACas9:gRNA complex. Indel frequencies at the endogenous target sequences was evaluated 72 hours after transfection by either T7E1 method or deep sequencing. Cell proliferation was analyzed over a period of 5 days using CellTiter Glow kits on GlowMax (Promega).

Figure 3A:
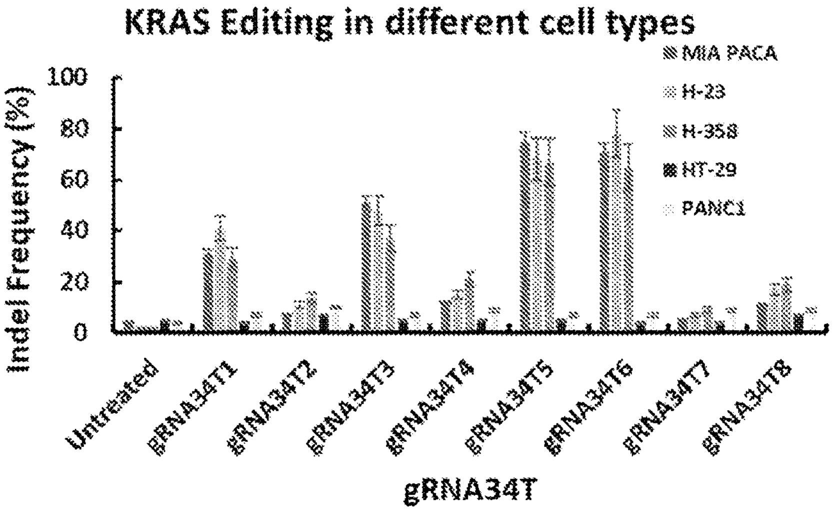
FIGS. 3A-3B show the evaluation of gRNAs targeting KRAS 35G>A mutant G12D KRAS on Mia-PACA, H-23, H-358, PANC1 and HT-29 cells. Cancer cells were treated with the different ADGN/Cas9mRNA/gRNA (0.15 μg/0.2 μg) complexes.
Figure 3B:
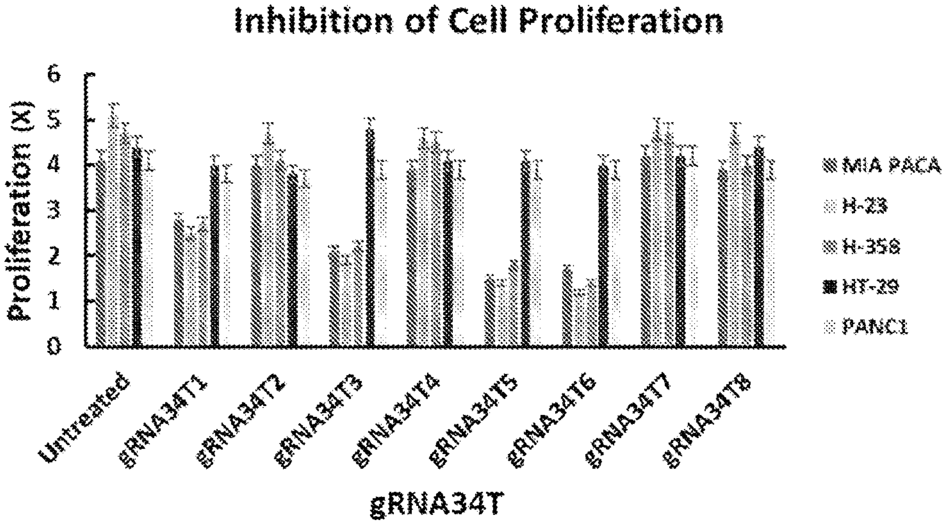

As reported in FIG. 3A, gRNA34T1, 34T3, 34T5 and 34T6 induced indel editing and efficient disruption of G12C mutant KRAS in cancer cells, but not of WT KRAS in HT29 cell or G12C KRAS mutation in PANC1 cells. In Contrast, gRNA34T2, 34T4, 34T7 and 34T8 are inefficient or less specific affecting wild type KRAS. Deep sequencing showed that delivery gRNA34T6 sgRNA resulted in indel frequencies of 71%, 78% and 67% in Mia-PACA, H23 and H358 cells, respectively. 34T5 sgRNA resulted in indel frequencies of 75%, 68% and 67% in Mia-PACA, H23 and H358 cells, respectively. 34T3 sgRNA resulted in indel frequencies of 51%, 48% and 37% in Mia-PACA, H23 and H358 cells, respectively. 34T1 sgRNA resulted in indel frequencies of 34%, 41% and 29% in Mia-PACA, H23 and H358 cells, respectively We next determined whether disruption of mutant KRAS can affect cancer cells proliferation. As reported in FIG. 3B, gRNA34T5, 34T6, 34T3 and 34T1 specifically inhibit proliferation or survival of Mia-PACA, H23 and H358 cells, but do not affected KRAS WT HT29 or HS-68 cells or G12C KRAS mutated PANC1 cells. gRNA34T6 blocked Mia-PACA, H23 and H358 cells proliferation by 75% and is 2 and 3 fold more efficient than gRNA34T5 and gRNA34T3. We have selected gRNA34T6 guide that efficiently target 34G>T (G12C) mutant KRAS without alteration of the wild-type allele.

Example 5. ADGN Mediated CRISPR Targeting KRAS G12D, G12V or G12C Mutation

In order to confirm the specificity of sgRNAs targeting G12V, G12C or G12D KRAS mutation, gRNA35T3 targeting G12V, gRNA34T6 targeting G12C, and gRNA35A5 targeting G12D were evaluated on a large panel of cancer cells harboring different KRAS mutations including SW403, SW480, PANC1, PK-45H, PK-1, MIA-PACA, H23, H358, HT-29, HS-68 and LS513. Cas9 mRNA (0.2 μg) and gRNA (0.4 μg) were associated with ADGN peptide at molar ratio 20/1 (peptide/nucleic acid). Cells were cultured in 48 well plate format and treated with free mRNACas9-gRNA, or ADGN/mRNACas9:gRNA complex. Indel frequencies at the endogenous target sequences was evaluated 72 hours after transfection by either T7E1 method and cell proliferation was analyzed over a period of 5 days using CellTiter Glow kits on GlowMax (Promega).

Figure 4A:
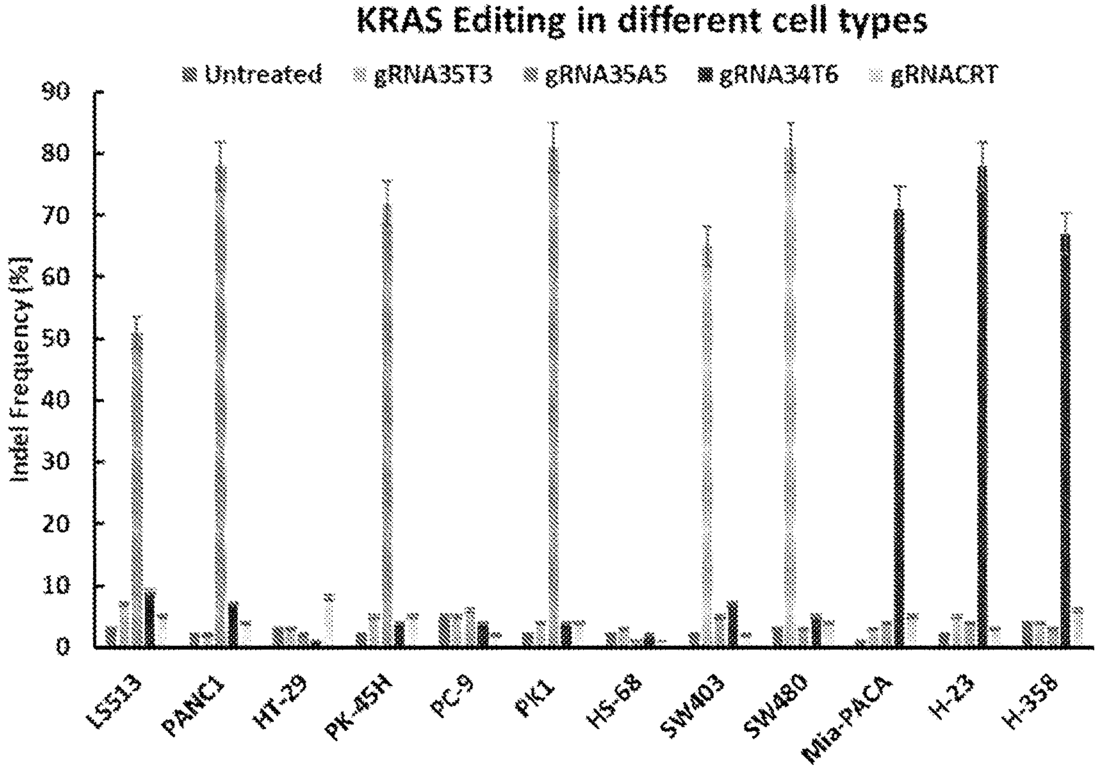
FIGS. 4A-4B show the evaluation of gRNAs targeting KRAS 35G>A, KRAS 35G>T, KRAS 34G>T mutants on different cell lines. SW403, SW480, PANC1, PK-45H, PK-1, MIA-PACA, NIH-H23, H358, HT-29, PC-9, HS-68 and LS513 cells were treated with ADGN/Cas9mRNA/gRNA (0.4 μg).
Figure 4B:
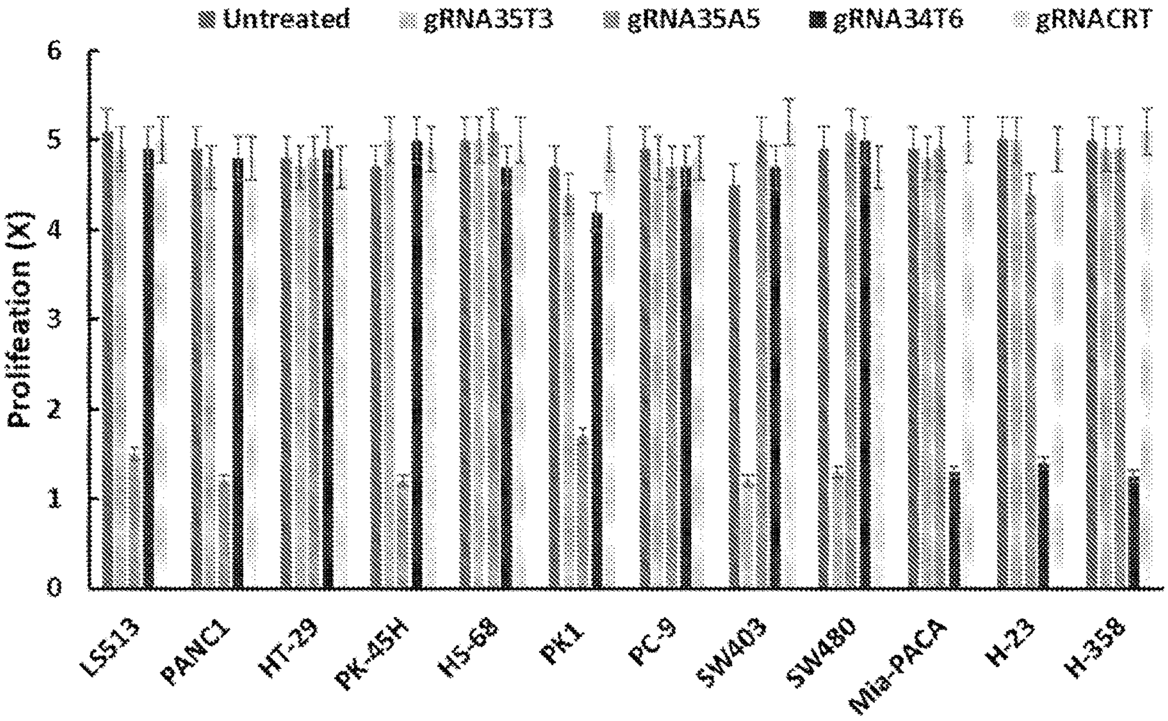

As reported in FIGS. 4A-4B, gRNA35A5 is highly specific for KRAS G12D mutated cancer cells, leading to indel frequency higher that 75% in PANC-1, PK-1, and PK-45H cells and does not alter G12V and G12C KRAS mutant cells or WT KRAS cells. gRNA35T3 is highly specific for KRAS G12V mutated cancer cells, leading to indel frequency higher that 65% in SW403 and SW480 cells and does not alter G12D and G12C KRAS mutant cells or WT KRAS cells. gRNA34T6 is highly specific for KRAS G12C mutated cancer cells, leading to indel frequency higher that 70% in Mia-PACA, H23 and H358 cells and does not alter G12D and G12V KRAS mutant cells or WT KRAS cells.

Example 6. ADGN Mediated CRISPR Targeting KRAS G12D or G12V Mutation Inhibit PI3K/Akt and MAPK Pathways In order to verify the specific effect of your lead sgRNA targeting G12V and G12D KRAS mutation, gRNA35A5 G12D and gRNA35T3 G12V on KRAS signal transduction pathway in PANC-1 and SW403 cells, we measured the levels of downstream signaling proteins that are activated by KRAS. We specifically looked for changes in key signaling pathways, such as mitogen-activated protein kinase (MAPK) or PI3K/Akt, which are known to be the major effector pathways of KRAS activation. Cas9 mRNA (0.2 μg) and gRNA (0.2 μg or 0.5 μg) were associated with ADGN peptide at molar ratio 20/1 (peptide/nucleic acid). PANC1 and SW403 cells were cultured in 48 well plate format and treated with free mRNACas9-gRNA, or ADGN/mRNACas9:gRNA complex. Levels of Erk and Akt phosphorylation were measured 48 h post transfection by western blot using phospho-Akt (Ser 473) (CST, #9271, RRID: AB_329825) and phospho-p44/42 MAPK (Erk1/2) (Thr202/Tyr204) (CST, #4370, RRID:AB_2315112).

Figure 5A:
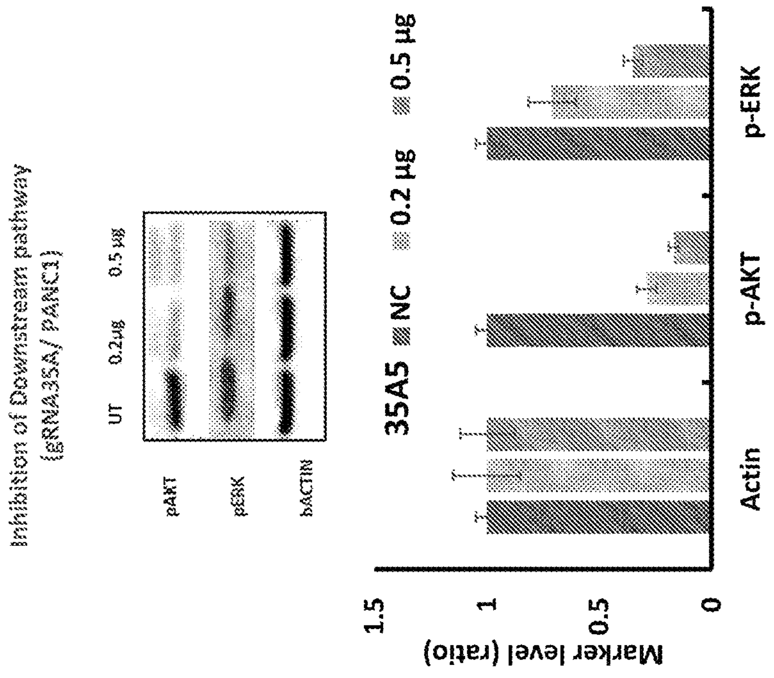
FIGS. 5A-5B show the impact of lead gRNAs targeting G12D and G12Vmutants on KRAS signaling pathway.
Figure 5B:
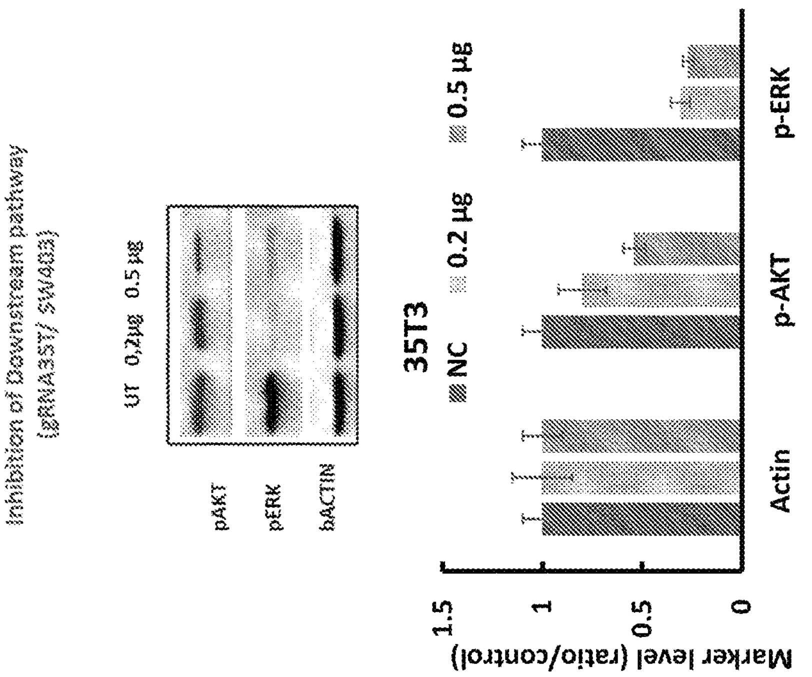

As reported in FIG. 5A-5B, Western blot results revealed that in both cases, gene editing of KRAS mutant caused a specific alteration of downstream signaling pathway. The knock-out of $KRAS^{G12D}$ using gRNA35A5 significantly reduced the level of p-AKT affecting the PI3K/Akt pathway (FIG. 5A). In contrast, the level of P-Erk is only reduced by 15%. The knock-out of $KRAS^{G12V}$ using gRNA35T3 significantly affected the level of p-Erk affecting the MAPK pathway and poorly Akt phosphorylation (FIG. 5B). Our results are in agreement with previous result showing that differences between KRAS mutants have been identified in tumors derived from animals. KRAS G12V, but not G12D, were able to interact with RAF1 and showed a high phosphorylation of ERK and KRAS G12V was unable to activate AKT despite its interaction with PI3K whereas KRAS G12D strongly activated AKT (Céspedes M, Sancho F, Guerrero S, Parreño M, Casanova I, Pavón M, et al. *Carcinogenesis*. (2006) 27:2190-200°).

Example 7. ADGN Peptides Mediated Target Delivery of CRISPR Components in the Tumors ADGN-100 and ADGN-106 peptides were selected in order to improve selective expression of Cas9 in the tumors and to increase the half-life of mRNA in the serum. Cas9 mRNA (10 μg) and gRNA (10 μg) were associated with ADGN-106, ADGN-100, ADGN-106-Hydro3, ADGN-100-Hydro3, ADGN-100-Hydro5, ADGN-106-Hydro5, ADGN-100-Hydro7 and ADGN-106-Hydro7. Female nude mice were subcutaneously injected with Human pancreatic carcinoma. Ten days after tumor implantation, mice received a single intravenous injection of free Cas9 or ADGN/mRNA Cas9/gRNA complexes. At 24 hours following injection, animals were sacrificed and tissues including lung, liver, brain, kidney, heart, spleen, blood, pancreas and tumor were collected. Tissues were homogenized and Cas9 expression was analyzed by ELISA using Cas9 monoclonal antibody (SBI clone 7A9).

TABLE 7

ADGN peptides for use in Cas9 expression in tumors.

| Cell-penetrating peptide | Sequence | SEQ ID NO |
|---|---|---|
| ADGN-100 | beta-AKWRSAGWRWRLWRVRSWSR-NH2 | 153 |
| ADGN-100-Hydro-3 | Ac-YIGSR-Ava-KWRSALWRWRLWRVRSWSR-NH2 | 162 |
| ADGN-100-Hydro-5 | Ac-YIGSR-Aun-KWRSALWRWRLWRVRSWSR-NH2 | 164 |
| ADGN-100 Hydro-7 | Ac-YIGSR-Ahx-KWRSALWRWRLWRVRSWSR-NH2 | 166 |
| ADGN-106 | beta-ALWRALWRLWRSLWRLLWKA-NH2 | 90 |
| ADGN-106-Hydro-3: | Ac-YIGSR-Ava-ALWRALWRLWRSLWRLLWK-NH2 | 96 or 265 |
| ADGN-106-Hydro-5 | Ac-YIGSR-Aun-ALWRALWRLWRSLWRLLWK-NH2 | 98 or 266 |
| ADGN-106 hydro-7 | Ac-YIGSR-Ahx-ALWRALWRLWRSLWRLLWK-NH2 | 100 |

Figure 6:
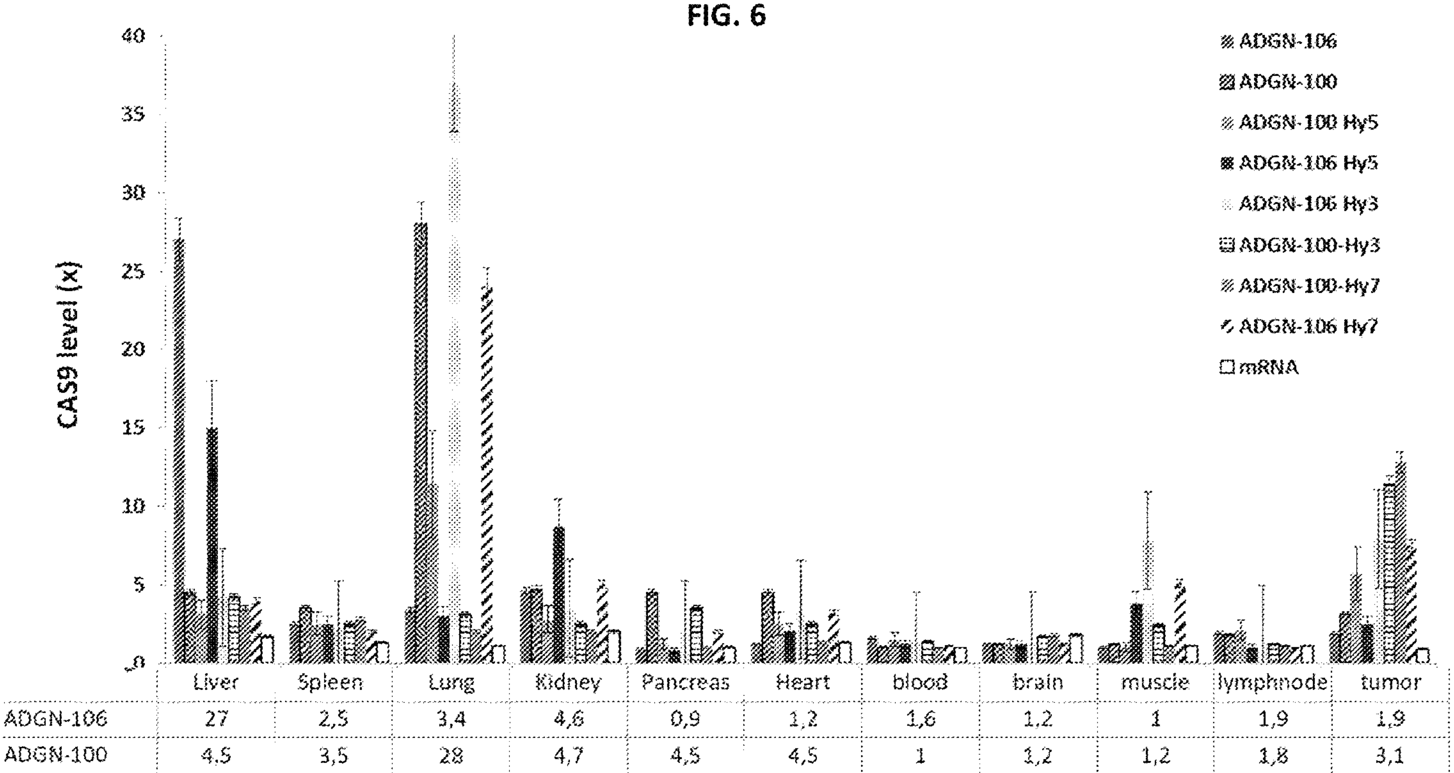
FIG. 6 shows quantification of Cas9 protein expression by ELISA in the different tissues and tumors following in vivo intravenous administration of CASmRNA/gRNA associated with different ADGN-peptides.

As shown in FIG. 6, the ADGN-100-Hy3, ADGN-100-Hy7, ADGN-106-Hy3 and ADGN-106-Hy7 peptides promote high Cas9 expression in tumors. The level of Cas-9 expression is increased by 4 to 6-fold in comparison to ADGN-100 and ADGN-106 peptides and at a level 10-fold that of background. ADGN-100-Hy3 and ADGN-100-Hy7 specifically target the tumor with no significant increase in Cas9 protein expression in the other tissues examined. In contrast, ADGN-106-Hy3 and ADGN-106-Hy7 targeted both tumor and lung, with a large Cas9 expression in the lung. The results demonstrated that ADGN-100-Hy3 and ADGN-100-Hy7 constitute a potent delivery method for in vivo target delivery of functional delivery of CRISPR components in the tumors.

ADGN-100-Hy3 and ADGN-100-Hy7 were selected for further in vivo evaluation.

Female nude mice 6-weeks of age were subcutaneous injected with PANC1 Human Pancreatic carcinoma cells (4 mice/group). 10 and 17 days after tumor cell administration, mice received IV injection of ADGN-100-Hy3/mRNA Cas9/gRNA and ADGN-100-Hy7/mRNA Cas9/gRNA nanoparticles. The level of Cas9 expression in the different tissues and tumors was analyzed by ELISA 24 hours after each injection (at D1 and D8) and 4/7 days after the second injection (D14). Tissues were homogenized and Cas9 expression was analyzed by ELISA on protein extract using antibody against CRISPR/Cas9.

Figure 7A:
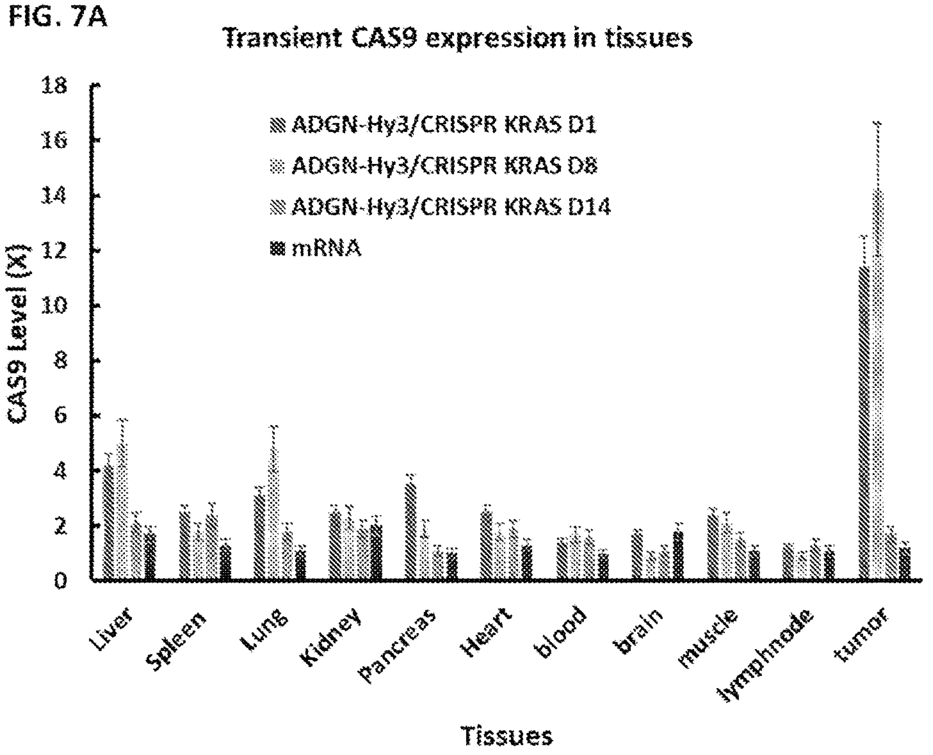
FIGS. 7A-7B show quantification of Cas9 protein expression by ELISA in the different tissues and tumors following in vivo IV administration of CAS mRNA/gRNA associated with ADGN-100 Hy3 (FIG. 7A) and ADGN-100-Hy7 (FIG. 7B) peptides.
Figure 7B:
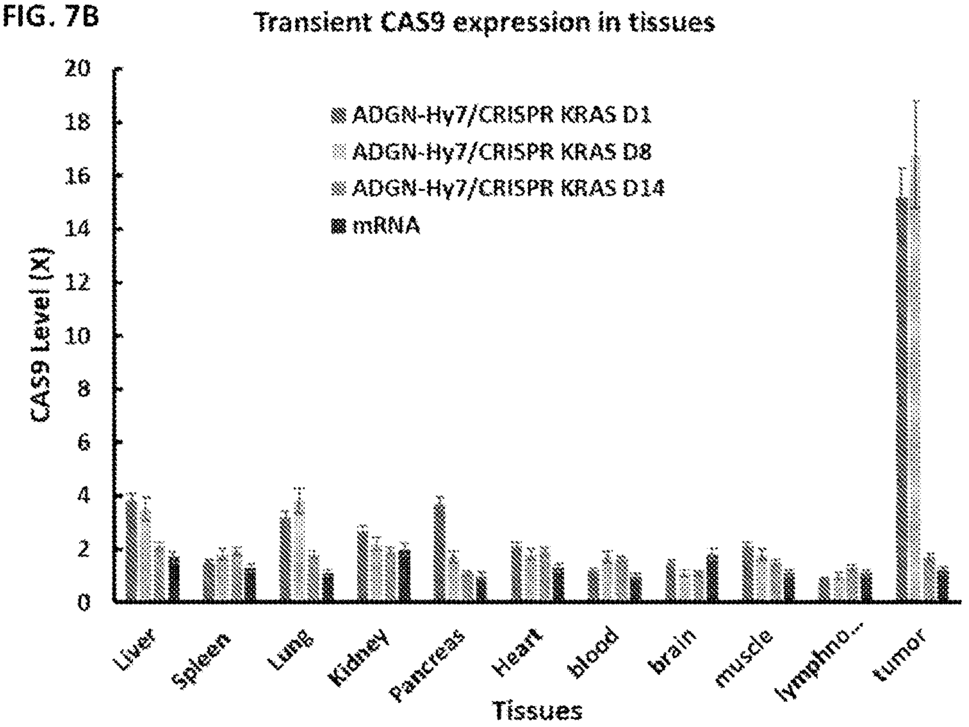

As reported in FIG. 7A-B, ADGN-100-Hy3 and ADGN-100-Hy7, respectively, mediated targeted delivery of Cas9 mRNA in tumors. High expression of Cas9 protein was observed in the tumors, at a level greater than 10-fold that of background (FIG. 7A-B). Cas9 expression was also observed in lung and liver, with levels about 2- to 3-fold that of background. No significant increase in Cas9 protein expression was detected in the other tissues examined. Cas9 expression in the tissues and tumor are close to background level 4 and 7 days after last injection.

Figure 8A:
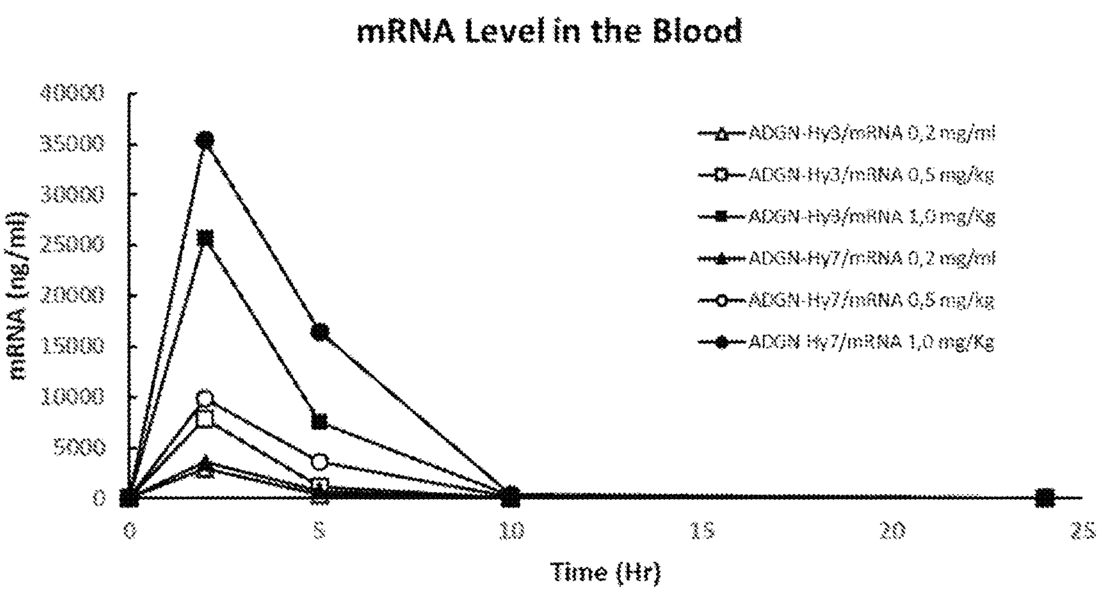
FIGS. 8A-8B show plasma concentration of Cas9-mRNA in mice treated intravenously with ADGN-Hy-3/mRNA Cas9/gRNA and ADGN-Hy7/mRNACas9:gRNA complexes. Mice bearing Panc1 tumors were treated with a single injection of ADGN/mRNA Cas9/gRNA nanoparticles at 0.2, 0.5 and 1.0 mg/kg. Cas9 mRNA level in the plasma was analyzed by Quantigen bDNA method. Graphs represent mean values (n=4). The calculated amount in picograms was normalized to the amount of plasma in the lysate and to the amount of lysate applied to the plate.
Figure 8B:
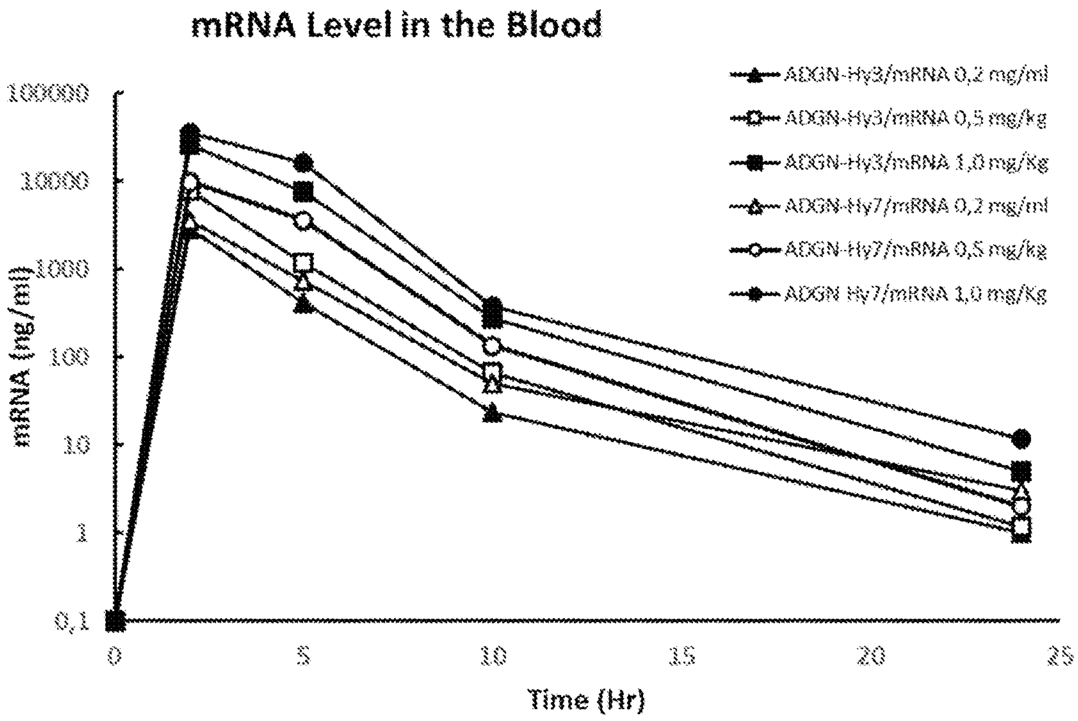

Example 8. ADGN-100 Hy3 and ADGN-100 Hy7 Nanocarrier Stabilized Cas9 mRNA in Serum We next evaluated the stability of the ADGN-100-Hy3 and ADGN-100-Hy7 nanoparticle in the serum. Female nude mice were subcutaneously injected with Human pancreatic carcinoma. Ten days after tumor cell administration, mice were treated intravenously with ADGN/mRNA Cas9/gRNA complex at 0.2 mg/kg, 0.5 mg/kg and 1.0 mg/kg. Cas9 mRNA level in the blood was analyzed by Quantigen bDNA method. The bioanalysis of plasma samples for quantification of Cas9mRNA levels was conducted according to the bDNA method for mRNA detection developed by QuantiGene (Affymetrix-USA). Plasma samples were directly diluted in lysis buffer. Signal amplification was carried out with oligonucleotides bound to the enzyme alkaline phosphatase. The calculated amount in picograms was normalized to the amount of plasma in the lysate and to the amount of lysate applied to the plate. As reported in FIG. 8A-8B, Cas9 mRNA levels in the blood are dose dependent with a moderate half-life of 4.2 hours and 5.0 hr, using ADGN-100-Hy3 and ADGN-100-Hy7, respectively. In both cases, Cas9 mRNA level declined to about 10 ng/ml or less in 24 hours.

Example 9. ADGN-Mediated CRISPR Gene Editing of KRAS Mutant Blocks Tumor Growth In Vivo We have evaluated whether targeting mutant KRAS can suppress tumor growth in vivo when administered intravenously using ADGN-100-Hy3 nanoparticles. Female nude mice 6-weeks of age were injected with either Human pancreatic carcinoma cell (Panc1-Luc) containing the 35G>A mutation or Human colorectal cancer cells (SW403) containing 35G>T KRAS mutation ($20\times10^6$ cells in 200 μl PBS). The animals were kept under pathogen-free conditions and fed and watered ad libitum, in cages of 2 to 4 animals (in compliance with recommended area surface/animal), in a dedicated room with a 12 h/12 h light/dark cycle at a constant temperature of 22° C. A period of 2 weeks was allowed for tumor development before the beginning of the experiments Mice were organized in five groups including 2 control groups G0 & G1 (6 animals per group) and 3 treatment groups (G3-G5) (6 animals per group). The different groups are:

For Panc1-mice:

G0: Control Untreated

G1: Naked Cas9 mRNA/gRNA35A5 1.0 mg/kg

G3: ADGN-100Hy3/mRNA/gRNA35A5 0.5 mg/kg

G4: ADGN-100Hy3/mRNA/gRNA35A5 1.0 mg/kg

G5: ADGN-100Hy3/mRNA/gRNA34T6 1.0 mg/kg

For SW-403 mice

G0: Control Untreated

G1: Naked Cas9 mRNA/gRNA35T3 1.0 mg/kg

G5: ADGN-100Hy3/mRNA/gRNA35T3 0.5 mg/kg

G7: ADGN-100Hy3/mRNA/gRNA35T3 1.0 mg/kg

G6: ADGN-100Hy3/mRNA/gRNA34T6 1.0 mg/kg

Animal were injected on day 1 and day 7. Mice received IV injection of 100 μl ADGN/mRNA complex in 5% glucose. PANC-1 tumor size was evaluated by bioluminescence imaging. Mice received an i.p. injection of 150 μg/g luciferin for non-invasive bioluminescence imaging (IVIS Kinetic; PerkinElmer, Waltham, MA, USA). Semi-quantitative data of luciferase-positive tumor cell signals were obtained using the manufacturer's software (Living Image; PerkinElmer). Results were expressed as photons/second (photons/s). Bioluminescence imaging was performed once a week. Results were then expressed as values relative to day 0. At Day 50 animals were sacrificed and tumors were harvested. SW403 tumor size was evaluated every 7 days using caliper. Results were then expressed as values relative to day 0. At Day 50 animals were sacrificed and tumors were harvested.

Figure 9A:
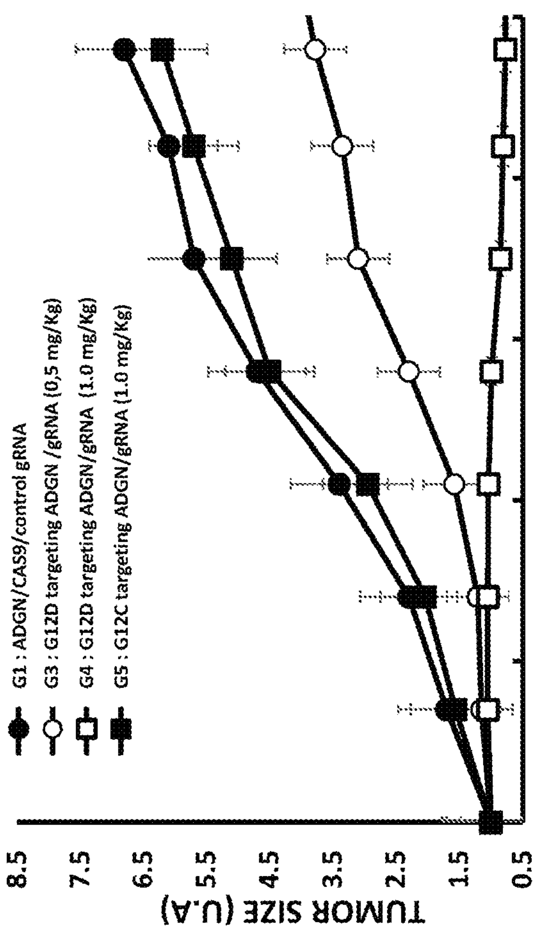
FIGS. 9A-9B show the potency of ADGN/Cas9/gRNA35A5 in vivo in a pancreas tumor model. A period of 3 weeks was allowed for PANC1 tumor development before the beginning of the treatments. Four groups of mice were identified Control Untreated mice (G1), ADGN-100Hy3/mRNA/gRNA35A5 0.5 mg/kg (G3), ADGN-100Hy3/mRNA/gRNA35A5 1.0 mg/kg (G4) and ADGN-100Hy3/mRNA/gRNA34T6 1.0 mg/kg (G5). Animal (6 animals per group) were intravenously (tail-vein) injected on day 0 and day 7. Tumor size was evaluated by bioluminescence imaging once a week.
Figure 9B:
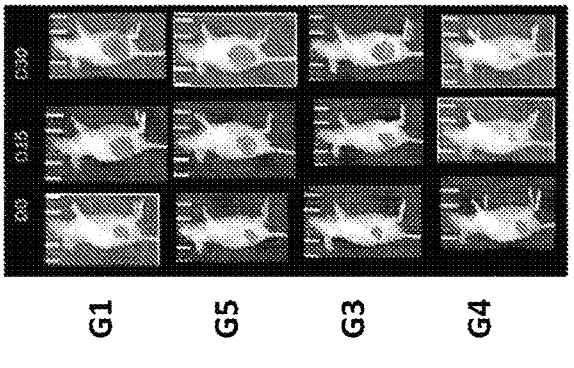

As reported in FIG. 9A-9B: in the control group, tumor size increased by 6.1 folds over a period of 48 days. IV administration of ADGN/Cas9/gRNA35A5 efficiently target 35G>A (G12D) mutant KRAS in vivo reducing the PANC1 tumor growth by 65% at 0.5 mg/kg. At 1 mg/kg dose, ADGN/gRNA35A5 abolished PANC1 tumor growth leading to 50% reduction of the tumor size compared to the original size. In contrast, ADGN/Cas9/gRNA34T6 targeting 34G>T (G12C) mutant KRAS does not impact PANC1 tumor growth. The results demonstrated that ADGN-100 Hy3 mediated efficient CRIPSR based editing of 35G>A (G12D) KRAS mutation in the tumors and inhibiting pancreas tumor growth.

Figure 10:
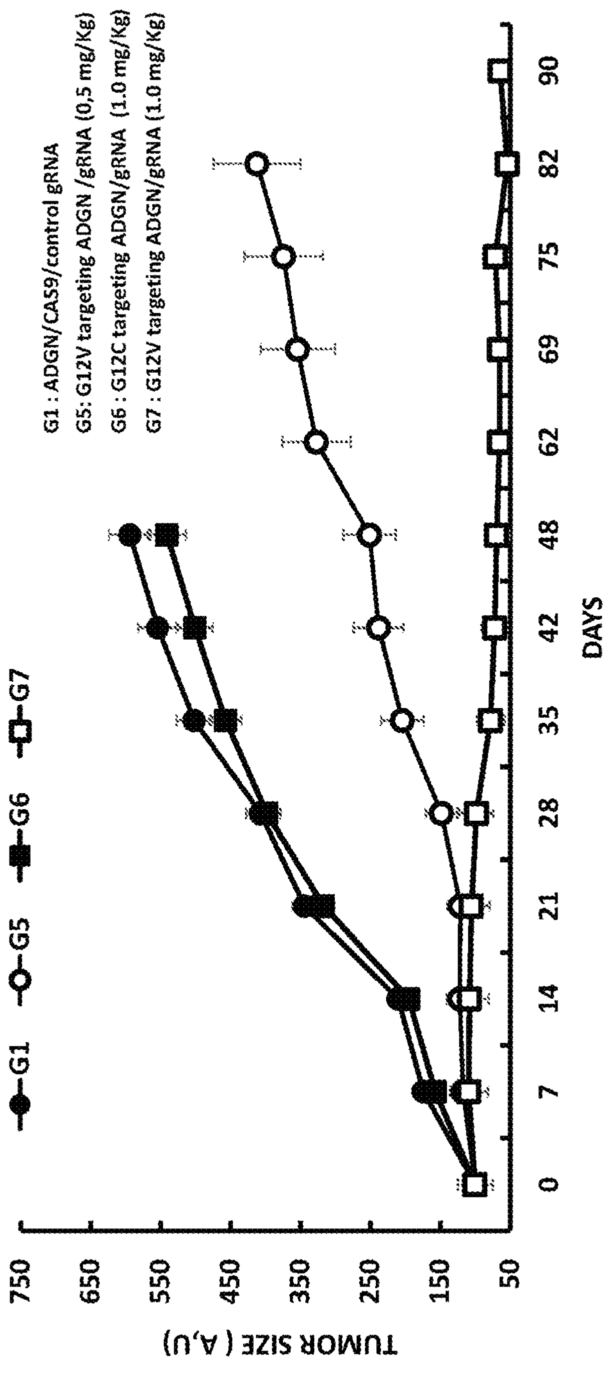
FIG. 10 shows the potency of ADGN/Cas9/gRNA35T3 in vivo in a colorectal tumor model. A period of 10 days was allowed for SW403 tumor development before the beginning of the treatments. Four groups of mice were identified Control Untreated mice (G1), ADGN-100Hy3/mRNA/gRNA35T3 0.5 mg/kg (G5), ADGN-100Hy3/mRNA/gRNA35T3 1.0 mg/kg (G7) and ADGN-100Hy3/mRNA/gRNA34T6 1.0 mg/kg (G6). Animal (6 animals per group) were intravenously (tail-vein) injected on day 0 and day 7. Tumor size was evaluated using caliper once a week.

As reported in FIG. 10: in the control group, SW403 tumor size increased by 5.9 folds over a period of 48 days. ADGN/Cas9/gRNA35T3 efficiently target 35G>T (G12V) mutant KRAS in vivo reducing the SW403 tumor growth by 65% at 0.5 mg/kg. At 1 mg/kg dose ADGN/gRNA35T3 abolished SW403 tumor growth leading to 62% reduction of the tumor size compared to the original size. In contrast, ADGN/Cas9/gRNA34T6 targeting 34G>T (G12C) mutant KRAS does not impact SW403 tumor growth. The results demonstrated that ADGN-100 Hy3 mediated efficient CRIPSR based editing of 35G>T (G12V) KRAS mutation in the tumors and inhibiting colorectal tumor growth.

Example 10. ADGN-Mediated CRISPR Gene Editing in Combination with a Second Agent It was also evaluated whether targeting mutant KRAS in combination with a chemotherapeutic agent can suppress tumor growth in vivo when administered intravenously using ADGN-100-Hy3 nanoparticles. Female nude mice 6-weeks of age were injected with either Human pancreatic carcinoma cell (Panc1-Luc) containing the 35G>A mutation, or Human colorectal cancer cells (SW403) containing 35G>T KRAS mutation ($20\times10^6$ cells in 200 μl PBS). The animals were kept under pathogen-free conditions and fed and watered ad libitum, in cages of 2 to 4 animals (in compliance with recommended area surface/animal), in a dedicated room with a 12 h/12 h light/dark cycle at a constant temperature of 22° C. A period of 2 weeks was allowed for tumor development before the beginning of the experiments For mice injected with PANC1 tumor, mice were organized in seven groups including 2 control groups G0 & G1 (6 animals per group) and 5 treatment groups (G3-G7) (6 animals per group). The different groups are:

G1: control untreated

G2: ADGN/mRNA Cas9/control gRNA

G3: G12D targeting ADGN/mRNACAS/gRNA dose 0.5 mg/kg

G4: G12D targeting ADGN/mRNACAS/gRNA dose 1.0 mg/kg

G5: G12D targeting ADGN/mRNACAS/gRNA/Abraxane (50 μg) dose 0.5 mg/kg

G6: G12D targeting ADGN/mRNACAS/gRNA/Abraxane (50 μg) dose 1.0 mg/kg

G7: Abraxane (50 μg) once a week dose

For mice injected with SW403 tumor, mice were organized in seven groups including 2 control groups G0 & G1 (6 animals per group) and 5 treatment groups (G3-G7) (6 animals per group). The different groups are:

G1: control/untreated

G2: ADGN/mRNA Cas9/control gRNA

G3: G12V targeting ADGN/mRNACAS/gRNA dose 0.5 mg/kg

G4: G12V targeting ADGN/mRNACAS/gRNA dose 1.0 mg/kg

G5: Capécitabine (200 μg)

G6: G12D targeting ADGN/mRNACAS/gRNA/dose 1.0 mg/kg

G7: G12V targeting ADGN/mRNACAS/gRNA/Capécitabine (200 μg) 0.5 mg/kg

Animal were injected ADGN/mRNA complex on day 1 and day 7. Mice received IV injection of 100 μl ADGN/mRNA complex in 5% glucose. PANC-1 tumor size was evaluated by bioluminescence imaging. Mice received an i.p. injection of 150 μg/g luciferin for non-invasive bioluminescence imaging (IVIS Kinetic; PerkinElmer, Waltham, MA, USA). Semi-quantitative data of luciferase-positive tumor cell signals were obtained using the manufacturer's software (Living Image; PerkinElmer). Results were expressed as photons/second (photons/s). Bioluminescence imaging was performed once a week. Results were then expressed as values relative to day 0. SW403 tumor size was evaluated every 7 days using caliper. Results were then expressed as values relative to day 0. At Day 90 animals were sacrificed and tumors were harvested.

Figure 11A:
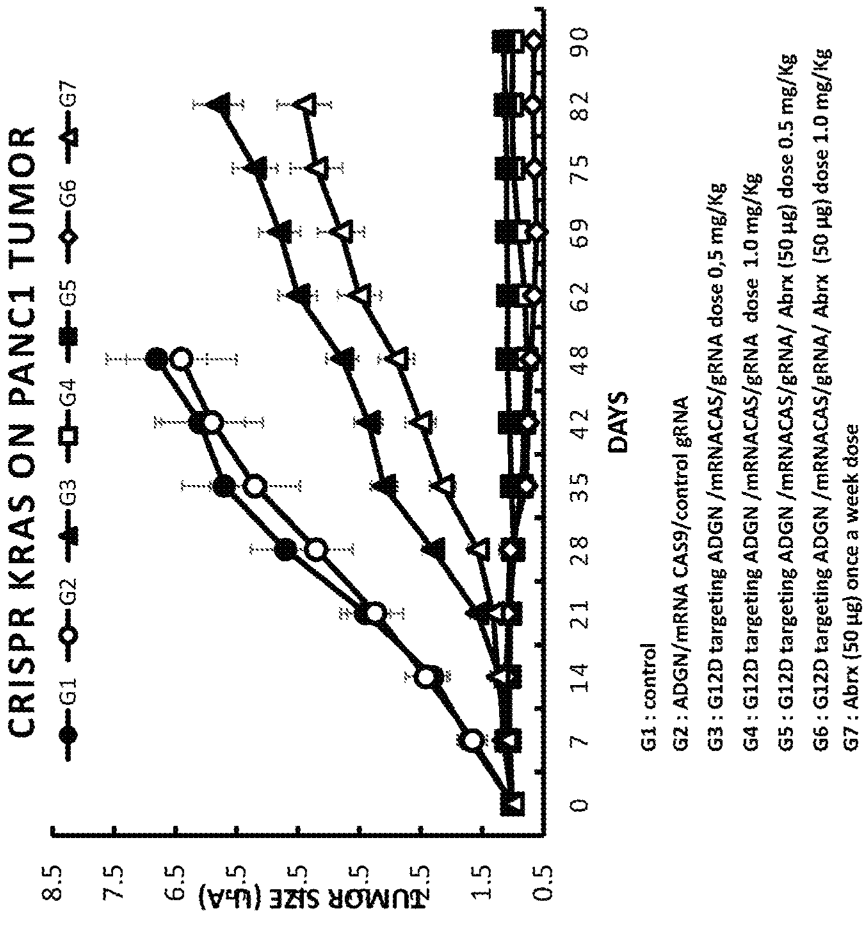
FIGS. 11A-11B show the potency of co-treatment of ADGN/Cas9/gRNA35A5 and Abraxane in vivo in a pancreas tumor mice model. A period of three weeks was allowed for PANC1 tumor development before the beginning of the treatments. Seven groups of mice were identified: control untreated mice (G1), ADGN/mRNA Cas9/control gRNA (G2), ADGN-100Hy3/mRNA/gRNA35A5 0.5 mg/kg (G3), ADGN-100Hy3/mRNA/gRNA35A5 1.0 mg/kg (G4), Abraxane (50 μg) and ADGN-100Hy3/mRNA/gRNA35A5 0.5 mg/kg (G5), Abraxane (50 μg) and ADGN-100Hy3/mRNA/gRNA35A5 1.0 mg/kg (G6) and Abraxane (50 μg) only (G7). For G2-G6, animals (6 animals per group) were intravenously (tail-vein) injected on day 0 and day 7 with ADGN/Cas9:sgRNA. For G5-G7, animals were intravenously (tail-vein) injected once a week with Abraxane (50 μg). Tumor size was evaluated by bioluminescence imaging once a week.
Figure 11B:
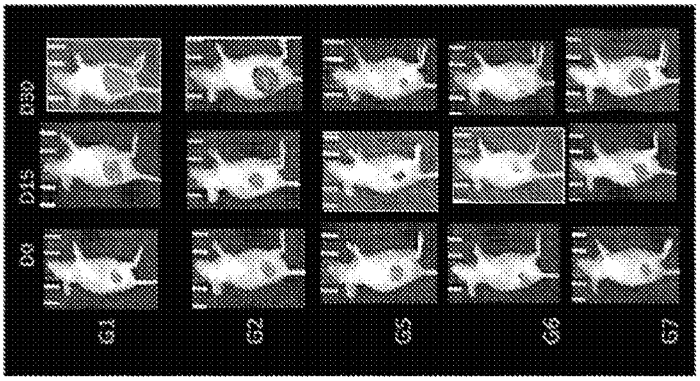

As reported in FIGS. 11A-11B, in the control group, and mice treated with ADGN/mRNA CAS9/control gRNA tumor size increased by 6.5 folds over a period of 48 days. IV administration of ADGN-100Hy3/CAS9/gRNA35A5 efficiently target 35G>A (G12D) mutant KRAS in vivo reducing the PANC1 tumor growth by 35% at 0.5 mg/kg. At 1 mg/kg dose, ADGN/gRNA35A5 abolished PANC1 tumor growth. Abraxane treatment reduced the PANC1 tumor growth by 42%; Combining Abraxane with ADGN/gRNA35A5 (0.5 mg/kg) abolished PANC1 tumor growth; Combining Abraxane with ADGN/gRNA35A5 (1.0 mg/kg) abolished tumor growth and reduced the size of initial the PANC1 tumor by 60%.

The results demonstrated a synergy between ADGN/CAS9/gRNA35A5 and Abraxane for the treatment of Panc 1 tumors and a potentialized inhibition of pancreas tumor growth.

Figure 12:
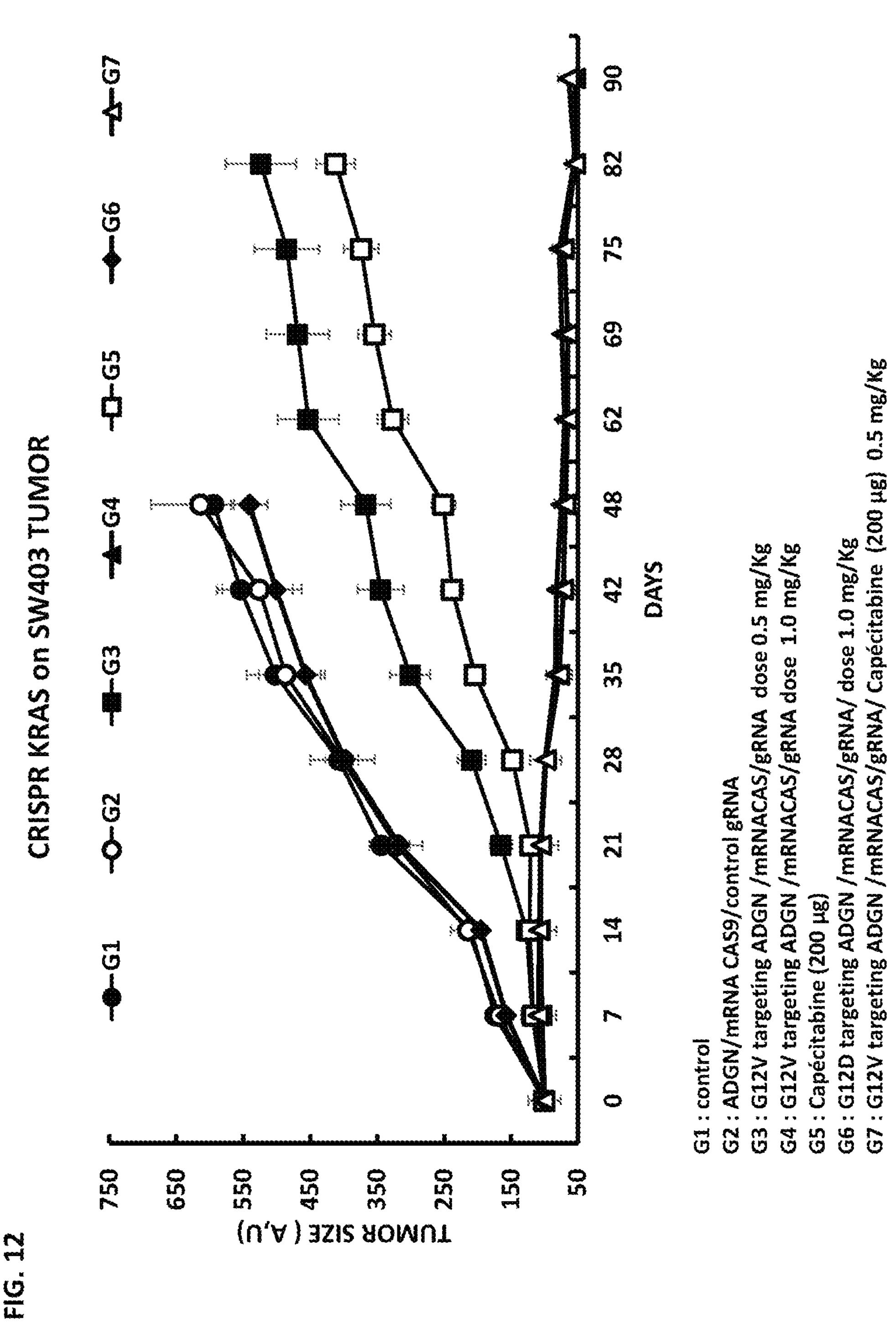
FIG. 12 shows the potency of co-treatment of ADGN/Cas9/gRNA35T3 and Capecitabine in vivo in a colorectal tumor mice model. Seven groups of mice were identified: control untreated mice (G1), ADGN/mRNA Cas9/control gRNA (G2), ADGN-100Hy3/mRNA/gRNA35T3 0.5 mg/kg (G3), ADGN-100Hy3/mRNA/gRNA35T3 1.0 mg/kg (G4), Capecitabine (200 μg) (G5), ADGN-100Hy3/mRNA/gRNA34T3 1.0 mg/kg (G6) and Capecitabine (200 μg) and ADGN-100Hy3/mRNA/gRNA34T3 0.5 mg/kg (G7). Animal (6 animals per group) were previously inoculated with SW403 tumor and treated by IV tail-vein injected on day 0 and day 7 with ADGN/Cas9/gRNA complexes (G2-G4, G6, and G7) and once a week with Capecitabine (200 μg) (G5 and G7). Tumor size was evaluated using caliper once a week.

As reported in FIG. 12, in the control group, and mice treated with ADGN/mRNA CAS9/control gRNA tumor size increased by 6.5 folds over a period of 48 days.

At day 90, IV administration of ADGN-100Hy3/mRNA/gRNA35T3 0.5 mg/kg efficiently target 35G>T (G12V) mutant KRAS in vivo reducing the SW403 tumor growth by 31% at 0.5 mg/kg. At 1 mg/kg dose, ADGN/gRNA35T3 abolished SW403 tumor growth. Capecitabine treatment reduced the SW403 tumor growth by 38%. Combining Capecitabine with ADGN/gRNA35T3 (0.5 mg/Kg) reduced the size of the initial SW403 tumor by 60%. The results demonstrated a synergy between ADGN/CAS9/gRNA35T3 and Capecitabine for the treatment of SW403 tumors and a potentialized inhibition of colorectal tumor growth.

Example 11. ADGN-Mediated Specific CRISPR Gene Editing of KRAS Mutants In Vivo The specificity of gRNA35A5 G12D and gRNA35T3 G12V for their targets in PANC-1 and SW403 tumors cells, have been analyzed. Female nude mice 6-weeks of age were injected with either Human pancreatic carcinoma cell (Panc1-Luc) containing the 35G>A mutation or Human colorectal cancer cells (SW403) containing 35G>T KRAS mutation ($20\times10^6$ cells in 200 μl PBS). A period of 2 weeks was allowed for tumor development before the beginning of the experiments.

Mice were organized in five groups including 2 control groups G0 & G1 (6 animals per group) and 3 treatment groups (G2-G4) (6 animals per group). The different groups are:

For Panc1-mice

G0: Control Untreated

G1: Naked Cas9 mRNA/gRNA35A5 1.0 mg/kg

G2: ADGN-100Hy3/mRNA/gRNA35A5 0.5 mg/kg

G3: ADGN-100Hy3/mRNA/gRNA35A5 1.0 mg/kg

G4: ADGN-100Hy3/mRNA/gRNA34T6 1.0 mg/kg

For SW-403 mice

G0: Control Untreated

G1: Naked Cas9 mRNA/gRNA35T3 1.0 mg/kg

G2: ADGN-100Hy3/mRNA/gRNA35T3 0.5 mg/kg

G3: ADGN-100Hy3/mRNA/gRNA35T3 1.0 mg/kg

G4: ADGN-100Hy3/mRNA/gRNA34T6 1.0 mg/kg

Figure 13A:
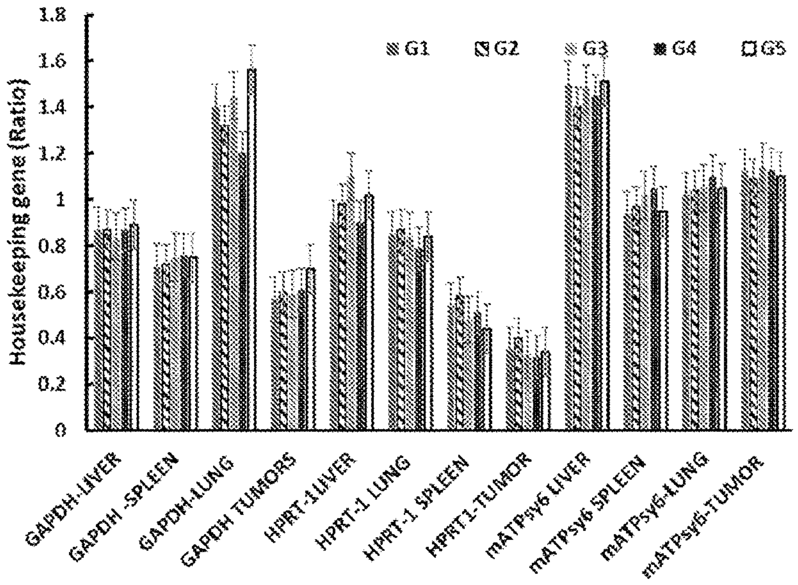
FIGS. 13A-13B show the expression levels of candidate housekeeping genes in different tissues and tumors after treatments. Animal (6 animals per group) were inoculated with PANC1 tumor cells (FIG. 13A) or SW403 tumor cells (FIG. 13B), and then intravenously (tail-vein) injected with ADGN/Cas9/gRNA complexes on day 0 and day 7.
Figure 13B:
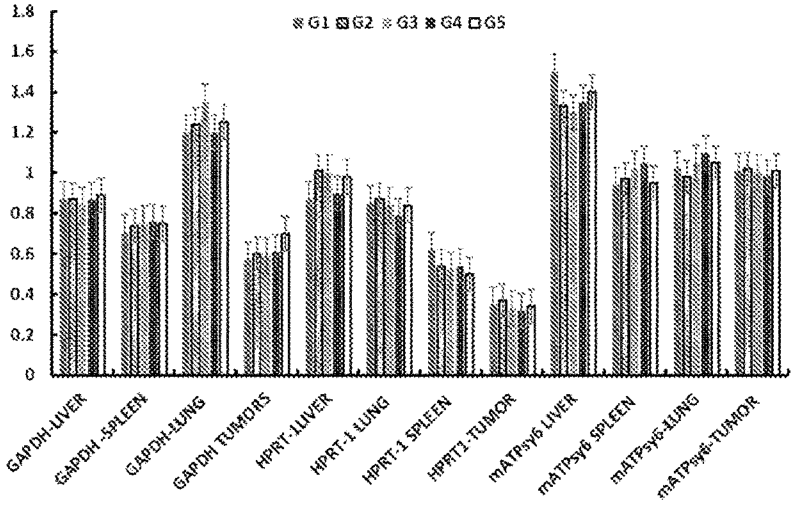

Animal were injected on day 1 and day 7. Mice received IV injection of 100 μl ADGN/mRNA complex in 5% glucose. At Day 50, animals were sacrificed and tissues/tumors were harvested. At Day 50 post treatment, level of expression of housekeeping genes; glyceraldehyde-3-phosphate dehydrogenase (GAPDH), HPRT-1 and mitochondrial ATP synthase 6 (mATPsy6) was evaluated by PCR in the tumor, liver, spleen and lung. As reported in FIGS. 13A-13B, animal analysis 50 days post treatment do not revealed any change in housekeeping genes in selected tissues including liver, lung, spleen and tumors.

Figure 14A:
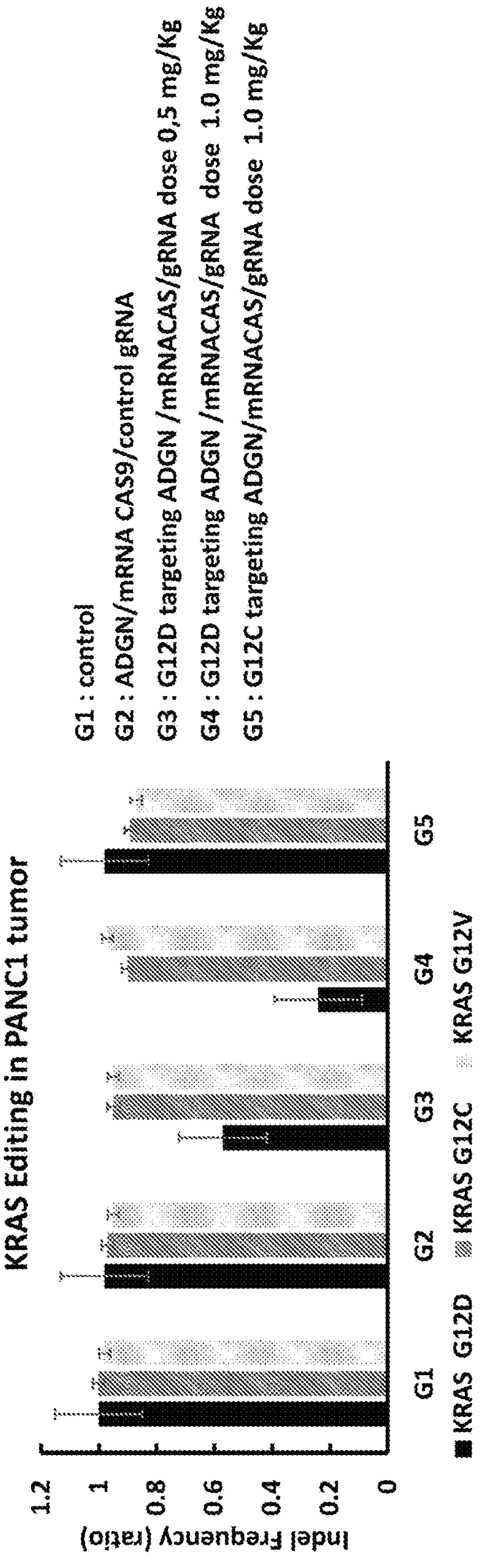
FIGS. 14A-14B show the level of gene editing associated to gRNAs targeting KRAS 35G>A, and KRAS 35G>T mutants on PANC1 and SW403 tumors. At Day 50 post treatment, indel frequencies at the endogenous target sequences in the PANC1 and SW403 tumors were determined by deep sequencing and compared to untreated mice.
Figure 14B:
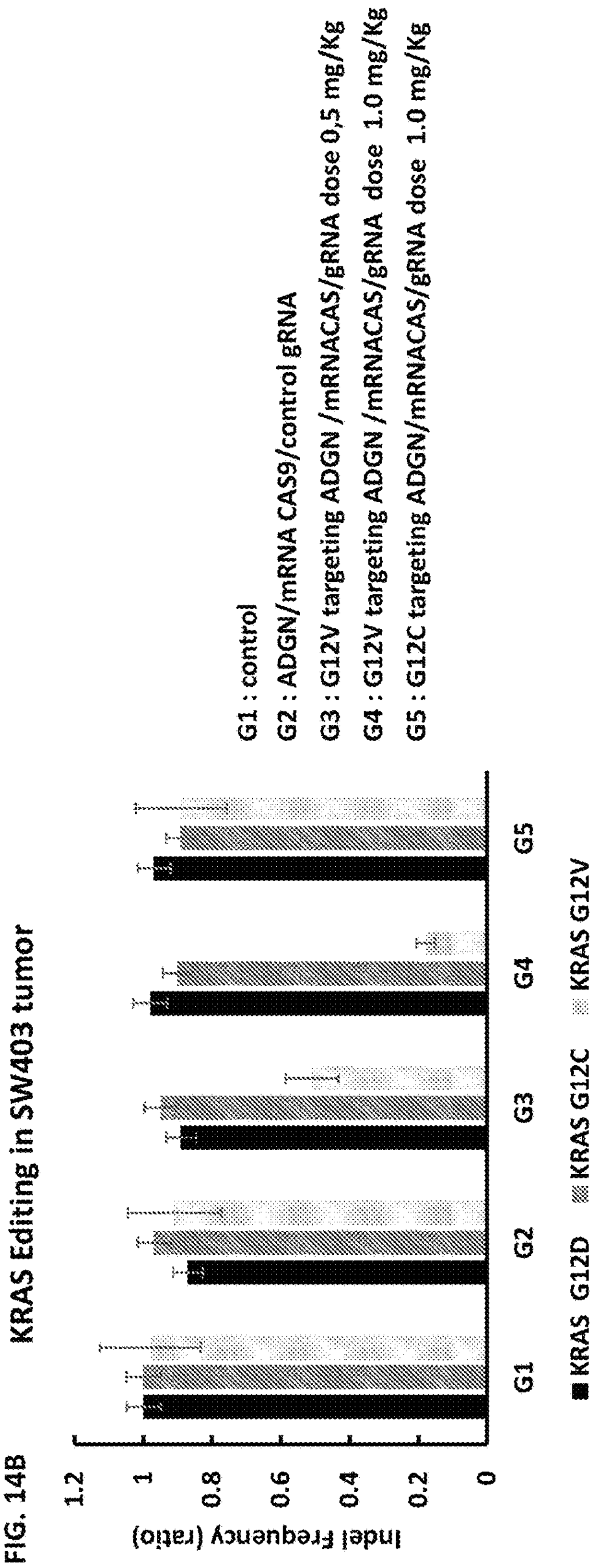
Figure 15A:
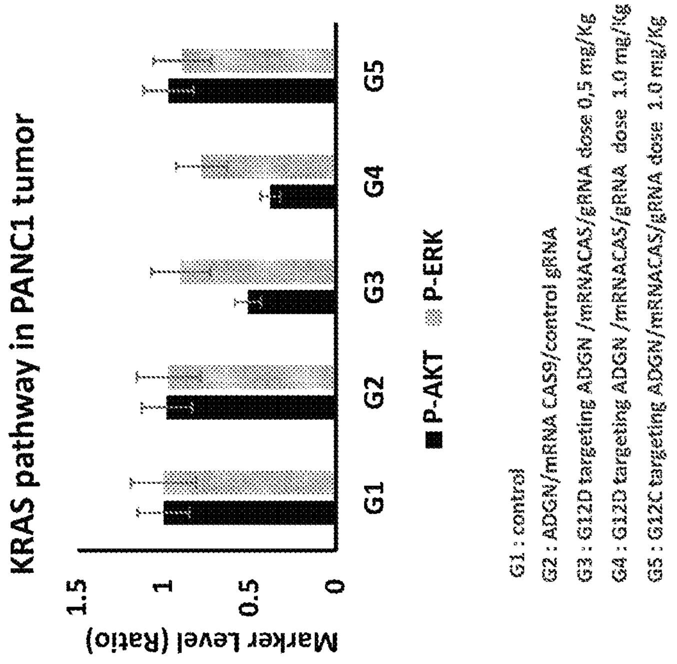
FIGS. 15A-15B show the impact of ADGN/Cas9/gRNAs targeting KRAS 35G>A, and KRAS 35G>T mutants in vivo treatment on KRAS signaling pathway in PANC1 (FIG. 15A) and SW403 tumors (FIG. 15B).
Figure 15B:
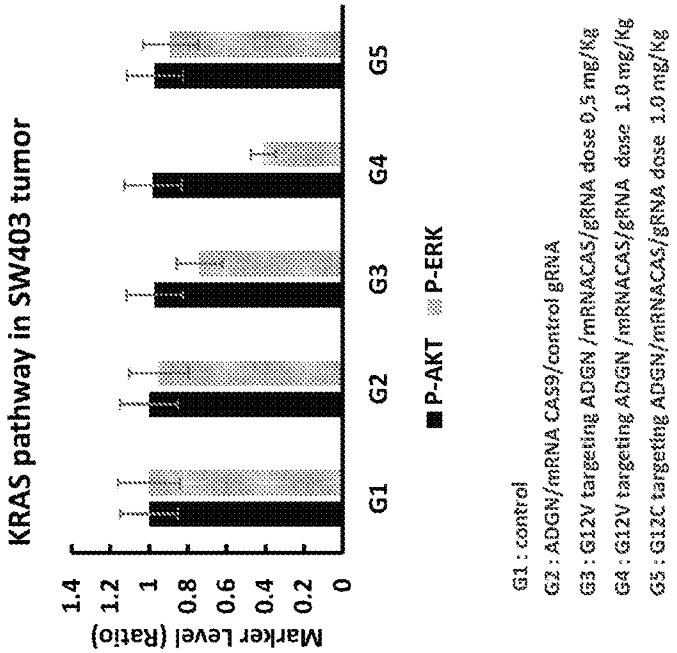

We analyzed the level of KRAS G12D or KRAS G12V gene editing by deep sequencing in PANC1 (FIG. 14A) and SW403 (FIG. 14B) tumors, respectively. As shown in FIGS. 14A-14B, deep sequencing showed that ADGN-Hy3/sgRNA35T3 sgRNA and ADGN-Hy3/sgRNA35A5 resulted in indel frequencies of 72% in SW403 tumor and of 76% in PANC-1 tumor, respectively. The level of downstream signaling proteins (pAKT and pERK) were quantified by ELISA on PANC1 and SW403 tumors. FIG. 15A demonstrated that the knock-out of $KRAS^{G12D}$ using gRNA35A5 significantly reduced the level of p-AKT and p-ERK in PANC1 tumors. The knock-out of $KRAS^{G12V}$ using gRNA35T3 significantly affected the level of p-ERK, but not of P-AKT in SW403 tumors (FIG. 15B). Given that targeting KRAS using Cas9/sgRNA can induce various secondary mutations at or near the target sites, deep sequencing shown similar level of secondary oncogenic mutations (G12D, G12V, G12C, G13D, G12R, G12A, and G12S) in KRAS-mutant cancer cells (SW403/PANC-1) or cells containing wild-type KRAS (HT29) either in vitro or in vivo.

Example 12. ADGN/CRISPR/KRAS Treatment are Well Tolerated In Vivo

Figure 16A:
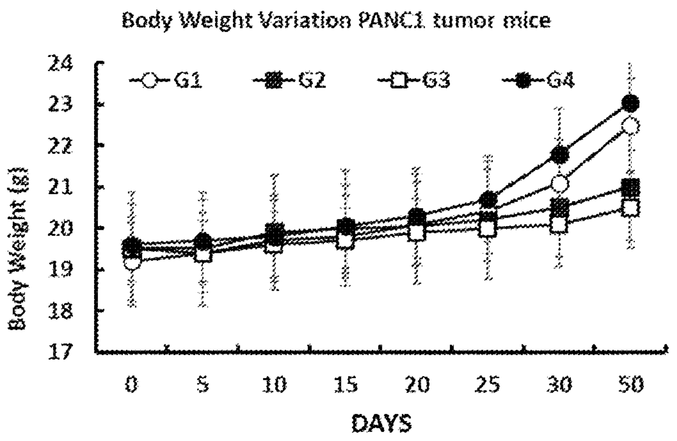
FIGS. 16A-16B show the impact of ADGN/Cas9/gRNAs targeting KRAS 35G>A, and KRAS 35G>T mutants in vivo treatment on animal weight in animals inoculated with PANC1 tumor cells (FIG. 16A) or SW403 tumor cells (FIG. 16B).
Figure 16B:
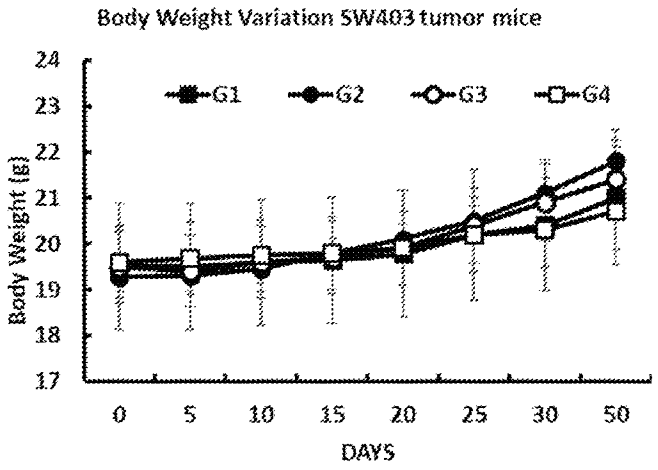
Figure 17A:
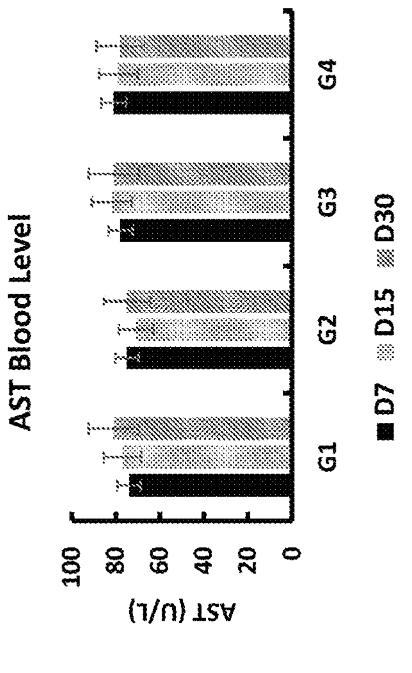
FIGS. 17A-17D show the impact of ADGN/Cas9/gRNAs targeting KRAS 35G>A mutant in vivo treatment on liver and renal markers in animals inoculated with PANC1 tumor cells. Four groups of mice were identified: control untreated mice (G1), ADGN-100Hy3/mRNA/gRNA35A5 0.5 mg/kg (G2), ADGN-100Hy3/mRNA/gRNA35A5 1.0 mg/kg (G3) and ADGN-100Hy3/mRNA/gRNA34T6 1.0 mg/kg (G4). Animal (6 animals per group) were intravenously (tail-vein) injected ADGN/Cas9/gRNA complexes on day 0 and day 7. Blood samples were collected in heparinized tubes and analyzed for plasma concentrations of blood urea nitrogen (BUN) (FIG. 17D), creatinine (FIG. 17C), aspartate aminotransferase (AST) (FIG. 17A), and alanine aminotransferase (ALT) (FIG. 17B) at D7, D15 and D30.
Figure 17B:
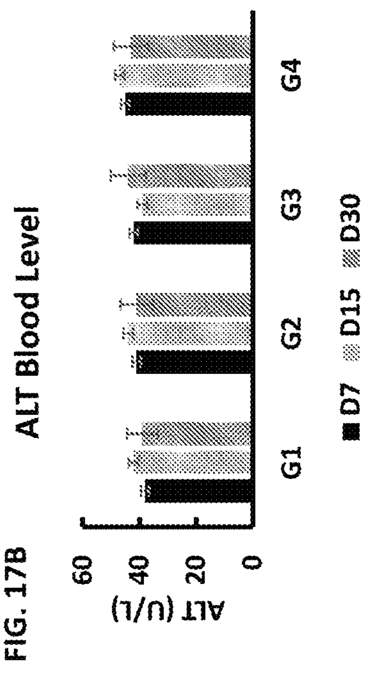
Figure 17C:
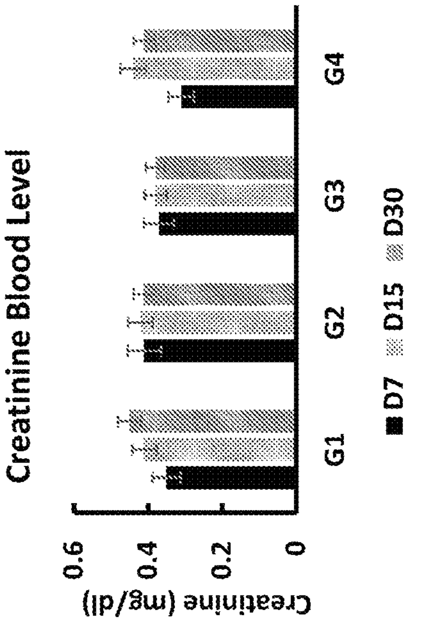
Figure 17D:
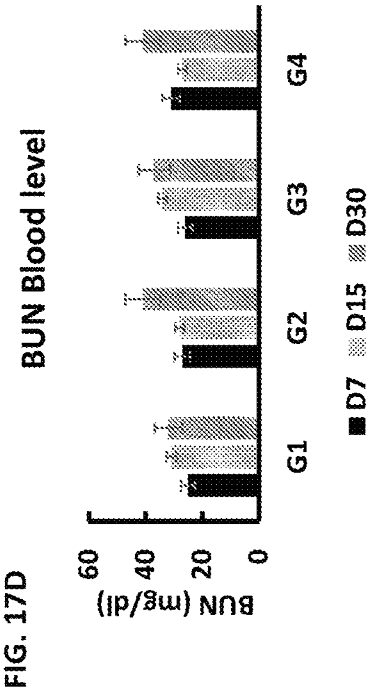

The toxicity and in vivo tolerability of ADGN/Cas9/gRNA35A5 and ADGN/Cas9/gRNA35T3 have been evaluated. Animals were treated on day 0 and day 7 intravenously with ADGN/Cas9/gRNA complex at 0.5 and 1.0 mg/kg. Animal weight was quantified at different time points (FIG. 16A-16B). Blood samples were collected in heparinized tubes and analyzed for plasma concentrations of blood urea nitrogen (BUN), creatinine, aspartate aminotransferase (AST), and alanine aminotransferase (ALT) at D7, D15 and D30. As reported in FIGS. 16A-16B, all treatments were well tolerated and no significant body weight loss was observed. No significant variation in BUN, AST, ALT and creatinine suggested a great tolerability of the treatment and a lack of renal and hepatic toxicity (FIG. 17A-17D).

Example 13

Table 8 lists a summary of cell-penetrating peptides that have been proven successful in delivering a CRISPR molecule (such as guide RNA described herein) into a cell in vivo (e.g., by intravenous (IV), intramuscular (IM), or subcutaneous (SQ) administration, or nebulization (NB) or intratracheal instillation). As shown, most of the cell-penetrating peptides were able to specifically target one or more organs.

TABLE 8

| CPP | SEQUENCES | IN VIVO | ROUTE | TARGETED ORGAN |
|---|---|---|---|---|
| ADGN-100a | beta-AKWRSAGWRWRLWRVRSWSR (SEQ ID NO: 154) | Mice | IV/IM/SQNB/ | LUNG/LIVER/KIDNEY/PANCREAS |
| ADGN-100b | beta-AKWRSALYRWRLWRVRSWSR (SEQ ID NO: 155) | Mice | IV/IM/SQ | LUNG/LIVER/KIDNEY/PANCREAS |
| ADGN-100 GALNAC | Ac-KWRSA(GALNAC)LWRWRLWRVRSWSR-NH2 (SEQ ID NO: 172) | Mice | IV/SQ | LIVER |
| ADGN-100-Hydro-3 | Ac-YIGSR-Ava-KWRSALWRWRLWRVRSWSR-NH2 (SEQ ID NO: 162) | Mice | IV/IM | TUMOR/LUNG |
| ADGN-100 Hydro-7 | Ac-YIGSR-Ahx-KWRSALWRWRLWRVRSWSR-NH2 (SEQ ID NO: 167) | Mice | IV/IM | TUMOR/LUNG |
| ADGN-100-PEG2 | Ac-(PEG)2-beta-A-KWRSALWRWRLWRVRSWSR-NH2 (SEQ ID NO: 158 or 267) | Mice | IV/IM | Lung/Liver/Spleen |
| ADGN-100-PEG7 | Ac-(PEG)7-beta A-KWRSALWRWRLWRVRSWSR-NH2 (SEQ ID NO: 157 or 268) | Mice | IV/IM | Lung/liver/kidney |
| ADGN-100-HYPEG2 | Ac-YIGSR-(PEG)2-βA-KWRSALWRWRLWRVRSWSR-NH2 (SEQ ID NO: 170 or 269) | Mice | IV/IM | Lung/Tumor |
| VEPEP-6 (ADGN-106) | beta-ALWRALWRLWRSLWRLLWKA (SEQ ID NO: 89 or 270) | Mice/Rat | IV/IM/NB/SQ | Liver/Lung |
| ADGN-106-Hydro-1 | Ac-YIGSR-(G)4-ALWRALWRLWRSLWRLLWKA-NH2 (SEQ ID NO: 94) | Mice | IV/IM | Lung/tumor |
| ADGN-106 hydro-2 | Ac-GYVS-(G)4-ALWRALWRLWRSLWRLLWKA-NH2 (SEQ ID NO: 95) | Mice | IV/IM | Liver/muscle |
| ADGN-106-Hydro-3: | Ac-YIGSR-Ava-ALWRALWRLWRSLWRLLWKA-NH2 (SEQ ID NO: 96) | Mice | IV/IM | Tumor/Lung |
| ADGN-106 hydro-4 | Ac-GYVS-Ava-ALWRALWRLWRSLWRLLWKA-NH2 (SEQ ID NO: 97) | Mice | IV/IM | Brain/Kidney |
| ADGN-106-Hydro-5 | Ac-YIGSR-Aun-ALWRALWRLWRSLWRLLWKA-NH2 (SEQ ID NO: 98) | Mice | IV/IM | Tumor/Lung/Pancreas/Liver |
| ADGN-106 hydro-6 | Ac-GYVS-Aun-ALWRALWRLWRSLWRLLWKA-NH2 (SEQ ID NO: 99) | Mice | IV/IM | Tumor/Pancreas/Lung |

TABLE 8-continued

| CPP | SEQUENCES | IN VIVO | ROUTE | TARGETED ORGAN |
|---|---|---|---|---|
| ADGN-106 hydro-7 | Ac-YIGSR-Ahx-ALWRALWRLWRSLWRLLWKA-NH2 (SEQ ID NO: 100) | Mice | IV/IM | Lung/Tumor |
| ADGN-106-PEG7 | Ac-(PEG)7-βALWRALWRLWRSLWRLLWKA-NH2 (SEQ ID NO: 92) | Mice | IV/IM | Lung |
| ADGN-106-PEG2 | Ac-(PEG)2-βALWRALWRLWRSLWRLLWKA-NH2 (SEQ ID NO: 93) | Mice | IV/IM | Lung/Kidney/Spleen |
| ADGN-106-HYPEG2 | Ac-YIGSR-(PEG)2-βALWRALWRLWRSLWRLLWKA-NH2 (SEQ ID NO: 105) | Mice | IV/IM | Tumor/Lung |
| ADGN-106-HYPEG4 | Ac-YIGSR-(PEG)4-βALWRALWRLWRSLWRLLWKA-NH2 (SEQ ID NO: 106) | Mice | IV/IM | Tumor/Lung |
| ADGN-106-TB | Ac-SYTSSTM-ava-βALWRALWRLWRSLWRLLWKA-NH2 (SEQ ID NO: 112) | Mice | IV/IM | Brain/Liver |
| ADGN-106-TC | Ac-THRPPNWSPVWPRALWRLWRSLWRLRWKA-NH2 (SEQ ID NO: 113) | Mice | IV/IM | Brain/Lung |
| ADGN-106-TD | Ac-CKTRRVPWRALWRLWRSLWRLLWKA-NH2 (SEQ ID NO: 114) | Mice | IV/IM | Muscle/Heart |
| ADGN-106-HYPEG7 | Ac-YIGSR-(PEG)7-βALWRALWRLWRSLWRLLWKA-NH2 (SEQ ID NO: 107) | Mice | IV/IM | Tumor/liver |

Table 9 below shows the SEQ ID Nos of the cell-penetrating peptides that are able to deliver a CRISPR molecule (such as guide RNA described herein) into a cell in vivo (e.g., by intravenous (IV), intramuscular (IM), or subcutaneous (SQ) administration, or nebulization (NB) or intratracheal instillation) based upon Table 8 and FIG. 6.

TABLE 9

| Organ | Heart | Brain | Muscle | lung | liver | kidney | pancreas | tumor | spleen |
|---|---|---|---|---|---|---|---|---|---|
| Cell-penetrating Peptide SEQ ID NO | 114, 153, 154, 96, 100, 101 | 97, 112, 113 | 95, ~~96,~~ 98, 114, 100, 101 | 89, 90, 92, 93, 94, 96, 98, 99, 100, 101, 105, 106, 107, 113, 137, 138, 153, 154, 155, 157, 158, 162, 164, 167, 170 | 89, 90, 95, 98, 112, 137, 138, 153, 154, 155, 158, 172, 164, 153, 157, 96, 162, 167, 100, 101 | 89, 90, 93, 96, 97, 98, 137, 100, 101, 138, 154, 155, 157 | 98, 99, 137, 138, 153, 154, 155, 162 | 94, 96, 98, 99, 100, 101, 105, 106, 107, 153, 154, 162, 164, 167, 170 | 93, 153, 154, 158 |

Example 14

Cancer Cell Lines.

All cell lines were obtained from the ATCC and the characteristics are reported in FIG. 24. Pancreatic cancer (PDAC): PANC1 Heterozygous for KRAS p.Gly12Asp (c.35G>A), PK 45H Homozygous for KRAS p.Gly12Asp (c.35G>A), PK1 Heterozygous for KRAS p.Gly12Asp (c.35G>A), MIA-PACA Homozygous for KRAS p.Gly12Cys (c.34G>T), ASPC-1 KRAS p.Gly12Asp (c.35G>A)

Colorectal cancer (CRC): SW480 Homozygous for KRAS p.Gly12Val (c.35G>T), SW403 Heterozygous for KRAS p.Gly12Val (c.35G>T), LS513 Heterozygous for KRAS p.Gly12Asp (c.35G>A), HT-29 WT KRAS and Homozygous for TP53 p.Arg273His (c.818G>A), HT-29 WT for KRAS Lung Cancer (NSCLC): NCI H23, CALU-1, H-2122, H358 Heterozygous for KRAS p.Gly12Cys (c.34G>T), H1299 WT for KRAS, H-2444, H-441 for KRAS p.Gly12Val (c.35G>T)

Specific Targeting Kras G12V Mutation in Cancer Cell Lines Using Adgn-121 Nanoparticle.

We have selected gRNA35T3 guide which is highly specific for KRAS G12V mutated cancer cells, leading to indel frequency higher that 70% in KRAS G12V mutated cancer cells. ADGN-121 nanoparticle corresponds to gRNA35T3 sgRNA/Cas9 mRNA (1/1 molar ratio) associated with ADGN peptide (ADGN-100-Hydro3 peptide) at molar ratio 20/1 (peptide/nucleic acid). ADGN-121 nanoparticles were evaluated on a large panel of cancer cells. Cells were cultured in 98 well plate format and treated with free mRNACas9-gRNA, or ADGN-121 (ADGN/mRNACas9-gRNA) complex (from 0.1-10 μM) on day 1. Cell proliferation was analyzed over a period of 5 days using CellTiter Glow kits on GlowMax (Promega) and cytotoxicity was analyzed at 72 hr after treatment using CellTiter Glow or MTT assays kits.

Figure 20:
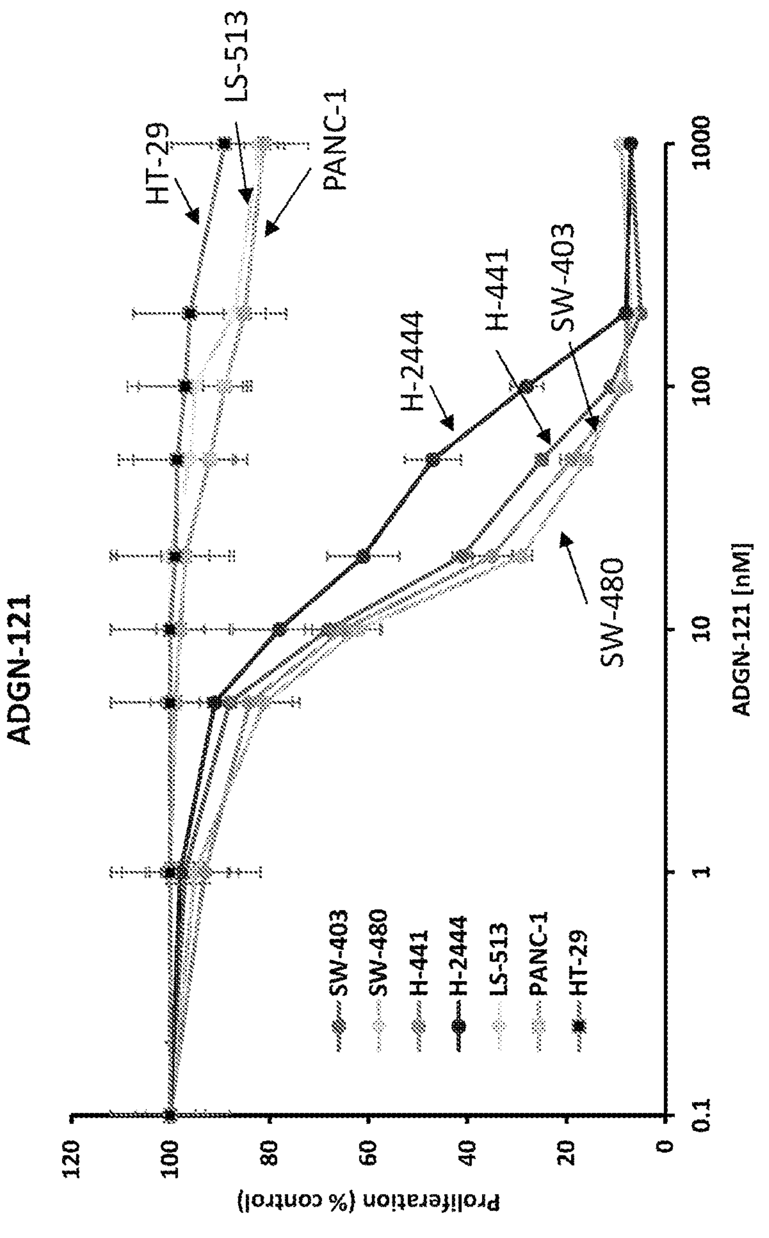
FIG. 20 shows the evaluation of ADGN-121 gRNAs targeting KRAS 35G>T mutant on different cell lines. SW403, SW480, PANC1, LS-513, HT-29, H-441, and H-2444 cells were treated with free mRNACas9-gRNA, or ADGN-121 (ADGN/mRNACas9-gRNA) complex (from 0.1 nM-10 μM) on day 1. Cell proliferation was analyzed over a period of 5 days using CellTiter Glow kits on GlowMax (Promega).

As reported in FIG. 20, ADGN-121 (gRNA35T3) inhibits specifically cell proliferation of all KRAS G12V mutated cancer cells. In contrast, ADGN-121 does not alter the proliferation of KRAS G12D (PANC-1, LS-513), and KRAS G12C (H-358, CALU-1) mutant cells or WT KRAS (HT-29, H-1299) cells. As reported in FIG. 25, ADGN-121 nanoparticles induced KRAS G12V editing in NSCLC and CRC cells with $IC_{50}$ value in a nanomolar range, between 10-50 nM. Analyzing ADGN-121 toxicity showed that toxicity occurs at concentration value (between 7-15 μM) which are 450 to 1000 folds higher than $IC_{50}$.

ADGN-100 Hydro3 peptide was used for this experiment. ADGN-106-Hydro3 has the same efficiency.

Specific Targeting Kras G12D Mutation in Cancer Cell Lines Using Adgn-123 Nanoparticle.

Figure 21:
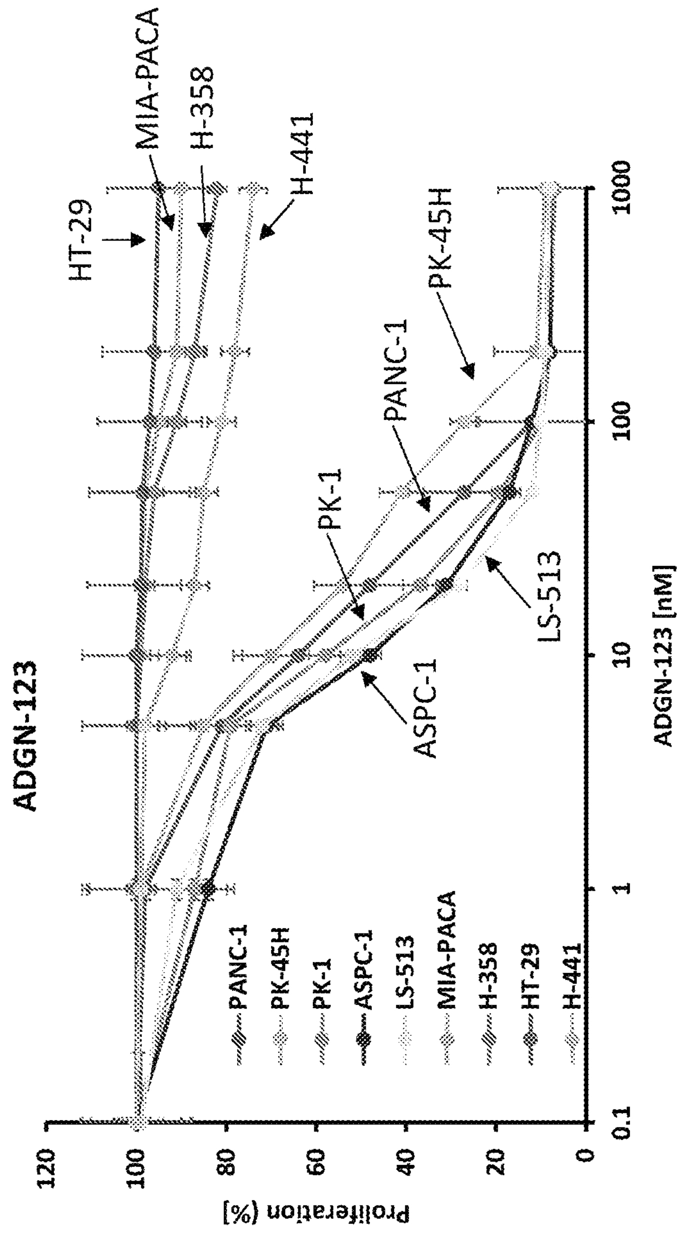
FIG. 21 shows the evaluation of ADGN-123 gRNAs targeting KRAS 35G>A mutant on different cell lines. PANC1, PK-45H, PK-1, ASPC-1, MIA-PACA, LS-513, H358, HT-29, and H-441 cells were treated with free mRNACas9-gRNA, or ADGN-123 (ADGN/mRNACas9-gRNA) complex (from 0.1 nM-10 μM) on day 1. Cell proliferation was analyzed over a period of 5 days using CellTiter Glow kits on GlowMax (Promega).

We have selected gRNA35A5 guide which is highly specific for KRAS G12D mutated cancer cells, leading to indel frequency higher that 70% in KRAS G12D mutated cancer cells. ADGN-123 nanoparticle corresponds to gRNA35A5 sgRNA/Cas9 mRNA (1/1 molar ratio) associated with ADGN peptide (ADGN-106-Hydro3 peptide) at molar ratio 20/1 (peptide/nucleic acid). ADGN-123 nanoparticles were evaluated on a large panel of cancer cells. Cells were cultured in 98 well plate format and treated with free mRNACas9-gRNA, or ADGN-123 (ADGN/mRNACas9-gRNA) complex (from 0.1-10 μM) on day 1. Cell proliferation was analyzed over a period of 5 days using CellTiter Glow kits on GlowMax (Promega) and cytotoxicity was analyzed at 72 hr after treatment using CellTiter Glow or MTT assays kits As reported in FIG. 21, ADGN-123 (gRNA35A5) inhibits specifically cell proliferation of all KRAS G12D mutated cancer cells. In contrast, ADGN-123 does not alter KRAS G12V (H-441, SW-480, SW-403) and KRAS G12C (H-358, MIA PACA) mutant cells or WT (HT-29) KRAS cells. As reported in FIG. 26, ADGN-123 nanoparticles induces KRAS G12D editing in PDA and CRC cells harboring KRAS G12D mutation, with $IC_{50}$ value in a nanomolar range, between 10-25 nM. Analyzing ADGN-123 toxicity showed that toxicity occurs at concentration value ($CC_{50}$ between 7-15 μM) which are 450 to 1000 folds higher than $IC_{50}$.

ADGN-106 Hydro3 peptide was used for this experiment. ADGN-100-Hydro3 has the same efficiency.

Specific Targeting Kras G12C Mutation in Cancer Cell Lines with ADGN-122

Figure 22:
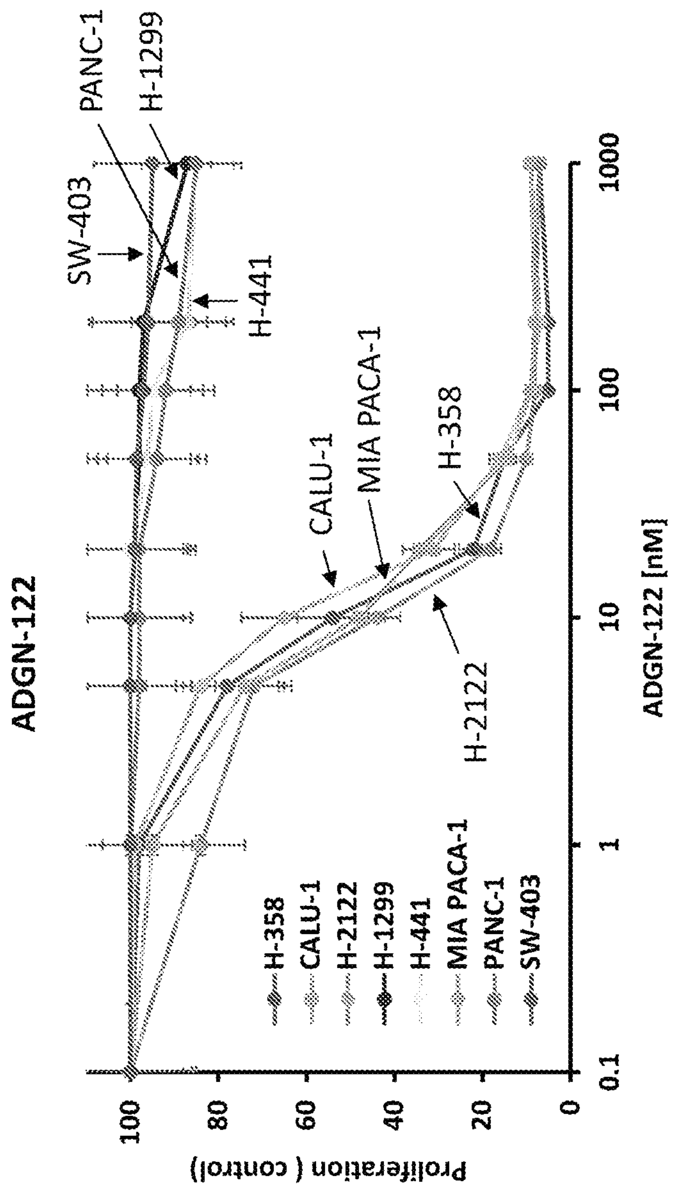
FIG. 22 shows the evaluation of ADGN-122 gRNAs targeting KRAS 34A>T mutant on different cell lines. SW403, PANC1, H358, CALU-1, H-2122, H-441, MIA-PACA, and H-1299 cells were treated with free mRNACas9-gRNA, or ADGN-122 (ADGN/mRNACas9-gRNA) complex (from 0.1 nM-10 μM) on day 1. Cell proliferation was analyzed over a period of 5 days using CellTiter Glow kits on GlowMax (Promega).
Figure 23:
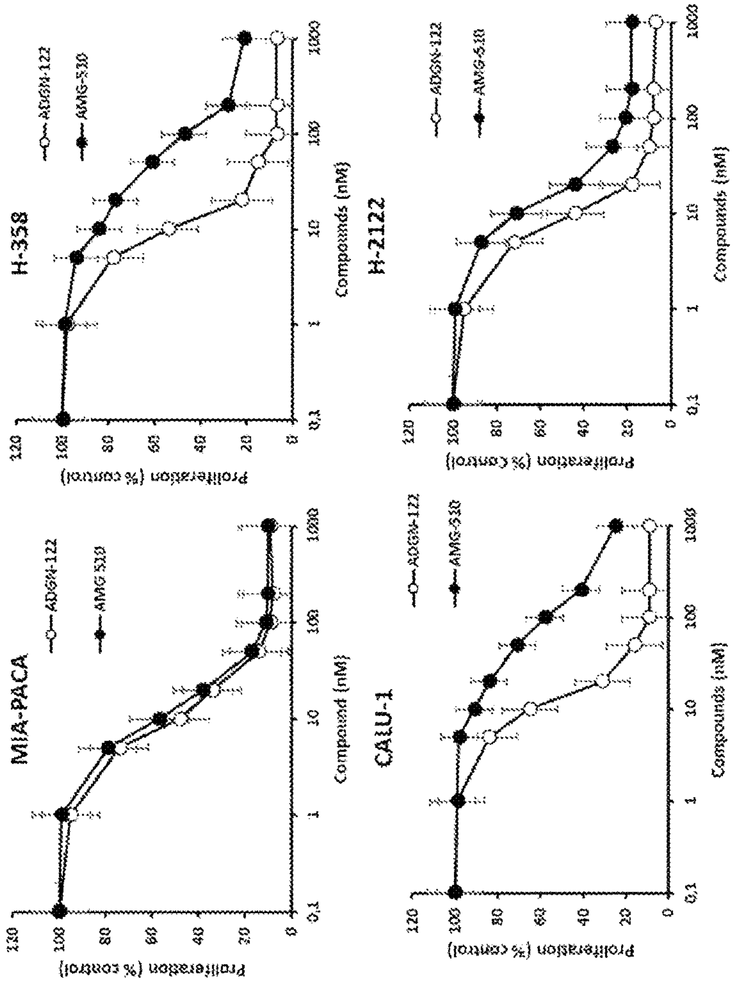
FIG. 23 shows the evaluation of AMG-510 and ADGN-122 targeting KRAS 34A>T mutant on different cell lines. H358, CALU-1, MIA-PACA and H-2122 cells were treated with or ADGN-122 (ADGN/mRNACas9-gRNA) complex and AMG-510 (from 0.1 nM-1000 nM) on day 1. Cell proliferation was analyzed over a period of 5 days using CellTiter Glow kits on GlowMax (Promega).

We have selected gRNA34T6 guide which is highly specific for KRAS G12C mutated cancer cells, leading to indel frequency higher that 70% in KRAS G12C mutated cancer cells. ADGN-122 nanoparticle corresponds to gRNA34T6 sgRNA/Cas9 mRNA (1/1 molar ratio) associated with ADGN peptide (ADGN-100-Hydro3 peptide) at molar ratio 20/1 (peptide/nucleic acid). ADGN-122 nanoparticles were evaluated on al large panel of cancer cells. Cells were cultured in 96 well plate format and treated with free mRNACas9-gRNA, or ADGN-122 (ADGN/mRNACas9-gRNA) complex (from 0.1-10 μM) on day 1. Cell proliferation was analyzed over a period of 5 days using CellTiter Glow kits on GlowMax (Promega) and cytotoxicity was analyzed at 72 hr after treatment using CellTiter Glow or MTT assays kits As reported in FIG. 22, ADGN-122 (gRNA34T6) inhibits specifically cell proliferation of all KRAS G12C mutated cancer cells. In contrast, ADGN-122 does not alter KRAS G12V (H-441, SW-480, SW-403) and KRAS G12D (PANC-1, ASPC-1) mutant cells or WT (H-1299) KRAS cells. As reported in FIG. 27, ADGN-122 nanoparticles induces KRAS G12C editing in PDA and NSCL cells harboring KRAS G12C mutation, with $IC_{50}$ value in a nanomolar range, between 10-16 nM. Analyzing ADGN-122 toxicity showed that toxicity occurs at concentration value ($CC_{50}$ between 7-15 μM) which are 800 to 1000 folds higher than $IC_{50}$.

ADGN-122/AMG-510 Comparison on Kras G12C Mutant Cell Lines

The AMG510 inhibitor, specifically targeting G12C KRAS, has shown efficacy in pre-clinical models of non-small cell lung cancers (NSCLCs) and has also been shown to enhance response to immune checkpoint blockade. AMG-510 is, however, specific for the G12C mutation and does not inhibit the G12D mutant KRAS. We have evaluated the potency of ADGN-122 versus AMG-510 on four different cancer cell lines harboring KRAS G12C mutation. (MIA PACA, H-358, CALU-1, H-2122). Cells were plated in 96 well plate format 24 hr prior treatment. Cells were treated with ADGN-122 or AMG-510 (1-1000 nM) on day 1. Cell proliferation was analyzed over a period of 5 days using CellTiter Glow kits on GlowMax (Promega) and cytotoxicity was analyzed at 72 hr after treatment using CellTiter Glow or MTT assays kits.

ADGN-122 efficiency is similar to AMG-510 in MIA PACA cells.

As reported in FIG. 20 and FIG. 28 both ADGN-122 and AMG-510 inhibit specifically proliferation of all KRAS G12C mutated cancer cells. ADGN-122 and AMG-510 have similar efficacy in PDA (MIA-PACA) cell. ADGN-122 is more efficient than AMG-510 in NSCLC cells. ADGN-122 is 3.7, 5.7 and 7.1 folds more potent than AMG-510, H-2122, H-358 and CALU-1 cells, respectively.

ADGN-100 Hydro3 peptide was used for this experiment. ADGN-106-Hydro3 has the same efficiency.

SEQUENCE TABLE

| SEQ ID NO | Description | Sequences |
|---|---|---|
| Exemplary KRAS G12V gRNA | | |
| 1. | G12V-gRNA35T1 | GTTGGAGCTGTTGGCGTAGGC |
| 2. | G12V-gRNA35T2 | CTTGTGGTAGTTGGAGCTGT |
| 3. | G12V-gRNA35T3 | GGTAGTTGGAGCTGTTGGCG |
| 4. | G12V gRNA35T4 | AGCTGTTGGCGTAGGCAAGA |

-continued

SEQUENCE TABLE

| SEQ ID NO | Description | Sequences |
|---|---|---|
| 5. | G12V-gRNA35T5 | TGTTGGCGTAGGCAAGAGTGCC |
| 6. | G12V-gRNA35T6 | GTTGGAGCTGTTGGCGTAGG |
| 7. | G12V-gRNA35T7 | TTGTGGTAGTTGGAGCTGTTG |
| 8. | G12V-gRNA35T8 | GTAGTTGGAGCTGTTGGCGT |
| 9. | G12V-gRNA35T9 | GCTGTTGGCGTAGGCAAGAGT |
| 10. | G12V-gRNA35T10 | TAGTTGGAGCTGTTGGCGT |
| 11. | G12V-gRNA35T11 | TGTTGGCGTAGGCAAGAGTGCCTTG |
| 12. | G12V gRNA | TTGTGGTAGTTGGAGCTGTT |
| 13. | G12V gRNA | TAGTTGGAGCTGTTGGCGTAG |
| 14. | G12V gRNA | GCTGTTGGCGTAGGCAAGAGA |
| | | **Exemplary KRAS G12D gRNA** |
| 15. | G12D-gRNA35A1 | CTTGTGGTAGTTGGAGCTGA |
| 16. | G12D-gRNA35A2 | GGTAGTTGGAGCTGATGGC |
| 17. | G12D-gRNA35A3 | AGCTGATGGCGTAGGCAAGA |
| 18. | G12D-gRNA35A4 | TGATGGCGTAGGCAAGAGTGCC |
| 19. | G12D-gRNA35A5 | AGTTGGAGCTGATGGCGT |
| 20. | G12D-gRNA35A6 | GTTGGAGCTGATGGCGTAGG |
| 21. | G12D-gRNA35A7 | GTAGTTGGAGCTGATGGCGT |
| 22. | G12D-gRNA35A8 | TTGTGGTAGTTGGAGCTGAT |
| 23. | G12D-gRNA35A9 | GCTGATGGCGTAGGCAAGAGA |
| 24. | G12D-gRNA35A10 | TAGTTGGAGCTGATGGCGT |
| 25. | G12D-gRNA35A11 | TGATGGCGTAGGCAAGAGTGCCTTG |
| 26. | G12D gRNA | TTGTGGTAGTTGGAGCTGAT |
| 27. | G12D gRNA | TAGTTGGAGCTGATGGCGTAG |
| 28. | G12D gRNA | GCTGATGGCGTAGGCAAGAGA |
| | | **Exemplary KRAS G12C gRNA** |
| 29. | G12C-gRNA34T1 | CTTGTGGTAGTTGGAGCTTG |
| 30. | G12C-gRNA34T2 | AGCTTGTGGCGTAGGCAAGA |
| 31. | G12C-gRNA34T3 | GTTGGAGCTTGTGGCGTAGGC |
| 32. | G12C-gRNA34T4 | GGTAGTTGGAGCTTGTGGC |
| 33. | G12C-gRNA34T5 | TTGTGGTAGTTGGAGCTTG |
| 34. | G12C-gRNA34T6 | GTAGTTGGAGCTTGTGGCGT |
| 35. | G12C-gRNA34T7 | GCTTGTGGCGTAGGCAAGAG |
| 36. | G12C-gRNA34T8 | CTTGTGGCGTAGGCAAGAGTGC |
| 37. | G12C-gRNA34T9 | CTTGTGGCGTAGGCAAGAGTGCCTTG |
| | | **Exemplary KRAS WT gRNA** |
| 38. | KRAS WT-gRNAWT1 | CTTGTGGTAGTTGGAGCTGG |
| 39. | KRAS WT-gRNAWT2 | TTGGATATTCTCGACACAGC |
| 40. | KRAS WT-gRNAWT3 | TCTCGACACAGCAGGTCAAG |
| 41. | KRAS WT-gRNAWT4 | GATGTACCTATGGTCCTAGT |
| 42. | KRAS WT-gRNAWT5 | GTCGAGAATATCCAAGAGAC |
| 43. | KRAS WT-gRNAWT6 | TCTCGACACAGCAGGTCAAG |
| | | **Exemplary cell-penetrating peptides VEPEP-3 peptides** |
| 44. | VEPEP-3 | $X_1X_2X_3X_4X_5X_2X_3X_4X_6X_7X_3X_8X_9X_{10}X_{11}X_{12}X_{13}$<br>$X_1$ is beta-A or S, $X_2$ is K, R or L, $X_3$ is F or W, $X_4$ is F, W or Y, $X_5$ is E, R or S, $X_6$ is R, T or S, $X_7$ is E, R, or S, $X_8$ is none, F or W, $X_9$ is P or R, $X_{10}$ is R or L, $X_{11}$ is K, W or R, $X_{12}$ is R or F, and $X_{13}$ is R or K |
| 45. | VEPEP-3 1 | $X_1X_2WX_4EX_2WX_4X_6X_7X_3PRX_{11}RX_{13}$<br>$X_1$ is beta-A or S, $X_2$ is R or K, $X_3$ is W or F, $X_4$ is F, W, or Y, $X_6$ is T or R, $X_7$ is E or R, $X_{11}$ is R or K, and $X_{13}$ is R or K |
| 46. | VEPEP-3 1a | $X_1$KWFERWFREWPRKRR<br>$X_1$ is beta-A or S |
| 47. | VEPEP-3 1b | $X_1$KWWERWWREWPRKRR<br>$X_1$ is beta-A or S |
| 48. | VEPEP-3 1c | $X_1$KWWERWWREWPRKRK<br>$X_1$ is beta-A or S |
| 49. | VEPEP-3 1d | $X_1$RWWEKWWTRWPRKRK<br>$X_1$ is beta-A or S |
| 50. | VEPEP-3 1e | $X_1$RWYEKWYTEFPRRRR<br>$X_1$ is beta-A or S |
| 51. | VEPEP-3 1S | $X_1KX_{14}$WWERWWR$X_{14}$WPRKRK<br>$X_1$ is beta-A or S and $X_{14}$ is a non-natural amino acid, and wherein there is a hydrocarbon linkage between the two non-natural amino acids |

-continued

SEQUENCE TABLE

| SEQ ID NO | Description | Sequences |
|---|---|---|
| 52. | VEPEP-3 2 | $X_1X_2X_3WX_5X_{10}XWX_6X_7WX_8X_9X_{10}WX_{12}R$<br>$X_1$ is beta-A or S, $X_2$ is K, R or L, $X_3$ is F or W, $X_5$ is R or S, $X_6$ is R or S, $X_7$ is R or S, $X_8$ is F or W, $X_9$ is R or P, $X_{10}$ is L or R, and $X_{12}$ is R or F |
| 53. | VEPEP-3 2a | $X_1$RWWRLWWRSWFRLWRR<br>$X_1$ is beta-A or S |
| 54. | VEPEP-3 2b | $X_1$LWWRRWWSRWWPRWRR<br>$X_1$ is beta-A or S |
| 55. | VEPEP-3 2c | $X_1$LWWSRWWRSWFRLWFR<br>$X_1$ is beta-A or S |
| 56. | VEPEP-3 2d | $X_1$KFWSRFWRSWFRLWRR<br>$X_1$ is beta-A or S |
| 57. | VEPEP-3 2S | $X_1$RWWX$_{14}$LWWRSWX$_{14}$RLWRR<br>$X_1$ is a beta-alanine or a serine and $X_{14}$ is a non-natural amino acid, and wherein there is a hydrocarbon linkage between the two non-natural amino acids |
| 58. | VEPEP-3a | beta-AKWFERWFREWPRKRR |
| 59. | VEPEP-3b | beta-AKWWERWWREWPRKRR |
| 60. | VEPEP-3C | ASSLNIA-Ava-KWWERWWREWPRKRR |
| 61. | VEPEP-3D | LSSRLDA-Ava-KWWERWWREWPRKRR |
| 62. | VEPEP-3E | Ac-SYTSSTM-ava-KWWERWWREWPRKRR |
| | | VEPEP-6 peptides |
| 63. | VEPEP-6 1 | $X_1LX_2RALWX_9LX_3X_9X_4LWX_9LX_5X_6X_7X_8$<br>$X_1$ is beta-A or S, $X_2$ is F or W, $X_3$ is L, W, C or I, $X_4$ is S, A, N or T, $X_5$ is L or W, $X_6$ is W or R, $X_7$ is K or R, $X_8$ is A or none, and $X_9$ is R or S |
| 64. | VEPEP-6 2 | $X_1LX_2LARWX_9LX_3X_9X_4LWX_9LX_5X_6X_7X_8$<br>$X_1$ is beta-A or S, $X_2$ is F or W, $X_3$ is L, W, C or I, $X_4$ is S, A, N or T, $X_5$ is L or W, $X_6$ is W or R, $X_7$ is K or R, $X_8$ is A or none, and $X_9$ is R or S |
| 65. | VEPEP-6 3 | $X_1LX_2ARLWX_9LX_3X_9X_4LWX_9LX_5X_6X_7X_8$<br>$X_1$ is beta-A or S, $X_2$ is F or W, $X_3$ is L, W, C or I, $X_4$ is S, A, N or T, $X_5$ is L or W, $X_6$ is W or R, $X_7$ is K or R, $X_8$ is A or none, and $X_9$ is R or S |
| 66. | VEPEP-6 4 | $X_1LX_2RALWRLX_3RX_4LWRLX_5X_6X_7X_8$<br>$X_1$ is beta-A or S, $X_2$ is F or W, $X_3$ is L, W, C or I, $X_4$ is S, A, N or T, $X_5$ is L or W, $X_6$ is W or R, $X_7$ is K or R, and $X_8$ is A or none |
| 67. | VEPEP-6 5 | $X_1LX_2RALWRLX_3RX_4LWRLX_5X_6KX_7$<br>$X_1$ is beta-A or S, $X_2$ is F or W, $X_3$ is L or W, $X_4$ is S, A or N, $X_5$ is L or W, $X_6$ is W or R, $X_7$ is A or none |
| 68. | VEPEP-6 6 | $X_1LFRALWRLLRX_2LWRLLWX_3$<br>$X_1$ is beta-A or S, $X_2$ is S or T,and $X_3$ is K or R |
| 69. | VEPEP-6 7 | $X_1LWRALWRLWRX_2LWRLLWX_3A$<br>$X_1$ is beta-A or S, $X_2$ is S or T, and $X_3$ is K or R |
| 70. | VEPEP-6 8 | $X_1LWRALWRLX_4RX_2LWRLWRX_3A$<br>$X_1$ is beta-A or S, $X_2$ is S or T, $X_3$ is K or R, and $X_4$ is L, C or I |
| 71. | VEPEP-6 9 | $X_1LWRALWRLWRX_2LWRLWRX_3A$<br>$X_1$ is beta-A or S, $X_2$ is S or T, and $X_3$ is K or R |
| 72. | VEPEP-6 10 | $X_1LWRALWRLX_5RALWRLLWX_3A$<br>$X_1$ is beta-A or S, $X_3$ is K or R, and $X_5$ is L or I |
| 73. | VEPEP-6 11 | $X_1LWRALWRLX_4RNLWRLLWX_3A$<br>$X_1$ is beta-A or S, $X_3$ is K or R, and $X_4$ is L, C or I |
| 74. | VEPEP-6a | Ac-$X_1$LFRALWRLLRSLWRLLWK-cysteamide<br>$X_1$ is beta-A or S |
| 75. | VEPEP-6b | Ac-$X_1$LWRALWRLWRSLWRLLWKA-cysteamide<br>$X_1$ is beta-A or S |
| 76. | VEPEP-6c | Ac-$X_1$WRALWRLLRSLWRLWRKA-cysteamide<br>$X_1$ is beta-A or S |
| 77. | VEPEP-6d | Ac-$X_1$LWRALWRLWRSLWRLWRKA-cysteamide<br>$X_1$ is beta-A or S |
| 78. | VEPEP-6e | Ac-$X_1$LWRALWRLLRALWRLLWKA-cysteamide<br>$X_1$ is beta-A or S |
| 79. | VEPEP-6f | Ac-$X_1$LWRALWRLLRNLWRLLWKA-cysteamide<br>$X_1$ is beta-A or S |
| 80. | ST-VEPEP-6a | Ac-$X_1$LFRALWR$_s$LLRS$_s$LWRLLWK-cysteamide<br>$X_1$ is beta-A or S and the residues followed by an inferior "s" are linked by a hydrocarbon linkage |
| 81. | ST-VEPEP-6aa | Ac-$X_1$LFLARWR$_s$LLRS$_s$LWRLLWK-cysteamide<br>$X_1$ is beta-A or S and the residues followed by an inferior "s" are linked by a hydrocarbon linkage |

-continued

SEQUENCE TABLE

| SEQ ID NO | Description | Sequences |
|---|---|---|
| 82. | ST-VEPEP-6ab | Ac-$X_1$LFRALW$S_s$LLR$S_s$LWRLLWK-cysteamide<br>$X_1$ is beta-A or S and the residues followed by an inferior "s" are linked by a hydrocarbon linkage |
| 83. | ST-VEPEP-6ad | Ac-$X_1$LFLARW$S_s$LLR$S_s$LWRLLWK-cysteamide<br>$X_1$ is beta-A or S and the residues followed by an inferior "s" are linked by a hydrocarbon linkage |
| 84. | ST-VEPEP-6b | Ac-$X_1$LFRALWRLL$R_s$SLW$S_s$LLWK-cysteamide<br>$X_1$ is beta-A or S and the residues followed by an inferior "s" are linked by a hydrocarbon linkage |
| 85. | ST-VEPEP-6ba | Ac-$X_1$LFLARWRLL$R_s$SLW$S_s$LLWK-cysteamide<br>$X_1$ is beta-A or S and the residues followed by an inferior "s" are linked by a hydrocarbon linkage |
| 86. | ST-VEPEP-6bb | Ac-$X_1$LFRALWRLL$S_s$SLW$S_s$LLWK-cysteamide<br>$X_1$ is beta-A or S and the residues followed by an inferior "s" are linked by a hydrocarbon linkage |
| 87. | ST-VEPEP-6bd | Ac-$X_1$LFLARWRLL$S_s$SLW$S_s$LLWK-cysteamide<br>$X_1$ is beta-A or S and the residues followed by an inferior "s" are linked by a hydrocarbon linkage |
| 88. | ST-VEPEP-6c | Ac-$X_1$LFA$R_s$LWRLLR$S_s$LWRLLWK-cysteamide<br>$X_1$ is beta-A or S and the residues followed by an inferior "s" are linked by a hydrocarbon linkage |
| 89. | VEPEP-6 (ADGN-106) | beta-ALWRALWRLWRSLWRLLWKA |
| 90. | ADGN-106 | beta-ALWRALWRLWRSLWRLLWKA-NH2 |
| 91. | ADGN-106-RI | AKWLLRWLSRWLRWLARWLR |
| 92. | ADGN-106-PEG7 | Ac-(PEG)7-βALWRALWRLWRSLWRLLWKA-NH2 |
| 93. | ADGN-106-PEG2 | Ac-(PEG)2-βALWRALWRLWRSLWRLLWKA-NH2 |
| 94. | ADGN-106-Hydro-1 | Ac-YIGSR-(G)4-ALWRALWRLWRSLWRLLWKA-NH2 |
| 95. | ADGN-106 hydro-2 | Ac-GYVS-(G)4-ALWRALWRLWRSLWRLLWKA-NH2 |
| 96. | ADGN-106-Hydro-3: | Ac-YIGSR-Ava-ALWRALWRLWRSLWRLLWKA-NH2<br>Ava is 5-amino pentanoic acid |
| 97. | ADGN-106 hydro-4 | Ac-GYVS-Ava-ALWRALWRLWRSLWRLLWKA-NH2<br>Ava is 5-amino pentanoic acid |
| 98. | ADGN-106-Hydro-5 | Ac-YIGSR-Aun-ALWRALWRLWRSLWRLLWKA-NH2<br>Aun is 11-amino-undecanoic acid |
| 99. | ADGN-106 hydro-6 | Ac-GYVS-Aun-ALWRALWRLWRSLWRLLWKA-NH2<br>Aun is 11-amino-undecanoic acid |
| 100. | ADGN-106 hydro-7 | Ac-YIGSR-Ahx-ALWRALWRLWRSLWRLLWK-NH2 |
| 101. | ADGN-106 hydro-7 | Ac-YIGSR-Ahx-ALWRALWRLWRSLWRLLWKA-NH2 |
| 102. | ADGN-106 hydro-8 | Ac-GYVS-Ahx-ALWRALWRLWRSLWRLLWKA-NH2 |
| 103. | ADGN-106-Hydro | Ac-YIGSR-βALWRALWRLWRSLWRLLWKA-NH2 |
| 104. | ADGN-106 Stearyl | Stearyl-βA-ALWRALWRLWRSLWRLLWKA-NH2 |
| 105. | ADGN-106-HYPEG2 | Ac-YIGSR-(PEG)2-βALWRALWRLWRSLWRLLWKA-NH2 |
| 106. | ADGN-106-HYPEG4 | Ac-YIGSR-(PEG)4-βALWRALWRLWRSLWRLLWKA-NH2 |
| 107. | ADGN-106-HYPEG7 | Ac-YIGSR-(PEG)7-βALWRALWRLWRSLWRLLWKA-NH2 |
| 108. | NA | |
| 109. | NA | |
| 110. | NA | |
| 111. | ADGN-106 gaLnaC | ALWRA(GalNac)LWRLWRSLWRLLWKA-NH2 |
| 112. | ADGN-106-TB | Ac-SYTSSTM-ava-βALWRALWRLWRSLWRLLWKA-NH2 |
| 113. | ADGN-106-TC | Ac-THRPPNWSPVWPRALWRLWRSLWRLRWKA-NH2 |
| 114. | ADGN-106-TD | Ac-CKTRRVPWRALWRLWRSLWRLLWKA-NH2 |
| 115. | | Ac-CKTRRVP-ava-WRALWRLWRSLWRLLWKA-NH2 |
| 116. | | Ac-CARPAR-ava-WRALWRLWRSLWRLLWK-NH2 |
| 117. | | Ac-THRPPNWSPV-ava-WRALWRLWRSLWRLRWK-NH2 |

VEPEP-9 peptides

| SEQ ID NO | Description | Sequences |
|---|---|---|
| 118. | VEPEP-9 1 | $X_1X_2X_3WWX_4X_5WAX_6X_3X_7X_8X_9X_{10}X_{11}X_{12}WX_{13}R$<br>$X_1$ is beta-A or S, $X_2$ is L or none, $X_3$ is R or none, $X_4$ is L, R or G, X5 is R, W or S, $X_6$ is S, P or T, $X_7$ is W or P, $X_8$ is F, A or R, $X_9$ is S, L, P or R, $X_{10}$ is R or S, $X_{11}$ is W or none, $X_{12}$ is A, R or none and $X_{13}$ is W or F, and wherein if $X_3$ is none, then $X_2$, $X_{11}$ and $X_{12}$ are none as well |
| 119. | VEPEP-9 2 | $X_1X_2RWWLRWAX_6RWX_8X_9X_{10}WX_{12}WX_{13}R$<br>$X_1$ is beta-A or S, $X_2$ is L or none, $X_6$ is S or P, $X_8$ is F or A, $X_9$ is S, L or P, $X_{10}$ is R or S, $X_{12}$ is A or R, and $X_{13}$ is W or F |
| 120. | VEPEP9a1 | $X_1$LRWWLRWASRWFSRWAWWR<br>$X_1$ is beta-A or S |
| 121. | VEPEP9a2 | $X_1$LRWWLRWASRWASRWAWFR<br>$X_1$ is beta-A or S |

-continued

SEQUENCE TABLE

| SEQ ID NO | Description | Sequences |
|---|---|---|
| 122. | VEPEP9b1 | $X_1$RWWLRWASRWALSWRWWR<br>$X_1$ is beta-A or S |
| 123. | VEPEP9b2 | $X_1$RWWLRWASRWFLSWRWWR<br>$X_1$ is beta-A or S |
| 124. | VEPEP9c1 | $X_1$RWWLRWAPRWFPSWRWWR<br>$X_1$ is beta-A or S |
| 125. | VEPEP9c2 | $X_1$RWWLRWASRWAPSWRWWR<br>$X_1$ is beta-A or S |
| 126. | VEPEP-9 3 | $X_1$WW$X_4$$X_5$WA$X_6$$X_7$$X_8$R$X_{10}$WWR<br>$X_1$ is beta-A or S, $X_4$ is R or G, $X_5$ is W or S, $X_6$ is S, T or P, $X_7$ is W or P, $X_8$ is A or R, and $X_{10}$ is S or R |
| 127. | VEPEP9d | $X_1$WWRWWASWARSWWR<br>$X_1$ is beta-A or S |
| 128. | VEPEP9e | $X_1$WWGSWATPRRRWWR<br>$X_1$ is beta-A or S |
| 129. | VEPEP9f | $X_1$WWRWWAPWARSWWR<br>$X_1$ is beta-A or S |
| 130. | VEPEP-9 | beta-ALRWWLRWASRWFSRWAWWR |
| 131. | VEPEP-9A | KSYDTY-ava-ALRWLRWASRWFSRWAWR |
| 132. | VEPEP-9 B | ac-CKRAVRWWLRWASRWFSRWAWWR |
| 133. | VEPEP-9 C | beta-A-RWWLRWASRWFSRWAWR |
| 134. | VEPEP-9D | KSYDTYAAETRRWASRWFSRWAWWR |
| | | ADGN-100 peptides |
| 135. | ADGN-100 | $X_1$KWRS$X_2$$X_3$$X_4$RWRLWR$X_5$$X_6$$X_7$$X_8$SR<br>$X_1$ is any amino acid or none, and $X_2$-$X_8$ are any amino acid |
| 136. | ADGN-100 1 | $X_1$KWRS$X_2$$X_3$$X_4$RWRLWR$X_5$$X_6$$X_7$$X_8$SR<br>$X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y |
| 137. | ADGN-100a | KWRSAGWRWRLWRVRSWSR |
| 138. | ADGN-100b | KWRSALYRWRLWRVRSWSR |
| 139. | ADGN-100c | KWRSALYRWRLWRSRSWSR |
| 140. | ADGN-100d | KWRSALYRWRLWRSALYSR |
| 141. | ADGN-100 aa | KWR$S_S$AGWR$_S$WRLWRVRSWSR<br>the residues marked with a subscript "S" are linked by a hydrocarbon linkage |
| 142. | ADGN-100 ab | KWR$S_S$AGWRWR$_S$LWRVRSWSR<br>the residues marked with a subscript "S" are linked by a hydrocarbon linkage |
| 143. | ADGN-100 ac | KWRSAGWR$_S$WRLWRVR$S_S$WSR<br>the residues marked with a subscript "S" are linked by a hydrocarbon linkage |
| 144. | ADGN-100 ba | KWR$S_S$ALYR$_S$WRLWRSRSWSR<br>the residues marked with a subscript "S" are linked by a hydrocarbon linkage |
| 145. | ADGN-100 bb | KWR$_S$SALYRWR$_S$LWRSRSWSR<br>the residues marked with a subscript "S" are linked by a hydrocarbon linkage |
| 146. | ADGN-100 be | KWRSALYR$_S$WRLWRSR$S_S$WSR<br>the residues marked with a subscript "S" are linked by a hydrocarbon linkage |
| 147. | ADGN-100 bd | KWRSALYRWR$_S$LWR$S_S$RSWSR<br>the residues marked with a subscript "S" are linked by a hydrocarbon linkage |
| 148. | ADGN-100 be | KWRSALYRWRLWR$S_S$RSW$S_S$R<br>the residues marked with a subscript "S" are linked by a hydrocarbon linkage |
| 149. | ADGN-100 ca | KWR$_S$SALYRWR$_S$LWRSALYSR<br>the residues marked with a subscript "S" are linked by a hydrocarbon linkage |
| 150. | ADGN-100 cb | KWR$S_S$ALYR$_S$WRLWRSALYSR<br>the residues marked with a subscript "S" are linked by a hydrocarbon linkage |
| 151. | ADGN-100 cc | KWRSALYRWR$_S$LWR$S_S$ALYSR<br>the residues marked with a subscript "S" are linked by a hydrocarbon linkage |
| 152. | ADGN-100 cd | KWRSALYRWRLWR$S_S$ALY$S_S$R<br>the residues marked with a subscript "S" are linked by a hydrocarbon linkage |
| 153. | ADGN-100 | beta-AKWRSAGWRWRLWRVRSWSR-NH2 |
| 154. | ADGN-100a (ADGN-100) | beta-AKWRSAGWRWRLWRVRSWSR |
| 155. | ADGN-100b | beta-AKWRSALYRWRLWRVRSWSR |

-continued

SEQUENCE TABLE

| SEQ ID NO | Description | Sequences |
|---|---|---|
| 156. | ADGN-100-RI | RSWSRVRWLRWRWGASRWK |
| 157. | ADGN-100-PEG7 | Ac-(PEG)7-bA-KWRSALWRWRLWRVRSWSR-NH2 |
| 158. | ADGN-100-PEG2 | Ac-(PEG)2-βA-KWRSALWRWRLWRVRSWSR-NH2 |
| 159. | ADGN-100 Stearyl | Stearyl-βA-KWRSALWRWRLWRVRSWSR-NH2 |
| 160. | ADGN-100-Hydro-1 | Ac-YIGSR-(G)4-KWRSALWRWRLWRVRSWSR-NH2 |
| 161. | ADGN-100 hydro-2 | Ac-GYVS-(G)4-KWRSALWRWRLWRVRSWSR-NH2 |
| 162. | ADGN-100-Hydro-3 | Ac-YIGSR-Ava-KWRSALWRWRLWRVRSWSR-NH2<br>Ava is 5-amino pentanoic acid |
| 163. | ADGN-100 hydro-4 | Ac-GYVS-Ava-KWRSALWRWRLWRVRSWSR-NH2<br>Ava is 5-amino pentanoic acid |
| 164. | ADGN-100-Hydro-5 | Ac-YIGSR-Aun-KWRSALWRWRLWRVRSWSR-NH2<br>Ann is 11-amino-undecanoic acid |
| 165. | ADGN-100 hydro-6 | Ac-GYVS-Aun-KWRSALWRWRLWRVRSWSR-NH2<br>Ann is 11-amino-undecanoic acid |
| 166. | ADGN-100-Hydro | Ac-YIGSR-βA-KWRSALWRWRLWRVRSWSR-NH2 |
| 167. | ADGN-100 Hydro-7 | Ac-YIGSR-Ahx-KWRSALWRWRLWRVRSWSR-NH2 |
| 168. | ADGN-102 core motif | RWRLWRWSR |
| 169. | ADGN-100 Hydro-8 | Ac-GYVS-Ahx-KWRSALWRWRLWRVRSWSR-NH2 |
| 170. | ADGN-100-HYPEG | Ac-YIGSR-(PEG)n-βA-KWRSALWRWRLWRVRSWSR-NH2<br>N = 2, 4, or 7 |
| 171. | | Ac-SYTSSTM-ava-KWRSALWRWRLWRVRSWSR-NH2 |
| 172. | ADGN-100 GALNAC | Ac-KWRSA(GALNAC)LWRWRLWRVRSWSR-NH2 |
| 173. | ADGN-101 | Ac-CARPARWRSAGWRWRLWRVRSWSR-NH2 |
| 174. | ADGN-102 | TGNYKALHPDHNGWRSALRWRLWRWSR-NH2 |
| 175. | | Ac-TGNYKALHPDHNG-ava-WRSALRWRLWRWSR-NH2 |
| | | **VEPEP-4 peptides** |
| 176. | VEPEP-4 | XWXRLXXXXXX<br>X in position 1 is beta-A or S; X in positions 3, 9 and 10 are, independently from each other, W or F; X in position 6 is R if X in position 8 is S, and X in position 6 is S if X in position 8 is R; X in position 7 is L or none; X in position 11 is R or none, and X in position 7 is L if X in position 11 is none |
| 177. | VEPEP-4 | $X_1$WWRLSLRWW<br>$X_1$ is beta-A or S |
| 178. | VEPEP-4 | $X_1$WFRLSLRFWR<br>$X_1$ is beta-A or S |
| 179. | VEPEP-4 | $X_1$WWRLRSWFR<br>$X_1$ is beta-A or S |
| 180. | VEPEP-4 | $X_1$WFRLSLRFW<br>$X_1$ is beta-A or S |
| | | **VEPEP-5 peptides** |
| 181. | VEPEP-5 | RXWXRLWXRLR<br>X in position 2 is R or S; and X in positions 4 and 8 are, independently from each other, W or F |
| 182. | VEPEP-5 | $X_1$WWRLWWRLR<br>$X_1$ is beta-A or S |
| 183. | VEPEP-5 | $X_1$WFRLWFRLR<br>$X_1$ is beta-A or S |
| 184. | VEPEP-5 | $X_1$WFRLWWRLR<br>$X_1$ is beta-A or S |
| 185. | VEPEP-5 | $X_1$WWRLWFRLR<br>$X_1$ is beta-A or S |
| 186. | VEPEP-5 | $X_1$RWWRLWWRL<br>$X_1$ is beta-A or S |
| 187. | VEPEP-5 | $X_1$RSWFRLWFR<br>$X_1$ is beta-A or S |
| | | **Other peptides** |
| 188. | PEP-1 | KETWWETWWTEWSQPKKKRKV |
| 189. | PEP-2 | KETWFETWFTEWSQPKKKRKV |
| 190. | PEP-3 | KWFETWFTEWPKKRK |
| 191. | MPG | GALFLGFLGAAGSTMGAWSQPKKKRKV |
| 192. | CADY | GLWRALWRLLRSLWRLLWKV |
| 193. | pANT | RQIKIWFQNRRMKWKKC |

-continued

SEQUENCE TABLE

| SEQ ID NO | Description | Sequences |
|---|---|---|
| 194. | TAT-HA2 | CRRRQRRKKRGGDIMGEWGNEIFGAIAGFLG |
| 195. | LAH4 | KKALLALALHHLAHLALHLALALKKAC |
| | | Exemplary targeting sequences |
| 196. | Targeting sequence | SYTSSTM |
| 197. | Targeting sequence | CKTRRVP |
| 198. | Targeting sequence | THRPPNWSPV |
| 199. | Targeting sequence | TGNYKALHPDHNG |
| 200. | Targeting sequence | CARPAR |
| 201. | Targeting sequence | YIGSR |
| 202. | Targeting sequence | GYVS |
| 203. | Targeting sequence | ASSLNIA |
| 204. | Targeting sequence | LSSRLDA |
| 205. | Targeting sequence | KSYDTY |
| | | Exemplary PAM sequences |
| 206. | PAM sequence | AGG |
| 207. | PAM sequence | TGG |
| 208. | PAM sequence | TAG |
| 209. | PAM sequence | GAG |
| 210. | PAM sequence | GCC |
| 211. | PAM sequence | ACG |
| | | Exemplary NLS sequences |
| 212. | NLS sequence | PKKKRKV |
| 213. | NLS sequence | KRPAATKKAGQAKKKK |
| 214. | NLS sequence | PAAKRVKLD |
| 215. | NLS sequence | RQRRNELKRSP |
| 216. | NLS sequence | NQSSNFGPMKGGNFGGRSSGPYGGGGQYFAKPRNQGGY |
| 217. | NLS sequence | RMRIZFKNKGKDTAELRRRRVEVSVELRKAKKDEQILKRRNV |
| 218. | NLS sequence | VSRKRPRP |
| 219. | NLS sequence | PPKKARED |
| 220. | NLS sequence | PQPKKKPL |
| 221. | NLS sequence | SALIKKKKKMAP |
| 222. | NLS sequence | DRLRR |
| 223. | NLS sequence | PKQKKRK |
| 224. | NLS sequence | RKLKKKIKKL |
| 225. | NLS sequence | REKKKFLKRR |
| 226. | NLS sequence | KRKGDEVDGVDEVAKKKSKK |
| 227. | NLS sequence | RKCLQAGMNLEARKTKK |
| | | Exemplary siRNAs targeting mutant form of KRAS |
| 228. | KRAS siRNA targeting G12C mutation (sense) | 5'-GUUGGAGCUUGUGGCGUAGTT-3' |
| 229. | KRAS siRNA targeting G12C mutation (anti-sense) | 5'-CUACGCCACCAGCUCCAACTT-3' |
| 230. | Factor VIII siRNA (sense) | 5'-GATGAGGCTATTCATGATGATT-3' |
| 231. | KRAS siRNA targeting Q61K mutation (sense) | 5'-GAAGUGCAUACACCGAGACTT-3' |
| 232. | KRAS siRNA targeting Q61K mutation (anti-sense) | 5'-GUCUCGGUGUAGCACUUCTT-3' |

-continued

SEQUENCE TABLE

| SEQ ID NO | Description | Sequences |
|---|---|---|
| 233. | KRAS siRNA targeting G12D mutation (sense) | 5'-GUUGGAGCUGUUGGCGUAGTT-3' |
| 234. | KRAS siRNA targeting G12D mutation (anti-sense) | 5'-CUACGCCAACAGCUCCAACTT-3' |
| 235. | targeting moiety | YVSK |
| 236. | targeting moiety | YIGS |
| 237. | targeting moiety | IGSR |
| 238. | targeting moiety | GYVSK |
| 239. | targeting moiety | GGGGS |
| 240. | targeting moiety | SGGGG |
| 241. | gRNA35T1 | TGGTAGTTGGAGCTGTTGGCGT |
| 242. | gRNA35T4 | AGCTGTTGGCGTAGGCAA |
| 243. | gRNA35T5 | TGTTGGCGTAGGCAAGAGT |
| 244. | gRNA35T6 | GTTGGAGCTGTTGGCGT |
| 245. | gRNA35T7 | TTGTGGTAGTTGGAGCTGT |
| 246. | gRNA35T9 | GCTGTTGGCGTAGGCAA |
| 247. | gRNA35A2 | GGTAGTTGGAGCTGATGGCG |
| 248. | gRNA35A3 | AGCTGATGGCGTAGGCAA |
| 249. | gRNA35A4 | TGATGGCGTAGGCAAGAGT |
| 250. | gRNA35A6 | GTTGGAGCTGATGGCGT |
| 251. | gRNA35A8 | TTGTGGTAGTTGGAGCTGA |
| 252. | gRNA35A9 | GCTGATGGCGTAGGCAA |
| 253. | gRNA34T2 | AGCTTGTGGCGTAGGCAA |
| 254. | gRNA34T3 | GTTGGAGCTTGTGGCGT |
| 255. | gRNA34T4 | GGTAGTTGGAGCTTGTGGCG |
| 256. | gRNA34T7 | GCTTGTGGCGTAGGCAA |
| 257. | gRNA34T8 | CTTGTGGCGTAGGCAAGAGT |
| 258. | Luciferase target site | ACAACTTTACCGACCGCGCC |
| 259. | ADGN-100-PEG2 | AKWRSALWRWRLWRVRSWSR |
| 260. | ADGN-100-HYPEG2 | YIGSR-AKWRSALWRWRLWRVRSWSR |
| 261. | ADGN-106-Hydro-3 | YIGSRXALWRALWRLWRSLWRLLWK |
| 262. | ADGN-106-Hydro-5 | YIGSR-Aun-ALWRALWRLWRSLWRLLWK |
| 263. | ADGN-106-PEG2 | ALWRALWRLWRSLWRLLWK |
| 264. | ADGN-106-HYPEG2 | YIGSR-ALWRALWRLWRSLWRLLWK |
| 265. | ADGN-106-Hydro-3: | YIGSRXALWRALWRLWRSLWRLLWK |
| 266. | ADGN-106-Hydro-5 | YIGSR-Aun-ALWRALWRLWRSLWRLLWK |
| 267. | ADGN-100-PEG2 | AKWRSALWRWRLWRVRSWSR |
| 268. | ADGN-100-PEG7 | AKWRSALWRWRLWRVRSWSR |
| 269. | ADGN-100-HYPEG2 | YIGSR-AKWRSALWRWRLWRVRSWSR |
| 270. | VEPEP-6 (ADGN-106) | ALWRALWRLWRSLWRLLWKAlung |
| 271. | gRNA34T10 | TTGTGGCGTAGGCAAGAGTGCCTTG |

The invention claimed is:

1. A non-naturally occurring polynucleotide comprising a guide RNA for targeting mutated KRAS comprising a specificity-determining CRISPR RNA (crRNA) comprising a nucleotide sequence substantially complementary to a target sequence selected from the group consisting of SEQ ID NOs: 1-37, 241-257 and 271, wherein the non-naturally occurring polynucleotide is comprised in a genome-editing complex, and wherein the genome-editing complex further comprises a cell-penetrating peptide comprising the amino acid sequence selected from the group consisting of SEQ ID NOs: 96, 162, and 167.

2. The non-naturally occurring polynucleotide of claim 1, wherein the guide RNA further comprises an auxiliary trans-activating crRNA (tracrRNA).

3. The non-naturally occurring polynucleotide of claim 1, wherein the nucleotide sequence substantially complementary to a target sequence is selected from the group consisting of SEQ ID NOs: 1, 3, 6, 8, 15, 16, 19-21, 23, 29, 31, 33, and 34.

4. The non-naturally occurring polynucleotide of claim 3, wherein the nucleotide sequence is 100% complementary to a target sequence selected from the group consisting of SEQ ID NOs: 3, 19, and 34.

5. The non-naturally occurring polynucleotide of claim 1, wherein the polynucleotide is chemically modified.

6. The non-naturally occurring polynucleotide of claim 1, wherein the guide RNA has a length of no more than about 200 nucleotides.

7. A genome-editing complex comprising a) a first cell-penetrating peptide, and b) a guide RNA targeting a mutated KRAS, wherein the guide RNA comprises a polynucleotide of claim 1, wherein the first cell-penetrating peptide comprises the amino acid sequence selected from the group consisting of SEQ ID NOs: 96, 162, and 167.

8. The genome-editing complex of claim 7, further comprising a DNA nuclease or a nucleotide sequence encoding the DNA nuclease.

9. The genome-editing complex of claim 7, wherein the first cell-penetrating peptide further comprises one or more moieties covalently linked to N-terminus of the first cell-penetrating peptide, and wherein the one or more moieties are selected from the group consisting of an acetyl, a fatty acid, a cholesterol, a poly-ethylene glycol, a nuclear localization signal, a nuclear export signal, an antibody, a polysaccharide, a linker moiety, and a targeting moiety.

10. The genome-editing complex of claim 9, wherein the first cell-penetrating peptide comprises a targeting moiety comprising a targeting peptide covalently linked to the N-terminus of the first cell-penetrating peptide.

11. The genome-editing complex of claim 7, wherein the first cell-penetrating peptide comprises a linker moiety selected from the group consisting of a polyglycine linker moiety, a PEG moiety, Aun, Ava, and Ahx.

12. The genome-editing complex of claim 7, wherein the first cell-penetrating peptide further comprises a carbohydrate moiety.

13. The genome-editing complex of claim 7, wherein the first cell-penetrating peptide is a retro-inverso peptide.

14. The genome-editing complex of claim 7, further comprising one or more additional guide RNAs comprising a different guide RNA sequence.

15. The genome-editing complex of claim 14, wherein at least two of the two or more guide RNAs target the same KRAS mutation.

16. A nanoparticle comprising the genome-editing complex of claim 7.

17. A pharmaceutical composition comprising the guide RNA of claim 1 and a pharmaceutically acceptable carrier.

18. A method of preparing the genome-editing complex of claim 7, comprising combining the first cell-penetrating peptide with the guide RNA, thereby forming the genome-editing complex.

19. A method of modifying mutated KRAS in a cell, comprising contacting the cell with guide RNA of claim 1.

20. A method of treating a cancer in an individual comprising administering the individual an effective amount of the pharmaceutical composition of claim 17.

21. The non-naturally occurring polynucleotide of claim 1, wherein the guide RNA for targeting mutated KRAS consists of a crRNA consisting of the nucleotide sequence having 100% complementarity to the target sequence of SEQ ID NO: 19.

* * * * *

SEQUENCE LISTING

<160> NUMBER OF SEQ ID NOS: 271

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct

<400> SEQUENCE: 1
gttggagctg ttggcgtagg c 21

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
cttgtggtag ttggagctgt 20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
ggtagttgga gctgttggcg 20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
agctgttggc gtaggcaaga 20

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct

<400> SEQUENCE: 5
tgttggcgta ggcaagagtg cc 22

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
gttggagctg ttggcgtagg 20

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
ttgtggtagt tggagctgtt g 21

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
gtagttggag ctgttggcgt 20

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
gctgttggcg taggcaagag t 21

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
tagttggagc tgttggcgt 19

<210> SEQ ID NO 11
<211> LENGTH: 25
<212> TYPE: DNA
<213> ORGANISM: Artificial Sequence
<220> FEATURE:
<223> OTHER INFORMATION: Synthetic Construct

<400> SEQUENCE: 11
tgttggcgta ggcaagagtg ccttg 25

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
ttgtggtagt tggagctgtt 20

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
tagttggagc tgttggcgta g 21

<210> SEQ ID NO 14
<211> LENGTH: 21
<212> TYPE: DNA
<213> ORGANISM: Artificial Sequence
<220> FEATURE:
<223> OTHER INFORMATION: Synthetic Construct

<400> SEQUENCE: 14
gctgttggcg taggcaagag a 21

<210> SEQ ID NO 15
<211> LENGTH: 20

<212> TYPE: DNA
<213> ORGANISM: Artificial Sequence
<220> FEATURE:
<223> OTHER INFORMATION: Synthetic Construct

<400> SEQUENCE: 15
cttgtggtag ttggagctga 20

<210> SEQ ID NO 16
<211> LENGTH: 19
<212> TYPE: DNA
<213> ORGANISM: Artificial Sequence
<220> FEATURE:
<223> OTHER INFORMATION: Synthetic Construct

<400> SEQUENCE: 16
ggtagttgga gctgatggc 19

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
agctgatggc gtaggcaaga 20

<210> SEQ ID NO 18
<211> LENGTH: 22
<212> TYPE: DNA
<213> ORGANISM: Artificial Sequence
<220> FEATURE:
<223> OTHER INFORMATION: Synthetic Construct

<400> SEQUENCE: 18
tgatggcgta ggcaagagtg cc 22

<210> SEQ ID NO 19
<211> LENGTH: 18
<212> TYPE: DNA
<213> ORGANISM: Artificial Sequence
<220> FEATURE:
<223> OTHER INFORMATION: Synthetic Construct

<400> SEQUENCE: 19
agttggagct gatggcgt 18

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
gttggagctg atggcgtagg 20

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
gtagttggag ctgatggcgt 20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
ttgtggtagt tggagctgat 20

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct

<400> SEQUENCE: 23
gctgatggcg taggcaagag a 21

<210> SEQ ID NO 24
<211> LENGTH: 19
<212> TYPE: DNA
<213> ORGANISM: Artificial Sequence
<220> FEATURE:
<223> OTHER INFORMATION: Synthetic Construct

<400> SEQUENCE: 24
tagttggagc tgatggcgt 19

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25
tgatggcgta ggcaagagtg ccttg 25

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
ttgtggtagt tggagctgat 20

<210> SEQ ID NO 27
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
tagttggagc tgatggcgta g 21

<210> SEQ ID NO 28
<211> LENGTH: 21
<212> TYPE: DNA
<213> ORGANISM: Artificial Sequence

```
<220> FEATURE:
<223> OTHER INFORMATION: Synthetic Construct

<400> SEQUENCE: 28

gctgatggcg taggcaagag a                                              21


<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29

cttgtggtag ttggagcttg                                                20


<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30

agcttgtggc gtaggcaaga                                                20


<210> SEQ ID NO 31
<211> LENGTH: 21
<212> TYPE: DNA
<213> ORGANISM: Artificial Sequence
<220> FEATURE:
<223> OTHER INFORMATION: Synthetic Construct

<400> SEQUENCE: 31

gttggagctt gtggcgtagg c                                              21


<210> SEQ ID NO 32
<211> LENGTH: 19
<212> TYPE: DNA
<213> ORGANISM: Artificial Sequence
<220> FEATURE:
<223> OTHER INFORMATION: Synthetic Construct

<400> SEQUENCE: 32

ggtagttgga gcttgtggc                                                 19


<210> SEQ ID NO 33
<211> LENGTH: 19
<212> TYPE: DNA
<213> ORGANISM: Artificial Sequence
<220> FEATURE:
<223> OTHER INFORMATION: Synthetic Construct

<400> SEQUENCE: 33

ttgtggtagt tggagcttg                                                 19


<210> SEQ ID NO 34
<211> LENGTH: 20
<212> TYPE: DNA
<213> ORGANISM: Artificial Sequence
<220> FEATURE:
<223> OTHER INFORMATION: Synthetic Construct

<400> SEQUENCE: 34

gtagttggag cttgtggcgt                                                20
```

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35
gcttgtggcg taggcaagag 20

<210> SEQ ID NO 36
<211> LENGTH: 22
<212> TYPE: DNA
<213> ORGANISM: Artificial Sequence
<220> FEATURE:
<223> OTHER INFORMATION: Synthetic Construct

<400> SEQUENCE: 36
cttgtggcgt aggcaagagt gc 22

<210> SEQ ID NO 37
<211> LENGTH: 26
<212> TYPE: DNA
<213> ORGANISM: Artificial Sequence
<220> FEATURE:
<223> OTHER INFORMATION: Synthetic Construct

<400> SEQUENCE: 37
cttgtggcgt aggcaagagt gccttg 26

<210> SEQ ID NO 38
<211> LENGTH: 20
<212> TYPE: DNA
<213> ORGANISM: Artificial Sequence
<220> FEATURE:
<223> OTHER INFORMATION: Synthetic Construct

<400> SEQUENCE: 38
cttgtggtag ttggagctgg 20

<210> SEQ ID NO 39
<211> LENGTH: 20
<212> TYPE: DNA
<213> ORGANISM: Artificial Sequence
<220> FEATURE:
<223> OTHER INFORMATION: Synthetic Construct

<400> SEQUENCE: 39
ttggatattc tcgacacagc 20

<210> SEQ ID NO 40
<211> LENGTH: 20
<212> TYPE: DNA
<213> ORGANISM: Artificial Sequence
<220> FEATURE:
<223> OTHER INFORMATION: Synthetic Construct

<400> SEQUENCE: 40
tctcgacaca gcaggtcaag 20

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct

<400> SEQUENCE: 41
gatgtaccta tggtcctagt 20

<210> SEQ ID NO 42
<211> LENGTH: 20
<212> TYPE: DNA
<213> ORGANISM: Artificial Sequence
<220> FEATURE:
<223> OTHER INFORMATION: Synthetic Construct

<400> SEQUENCE: 42
gtcgagaata tccaagagac 20

<210> SEQ ID NO 43
<211> LENGTH: 20
<212> TYPE: DNA
<213> ORGANISM: Artificial Sequence
<220> FEATURE:
<223> OTHER INFORMATION: Synthetic Construct

<400> SEQUENCE: 43
tctcgacaca gcaggtcaag 20

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 2, 6
<223> OTHER INFORMATION: Xaa = K, R or L
<220> FEATURE:
<221> NAME/KEY: VARIANT
<222> LOCATION: 3, 7, 11
<223> OTHER INFORMATION: Xaa = F or W
<220> FEATURE:
<221> NAME/KEY: VARIANT
<222> LOCATION: 4, 8
<223> OTHER INFORMATION: Xaa = F, W or Y
<220> FEATURE:
<221> NAME/KEY: VARIANT
<222> LOCATION: 5
<223> OTHER INFORMATION: Xaa = E, R or S
<220> FEATURE:
<221> NAME/KEY: VARIANT
<222> LOCATION: 9
<223> OTHER INFORMATION: Xaa = R, T or S
<220> FEATURE:
<221> NAME/KEY: VARIANT
<222> LOCATION: 10
<223> OTHER INFORMATION: Xaa = E, R, or S
<220> FEATURE:
<221> NAME/KEY: VARIANT
<222> LOCATION: 12
<223> OTHER INFORMATION: Xaa = absent, F or W
<220> FEATURE:
<221> NAME/KEY: VARIANT
<222> LOCATION: 13
<223> OTHER INFORMATION: Xaa = P or R
<220> FEATURE:
<221> NAME/KEY: VARIANT
<222> LOCATION: 14
<223> OTHER INFORMATION: Xaa = R or L
<220> FEATURE:
<221> NAME/KEY: VARIANT
<222> LOCATION: 15

<223> OTHER INFORMATION: Xaa = K, W or R
<220> FEATURE:
<221> NAME/KEY: VARIANT
<222> LOCATION: 16
<223> OTHER INFORMATION: Xaa = R or F
<220> FEATURE:
<221> NAME/KEY: VARIANT
<222> LOCATION: 17
<223> OTHER INFORMATION: Xaa = R or K

<400> SEQUENCE: 44

Xaa Xaa Xaa Xaa Xaa Xaa Xaa Xaa Xaa Xaa Xaa Xaa Xaa Xaa Xaa Xaa
1 5 10 15

Xaa

<210> SEQ ID NO 45
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 2, 6
<223> OTHER INFORMATION: Xaa = R or K
<220> FEATURE:
<221> NAME/KEY: VARIANT
<222> LOCATION: 4, 8
<223> OTHER INFORMATION: Xaa = F, W, or Y
<220> FEATURE:
<221> NAME/KEY: VARIANT
<222> LOCATION: 9
<223> OTHER INFORMATION: Xaa = T or R
<220> FEATURE:
<221> NAME/KEY: VARIANT
<222> LOCATION: 10
<223> OTHER INFORMATION: Xaa = E or R
<220> FEATURE:
<221> NAME/KEY: VARIANT
<222> LOCATION: 11
<223> OTHER INFORMATION: Xaa = W or F
<220> FEATURE:
<221> NAME/KEY: VARIANT
<222> LOCATION: 14
<223> OTHER INFORMATION: Xaa = R or K
<220> FEATURE:
<221> NAME/KEY: VARIANT
<222> LOCATION: 16
<223> OTHER INFORMATION: Xaa = R or K

<400> SEQUENCE: 45

Xaa Xaa Trp Xaa Glu Xaa Trp Xaa Xaa Xaa Xaa Pro Arg Xaa Arg Xaa
1 5 10 15

<210> SEQ ID NO 46
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 46

Xaa Lys Trp Phe Glu Arg Trp Phe Arg Glu Trp Pro Arg Lys Arg Arg
1 5 10 15

<210> SEQ ID NO 47
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 47

Xaa Lys Trp Trp Glu Arg Trp Trp Arg Glu Trp Pro Arg Lys Arg Arg
1 5 10 15

<210> SEQ ID NO 48
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 48

Xaa Lys Trp Trp Glu Arg Trp Trp Arg Glu Trp Pro Arg Lys Arg Lys
1 5 10 15

<210> SEQ ID NO 49
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 49

Xaa Arg Trp Trp Glu Lys Trp Trp Thr Arg Trp Pro Arg Lys Arg Lys
1 5 10 15

<210> SEQ ID NO 50
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 50

Xaa Arg Trp Tyr Glu Lys Trp Tyr Thr Glu Phe Pro Arg Arg Arg Arg
1 5 10 15

<210> SEQ ID NO 51
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3, 11
<223> OTHER INFORMATION: Xaa = non-natural amino acids
<220> FEATURE:
<221> NAME/KEY: VARIANT
<222> LOCATION: 3, 11
<223> OTHER INFORMATION: Linked by hydrocarbon linkage

<400> SEQUENCE: 51

```
Xaa Lys Xaa Trp Trp Glu Arg Trp Trp Arg Xaa Trp Pro Arg Lys Arg
1               5                   10                  15

Lys
```

<210> SEQ ID NO 52
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 2
<223> OTHER INFORMATION: Xaa = K, R or L
<220> FEATURE:
<221> NAME/KEY: VARIANT
<222> LOCATION: 3, 7
<223> OTHER INFORMATION: Xaa = F or W
<220> FEATURE:
<221> NAME/KEY: VARIANT
<222> LOCATION: 5
<223> OTHER INFORMATION: Xaa = R or S
<220> FEATURE:
<221> NAME/KEY: VARIANT
<222> LOCATION: 6, 14
<223> OTHER INFORMATION: Xaa = L or R
<220> FEATURE:
<221> NAME/KEY: VARIANT
<222> LOCATION: 9
<223> OTHER INFORMATION: Xaa = R or S
<220> FEATURE:
<221> NAME/KEY: VARIANT
<222> LOCATION: 10
<223> OTHER INFORMATION: Xaa = R or S
<220> FEATURE:
<221> NAME/KEY: VARIANT
<222> LOCATION: 12
<223> OTHER INFORMATION: Xaa = F or W
<220> FEATURE:
<221> NAME/KEY: VARIANT
<222> LOCATION: 13
<223> OTHER INFORMATION: Xaa = R or P
<220> FEATURE:
<221> NAME/KEY: VARIANT
<222> LOCATION: 16
<223> OTHER INFORMATION: Xaa = R or F

<400> SEQUENCE: 52

```
Xaa Xaa Xaa Trp Xaa Xaa Xaa Trp Xaa Xaa Trp Xaa Xaa Xaa Trp Xaa
1               5                   10                  15

Arg
```

<210> SEQ ID NO 53
<211> LENGTH: 17
<212> TYPE: PRT
<213> ORGANISM: Artificial Sequence
<220> FEATURE:
<223> OTHER INFORMATION: Synthetic Construct
<220> FEATURE:

```
<221> NAME/KEY: VARIANT
<222> LOCATION: 1
<223> OTHER INFORMATION: Xaa = beta-A or S

<400> SEQUENCE: 53

Xaa Arg Trp Trp Arg Leu Trp Trp Arg Ser Trp Phe Arg Leu Trp Arg
1               5                   10                  15

Arg


<210> SEQ ID NO 54
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 54

Xaa Leu Trp Trp Arg Arg Trp Trp Ser Arg Trp Trp Pro Arg Trp Arg
1               5                   10                  15

Arg


<210> SEQ ID NO 55
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 55

Xaa Leu Trp Trp Ser Arg Trp Trp Arg Ser Trp Phe Arg Leu Trp Phe
1               5                   10                  15

Arg


<210> SEQ ID NO 56
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 56

Xaa Lys Phe Trp Ser Arg Phe Trp Arg Ser Trp Phe Arg Leu Trp Arg
1               5                   10                  15

Arg


<210> SEQ ID NO 57
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
```

```
<220> FEATURE:
<221> NAME/KEY: VARIANT
<222> LOCATION: 5, 12
<223> OTHER INFORMATION: Xaa = non-natural amino acids
<220> FEATURE:
<221> NAME/KEY: VARIANT
<222> LOCATION: 5, 12
<223> OTHER INFORMATION: Linked by hydrocarbon linkage

<400> SEQUENCE: 57

Xaa Arg Trp Trp Xaa Leu Trp Trp Arg Ser Trp Xaa Arg Leu Trp Arg
1               5                   10                  15

Arg


<210> SEQ ID NO 58
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 58

Ala Lys Trp Phe Glu Arg Trp Phe Arg Glu Trp Pro Arg Lys Arg Arg
1               5                   10                  15


<210> SEQ ID NO 59
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 59

Ala Lys Trp Trp Glu Arg Trp Trp Arg Glu Trp Pro Arg Lys Arg Arg
1               5                   10                  15


<210> SEQ ID NO 60
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8
<223> OTHER INFORMATION: Xaa = 5-amino pentanoic acid

<400> SEQUENCE: 60

Ala Ser Ser Leu Asn Ile Ala Xaa Lys Trp Trp Glu Arg Trp Trp Arg
1               5                   10                  15

Glu Trp Pro Arg Lys Arg Arg
            20


<210> SEQ ID NO 61
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
```

<222> LOCATION: 8
<223> OTHER INFORMATION: Xaa = 5-amino pentanoic acid

<400> SEQUENCE: 61

```
Leu Ser Ser Arg Leu Asp Ala Xaa Lys Trp Trp Glu Arg Trp Trp Arg
1               5                   10                  15

Glu Trp Pro Arg Lys Arg Arg
            20
```

<210> SEQ ID NO 62
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8
<223> OTHER INFORMATION: Xaa = 5-amino pentanoic acid

<400> SEQUENCE: 62

```
Ser Tyr Thr Ser Ser Thr Met Xaa Lys Trp Trp Glu Arg Trp Trp Arg
1               5                   10                  15

Glu Trp Pro Arg Lys Arg Arg
            20
```

<210> SEQ ID NO 63
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3
<223> OTHER INFORMATION: Xaa = F or W
<220> FEATURE:
<221> NAME/KEY: VARIANT
<222> LOCATION: 8
<223> OTHER INFORMATION: Xaa = R or S
<220> FEATURE:
<221> NAME/KEY: VARIANT
<222> LOCATION: 10
<223> OTHER INFORMATION: Xaa = L, W, C or I
<220> FEATURE:
<221> NAME/KEY: VARIANT
<222> LOCATION: 11
<223> OTHER INFORMATION: Xaa = R or S
<220> FEATURE:
<221> NAME/KEY: VARIANT
<222> LOCATION: 12
<223> OTHER INFORMATION: Xaa = S, A, N or T
<220> FEATURE:
<221> NAME/KEY: VARIANT
<222> LOCATION: 15
<223> OTHER INFORMATION: Xaa = R or S
<220> FEATURE:
<221> NAME/KEY: VARIANT
<222> LOCATION: 17
<223> OTHER INFORMATION: Xaa = L or W
<220> FEATURE:
<221> NAME/KEY: VARIANT
<222> LOCATION: 18
<223> OTHER INFORMATION: Xaa = W or R
<220> FEATURE:
<221> NAME/KEY: VARIANT
<222> LOCATION: 19
<223> OTHER INFORMATION: Xaa = K or R
<220> FEATURE:

<221> NAME/KEY: VARIANT
<222> LOCATION: 20
<223> OTHER INFORMATION: Xaa = A or none

<400> SEQUENCE: 63

```
Xaa Leu Xaa Arg Ala Leu Trp Xaa Leu Xaa Xaa Xaa Leu Trp Xaa Leu
1               5                   10                  15

Xaa Xaa Xaa Xaa
            20
```

<210> SEQ ID NO 64
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3
<223> OTHER INFORMATION: Xaa = F or W
<220> FEATURE:
<221> NAME/KEY: VARIANT
<222> LOCATION: 8
<223> OTHER INFORMATION: Xaa = R or S
<220> FEATURE:
<221> NAME/KEY: VARIANT
<222> LOCATION: 10
<223> OTHER INFORMATION: Xaa = L, W, C or I
<220> FEATURE:
<221> NAME/KEY: VARIANT
<222> LOCATION: 11
<223> OTHER INFORMATION: Xaa = R or S
<220> FEATURE:
<221> NAME/KEY: VARIANT
<222> LOCATION: 12
<223> OTHER INFORMATION: Xaa = S, A, N or T
<220> FEATURE:
<221> NAME/KEY: VARIANT
<222> LOCATION: 15
<223> OTHER INFORMATION: Xaa = R or S
<220> FEATURE:
<221> NAME/KEY: VARIANT
<222> LOCATION: 17
<223> OTHER INFORMATION: Xaa = L or W
<220> FEATURE:
<221> NAME/KEY: VARIANT
<222> LOCATION: 18
<223> OTHER INFORMATION: Xaa = W or R
<220> FEATURE:
<221> NAME/KEY: VARIANT
<222> LOCATION: 19
<223> OTHER INFORMATION: Xaa = K or R
<220> FEATURE:
<221> NAME/KEY: VARIANT
<222> LOCATION: 20
<223> OTHER INFORMATION: Xaa = A or none

<400> SEQUENCE: 64

```
Xaa Leu Xaa Leu Ala Arg Trp Xaa Leu Xaa Xaa Xaa Leu Trp Xaa Leu
1               5                   10                  15

Xaa Xaa Xaa Xaa
            20
```

<210> SEQ ID NO 65
<211> LENGTH: 20
<212> TYPE: PRT
<213> ORGANISM: Artificial Sequence
<220> FEATURE:
<223> OTHER INFORMATION: Synthetic Construct

```
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3
<223> OTHER INFORMATION: Xaa = F or W
<220> FEATURE:
<221> NAME/KEY: VARIANT
<222> LOCATION: 8
<223> OTHER INFORMATION: Xaa = R or S
<220> FEATURE:
<221> NAME/KEY: VARIANT
<222> LOCATION: 10
<223> OTHER INFORMATION: Xaa = L, W, C or I
<220> FEATURE:
<221> NAME/KEY: VARIANT
<222> LOCATION: 11
<223> OTHER INFORMATION: Xaa = R or S
<220> FEATURE:
<221> NAME/KEY: VARIANT
<222> LOCATION: 12
<223> OTHER INFORMATION: Xaa = S, A, N or T
<220> FEATURE:
<221> NAME/KEY: VARIANT
<222> LOCATION: 15
<223> OTHER INFORMATION: Xaa = R or S
<220> FEATURE:
<221> NAME/KEY: VARIANT
<222> LOCATION: 17
<223> OTHER INFORMATION: Xaa = L or W
<220> FEATURE:
<221> NAME/KEY: VARIANT
<222> LOCATION: 18
<223> OTHER INFORMATION: Xaa = W or R
<220> FEATURE:
<221> NAME/KEY: VARIANT
<222> LOCATION: 19
<223> OTHER INFORMATION: Xaa = K or R
<220> FEATURE:
<221> NAME/KEY: VARIANT
<222> LOCATION: 20
<223> OTHER INFORMATION: Xaa = A or none

<400> SEQUENCE: 65

Xaa Leu Xaa Ala Arg Leu Trp Xaa Leu Xaa Xaa Xaa Leu Trp Xaa Leu
1               5                   10                  15

Xaa Xaa Xaa Xaa
            20


<210> SEQ ID NO 66
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3
<223> OTHER INFORMATION: Xaa = F or W
<220> FEATURE:
<221> NAME/KEY: VARIANT
<222> LOCATION: 10
<223> OTHER INFORMATION: Xaa = L, W, C or I
<220> FEATURE:
<221> NAME/KEY: VARIANT
<222> LOCATION: 12
<223> OTHER INFORMATION: Xaa = S, A, N or T
<220> FEATURE:
<221> NAME/KEY: VARIANT
<222> LOCATION: 17
```

<223> OTHER INFORMATION: Xaa = L or W
<220> FEATURE:
<221> NAME/KEY: VARIANT
<222> LOCATION: 18
<223> OTHER INFORMATION: Xaa = W or R
<220> FEATURE:
<221> NAME/KEY: VARIANT
<222> LOCATION: 19
<223> OTHER INFORMATION: Xaa = K or R
<220> FEATURE:
<221> NAME/KEY: VARIANT
<222> LOCATION: 20
<223> OTHER INFORMATION: Xaa = A or none

<400> SEQUENCE: 66

```
Xaa Leu Xaa Arg Ala Leu Trp Arg Leu Xaa Arg Xaa Leu Trp Arg Leu
1               5                   10                  15

Xaa Xaa Xaa Xaa
            20
```

<210> SEQ ID NO 67
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3
<223> OTHER INFORMATION: Xaa = F or W
<220> FEATURE:
<221> NAME/KEY: VARIANT
<222> LOCATION: 10
<223> OTHER INFORMATION: Xaa = L or W
<220> FEATURE:
<221> NAME/KEY: VARIANT
<222> LOCATION: 12
<223> OTHER INFORMATION: Xaa = S, A, or N
<220> FEATURE:
<221> NAME/KEY: VARIANT
<222> LOCATION: 17
<223> OTHER INFORMATION: Xaa = L or W
<220> FEATURE:
<221> NAME/KEY: VARIANT
<222> LOCATION: 18
<223> OTHER INFORMATION: Xaa = W or R
<220> FEATURE:
<221> NAME/KEY: VARIANT
<222> LOCATION: 20
<223> OTHER INFORMATION: Xaa = A or none

<400> SEQUENCE: 67

```
Xaa Leu Xaa Arg Ala Leu Trp Arg Leu Xaa Arg Xaa Leu Trp Arg Leu
1               5                   10                  15

Xaa Xaa Lys Xaa
            20
```

<210> SEQ ID NO 68
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 12
<223> OTHER INFORMATION: Xaa = S or T
<220> FEATURE:
<221> NAME/KEY: VARIANT
<222> LOCATION: 19
<223> OTHER INFORMATION: Xaa = K or R

<400> SEQUENCE: 68

Xaa Leu Phe Arg Ala Leu Trp Arg Leu Leu Arg Xaa Leu Trp Arg Leu
1 5 10 15

Leu Trp Xaa

<210> SEQ ID NO 69
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 12
<223> OTHER INFORMATION: Xaa = S or T
<220> FEATURE:
<221> NAME/KEY: VARIANT
<222> LOCATION: 19
<223> OTHER INFORMATION: Xaa = K or R

<400> SEQUENCE: 69

Xaa Leu Trp Arg Ala Leu Trp Arg Leu Trp Arg Xaa Leu Trp Arg Leu
1 5 10 15

Leu Trp Xaa Ala
20

<210> SEQ ID NO 70
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 10
<223> OTHER INFORMATION: Xaa = L, C or I
<220> FEATURE:
<221> NAME/KEY: VARIANT
<222> LOCATION: 12
<223> OTHER INFORMATION: Xaa = S or T
<220> FEATURE:
<221> NAME/KEY: VARIANT
<222> LOCATION: 19
<223> OTHER INFORMATION: Xaa = K or R

<400> SEQUENCE: 70

Xaa Leu Trp Arg Ala Leu Trp Arg Leu Xaa Arg Xaa Leu Trp Arg Leu
1 5 10 15

Trp Arg Xaa Ala
20

<210> SEQ ID NO 71
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 12
<223> OTHER INFORMATION: Xaa = S or T
<220> FEATURE:
<221> NAME/KEY: VARIANT
<222> LOCATION: 19
<223> OTHER INFORMATION: Xaa = K or R

<400> SEQUENCE: 71

Xaa Leu Trp Arg Ala Leu Trp Arg Leu Trp Arg Xaa Leu Trp Arg Leu
1               5                   10                  15

Trp Arg Xaa Ala
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 10
<223> OTHER INFORMATION: Xaa = L or I
<220> FEATURE:
<221> NAME/KEY: VARIANT
<222> LOCATION: 19
<223> OTHER INFORMATION: Xaa = K or R

<400> SEQUENCE: 72

Xaa Leu Trp Arg Ala Leu Trp Arg Leu Xaa Arg Ala Leu Trp Arg Leu
1               5                   10                  15

Leu Trp Xaa Ala
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 10
<223> OTHER INFORMATION: Xaa = L, C or I
<220> FEATURE:
<221> NAME/KEY: VARIANT
<222> LOCATION: 19
<223> OTHER INFORMATION: Xaa = K or R

<400> SEQUENCE: 73

Xaa Leu Trp Arg Ala Leu Trp Arg Leu Xaa Arg Asn Leu Trp Arg Leu
1               5                   10                  15

Leu Trp Xaa Ala
            20

<210> SEQ ID NO 74
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 19
<223> OTHER INFORMATION: Modified as shown in Sequence Table of the specification

<400> SEQUENCE: 74

```
Xaa Leu Phe Arg Ala Leu Trp Arg Leu Leu Arg Ser Leu Trp Arg Leu
1               5                   10                  15

Leu Trp Lys
```

<210> SEQ ID NO 75
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 20
<223> OTHER INFORMATION: Modified as shown in Sequence Table of the specification

<400> SEQUENCE: 75

```
Xaa Leu Trp Arg Ala Leu Trp Arg Leu Trp Arg Ser Leu Trp Arg Leu
1               5                   10                  15

Leu Trp Lys Ala
            20
```

<210> SEQ ID NO 76
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 20
<223> OTHER INFORMATION: Modified as shown in Sequence Table of the specification

<400> SEQUENCE: 76

```
Xaa Leu Trp Arg Ala Leu Trp Arg Leu Leu Arg Ser Leu Trp Arg Leu
1               5                   10                  15

Trp Arg Lys Ala
            20
```

<210> SEQ ID NO 77
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 20
<223> OTHER INFORMATION: Modified as shown in Sequence Table of the specification

<400> SEQUENCE: 77

Xaa Leu Trp Arg Ala Leu Trp Arg Leu Trp Arg Ser Leu Trp Arg Leu
1 5 10 15

Trp Arg Lys Ala
20

<210> SEQ ID NO 78
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 20
<223> OTHER INFORMATION: Modified as shown in Sequence Table of the specification

<400> SEQUENCE: 78

Xaa Leu Trp Arg Ala Leu Trp Arg Leu Leu Arg Ala Leu Trp Arg Leu
1 5 10 15

Leu Trp Lys Ala
20

<210> SEQ ID NO 79
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 20
<223> OTHER INFORMATION: Modified as shown in Sequence Table of the specification

<400> SEQUENCE: 79

Xaa Leu Trp Arg Ala Leu Trp Arg Leu Leu Arg Asn Leu Trp Arg Leu
1 5 10 15

Leu Trp Lys Ala
20

<210> SEQ ID NO 80
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 8, 12
<223> OTHER INFORMATION: Modified as shown in Sequence Table of the specification

<400> SEQUENCE: 80

Xaa Leu Phe Arg Ala Leu Trp Arg Leu Leu Arg Ser Leu Trp Arg Leu
1 5 10 15

Leu Trp Lys

<210> SEQ ID NO 81
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 8, 12
<223> OTHER INFORMATION: Modified as shown in Sequence Table of the specification

<400> SEQUENCE: 81

Xaa Leu Phe Leu Ala Arg Trp Arg Leu Leu Arg Ser Leu Trp Arg Leu
1 5 10 15

Leu Trp Lys

<210> SEQ ID NO 82
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 8, 12
<223> OTHER INFORMATION: Modified as shown in Sequence Table of the specification

<400> SEQUENCE: 82

Xaa Leu Phe Arg Ala Leu Trp Ser Leu Leu Arg Ser Leu Trp Arg Leu
1 5 10 15

Leu Trp Lys

<210> SEQ ID NO 83
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 8, 12
<223> OTHER INFORMATION: Modified as shown in Sequence Table of the specification

<400> SEQUENCE: 83

Xaa Leu Phe Leu Ala Arg Trp Ser Leu Leu Arg Ser Leu Trp Arg Leu
1 5 10 15

Leu Trp Lys

<210> SEQ ID NO 84
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 11, 15
<223> OTHER INFORMATION: Modified as shown in Sequence Table of the specification

<400> SEQUENCE: 84

Xaa Leu Phe Arg Ala Leu Trp Arg Leu Leu Arg Ser Leu Trp Ser Leu
1 5 10 15

Leu Trp Lys

<210> SEQ ID NO 85
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 11, 15
<223> OTHER INFORMATION: Modified as shown in Sequence Table of the specification

<400> SEQUENCE: 85

Xaa Leu Phe Leu Ala Arg Trp Arg Leu Leu Arg Ser Leu Trp Ser Leu
1 5 10 15

Leu Trp Lys

<210> SEQ ID NO 86
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 11, 15
<223> OTHER INFORMATION: Modified as shown in Sequence Table of the specification

<400> SEQUENCE: 86

Xaa Leu Phe Arg Ala Leu Trp Arg Leu Leu Ser Ser Leu Trp Ser Leu
1 5 10 15

Leu Trp Lys

```
<210> SEQ ID NO 87
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 11, 15
<223> OTHER INFORMATION: Modified as shown in Sequence Table of the
      specification

<400> SEQUENCE: 87

Xaa Leu Phe Leu Ala Arg Trp Arg Leu Leu Ser Ser Leu Trp Ser Leu
1               5                   10                  15

Leu Trp Lys


<210> SEQ ID NO 88
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1, 5, 12
<223> OTHER INFORMATION: Modified as shown in Sequence Table of the
      specification

<400> SEQUENCE: 88

Xaa Leu Phe Ala Arg Leu Trp Arg Leu Leu Arg Ser Leu Trp Arg Leu
1               5                   10                  15

Leu Trp Lys


<210> SEQ ID NO 89
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 89

Ala Leu Trp Arg Ala Leu Trp Arg Leu Trp Arg Ser Leu Trp Arg Leu
1               5                   10                  15

Leu Trp Lys Ala
            20


<210> SEQ ID NO 90
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
```

```
<223> OTHER INFORMATION: beta-A
<220> FEATURE:
<221> NAME/KEY: VARIANT
<222> LOCATION: 20
<223> OTHER INFORMATION: Modified as shown in Sequence Table of the
      specification

<400> SEQUENCE: 90

Ala Leu Trp Arg Ala Leu Trp Arg Leu Trp Arg Ser Leu Trp Arg Leu
1               5                   10                  15

Leu Trp Lys Ala
            20


<210> SEQ ID NO 91
<211> LENGTH: 20
<212> TYPE: PRT
<213> ORGANISM: Artificial Sequence
<220> FEATURE:
<223> OTHER INFORMATION: Synthetic Construct

<400> SEQUENCE: 91

Ala Lys Trp Leu Leu Arg Trp Leu Ser Arg Trp Leu Arg Trp Leu Ala
1               5                   10                  15

Arg Trp Leu Arg
            20


<210> SEQ ID NO 92
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 20
<223> OTHER INFORMATION: Modified as shown in Sequence Table of the
      specification

<400> SEQUENCE: 92

Ala Leu Trp Arg Ala Leu Trp Arg Leu Trp Arg Ser Leu Trp Arg Leu
1               5                   10                  15

Leu Trp Lys Ala
            20


<210> SEQ ID NO 93
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 20
<223> OTHER INFORMATION: Modified as shown in Sequence Table of the
      specification

<400> SEQUENCE: 93

Ala Leu Trp Arg Ala Leu Trp Arg Leu Trp Arg Ser Leu Trp Arg Leu
1               5                   10                  15

Leu Trp Lys Ala
            20


<210> SEQ ID NO 94
<211> LENGTH: 29
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: VARIANT
<222> LOCATION: 1, 29
<223> OTHER INFORMATION: Modified as shown in Sequence Table of the
      specification

<400> SEQUENCE: 94

Tyr Ile Gly Ser Arg Gly Gly Gly Gly Ala Leu Trp Arg Ala Leu Trp
1               5                   10                  15

Arg Leu Trp Arg Ser Leu Trp Arg Leu Leu Trp Lys Ala
            20                  25


<210> SEQ ID NO 95
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 28
<223> OTHER INFORMATION: Modified as shown in Sequence Table of the
      specification

<400> SEQUENCE: 95

Gly Tyr Val Ser Gly Gly Gly Gly Ala Leu Trp Arg Ala Leu Trp Arg
1               5                   10                  15

Leu Trp Arg Ser Leu Trp Arg Leu Leu Trp Lys Ala
            20                  25


<210> SEQ ID NO 96
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 26
<223> OTHER INFORMATION: Modified as shown in Sequence Table of the
      specification
<220> FEATURE:
<221> NAME/KEY: VARIANT
<222> LOCATION: 6
<223> OTHER INFORMATION: Xaa = 5-amino pentanoic acid

<400> SEQUENCE: 96

Tyr Ile Gly Ser Arg Xaa Ala Leu Trp Arg Ala Leu Trp Arg Leu Trp
1               5                   10                  15

Arg Ser Leu Trp Arg Leu Leu Trp Lys Ala
            20                  25


<210> SEQ ID NO 97
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the
      specification
<220> FEATURE:
<221> NAME/KEY: VARIANT
<222> LOCATION: 5
<223> OTHER INFORMATION: Xaa = 5-amino pentanoic acid

<400> SEQUENCE: 97
```

Gly Tyr Val Ser Xaa Ala Leu Trp Arg Ala Leu Trp Arg Leu Trp Arg
1 5 10 15

Ser Leu Trp Arg Leu Leu Trp Lys Ala
20 25

<210> SEQ ID NO 98
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 26
<223> OTHER INFORMATION: Modified as shown in Sequence Table of the specification
<220> FEATURE:
<221> NAME/KEY: VARIANT
<222> LOCATION: 6
<223> OTHER INFORMATION: Xaa = 11-amino-undecanoic acid

<400> SEQUENCE: 98

Tyr Ile Gly Ser Arg Xaa Ala Leu Trp Arg Ala Leu Trp Arg Leu Trp
1 5 10 15

Arg Ser Leu Trp Arg Leu Leu Trp Lys Ala
20 25

<210> SEQ ID NO 99
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification
<220> FEATURE:
<221> NAME/KEY: VARIANT
<222> LOCATION: 5
<223> OTHER INFORMATION: Xaa = 11-amino-undecanoic acid

<400> SEQUENCE: 99

Gly Tyr Val Ser Xaa Ala Leu Trp Arg Ala Leu Trp Arg Leu Trp Arg
1 5 10 15

Ser Leu Trp Arg Leu Leu Trp Lys Ala
20 25

<210> SEQ ID NO 100
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification
<220> FEATURE:
<221> NAME/KEY: VARIANT
<222> LOCATION: 6
<223> OTHER INFORMATION: Xaa = Ahx

<400> SEQUENCE: 100

Tyr Ile Gly Ser Arg Xaa Ala Leu Trp Arg Ala Leu Trp Arg Leu Trp
1 5 10 15

Arg Ser Leu Trp Arg Leu Leu Trp Lys
20 25

<210> SEQ ID NO 101
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 26
<223> OTHER INFORMATION: Modified as shown in Sequence Table of the specification
<220> FEATURE:
<221> NAME/KEY: VARIANT
<222> LOCATION: 6
<223> OTHER INFORMATION: Xaa = Ahx

<400> SEQUENCE: 101

Tyr Ile Gly Ser Arg Xaa Ala Leu Trp Arg Ala Leu Trp Arg Leu Trp
1 5 10 15

Arg Ser Leu Trp Arg Leu Leu Trp Lys Ala
20 25

<210> SEQ ID NO 102
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification
<220> FEATURE:
<221> NAME/KEY: VARIANT
<222> LOCATION: 5
<223> OTHER INFORMATION: Xaa = Ahx

<400> SEQUENCE: 102

Gly Tyr Val Ser Xaa Ala Leu Trp Arg Ala Leu Trp Arg Leu Trp Arg
1 5 10 15

Ser Leu Trp Arg Leu Leu Trp Lys Ala
20 25

<210> SEQ ID NO 103
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification

<400> SEQUENCE: 103

Tyr Ile Gly Ser Arg Ala Leu Trp Arg Ala Leu Trp Arg Leu Trp Arg
1 5 10 15

Ser Leu Trp Arg Leu Leu Trp Lys Ala
20 25

<210> SEQ ID NO 104
<211> LENGTH: 21
<212> TYPE: PRT
<213> ORGANISM: Artificial Sequence

```
<220> FEATURE:
<223> OTHER INFORMATION: Synthetic Construct
<220> FEATURE:
<221> NAME/KEY: VARIANT
<222> LOCATION: 1, 21
<223> OTHER INFORMATION: Modified as shown in Sequence Table of the
      specification

<400> SEQUENCE: 104

Ala Ala Leu Trp Arg Ala Leu Trp Arg Leu Trp Arg Ser Leu Trp Arg
1               5                   10                  15

Leu Leu Trp Lys Ala
            20


<210> SEQ ID NO 105
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 5, 6, 25
<223> OTHER INFORMATION: Modified as shown in Sequence Table of the
      specification

<400> SEQUENCE: 105

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25


<210> SEQ ID NO 106
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 5, 6, 25
<223> OTHER INFORMATION: Modified as shown in Sequence Table of the
      specification

<400> SEQUENCE: 106

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25


<210> SEQ ID NO 107
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 5, 6, 25
<223> OTHER INFORMATION: Modified as shown in Sequence Table of the
      specification

<400> SEQUENCE: 107

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25
```

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: GalNac
<220> FEATURE:
<221> NAME/KEY: VARIANT
<222> LOCATION: 21
<223> OTHER INFORMATION: Modified as shown in Sequence Table of the specification

<400> SEQUENCE: 111

```
Ala Leu Trp Arg Ala Xaa Leu Trp Arg Leu Trp Arg Ser Leu Trp Arg
1               5                   10                  15

Leu Leu Trp Lys Ala
            20
```

<210> SEQ ID NO 112
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 28
<223> OTHER INFORMATION: Modified as shown in Sequence Table of the specification
<220> FEATURE:
<221> NAME/KEY: VARIANT
<222> LOCATION: 8
<223> OTHER INFORMATION: Xaa = 5-amino pentanoic acid

<400> SEQUENCE: 112

```
Ser Tyr Thr Ser Ser Thr Met Xaa Ala Leu Trp Arg Ala Leu Trp Arg
1               5                   10                  15

Leu Trp Arg Ser Leu Trp Arg Leu Leu Trp Lys Ala
            20                  25
```

<210> SEQ ID NO 113
<211> LENGTH: 29
<212> TYPE: PRT
<213> ORGANISM: Artificial Sequence
<220> FEATURE:
<223> OTHER INFORMATION: Synthetic Construct
<220> FEATURE:

<221> NAME/KEY: VARIANT
<222> LOCATION: 1, 29
<223> OTHER INFORMATION: Modified as shown in Sequence Table of the
      specification

<400> SEQUENCE: 113

```
Thr His Arg Pro Pro Asn Trp Ser Pro Val Trp Pro Arg Ala Leu Trp
1               5                   10                  15

Arg Leu Trp Arg Ser Leu Trp Arg Leu Arg Trp Lys Ala
            20                  25
```

<210> SEQ ID NO 114
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the
      specification

<400> SEQUENCE: 114

```
Cys Lys Thr Arg Arg Val Pro Trp Arg Ala Leu Trp Arg Leu Trp Arg
1               5                   10                  15

Ser Leu Trp Arg Leu Leu Trp Lys Ala
            20                  25
```

<210> SEQ ID NO 115
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 26
<223> OTHER INFORMATION: Modified as shown in Sequence Table of the
      specification
<220> FEATURE:
<221> NAME/KEY: VARIANT
<222> LOCATION: 8
<223> OTHER INFORMATION: Xaa = 5-amino pentanoic acid

<400> SEQUENCE: 115

```
Cys Lys Thr Arg Arg Val Pro Xaa Trp Arg Ala Leu Trp Arg Leu Trp
1               5                   10                  15

Arg Ser Leu Trp Arg Leu Leu Trp Lys Ala
            20                  25
```

<210> SEQ ID NO 116
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 24
<223> OTHER INFORMATION: Modified as shown in Sequence Table of the
      specification
<220> FEATURE:
<221> NAME/KEY: VARIANT
<222> LOCATION: 7
<223> OTHER INFORMATION: Xaa = 5-amino pentanoic acid

<400> SEQUENCE: 116

```
Cys Ala Arg Pro Ala Arg Xaa Trp Arg Ala Leu Trp Arg Leu Trp Arg
```

1 5 10 15

Ser Leu Trp Arg Leu Leu Trp Lys
20

<210> SEQ ID NO 117
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 28
<223> OTHER INFORMATION: Modified as shown in Sequence Table of the specification
<220> FEATURE:
<221> NAME/KEY: VARIANT
<222> LOCATION: 11
<223> OTHER INFORMATION: Xaa = 5-amino pentanoic acid

<400> SEQUENCE: 117

Thr His Arg Pro Pro Asn Trp Ser Pro Val Xaa Trp Arg Ala Leu Trp
1 5 10 15

Arg Leu Trp Arg Ser Leu Trp Arg Leu Arg Trp Lys
20 25

<210> SEQ ID NO 118
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 2
<223> OTHER INFORMATION: Xaa = L or (if Xaa at position 3 is absent)
<220> FEATURE:
<221> NAME/KEY: VARIANT
<222> LOCATION: 3
<223> OTHER INFORMATION: Xaa = R or none
<220> FEATURE:
<221> NAME/KEY: VARIANT
<222> LOCATION: 6
<223> OTHER INFORMATION: Xaa = L, R or G
<220> FEATURE:
<221> NAME/KEY: VARIANT
<222> LOCATION: 7
<223> OTHER INFORMATION: Xaa = R, W or S
<220> FEATURE:
<221> NAME/KEY: VARIANT
<222> LOCATION: 10
<223> OTHER INFORMATION: Xaa = S, P or T
<220> FEATURE:
<221> NAME/KEY: VARIANT
<222> LOCATION: 11
<223> OTHER INFORMATION: Xaa = R or none
<220> FEATURE:
<221> NAME/KEY: VARIANT
<222> LOCATION: 12
<223> OTHER INFORMATION: Xaa = W or P
<220> FEATURE:
<221> NAME/KEY: VARIANT
<222> LOCATION: 13
<223> OTHER INFORMATION: Xaa = F, A or R
<220> FEATURE:
<221> NAME/KEY: VARIANT
<222> LOCATION: 14
<223> OTHER INFORMATION: Xaa = S, L, P or R
<220> FEATURE:
<221> NAME/KEY: VARIANT
<222> LOCATION: 15
<223> OTHER INFORMATION: Xaa = R or S
<220> FEATURE:
<221> NAME/KEY: VARIANT
<222> LOCATION: 16
<223> OTHER INFORMATION: Xaa = W or none (if Xaa at position 3 is absent)
<220> FEATURE:
<221> NAME/KEY: VARIANT
<222> LOCATION: 17
<223> OTHER INFORMATION: Xaa = A, R or none (if Xaa at position 3 is absent)
<220> FEATURE:
<221> NAME/KEY: VARIANT
<222> LOCATION: 19
<223> OTHER INFORMATION: Xaa = W or F

<400> SEQUENCE: 118

```
Xaa Xaa Xaa Trp Trp Xaa Xaa Trp Ala Xaa Xaa Xaa Xaa Xaa Xaa Xaa
1               5                   10                  15

Xaa Trp Xaa Arg
            20
```

<210> SEQ ID NO 119
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 2
<223> OTHER INFORMATION: Xaa = L or none
<220> FEATURE:
<221> NAME/KEY: VARIANT
<222> LOCATION: 10
<223> OTHER INFORMATION: Xaa = S or P
<220> FEATURE:
<221> NAME/KEY: VARIANT
<222> LOCATION: 13
<223> OTHER INFORMATION: Xaa = F or A
<220> FEATURE:
<221> NAME/KEY: VARIANT
<222> LOCATION: 14
<223> OTHER INFORMATION: Xaa = S, L or P
<220> FEATURE:
<221> NAME/KEY: VARIANT
<222> LOCATION: 15
<223> OTHER INFORMATION: Xaa = R or S
<220> FEATURE:
<221> NAME/KEY: VARIANT
<222> LOCATION: 17
<223> OTHER INFORMATION: Xaa = A or R
<220> FEATURE:
<221> NAME/KEY: VARIANT
<222> LOCATION: 19
<223> OTHER INFORMATION: Xaa = W or F

<400> SEQUENCE: 119

```
Xaa Xaa Arg Trp Trp Leu Arg Trp Ala Xaa Arg Trp Xaa Xaa Xaa Trp
1               5                   10                  15

Xaa Trp Xaa Arg
            20
```

<210> SEQ ID NO 120
<211> LENGTH: 20
<212> TYPE: PRT
<213> ORGANISM: Artificial Sequence
<220> FEATURE:

<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 120

```
Xaa Leu Arg Trp Trp Leu Arg Trp Ala Ser Arg Trp Phe Ser Arg Trp
1               5                   10                  15

Ala Trp Trp Arg
            20
```

<210> SEQ ID NO 121
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 121

```
Xaa Leu Arg Trp Trp Leu Arg Trp Ala Ser Arg Trp Ala Ser Arg Trp
1               5                   10                  15

Ala Trp Phe Arg
            20
```

<210> SEQ ID NO 122
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 122

```
Xaa Arg Trp Trp Leu Arg Trp Ala Ser Arg Trp Ala Leu Ser Trp Arg
1               5                   10                  15

Trp Trp Arg
```

<210> SEQ ID NO 123
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 123

```
Xaa Arg Trp Trp Leu Arg Trp Ala Ser Arg Trp Phe Leu Ser Trp Arg
1               5                   10                  15

Trp Trp Arg
```

<210> SEQ ID NO 124
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 124

Xaa Arg Trp Trp Leu Arg Trp Ala Pro Arg Trp Phe Pro Ser Trp Arg
1 5 10 15

Trp Trp Arg

<210> SEQ ID NO 125
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 125

Xaa Arg Trp Trp Leu Arg Trp Ala Ser Arg Trp Ala Pro Ser Trp Arg
1 5 10 15

Trp Trp Arg

<210> SEQ ID NO 126
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 4
<223> OTHER INFORMATION: Xaa = R or G
<220> FEATURE:
<221> NAME/KEY: VARIANT
<222> LOCATION: 5
<223> OTHER INFORMATION: Xaa = W or S
<220> FEATURE:
<221> NAME/KEY: VARIANT
<222> LOCATION: 8
<223> OTHER INFORMATION: Xaa = S, T or P
<220> FEATURE:
<221> NAME/KEY: VARIANT
<222> LOCATION: 9
<223> OTHER INFORMATION: Xaa = W or P
<220> FEATURE:
<221> NAME/KEY: VARIANT
<222> LOCATION: 10
<223> OTHER INFORMATION: Xaa = A or R
<220> FEATURE:
<221> NAME/KEY: VARIANT
<222> LOCATION: 12
<223> OTHER INFORMATION: Xaa = S or R

<400> SEQUENCE: 126

Xaa Trp Trp Xaa Xaa Trp Ala Xaa Xaa Xaa Arg Xaa Trp Trp Arg
1 5 10 15

<210> SEQ ID NO 127
<211> LENGTH: 15
<212> TYPE: PRT
<213> ORGANISM: Artificial Sequence
<220> FEATURE:
<223> OTHER INFORMATION: Synthetic Construct

```
<220> FEATURE:
<221> NAME/KEY: VARIANT
<222> LOCATION: 1
<223> OTHER INFORMATION: Xaa = beta-A or S

<400> SEQUENCE: 127

Xaa Trp Trp Arg Trp Trp Ala Ser Trp Ala Arg Ser Trp Trp Arg
1               5                   10                  15


<210> SEQ ID NO 128
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 128

Xaa Trp Trp Gly Ser Trp Ala Thr Pro Arg Arg Arg Trp Trp Arg
1               5                   10                  15


<210> SEQ ID NO 129
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 129

Xaa Trp Trp Arg Trp Trp Ala Pro Trp Ala Arg Ser Trp Trp Arg
1               5                   10                  15


<210> SEQ ID NO 130
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 130

Ala Leu Arg Trp Trp Leu Arg Trp Ala Ser Arg Trp Phe Ser Arg Trp
1               5                   10                  15

Ala Trp Trp Arg
            20


<210> SEQ ID NO 131
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = 5-amino pentanoic acid

<400> SEQUENCE: 131

Lys Ser Tyr Asp Thr Tyr Xaa Ala Leu Arg Trp Leu Arg Trp Ala Ser
```

```
1               5                   10                  15

Arg Trp Phe Ser Arg Trp Ala Trp Arg
            20                  25


<210> SEQ ID NO 132
<211> LENGTH: 23
<212> TYPE: PRT
<213> ORGANISM: Artificial Sequence
<220> FEATURE:
<223> OTHER INFORMATION: Synthetic Construct

<400> SEQUENCE: 132

Cys Lys Arg Ala Val Arg Trp Trp Leu Arg Trp Ala Ser Arg Trp Phe
1               5                   10                  15

Ser Arg Trp Ala Trp Trp Arg
            20


<210> SEQ ID NO 133
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-R

<400> SEQUENCE: 133

Arg Trp Trp Leu Arg Trp Ala Ser Arg Trp Phe Ser Arg Trp Ala Trp
1               5                   10                  15

Arg


<210> SEQ ID NO 134
<211> LENGTH: 25
<212> TYPE: PRT
<213> ORGANISM: Artificial Sequence
<220> FEATURE:
<223> OTHER INFORMATION: Synthetic Construct

<400> SEQUENCE: 134

Lys Ser Tyr Asp Thr Tyr Ala Ala Glu Thr Arg Arg Trp Ala Ser Arg
1               5                   10                  15

Trp Phe Ser Arg Trp Ala Trp Trp Arg
            20                  25


<210> SEQ ID NO 135
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Any Amino Acid or none
<220> FEATURE:
<221> NAME/KEY: VARIANT
<222> LOCATION: 6, 7, 8, 15, 16, 17, 18
<223> OTHER INFORMATION: Xaa = Any Amino Acid

<400> SEQUENCE: 135

Xaa Lys Trp Arg Ser Xaa Xaa Xaa Arg Trp Arg Leu Trp Arg Xaa Xaa
1               5                   10                  15

Xaa Xaa Ser Arg
            20
```

<210> SEQ ID NO 136
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A, S, or none
<220> FEATURE:
<221> NAME/KEY: VARIANT
<222> LOCATION: 6
<223> OTHER INFORMATION: Xaa = A or V
<220> FEATURE:
<221> NAME/KEY: VARIANT
<222> LOCATION: 7
<223> OTHER INFORMATION: Xaa = G or L
<220> FEATURE:
<221> NAME/KEY: VARIANT
<222> LOCATION: 8
<223> OTHER INFORMATION: Xaa = W or Y
<220> FEATURE:
<221> NAME/KEY: VARIANT
<222> LOCATION: 15
<223> OTHER INFORMATION: Xaa = V or S
<220> FEATURE:
<221> NAME/KEY: VARIANT
<222> LOCATION: 16
<223> OTHER INFORMATION: Xaa = R, V, or A
<220> FEATURE:
<221> NAME/KEY: VARIANT
<222> LOCATION: 17
<223> OTHER INFORMATION: Xaa = S or L
<220> FEATURE:
<221> NAME/KEY: VARIANT
<222> LOCATION: 18
<223> OTHER INFORMATION: Xaa = W or Y

<400> SEQUENCE: 136

```
Xaa Lys Trp Arg Ser Xaa Xaa Xaa Arg Trp Arg Leu Trp Arg Xaa Xaa
1               5                   10                  15

Xaa Xaa Ser Arg
            20
```

<210> SEQ ID NO 137
<211> LENGTH: 19
<212> TYPE: PRT
<213> ORGANISM: Artificial Sequence
<220> FEATURE:
<223> OTHER INFORMATION: Synthetic Construct

<400> SEQUENCE: 137

```
Lys Trp Arg Ser Ala Gly Trp Arg Trp Arg Leu Trp Arg Val Arg Ser
1               5                   10                  15

Trp Ser Arg
```

<210> SEQ ID NO 138
<211> LENGTH: 19
<212> TYPE: PRT
<213> ORGANISM: Artificial Sequence
<220> FEATURE:
<223> OTHER INFORMATION: Synthetic Construct

<400> SEQUENCE: 138

```
Lys Trp Arg Ser Ala Leu Tyr Arg Trp Arg Leu Trp Arg Val Arg Ser
1               5                   10                  15

Trp Ser Arg
```

<210> SEQ ID NO 139
<211> LENGTH: 19
<212> TYPE: PRT
<213> ORGANISM: Artificial Sequence
<220> FEATURE:
<223> OTHER INFORMATION: Synthetic Construct

<400> SEQUENCE: 139

```
Lys Trp Arg Ser Ala Leu Tyr Arg Trp Arg Leu Trp Arg Ser Arg Ser
1               5                   10                  15

Trp Ser Arg
```

<210> SEQ ID NO 140
<211> LENGTH: 19
<212> TYPE: PRT
<213> ORGANISM: Artificial Sequence
<220> FEATURE:
<223> OTHER INFORMATION: Synthetic Construct

<400> SEQUENCE: 140

```
Lys Trp Arg Ser Ala Leu Tyr Arg Trp Arg Leu Trp Arg Ser Ala Leu
1               5                   10                  15

Tyr Ser Arg
```

<210> SEQ ID NO 141
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 8
<223> OTHER INFORMATION: Linked by hydrocarbon linkage

<400> SEQUENCE: 141

```
Lys Trp Arg Ser Ala Gly Trp Arg Trp Arg Leu Trp Arg Val Arg Ser
1               5                   10                  15

Trp Ser Arg
```

<210> SEQ ID NO 142
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 10
<223> OTHER INFORMATION: Linked by hydrocarbon linkage

<400> SEQUENCE: 142

```
Lys Trp Arg Ser Ala Gly Trp Arg Trp Arg Leu Trp Arg Val Arg Ser
1               5                   10                  15

Trp Ser Arg
```

<210> SEQ ID NO 143
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8, 15
<223> OTHER INFORMATION: Linked by hydrocarbon linkage

<400> SEQUENCE: 143

Lys Trp Arg Ser Ala Gly Trp Arg Trp Arg Leu Trp Arg Val Arg Ser
1 5 10 15

Trp Ser Arg

<210> SEQ ID NO 144
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 8
<223> OTHER INFORMATION: Linked by hydrocarbon linkage

<400> SEQUENCE: 144

Lys Trp Arg Ser Ala Leu Tyr Arg Trp Arg Leu Trp Arg Ser Arg Ser
1 5 10 15

Trp Ser Arg

<210> SEQ ID NO 145
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 10
<223> OTHER INFORMATION: Linked by hydrocarbon linkage

<400> SEQUENCE: 145

Lys Trp Arg Ser Ala Leu Tyr Arg Trp Arg Leu Trp Arg Ser Arg Ser
1 5 10 15

Trp Ser Arg

<210> SEQ ID NO 146
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8, 15
<223> OTHER INFORMATION: Linked by hydrocarbon linkage

<400> SEQUENCE: 146

Lys Trp Arg Ser Ala Leu Tyr Arg Trp Arg Leu Trp Arg Ser Arg Ser
1 5 10 15

Trp Ser Arg

<210> SEQ ID NO 147
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10, 14
<223> OTHER INFORMATION: Linked by hydrocarbon linkage

<400> SEQUENCE: 147

Lys Trp Arg Ser Ala Leu Tyr Arg Trp Arg Leu Trp Arg Ser Arg Ser
1 5 10 15

Trp Ser Arg

<210> SEQ ID NO 148
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 14, 18
<223> OTHER INFORMATION: Linked by hydrocarbon linkage

<400> SEQUENCE: 148

Lys Trp Arg Ser Ala Leu Tyr Arg Trp Arg Leu Trp Arg Ser Arg Ser
1 5 10 15

Trp Ser Arg

<210> SEQ ID NO 149
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 10
<223> OTHER INFORMATION: Linked by hydrocarbon linkage

<400> SEQUENCE: 149

Lys Trp Arg Ser Ala Leu Tyr Arg Trp Arg Leu Trp Arg Ser Ala Leu
1 5 10 15

Tyr Ser Arg

<210> SEQ ID NO 150
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 8
<223> OTHER INFORMATION: Linked by hydrocarbon linkage

<400> SEQUENCE: 150

Lys Trp Arg Ser Ala Leu Tyr Arg Trp Arg Leu Trp Arg Ser Ala Leu
1 5 10 15

Tyr Ser Arg

<210> SEQ ID NO 151
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10, 14
<223> OTHER INFORMATION: Linked by hydrocarbon linkage

<400> SEQUENCE: 151

Lys Trp Arg Ser Ala Leu Tyr Arg Trp Arg Leu Trp Arg Ser Ala Leu
1 5 10 15

Tyr Ser Arg

<210> SEQ ID NO 152
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 14, 18
<223> OTHER INFORMATION: Linked by hydrocarbon linkage

<400> SEQUENCE: 152

Lys Trp Arg Ser Ala Leu Tyr Arg Trp Arg Leu Trp Arg Ser Ala Leu
1 5 10 15

Tyr Ser Arg

<210> SEQ ID NO 153
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 20
<223> OTHER INFORMATION: Modified as shown in Sequence Table of the specification

<400> SEQUENCE: 153

Ala Lys Trp Arg Ser Ala Gly Trp Arg Trp Arg Leu Trp Arg Val Arg
1 5 10 15

Ser Trp Ser Arg
20

<210> SEQ ID NO 154
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 154

Ala Lys Trp Arg Ser Ala Gly Trp Arg Trp Arg Leu Trp Arg Val Arg
1 5 10 15

Ser Trp Ser Arg
20

<210> SEQ ID NO 155
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 155

Ala Lys Trp Arg Ser Ala Leu Tyr Arg Trp Arg Leu Trp Arg Val Arg
1 5 10 15

Ser Trp Ser Arg
20

<210> SEQ ID NO 156
<211> LENGTH: 19
<212> TYPE: PRT
<213> ORGANISM: Artificial Sequence
<220> FEATURE:
<223> OTHER INFORMATION: Synthetic Construct

<400> SEQUENCE: 156

Arg Ser Trp Ser Arg Val Arg Trp Leu Arg Trp Arg Trp Gly Ala Ser
1 5 10 15

Arg Trp Lys

<210> SEQ ID NO 157
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 20
<223> OTHER INFORMATION: Modified as shown in Sequence Table of the specification

<400> SEQUENCE: 157

Ala Lys Trp Arg Ser Ala Leu Trp Arg Trp Arg Leu Trp Arg Val Arg
1 5 10 15

Ser Trp Ser Arg
20

<210> SEQ ID NO 158
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 20
<223> OTHER INFORMATION: Modified as shown in Sequence Table of the specification

<400> SEQUENCE: 158

Ala Lys Trp Arg Ser Ala Leu Trp Arg Trp Arg Leu Trp Arg Val Arg
1 5 10 15

Ser Trp Ser Arg
20

<210> SEQ ID NO 159
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 20
<223> OTHER INFORMATION: Modified as shown in Sequence Table of the specification

<400> SEQUENCE: 159

Ala Lys Trp Arg Ser Ala Leu Trp Arg Trp Arg Leu Trp Arg Val Arg
1 5 10 15

Ser Trp Ser Arg

20

<210> SEQ ID NO 160
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 28
<223> OTHER INFORMATION: Modified as shown in Sequence Table of the specification

<400> SEQUENCE: 160

```
Tyr Ile Gly Ser Arg Gly Gly Gly Gly Lys Trp Arg Ser Ala Leu Trp
1               5                   10                  15

Arg Trp Arg Leu Trp Arg Val Arg Ser Trp Ser Arg
            20                  25
```

<210> SEQ ID NO 161
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 27
<223> OTHER INFORMATION: Modified as shown in Sequence Table of the specification

<400> SEQUENCE: 161

```
Gly Tyr Val Ser Gly Gly Gly Gly Lys Trp Arg Ser Ala Leu Trp Arg
1               5                   10                  15

Trp Arg Leu Trp Arg Val Arg Ser Trp Ser Arg
            20                  25
```

<210> SEQ ID NO 162
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification
<220> FEATURE:
<221> NAME/KEY: VARIANT
<222> LOCATION: 6
<223> OTHER INFORMATION: Xaa = 5-amino pentanoic acid

<400> SEQUENCE: 162

```
Tyr Ile Gly Ser Arg Xaa Lys Trp Arg Ser Ala Leu Trp Arg Trp Arg
1               5                   10                  15

Leu Trp Arg Val Arg Ser Trp Ser Arg
            20                  25
```

<210> SEQ ID NO 163
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 24

<223> OTHER INFORMATION: Modified as shown in Sequence Table of the
      specification
<220> FEATURE:
<221> NAME/KEY: VARIANT
<222> LOCATION: 5
<223> OTHER INFORMATION: Xaa = 5-amino pentanoic acid

<400> SEQUENCE: 163

Gly Tyr Val Ser Xaa Lys Trp Arg Ser Ala Leu Trp Arg Trp Arg Leu
1               5                   10                  15

Trp Arg Val Arg Ser Trp Ser Arg
            20

<210> SEQ ID NO 164
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the
      specification
<220> FEATURE:
<221> NAME/KEY: VARIANT
<222> LOCATION: 6
<223> OTHER INFORMATION: Xaa = 11-amino-undecanoic acid

<400> SEQUENCE: 164

Tyr Ile Gly Ser Arg Xaa Lys Trp Arg Ser Ala Leu Trp Arg Trp Arg
1               5                   10                  15

Leu Trp Arg Val Arg Ser Trp Ser Arg
            20                  25

<210> SEQ ID NO 165
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 24
<223> OTHER INFORMATION: Modified as shown in Sequence Table of the
      specification
<220> FEATURE:
<221> NAME/KEY: VARIANT
<222> LOCATION: 5
<223> OTHER INFORMATION: Xaa = 11-amino-undecanoic acid

<400> SEQUENCE: 165

Gly Tyr Val Ser Xaa Lys Trp Arg Ser Ala Leu Trp Arg Trp Arg Leu
1               5                   10                  15

Trp Arg Val Arg Ser Trp Ser Arg
            20

<210> SEQ ID NO 166
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the
      specification

<400> SEQUENCE: 166

Tyr Ile Gly Ser Arg Ala Lys Trp Arg Ser Ala Leu Trp Arg Trp Arg
1 5 10 15

Leu Trp Arg Val Arg Ser Trp Ser Arg
20 25

<210> SEQ ID NO 167
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification
<220> FEATURE:
<221> NAME/KEY: VARIANT
<222> LOCATION: 6
<223> OTHER INFORMATION: Xaa = Ahx

<400> SEQUENCE: 167

Tyr Ile Gly Ser Arg Xaa Lys Trp Arg Ser Ala Leu Trp Arg Trp Arg
1 5 10 15

Leu Trp Arg Val Arg Ser Trp Ser Arg
20 25

<210> SEQ ID NO 168
<211> LENGTH: 9
<212> TYPE: PRT
<213> ORGANISM: Artificial Sequence
<220> FEATURE:
<223> OTHER INFORMATION: Synthetic Construct

<400> SEQUENCE: 168

Arg Trp Arg Leu Trp Arg Trp Ser Arg
1 5

<210> SEQ ID NO 169
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 24
<223> OTHER INFORMATION: Modified as shown in Sequence Table of the specification
<220> FEATURE:
<221> NAME/KEY: VARIANT
<222> LOCATION: 5
<223> OTHER INFORMATION: Xaa = Ahx

<400> SEQUENCE: 169

Gly Tyr Val Ser Xaa Lys Trp Arg Ser Ala Leu Trp Arg Trp Arg Leu
1 5 10 15

Trp Arg Val Arg Ser Trp Ser Arg
20

<210> SEQ ID NO 170
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification

<400> SEQUENCE: 170

Tyr Ile Gly Ser Arg Ala Lys Trp Arg Ser Ala Leu Trp Arg Trp Arg
1 5 10 15

Leu Trp Arg Val Arg Ser Trp Ser Arg
20 25

<210> SEQ ID NO 171
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 27
<223> OTHER INFORMATION: Modified as shown in Sequence Table of the specification
<220> FEATURE:
<221> NAME/KEY: VARIANT
<222> LOCATION: 8
<223> OTHER INFORMATION: Xaa = 5-amino pentanoic acid

<400> SEQUENCE: 171

Ser Tyr Thr Ser Ser Thr Met Xaa Lys Trp Arg Ser Ala Leu Trp Arg
1 5 10 15

Trp Arg Leu Trp Arg Val Arg Ser Trp Ser Arg
20 25

<210> SEQ ID NO 172
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 20
<223> OTHER INFORMATION: Modified as shown in Sequence Table of the specification
<220> FEATURE:
<221> NAME/KEY: VARIANT
<222> LOCATION: 6
<223> OTHER INFORMATION: Xaa = GalNac

<400> SEQUENCE: 172

Lys Trp Arg Ser Ala Xaa Leu Trp Arg Trp Arg Leu Trp Arg Val Arg
1 5 10 15

Ser Trp Ser Arg
20

<210> SEQ ID NO 173
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 24
<223> OTHER INFORMATION: Modified as shown in Sequence Table of the specification

<400> SEQUENCE: 173

Cys Ala Arg Pro Ala Arg Trp Arg Ser Ala Gly Trp Arg Trp Arg Leu
1 5 10 15

```
Trp Arg Val Arg Ser Trp Ser Arg
            20


<210> SEQ ID NO 174
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 27
<223> OTHER INFORMATION: Modified as shown in Sequence Table of the
      specification

<400> SEQUENCE: 174

Thr Gly Asn Tyr Lys Ala Leu His Pro Asp His Asn Gly Trp Arg Ser
1               5                   10                  15

Ala Leu Arg Trp Arg Leu Trp Arg Trp Ser Arg
            20                  25


<210> SEQ ID NO 175
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 28
<223> OTHER INFORMATION: Modified as shown in Sequence Table of the
      specification
<220> FEATURE:
<221> NAME/KEY: VARIANT
<222> LOCATION: 14
<223> OTHER INFORMATION: Xaa = 5-amino pentanoic acid

<400> SEQUENCE: 175

Thr Gly Asn Tyr Lys Ala Leu His Pro Asp His Asn Gly Xaa Trp Arg
1               5                   10                  15

Ser Ala Leu Arg Trp Arg Leu Trp Arg Trp Ser Arg
            20                  25


<210> SEQ ID NO 176
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3
<223> OTHER INFORMATION: Xaa = W or F
<220> FEATURE:
<221> NAME/KEY: VARIANT
<222> LOCATION: 6
<223> OTHER INFORMATION: Xaa = R if X in position 8 is S, or
      S if X in position 8 is R
<220> FEATURE:
<221> NAME/KEY: VARIANT
<222> LOCATION: 7
<223> OTHER INFORMATION: Xaa = L or none, or
      L if X in position 11 is none
<220> FEATURE:
<221> NAME/KEY: VARIANT
<222> LOCATION: 8
<223> OTHER INFORMATION: Xaa = Any Amino Acid
```

<220> FEATURE:
<221> NAME/KEY: VARIANT
<222> LOCATION: 9
<223> OTHER INFORMATION: Xaa = W or F
<220> FEATURE:
<221> NAME/KEY: VARIANT
<222> LOCATION: 10
<223> OTHER INFORMATION: Xaa = W or F
<220> FEATURE:
<221> NAME/KEY: VARIANT
<222> LOCATION: 11
<223> OTHER INFORMATION: Xaa = R or none

<400> SEQUENCE: 176

Xaa Trp Xaa Arg Leu Xaa Xaa Xaa Xaa Xaa Xaa
1 5 10

<210> SEQ ID NO 177
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 177

Xaa Trp Trp Arg Leu Ser Leu Arg Trp Trp
1 5 10

<210> SEQ ID NO 178
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 178

Xaa Trp Phe Arg Leu Ser Leu Arg Phe Trp Arg
1 5 10

<210> SEQ ID NO 179
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 179

Xaa Trp Trp Arg Leu Arg Ser Trp Phe Arg
1 5 10

<210> SEQ ID NO 180
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1

<223> OTHER INFORMATION: Xaa = beta-A or S

<400> SEQUENCE: 180

Xaa Trp Phe Arg Leu Ser Leu Arg Phe Trp
1 5 10

<210> SEQ ID NO 181
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = R or S
<220> FEATURE:
<221> NAME/KEY: VARIANT
<222> LOCATION: 4, 8
<223> OTHER INFORMATION: Xaa = W or F

<400> SEQUENCE: 181

Arg Xaa Trp Xaa Arg Leu Trp Xaa Arg Leu Arg
1 5 10

<210> SEQ ID NO 182
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 182

Xaa Trp Trp Arg Leu Trp Trp Arg Leu Arg
1 5 10

<210> SEQ ID NO 183
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 183

Xaa Trp Phe Arg Leu Trp Phe Arg Leu Arg
1 5 10

<210> SEQ ID NO 184
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 184

Xaa Trp Phe Arg Leu Trp Trp Arg Leu Arg
1 5 10

```
<210> SEQ ID NO 185
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 185

Xaa Trp Trp Arg Leu Trp Phe Arg Leu Arg
1               5                   10


<210> SEQ ID NO 186
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 186

Xaa Arg Trp Trp Arg Leu Trp Trp Arg Leu
1               5                   10


<210> SEQ ID NO 187
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 187

Xaa Arg Ser Trp Phe Arg Leu Trp Phe Arg
1               5                   10


<210> SEQ ID NO 188
<211> LENGTH: 21
<212> TYPE: PRT
<213> ORGANISM: Artificial Sequence
<220> FEATURE:
<223> OTHER INFORMATION: Synthetic Construct

<400> SEQUENCE: 188

Lys Glu Thr Trp Trp Glu Thr Trp Trp Thr Glu Trp Ser Gln Pro Lys
1               5                   10                  15

Lys Lys Arg Lys Val
            20


<210> SEQ ID NO 189
<211> LENGTH: 21
<212> TYPE: PRT
<213> ORGANISM: Artificial Sequence
<220> FEATURE:
<223> OTHER INFORMATION: Synthetic Construct

<400> SEQUENCE: 189

Lys Glu Thr Trp Phe Glu Thr Trp Phe Thr Glu Trp Ser Gln Pro Lys
1               5                   10                  15
```

Lys Lys Arg Lys Val
20

<210> SEQ ID NO 190
<211> LENGTH: 15
<212> TYPE: PRT
<213> ORGANISM: Artificial Sequence
<220> FEATURE:
<223> OTHER INFORMATION: Synthetic Construct

<400> SEQUENCE: 190

Lys Trp Phe Glu Thr Trp Phe Thr Glu Trp Pro Lys Lys Arg Lys
1 5 10 15

<210> SEQ ID NO 191
<211> LENGTH: 27
<212> TYPE: PRT
<213> ORGANISM: Artificial Sequence
<220> FEATURE:
<223> OTHER INFORMATION: Synthetic Construct

<400> SEQUENCE: 191

Gly Ala Leu Phe Leu Gly Phe Leu Gly Ala Ala Gly Ser Thr Met Gly
1 5 10 15

Ala Trp Ser Gln Pro Lys Lys Lys Arg Lys Val
20 25

<210> SEQ ID NO 192
<211> LENGTH: 20
<212> TYPE: PRT
<213> ORGANISM: Artificial Sequence
<220> FEATURE:
<223> OTHER INFORMATION: Synthetic Construct

<400> SEQUENCE: 192

Gly Leu Trp Arg Ala Leu Trp Arg Leu Leu Arg Ser Leu Trp Arg Leu
1 5 10 15

Leu Trp Lys Val
20

<210> SEQ ID NO 193
<211> LENGTH: 17
<212> TYPE: PRT
<213> ORGANISM: Artificial Sequence
<220> FEATURE:
<223> OTHER INFORMATION: Synthetic Construct

<400> SEQUENCE: 193

Arg Gln Ile Lys Ile Trp Phe Gln Asn Arg Arg Met Lys Trp Lys Lys
1 5 10 15

Cys

<210> SEQ ID NO 194
<211> LENGTH: 31
<212> TYPE: PRT
<213> ORGANISM: Artificial Sequence
<220> FEATURE:
<223> OTHER INFORMATION: Synthetic Construct

<400> SEQUENCE: 194

Cys Arg Arg Arg Gln Arg Arg Lys Lys Arg Gly Gly Asp Ile Met Gly
1 5 10 15

Glu Trp Gly Asn Glu Ile Phe Gly Ala Ile Ala Gly Phe Leu Gly
20 25 30

<210> SEQ ID NO 195
<211> LENGTH: 27
<212> TYPE: PRT
<213> ORGANISM: Artificial Sequence
<220> FEATURE:
<223> OTHER INFORMATION: Synthetic Construct

<400> SEQUENCE: 195

Lys Lys Ala Leu Leu Ala Leu Ala Leu His His Leu Ala His Leu Ala
1               5                   10                  15

Leu His Leu Ala Leu Ala Leu Lys Lys Ala Cys
            20                  25

<210> SEQ ID NO 196
<211> LENGTH: 7
<212> TYPE: PRT
<213> ORGANISM: Artificial Sequence
<220> FEATURE:
<223> OTHER INFORMATION: Synthetic Construct

<400> SEQUENCE: 196

Ser Tyr Thr Ser Ser Thr Met
1               5

<210> SEQ ID NO 197
<211> LENGTH: 7
<212> TYPE: PRT
<213> ORGANISM: Artificial Sequence
<220> FEATURE:
<223> OTHER INFORMATION: Synthetic Construct

<400> SEQUENCE: 197

Cys Lys Thr Arg Arg Val Pro
1               5

<210> SEQ ID NO 198
<211> LENGTH: 10
<212> TYPE: PRT
<213> ORGANISM: Artificial Sequence
<220> FEATURE:
<223> OTHER INFORMATION: Synthetic Construct

<400> SEQUENCE: 198

Thr His Arg Pro Pro Asn Trp Ser Pro Val
1               5                   10

<210> SEQ ID NO 199
<211> LENGTH: 13
<212> TYPE: PRT
<213> ORGANISM: Artificial Sequence
<220> FEATURE:
<223> OTHER INFORMATION: Synthetic Construct

<400> SEQUENCE: 199

Thr Gly Asn Tyr Lys Ala Leu His Pro Asp His Asn Gly
1               5                   10

<210> SEQ ID NO 200
<211> LENGTH: 6
<212> TYPE: PRT
<213> ORGANISM: Artificial Sequence
<220> FEATURE:
<223> OTHER INFORMATION: Synthetic Construct

<400> SEQUENCE: 200

Cys Ala Arg Pro Ala Arg
1 5

<210> SEQ ID NO 201
<211> LENGTH: 5
<212> TYPE: PRT
<213> ORGANISM: Artificial Sequence
<220> FEATURE:
<223> OTHER INFORMATION: Synthetic Construct

<400> SEQUENCE: 201

Tyr Ile Gly Ser Arg
1 5

<210> SEQ ID NO 202
<211> LENGTH: 4
<212> TYPE: PRT
<213> ORGANISM: Artificial Sequence
<220> FEATURE:
<223> OTHER INFORMATION: Synthetic Construct

<400> SEQUENCE: 202

Gly Tyr Val Ser
1

<210> SEQ ID NO 203
<211> LENGTH: 7
<212> TYPE: PRT
<213> ORGANISM: Artificial Sequence
<220> FEATURE:
<223> OTHER INFORMATION: Synthetic Construct

<400> SEQUENCE: 203

Ala Ser Ser Leu Asn Ile Ala
1 5

<210> SEQ ID NO 204
<211> LENGTH: 7
<212> TYPE: PRT
<213> ORGANISM: Artificial Sequence
<220> FEATURE:
<223> OTHER INFORMATION: Synthetic Construct

<400> SEQUENCE: 204

Leu Ser Ser Arg Leu Asp Ala
1 5

<210> SEQ ID NO 205
<211> LENGTH: 6
<212> TYPE: PRT
<213> ORGANISM: Artificial Sequence
<220> FEATURE:
<223> OTHER INFORMATION: Synthetic Construct

<400> SEQUENCE: 205

Lys Ser Tyr Asp Thr Tyr
1 5

<210> SEQ ID NO 206
<211> LENGTH: 3
<212> TYPE: PRT
<213> ORGANISM: Artificial Sequence
<220> FEATURE:
<223> OTHER INFORMATION: Synthetic Construct

<400> SEQUENCE: 206

Ala Gly Gly

1

<210> SEQ ID NO 207
<211> LENGTH: 3
<212> TYPE: PRT
<213> ORGANISM: Artificial Sequence
<220> FEATURE:
<223> OTHER INFORMATION: Synthetic Construct

<400> SEQUENCE: 207

Thr Gly Gly
1

<210> SEQ ID NO 208
<211> LENGTH: 3
<212> TYPE: PRT
<213> ORGANISM: Artificial Sequence
<220> FEATURE:
<223> OTHER INFORMATION: Synthetic Construct

<400> SEQUENCE: 208

Thr Ala Gly
1

<210> SEQ ID NO 209
<211> LENGTH: 3
<212> TYPE: PRT
<213> ORGANISM: Artificial Sequence
<220> FEATURE:
<223> OTHER INFORMATION: Synthetic Construct

<400> SEQUENCE: 209

Gly Ala Gly
1

<210> SEQ ID NO 210
<211> LENGTH: 3
<212> TYPE: PRT
<213> ORGANISM: Artificial Sequence
<220> FEATURE:
<223> OTHER INFORMATION: Synthetic Construct

<400> SEQUENCE: 210

Gly Cys Cys
1

<210> SEQ ID NO 211
<211> LENGTH: 3
<212> TYPE: PRT
<213> ORGANISM: Artificial Sequence
<220> FEATURE:
<223> OTHER INFORMATION: Synthetic Construct

<400> SEQUENCE: 211

Ala Cys Gly
1

<210> SEQ ID NO 212
<211> LENGTH: 7
<212> TYPE: PRT
<213> ORGANISM: Artificial Sequence
<220> FEATURE:
<223> OTHER INFORMATION: Synthetic Construct

<400> SEQUENCE: 212

Pro Lys Lys Lys Arg Lys Val
1               5

<210> SEQ ID NO 213
<211> LENGTH: 16
<212> TYPE: PRT
<213> ORGANISM: Artificial Sequence
<220> FEATURE:
<223> OTHER INFORMATION: Synthetic Construct

<400> SEQUENCE: 213

Lys Arg Pro Ala Ala Thr Lys Lys Ala Gly Gln Ala Lys Lys Lys Lys
1               5                   10                  15

<210> SEQ ID NO 214
<211> LENGTH: 9
<212> TYPE: PRT
<213> ORGANISM: Artificial Sequence
<220> FEATURE:
<223> OTHER INFORMATION: Synthetic Construct

<400> SEQUENCE: 214

Pro Ala Ala Lys Arg Val Lys Leu Asp
1               5

<210> SEQ ID NO 215
<211> LENGTH: 11
<212> TYPE: PRT
<213> ORGANISM: Artificial Sequence
<220> FEATURE:
<223> OTHER INFORMATION: Synthetic Construct

<400> SEQUENCE: 215

Arg Gln Arg Arg Asn Glu Leu Lys Arg Ser Pro
1               5                   10

<210> SEQ ID NO 216
<211> LENGTH: 38
<212> TYPE: PRT
<213> ORGANISM: Artificial Sequence
<220> FEATURE:
<223> OTHER INFORMATION: Synthetic Construct

<400> SEQUENCE: 216

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 217
<211> LENGTH: 42
<212> TYPE: PRT
<213> ORGANISM: Artificial Sequence
<220> FEATURE:
<223> OTHER INFORMATION: Synthetic Construct

<400> SEQUENCE: 217

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 218
<211> LENGTH: 8
<212> TYPE: PRT
<213> ORGANISM: Artificial Sequence
<220> FEATURE:
<223> OTHER INFORMATION: Synthetic Construct

<400> SEQUENCE: 218

Val Ser Arg Lys Arg Pro Arg Pro
1               5

<210> SEQ ID NO 219
<211> LENGTH: 8
<212> TYPE: PRT
<213> ORGANISM: Artificial Sequence
<220> FEATURE:
<223> OTHER INFORMATION: Synthetic Construct

<400> SEQUENCE: 219

Pro Pro Lys Lys Ala Arg Glu Asp
1               5

<210> SEQ ID NO 220
<211> LENGTH: 8
<212> TYPE: PRT
<213> ORGANISM: Homo sapiens

<400> SEQUENCE: 220

Pro Gln Pro Lys Lys Lys Pro Leu
1               5

<210> SEQ ID NO 221
<211> LENGTH: 12
<212> TYPE: PRT
<213> ORGANISM: Mus musculus

<400> SEQUENCE: 221

Ser Ala Leu Ile Lys Lys Lys Lys Lys Met Ala Pro
1               5                   10

<210> SEQ ID NO 222
<211> LENGTH: 5
<212> TYPE: PRT
<213> ORGANISM: Influenza virus NS1

<400> SEQUENCE: 222

Asp Arg Leu Arg Arg
1               5

<210> SEQ ID NO 223
<211> LENGTH: 7
<212> TYPE: PRT
<213> ORGANISM: Influenza virus NS1

<400> SEQUENCE: 223

Pro Lys Gln Lys Lys Arg Lys
1               5

<210> SEQ ID NO 224
<211> LENGTH: 10
<212> TYPE: PRT
<213> ORGANISM: Hepatitis virus

<400> SEQUENCE: 224

Arg Lys Leu Lys Lys Lys Ile Lys Lys Leu
1               5                   10

<210> SEQ ID NO 225
<211> LENGTH: 10
<212> TYPE: PRT
<213> ORGANISM: Mus musculus

<400> SEQUENCE: 225

Arg Glu Lys Lys Lys Phe Leu Lys Arg Arg
1               5                   10

<210> SEQ ID NO 226
<211> LENGTH: 20
<212> TYPE: PRT
<213> ORGANISM: Homo sapiens

<400> SEQUENCE: 226

Lys Arg Lys Gly Asp Glu Val Asp Gly Val Asp Glu Val Ala Lys Lys
1               5                   10                  15

Lys Ser Lys Lys
            20

<210> SEQ ID NO 227
<211> LENGTH: 17
<212> TYPE: PRT
<213> ORGANISM: Homo sapiens

<400> SEQUENCE: 227

Arg Lys Cys Leu Gln Ala Gly Met Asn Leu Glu Ala Arg Lys Thr Lys
1               5                   10                  15

Lys

<210> SEQ ID NO 228
<211> LENGTH: 21
<212> TYPE: RNA
<213> ORGANISM: Artificial Sequence
<220> FEATURE:
<223> OTHER INFORMATION: Synthetic Construct

<400> SEQUENCE: 228
guuggagcuu guggcguagt t                                              21

<210> SEQ ID NO 229
<211> LENGTH: 21
<212> TYPE: RNA
<213> ORGANISM: Artificial Sequence
<220> FEATURE:
<223> OTHER INFORMATION: Synthetic Construct

<400> SEQUENCE: 229
cuacgccacc agcuccaact t                                              21

<210> SEQ ID NO 230
<211> LENGTH: 22
<212> TYPE: RNA
<213> ORGANISM: Artificial Sequence
<220> FEATURE:
<223> OTHER INFORMATION: Synthetic Construct

<400> SEQUENCE: 230
gatgaggcta ttcatgatga tt                                             22

<210> SEQ ID NO 231
<211> LENGTH: 21
<212> TYPE: RNA

<213> ORGANISM: Artificial Sequence
<220> FEATURE:
<223> OTHER INFORMATION: Synthetic Construct

<400> SEQUENCE: 231
gaagugcaua caccgagact t 21

<210> SEQ ID NO 232
<211> LENGTH: 20
<212> TYPE: RNA
<213> ORGANISM: Artificial Sequence
<220> FEATURE:
<223> OTHER INFORMATION: Synthetic Construct

<400> SEQUENCE: 232
gucucggugu agcacuuctt 20

<210> SEQ ID NO 233
<211> LENGTH: 21
<212> TYPE: RNA
<213> ORGANISM: Artificial Sequence
<220> FEATURE:
<223> OTHER INFORMATION: Synthetic Construct

<400> SEQUENCE: 233
guuggagcug uuggcguagt t 21

<210> SEQ ID NO 234
<211> LENGTH: 21
<212> TYPE: RNA
<213> ORGANISM: Artificial Sequence
<220> FEATURE:
<223> OTHER INFORMATION: Synthetic Construct

<400> SEQUENCE: 234
cuacgccaac agcuccaact t 21

<210> SEQ ID NO 235
<211> LENGTH: 4
<212> TYPE: PRT
<213> ORGANISM: Artificial Sequence
<220> FEATURE:
<223> OTHER INFORMATION: Synthetic Construct

<400> SEQUENCE: 235

Tyr Val Ser Lys
1

<210> SEQ ID NO 236
<211> LENGTH: 4
<212> TYPE: PRT
<213> ORGANISM: Artificial Sequence
<220> FEATURE:
<223> OTHER INFORMATION: Synthetic Construct

<400> SEQUENCE: 236

Tyr Ile Gly Ser
1

<210> SEQ ID NO 237
<211> LENGTH: 4
<212> TYPE: PRT
<213> ORGANISM: Artificial Sequence
<220> FEATURE:
<223> OTHER INFORMATION: Synthetic Construct

<400> SEQUENCE: 237

Ile Gly Ser Arg
1

<210> SEQ ID NO 238
<211> LENGTH: 5
<212> TYPE: PRT
<213> ORGANISM: Artificial Sequence
<220> FEATURE:
<223> OTHER INFORMATION: Synthetic Construct

<400> SEQUENCE: 238

Gly Tyr Val Ser Lys
1 5

<210> SEQ ID NO 239
<211> LENGTH: 5
<212> TYPE: PRT
<213> ORGANISM: Artificial Sequence
<220> FEATURE:
<223> OTHER INFORMATION: Synthetic Construct

<400> SEQUENCE: 239

Gly Gly Gly Gly Ser
1 5

<210> SEQ ID NO 240
<211> LENGTH: 5
<212> TYPE: PRT
<213> ORGANISM: Artificial Sequence
<220> FEATURE:
<223> OTHER INFORMATION: Synthetic Construct

<400> SEQUENCE: 240

Ser Gly Gly Gly Gly
1 5

<210> SEQ ID NO 241
<211> LENGTH: 22
<212> TYPE: DNA
<213> ORGANISM: Artificial Sequence
<220> FEATURE:
<223> OTHER INFORMATION: Synthetic Construct

<400> SEQUENCE: 241
tggtagttgg agctgttggc gt 22

<210> SEQ ID NO 242
<211> LENGTH: 18
<212> TYPE: DNA
<213> ORGANISM: Artificial Sequence
<220> FEATURE:
<223> OTHER INFORMATION: Synthetic Construct

<400> SEQUENCE: 242
agctgttggc gtaggcaa 18

<210> SEQ ID NO 243
<211> LENGTH: 19
<212> TYPE: DNA
<213> ORGANISM: Artificial Sequence
<220> FEATURE:
<223> OTHER INFORMATION: Synthetic Construct

<400> SEQUENCE: 243
tgttggcgta ggcaagagt 19

<210> SEQ ID NO 244
<211> LENGTH: 17
<212> TYPE: DNA
<213> ORGANISM: Artificial Sequence
<220> FEATURE:
<223> OTHER INFORMATION: Synthetic Construct

<400> SEQUENCE: 244
gttggagctg ttggcgt 17

<210> SEQ ID NO 245
<211> LENGTH: 19
<212> TYPE: DNA
<213> ORGANISM: Artificial Sequence
<220> FEATURE:
<223> OTHER INFORMATION: Synthetic Construct

<400> SEQUENCE: 245
ttgtggtagt tggagctgt 19

<210> SEQ ID NO 246
<211> LENGTH: 17
<212> TYPE: DNA
<213> ORGANISM: Artificial Sequence
<220> FEATURE:
<223> OTHER INFORMATION: Synthetic Construct

<400> SEQUENCE: 246
gctgttggcg taggcaa 17

<210> SEQ ID NO 247
<211> LENGTH: 20
<212> TYPE: DNA
<213> ORGANISM: Artificial Sequence
<220> FEATURE:
<223> OTHER INFORMATION: Synthetic Construct

<400> SEQUENCE: 247
ggtagttgga gctgatggcg 20

<210> SEQ ID NO 248
<211> LENGTH: 18
<212> TYPE: DNA
<213> ORGANISM: Artificial Sequence
<220> FEATURE:
<223> OTHER INFORMATION: Synthetic Construct

<400> SEQUENCE: 248
agctgatggc gtaggcaa 18

<210> SEQ ID NO 249
<211> LENGTH: 19
<212> TYPE: DNA
<213> ORGANISM: Artificial Sequence
<220> FEATURE:
<223> OTHER INFORMATION: Synthetic Construct

<400> SEQUENCE: 249
tgatggcgta ggcaagagt 19

<210> SEQ ID NO 250
<211> LENGTH: 17
<212> TYPE: DNA
<213> ORGANISM: Artificial Sequence
<220> FEATURE:
<223> OTHER INFORMATION: Synthetic Construct

<400> SEQUENCE: 250
gttggagctg atggcgt 17

<210> SEQ ID NO 251
<211> LENGTH: 19
<212> TYPE: DNA
<213> ORGANISM: Artificial Sequence
<220> FEATURE:
<223> OTHER INFORMATION: Synthetic Construct

<400> SEQUENCE: 251
ttgtggtagt tggagctga 19

<210> SEQ ID NO 252
<211> LENGTH: 17
<212> TYPE: DNA
<213> ORGANISM: Artificial Sequence
<220> FEATURE:
<223> OTHER INFORMATION: Synthetic Construct

<400> SEQUENCE: 252
gctgatggcg taggcaa 17

<210> SEQ ID NO 253
<211> LENGTH: 18
<212> TYPE: DNA
<213> ORGANISM: Artificial Sequence
<220> FEATURE:
<223> OTHER INFORMATION: Synthetic Construct

<400> SEQUENCE: 253
agcttgtggc gtaggcaa 18

<210> SEQ ID NO 254
<211> LENGTH: 17
<212> TYPE: DNA
<213> ORGANISM: Artificial Sequence
<220> FEATURE:
<223> OTHER INFORMATION: Synthetic Construct

<400> SEQUENCE: 254
gttggagctt gtggcgt 17

<210> SEQ ID NO 255
<211> LENGTH: 20
<212> TYPE: DNA
<213> ORGANISM: Artificial Sequence
<220> FEATURE:
<223> OTHER INFORMATION: Synthetic Construct

<400> SEQUENCE: 255
ggtagttgga gcttgtggcg 20

<210> SEQ ID NO 256
<211> LENGTH: 17
<212> TYPE: DNA
<213> ORGANISM: Artificial Sequence
<220> FEATURE:
<223> OTHER INFORMATION: Synthetic Construct

<400> SEQUENCE: 256
gcttgtggcg taggcaa 17

<210> SEQ ID NO 257

<211> LENGTH: 20
<212> TYPE: DNA
<213> ORGANISM: Artificial Sequence
<220> FEATURE:
<223> OTHER INFORMATION: Synthetic Construct

<400> SEQUENCE: 257
cttgtggcgt aggcaagagt 20

<210> SEQ ID NO 258
<211> LENGTH: 20
<212> TYPE: DNA
<213> ORGANISM: Artificial Sequence
<220> FEATURE:
<223> OTHER INFORMATION: Synthetic Construct

<400> SEQUENCE: 258
acaactttac cgaccgcgcc 20

<210> SEQ ID NO 259
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 20
<223> OTHER INFORMATION: Modified as shown in Sequence Table of the specification

<400> SEQUENCE: 259

```
Ala Lys Trp Arg Ser Ala Leu Trp Arg Trp Arg Leu Trp Arg Val Arg
1               5                   10                  15

Ser Trp Ser Arg
            20
```

<210> SEQ ID NO 260
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification

<400> SEQUENCE: 260

```
Tyr Ile Gly Ser Arg Ala Lys Trp Arg Ser Ala Leu Trp Arg Trp Arg
1               5                   10                  15

Leu Trp Arg Val Arg Ser Trp Ser Arg
            20                  25
```

<210> SEQ ID NO 261
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification
<220> FEATURE:
<221> NAME/KEY: VARIANT
<222> LOCATION: 6

<223> OTHER INFORMATION: Xaa = 5-amino pentanoic acid

<400> SEQUENCE: 261

Tyr Ile Gly Ser Arg Xaa Ala Leu Trp Arg Ala Leu Trp Arg Leu Trp
1 5 10 15

Arg Ser Leu Trp Arg Leu Leu Trp Lys
20 25

<210> SEQ ID NO 262
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification
<220> FEATURE:
<221> NAME/KEY: VARIANT
<222> LOCATION: 6
<223> OTHER INFORMATION: Xaa = 11-amino-undecanoic acid

<400> SEQUENCE: 262

Tyr Ile Gly Ser Arg Xaa Ala Leu Trp Arg Ala Leu Trp Arg Leu Trp
1 5 10 15

Arg Ser Leu Trp Arg Leu Leu Trp Lys
20 25

<210> SEQ ID NO 263
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 19
<223> OTHER INFORMATION: Modified as shown in Sequence Table of the specification

<400> SEQUENCE: 263

Ala Leu Trp Arg Ala Leu Trp Arg Leu Trp Arg Ser Leu Trp Arg Leu
1 5 10 15

Leu Trp Lys

<210> SEQ ID NO 264
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 24
<223> OTHER INFORMATION: Modified as shown in Sequence Table of the specification

<400> SEQUENCE: 264

Tyr Ile Gly Ser Arg Ala Leu Trp Arg Ala Leu Trp Arg Leu Trp Arg
1 5 10 15

Ser Leu Trp Arg Leu Leu Trp Lys
20

<210> SEQ ID NO 265
<211> LENGTH: 25

<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification
<220> FEATURE:
<221> NAME/KEY: VARIANT
<222> LOCATION: 6
<223> OTHER INFORMATION: Xaa = 5-amino pentanoic acid

<400> SEQUENCE: 265

```
Tyr Ile Gly Ser Arg Xaa Ala Leu Trp Arg Ala Leu Trp Arg Leu Trp
1               5                   10                  15

Arg Ser Leu Trp Arg Leu Leu Trp Lys
            20                  25
```

<210> SEQ ID NO 266
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification
<220> FEATURE:
<221> NAME/KEY: VARIANT
<222> LOCATION: 6
<223> OTHER INFORMATION: Xaa = 11-amino-undecanoic acid

<400> SEQUENCE: 266

```
Tyr Ile Gly Ser Arg Xaa Ala Leu Trp Arg Ala Leu Trp Arg Leu Trp
1               5                   10                  15

Arg Ser Leu Trp Arg Leu Leu Trp Lys
            20                  25
```

<210> SEQ ID NO 267
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 20
<223> OTHER INFORMATION: Modified as shown in Sequence Table of the specification

<400> SEQUENCE: 267

```
Ala Lys Trp Arg Ser Ala Leu Trp Arg Trp Arg Leu Trp Arg Val Arg
1               5                   10                  15

Ser Trp Ser Arg
            20
```

<210> SEQ ID NO 268
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 20
<223> OTHER INFORMATION: Modified as shown in Sequence Table of the specification

<400> SEQUENCE: 268

```
Ala Lys Trp Arg Ser Ala Leu Trp Arg Trp Arg Leu Trp Arg Val Arg
1               5                   10                  15

Ser Trp Ser Arg
            20
```

<210> SEQ ID NO 269
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 25
<223> OTHER INFORMATION: Modified as shown in Sequence Table of the specification

<400> SEQUENCE: 269

```
Tyr Ile Gly Ser Arg Ala Lys Trp Arg Ser Ala Leu Trp Arg Trp Arg
1               5                   10                  15

Leu Trp Arg Val Arg Ser Trp Ser Arg
            20                  25
```

<210> SEQ ID NO 270
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 270

```
Ala Leu Trp Arg Ala Leu Trp Arg Leu Trp Arg Ser Leu Trp Arg Leu
1               5                   10                  15

Leu Trp Lys Ala
            20
```

<210> SEQ ID NO 271
<211> LENGTH: 25
<212> TYPE: DNA
<213> ORGANISM: Artificial Sequence
<220> FEATURE:
<223> OTHER INFORMATION: Synthetic Construct

<400> SEQUENCE: 271

```
ttgtggcgta ggcaagagtg ccttg                                           25
```